(12) United States Patent
Haskell

(10) Patent No.: US 9,788,908 B1
(45) Date of Patent: Oct. 17, 2017

(54) EXTERNAL FIXATOR DEFORMITY CORRECTION SYSTEMS AND METHODS

(71) Applicant: Stryker European Holdings I, LLC, Kalamazoo, MI (US)

(72) Inventor: Andrew Haskell, Burlingame, CA (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/630,010

(22) Filed: Jun. 22, 2017

Related U.S. Application Data

(63) Continuation of application No. 15/350,220, filed on Nov. 14, 2016, which is a continuation of application No. 14/617,321, filed on Feb. 9, 2015, now Pat. No. 9,524,581, which is a continuation of application No. 14/165,420, filed on Jan. 27, 2014, now Pat. No. 8,952,986, which is a continuation of application No.
(Continued)

(51) Int. Cl.
| | |
|---|---|
| *G09G 5/00* | (2006.01) |
| *A61B 34/10* | (2016.01) |
| *G06T 19/20* | (2011.01) |
| *A61B 17/62* | (2006.01) |
| *G06F 3/0486* | (2013.01) |

(52) U.S. Cl.
CPC .............. *A61B 34/10* (2016.02); *G06T 19/20* (2013.01); *A61B 17/62* (2013.01); *A61B 2034/104* (2016.02); *A61B 2034/105* (2016.02); *G06F 3/0486* (2013.01); *G06T 2200/24* (2013.01); *G06T 2219/2004* (2013.01); *G06T 2219/2016* (2013.01)

(58) Field of Classification Search
None
See application file for complete search history.

(56) References Cited

U.S. PATENT DOCUMENTS

| | | |
|---|---|---|
| 5,546,942 A | 8/1996 | Zhang |
| 5,681,309 A | 10/1997 | Ross, Jr. et al. |

(Continued)

FOREIGN PATENT DOCUMENTS

| | | |
|---|---|---|
| DE | 102006048451 A1 | 4/2008 |
| RU | 2448663 C1 | 5/2012 |

(Continued)

OTHER PUBLICATIONS

European Patent Office (ISA), International Search Report and Written Opinion dated Jun. 25, 2013 for International Application No. PCT/US2013/024548,International filing date Feb. 3, 2013.

(Continued)

*Primary Examiner* — Peter Hoang
(74) *Attorney, Agent, or Firm* — Lerner, David, Littenberg, Krumholz & Mentlik, LLP

(57) ABSTRACT

In some embodiments, a synthetic (virtual) orthopedic treatment device (e.g. a virtual external fixator representing a physical fixator attachable to a patient's anatomic structure) is displayed concurrently in two views (e.g. anterior-posterior and lateral) along corresponding digital medical images (e.g. X-rays), and rotation/translation user input received along one of the images is used to concurrently control both displays of the orthopedic treatment device to reflect the rotation/translation user input.

21 Claims, 104 Drawing Sheets

Related U.S. Application Data

13/758,814, filed on Feb. 4, 2013, now Pat. No. 8,654,150.

(60) Provisional application No. 61/594,519, filed on Feb. 3, 2012.

(56) References Cited

U.S. PATENT DOCUMENTS

| | | | |
|---|---|---|---|
| 5,702,389 A | 12/1997 | Taylor et al. | |
| 5,728,095 A | 3/1998 | Taylor et al. | |
| 5,824,085 A | 10/1998 | Sahay et al. | |
| 5,880,976 A | 3/1999 | DiGioia, III et al. | |
| 5,891,143 A | 4/1999 | Taylor et al. | |
| 5,971,984 A | 10/1999 | Taylor et al. | |
| 6,030,386 A | 2/2000 | Taylor et al. | |
| 6,129,727 A | 10/2000 | Austin et al. | |
| 6,205,411 B1 | 3/2001 | DiGioia, III et al. | |
| 6,701,174 B1 | 3/2004 | Krause et al. | |
| 6,711,432 B1 | 3/2004 | Krause et al. | |
| 7,039,225 B2 | 5/2006 | Tanaka et al. | |
| 7,280,683 B2 | 10/2007 | Bi et al. | |
| 7,388,972 B2 | 6/2008 | Kitson | |
| 7,394,946 B2 | 7/2008 | Dewaele | |
| 7,547,307 B2 | 6/2009 | Carson et al. | |
| RE40,914 E | 9/2009 | Taylor et al. | |
| 7,837,621 B2 | 11/2010 | Krause et al. | |
| 8,055,487 B2 | 11/2011 | James | |
| 8,157,800 B2 | 4/2012 | Vvedensky et al. | |
| 8,257,353 B2 | 9/2012 | Wong et al. | |
| 8,296,094 B2 | 10/2012 | Harrison et al. | |
| 8,419,732 B2 | 4/2013 | Mullaney | |
| 8,439,914 B2 | 5/2013 | Ross et al. | |
| 8,654,150 B2 | 2/2014 | Haskell | |
| 8,731,885 B2 | 5/2014 | Iannotti et al. | |
| 8,777,946 B2 | 7/2014 | Lindahl et al. | |
| 8,864,750 B2 | 10/2014 | Ross et al. | |
| 8,945,128 B2 | 2/2015 | Singh et al. | |
| 8,952,986 B2 | 2/2015 | Haskell | |
| 9,204,937 B2 | 12/2015 | Edelhauser et al. | |
| 2002/0010465 A1 | 1/2002 | Koo et al. | |
| 2003/0191466 A1 | 10/2003 | Austin et al. | |
| 2004/0039259 A1 | 2/2004 | Krause et al. | |
| 2004/0068187 A1 | 4/2004 | Krause et al. | |
| 2004/0073211 A1 | 4/2004 | Austin et al. | |
| 2004/0073212 A1 | 4/2004 | Kim | |
| 2005/0054917 A1 | 3/2005 | Kitson | |
| 2005/0215997 A1 | 9/2005 | Austin et al. | |
| 2006/0276786 A1 | 12/2006 | Brinker | |
| 2008/0234554 A1 | 9/2008 | Vvedensky et al. | |
| 2008/0319448 A1 | 12/2008 | Lavallee et al. | |
| 2010/0087819 A1 | 4/2010 | Mullaney | |
| 2010/0286995 A1 | 11/2010 | Pekar et al. | |
| 2011/0004199 A1 | 1/2011 | Ross et al. | |
| 2011/0103556 A1 | 5/2011 | Carn | |
| 2011/0103676 A1 | 5/2011 | Mullaney | |
| 2011/0116041 A1 | 5/2011 | Hartung et al. | |
| 2011/0313418 A1 | 12/2011 | Nikonovas | |
| 2012/0130687 A1 | 5/2012 | Otto et al. | |
| 2012/0330312 A1 | 12/2012 | Burgherr et al. | |
| 2013/0121612 A1 | 5/2013 | Falco, Jr. et al. | |
| 2014/0236153 A1 | 8/2014 | Edelhauser | |
| 2016/0045225 A1 | 2/2016 | Edelhauser et al. | |

FOREIGN PATENT DOCUMENTS

| | | |
|---|---|---|
| RU | 2471447 C1 | 1/2013 |
| RU | 2489106 C2 | 8/2013 |
| WO | 2010104567 A1 | 9/2010 |

OTHER PUBLICATIONS

LITOS GmbH, "Ilizarov Hexapod System," available from http://d3llyibkg2zj6z.cloudfront.net/ImagemAnexo/Ilozarov-Hexapod-System.-PDF, dated May 23, 2007.

Extended European Seach Report for Application No. 14154820.6 dated Jun. 16, 2014.

Response Ortho LLC, Smart Correction Computer Assisted Circular Hexapod System Brochure, date not known.

Vreden Russian Research Institute of Traumatology and Orthopedics Ortho-SUV Ltd., Deformity Correction and Fracture Treatment by Software-based Ortho-SUV Frame, Saint-Petersburg, 2013.

IMED Surgical, Adam Frame with Paley's Method, Workshop, Oct. 2010.

Craveiro-Lopes, MD, Software Assisted "Ortho-SUV Frame", Int'l Congress on External Fixation & Bone Reconstruction, Oct. 22, 2010.

Smart Correction, Computer-Assisted Circular External Fixator System, website printout, Feb. 2, 2011.

EXTERNAL FIXATOR DEFORMITY CORRECTION SYSTEMS AND METHODS

CROSS-REFERENCE TO RELATED APPLICATIONS

This application is a continuation of U.S. patent application Ser. No. 15/350,220, filed Nov. 14, 2016, which is a continuation of U.S. patent application Ser. No. 14/617,321, filed Feb. 9, 2015, issued on Dec. 20, 2016 as U.S. Pat. No. 9,524,581, which is a continuation of U.S. patent application Ser. No. 14/165,420, filed Jan. 27, 2014, issued on Feb. 10, 2015 as U.S. Pat. No. 8,952,986, which is a continuation of U.S. patent application Ser. No. 13/758,814, filed Feb. 4, 2013, issued on Feb. 18, 2014 as U.S. Pat. No. 8,654,150, which claims the benefit of the filing date of U.S. Provisional Application No. 61/594,519, filed Feb. 3, 2012, all of which are incorporated herein by reference in their entireties.

BACKGROUND

The invention relates to systems and methods for correcting bone deformities using external fixators, and in particular to using systems to plan and optimize bone deformity correction treatment with external fixators.

Patients with bone deformities suffer from a reduced quality of life: they may suffer from difficulties in standing, walking, or using limbs. Bone deformities can be congenital, or the result of a fracture that did not heal properly. These deformities can include axial, sagittal, or coronal plane deformities, translational or rotational deformities and malunion or non-union deformities, or, in complex cases, more than one type of deformity.

The bone deformities are often treated with surgery. For example, surgeons may use metal implants to improve the geometry of a deformed bone; however, inert metal implants are not as flexible in their ability to reform natural bone in something close to normal anatomical geometry. As an alternative, surgeons may perform an osteotomy—a cut in the bone—and then attach an external fixator to support the growing bone while the bone deformity is corrected. The Taylor Spatial Frame (TSF) is a commonly-used external fixator comprising rings interconnected by struts. After the osteotomy, the surgeon may insert pins through the superior and inferior sections of the bone. These pins are attached to external rings so that one ring is roughly perpendicular to the superior section of the bone, and the other ring is roughly perpendicular to the inferior section of the bone. The surgeon may attach adjustable struts to these rings so that the rings are held together by the struts. Each strut has a predetermined attachment point to each ring. Because the rings are each fixed to a section of bone, and because the rings are now joined by flexible struts, the bones can be moved with six degrees of freedom relative to each other.

After the surgery to attach these rings and struts, a surgeon may take orthogonal x-rays of the apparatus on the patient's leg. The surgeon may make a number of measurements from the x-ray images, including distances and angles of both the tibia and the rings and struts. The surgeon may then use the numerical measurements to calculate the bone correction needed and prescribe for the patient the length of each strut to be adjusted each day. Typically, daily adjustments will be made, realigning the sections of the bone at a rate that allows new bone to form ultimately yielding natural bone in a geometry that comes close to normal anatomy and function.

Such calculations are usually time-consuming and usually rely on the assumptions that each ring is perfectly perpendicular to the bone segment to which it is attached. This may require a surgeon to spend extra time in the operating room to assure that each ring is perpendicular to each corresponding bone segment. If a ring is not perpendicular to its corresponding bone segment, error will be entered and the resulting prescription for strut adjustments will not be accurate.

This system of two rings and six struts may be chosen for several reasons. First, the system allows a surgeon to move the two bone segments with six degrees of freedom relative to each other, thereby giving the surgeon the freedom to treat many types of deformities. The system may be strong enough to support body weight so that a patient can be ambulatory while healing occurs.

The shortcomings of the procedure include the difficulty and lack of accuracy in using a ruler and protractor on an x-ray print-out, or digital system not related to the prescription calculation program, to measure distances and angles, the amount of time involved in performing all the calculations needed to generate the patient prescription, and the surgical difficulty in positioning the external fixator exactly with respect to the patient's bone.

It would thus be desirable to develop a system that would allow easy and accurate measurements of bones and bone deformities, and easily generate accurate prescriptions for strut lengths for the bone correction treatment.

SUMMARY

According to one aspect, a computer system comprises a microprocessor configured to execute instructions to: generate a first display of an orthopedic treatment device superimposed on a display of a first digital medical image, the display of the first digital medical image displaying a first view of a patient's anatomical structure, the first display of the orthopedic treatment device being a first graphical representation of a synthetic orthopedic treatment device representing a physical orthopedic treatment device; substantially concurrently with generating the first display of the orthopedic treatment device superimposed on the display of the first digital medical image, generate a second display of the orthopedic treatment device superimposed on a display of a second digital image, the display of the second digital medical image displaying a second view of the patient's anatomical structure from a different angle than the first view, the second display of the orthopedic treatment device being a second graphical representation of the synthetic orthopedic treatment device; receive user input entered graphically on the first display of the orthopedic treatment device superimposed on the display of the first digital medical image, the user input controlling a motion of the synthetic orthopedic treatment device; and in response to receiving the user input, update the first display of the orthopedic treatment device superimposed on the display of a first digital medical image and the second display of the orthopedic treatment device superimposed on the display of a second digital image to reflect the motion of the synthetic orthopedic treatment device.

According to another aspect, a non-transitory computer-readable medium encodes instructions which, when executed by a microprocessor of a computer system, cause the computer system to: generate a first display of an orthopedic treatment device superimposed on a display of a first digital medical image, the display of the first digital medical image displaying a first view of a patient's anatomical structure, the first display of the orthopedic treatment device being a first graphical representation of a synthetic orthopedic treatment device representing a physical orthopedic treatment device; substantially concurrently with generating the first display of the orthopedic treatment device superimposed on the display of the first digital medical image, generate a second display of the orthopedic treatment device superimposed on a display of a second digital image, the display of the second digital medical image displaying a second view of the patient's anatomical structure from a different angle than the first view, the second display of the orthopedic treatment device being a second graphical representation of the synthetic orthopedic treatment device; receive user input entered graphically on the first display of the orthopedic treatment device superimposed on the display of the first digital medical image, the user input controlling a motion of the synthetic orthopedic treatment device; and in response to receiving the user input, update the first display of the orthopedic treatment device superimposed on the display of a first digital medical image and the second display of the orthopedic treatment device superimposed on the display of a second digital image to reflect the motion of the synthetic orthopedic treatment device.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Azimuthal rotation of a ring refers to rotation of the ring about an axis passing through a center of the ring and normal to a major plane of the ring. Axial rotation of a ring refers to a non-azimuthal rotation of the ring, i.e. to a rotation about an axis different from the axis passing through the center of the ring and normal to the major plane of the ring; an axial rotation may be performed about an axis lying in the major plane of the ring, about a point along the ring or tangent to the ring, or about another axis. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links. According to some embodiments, the present invention provides, inter alia, computer systems comprising hardware (e.g. one or more processors and associated memory) programmed to perform the methods described herein, as well as computer-readable media encoding instructions to perform the methods described herein.

The following description illustrates embodiments of the invention by way of example and not necessarily by way of limitation.

Hardware Environment

Figure 1:
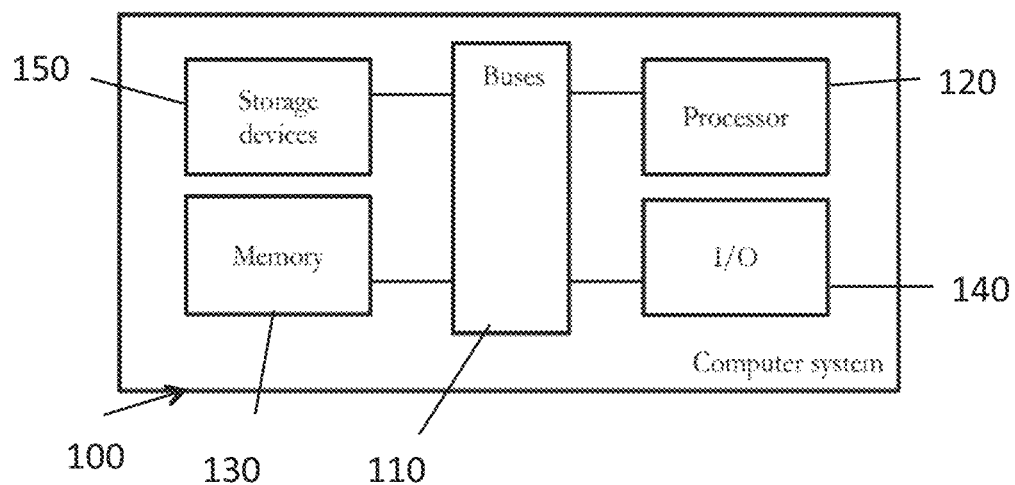
FIG. 1 shows a hardware configuration of an exemplary computer system, which may be used to implement at least part of the embodiments of the present invention.

FIG. 1 shows a hardware configuration of an exemplary computer system 100 which may be used to implement at least part of the embodiments of the present invention. As shown in FIG. 1, one or more buses 110 connect a processor (CPU) 120, memory 130, input (e.g. mouse, keyboard) and output devices (e.g. display, speakers, haptic/vibration generator) 140, and storage devices (e.g. hard drive) 150. Software as described below may run on one or more computer systems such as the one shown in FIG. 1.

Figure 2:
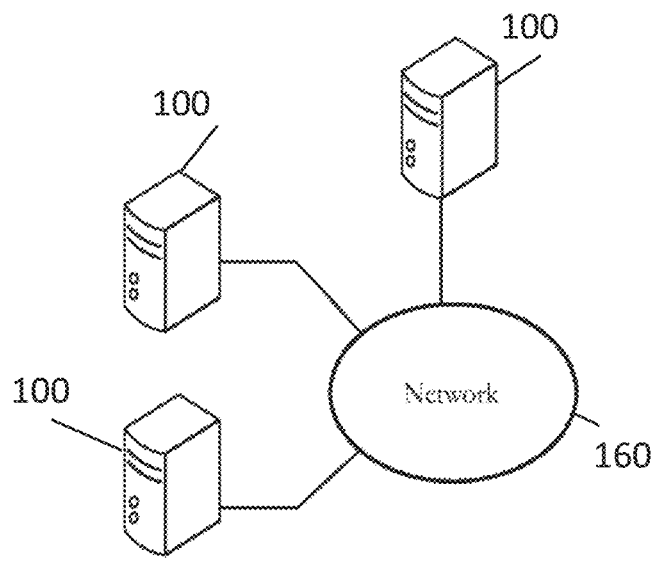
FIG. 2 shows multiple computer systems may be interconnected through a wide-area network such as the Internet, suitable for implementing some embodiments of the present invention.

As shown in FIG. 2, multiple computer systems 100 may be interconnected through a wide-area network 160 such as the Internet in some embodiments of the present invention. Bone deformity correction software running on one system 100 may be accessible through an interface (e.g. web interface, or application software interface) running on a different system 100. In some embodiments, some of the steps described below (e.g. diagnostic/X-ray image generation and storage, fixator model computations and storage) may be performed using on a server system 100, while other steps (e.g. receiving user input, generating graphical representations of fixator rings and struts, etc.) may be performed on a client system 100.

Software running on one or more computer systems 100 is described below with reference to various tabs used to organize the software capabilities. In some embodiments, the software includes image placement, segment placement, ring definition, ring placement, segment translation, correction setting, and correction prescription functions, each accessible and controllable by a user through an associated tab in a graphical user interface.

Place Image (ID, Sessions and Import Images) Tab

Figure 3:
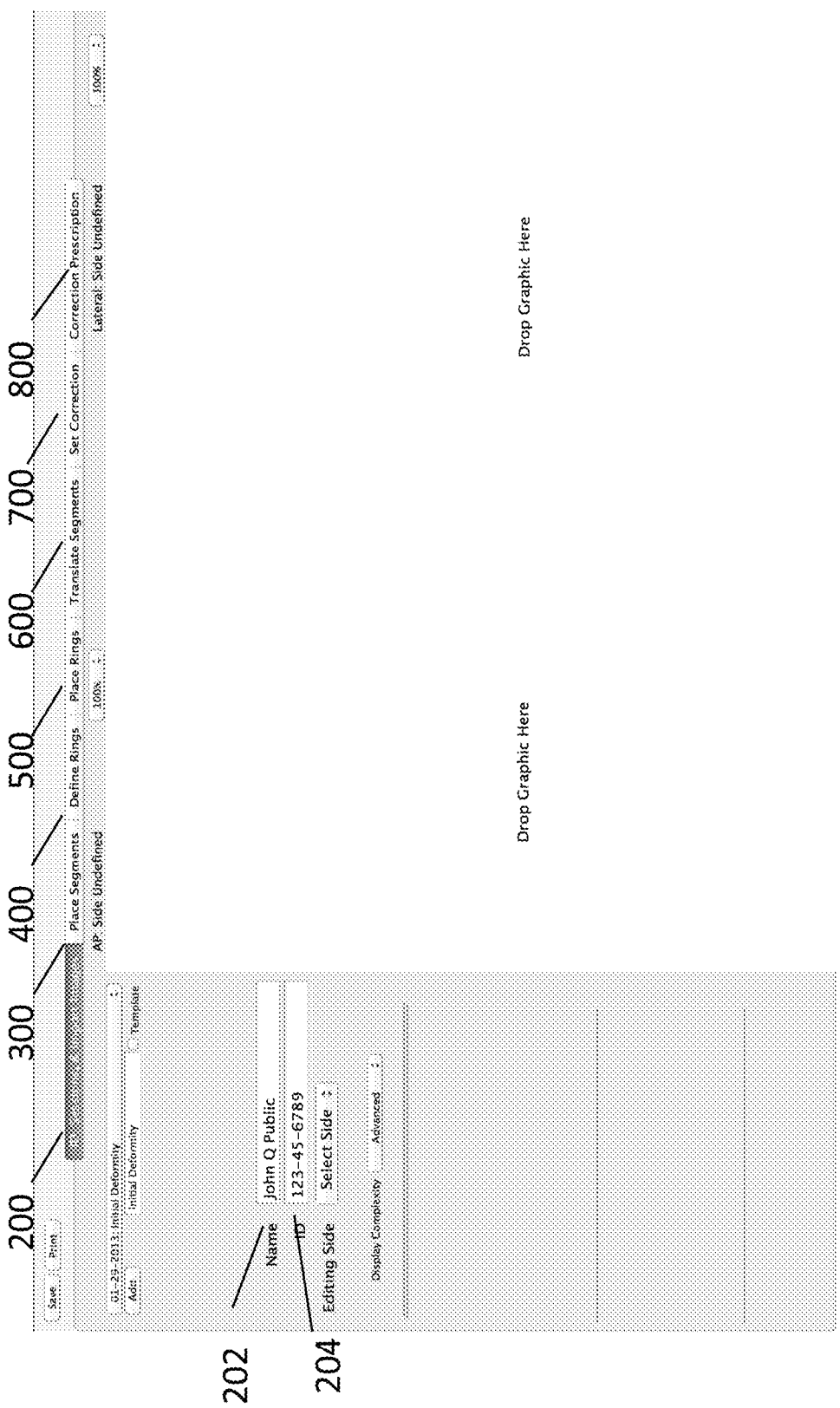
FIG. 3 shows screen shot of the "ID, SESSIONS, & IMPORT IMAGES" box, according to some embodiments of the present invention.

In some embodiments, a patient record for the bone deformity correction treatment program is created by a user using a graphical user interface. FIG. 3 shows a screen shot of an introductory "ID, SESSIONS, & IMPORT IMAGES" input section 200, which allows a user to enter data for a patient information record that can be saved. Introductory input section 200 includes data entry fields for a number of patient identifiers such as a patient name field 202, a medical record number or ID field 204, and a deformity type field. In some embodiments, multiple days' worth of information and calculations for the same patient may be saved. For example, preoperative templating, intraoperative images, and a number of postoperative images on different days can be saved.

In some embodiments, the system also allows the user to save/store multiple images and correction calculations for the same patient and to update the correction in real-time during the correction period, rather than waiting for the end of a correction prescription, described below. Real-time updating facilitates arriving at a desired outcome in a shorter time by error correcting during, rather than after, the user input process.

As shown in FIG. 3, once the patient record has been created, a user of the system can enter data identified by each of multiple tabs placed on the top side of the screen: "ID, SESSIONS, & IMPORT IMAGES" 200, "PLACE SEGMENTS" 300, "DEFINE RINGS" 400, "PLACE RINGS" 500, "TRANSLATE SEGMENTS" 600, "SET CORRECTION" 700, and "CORRECTION PRESCRIPTION" 800.

Figure 4:
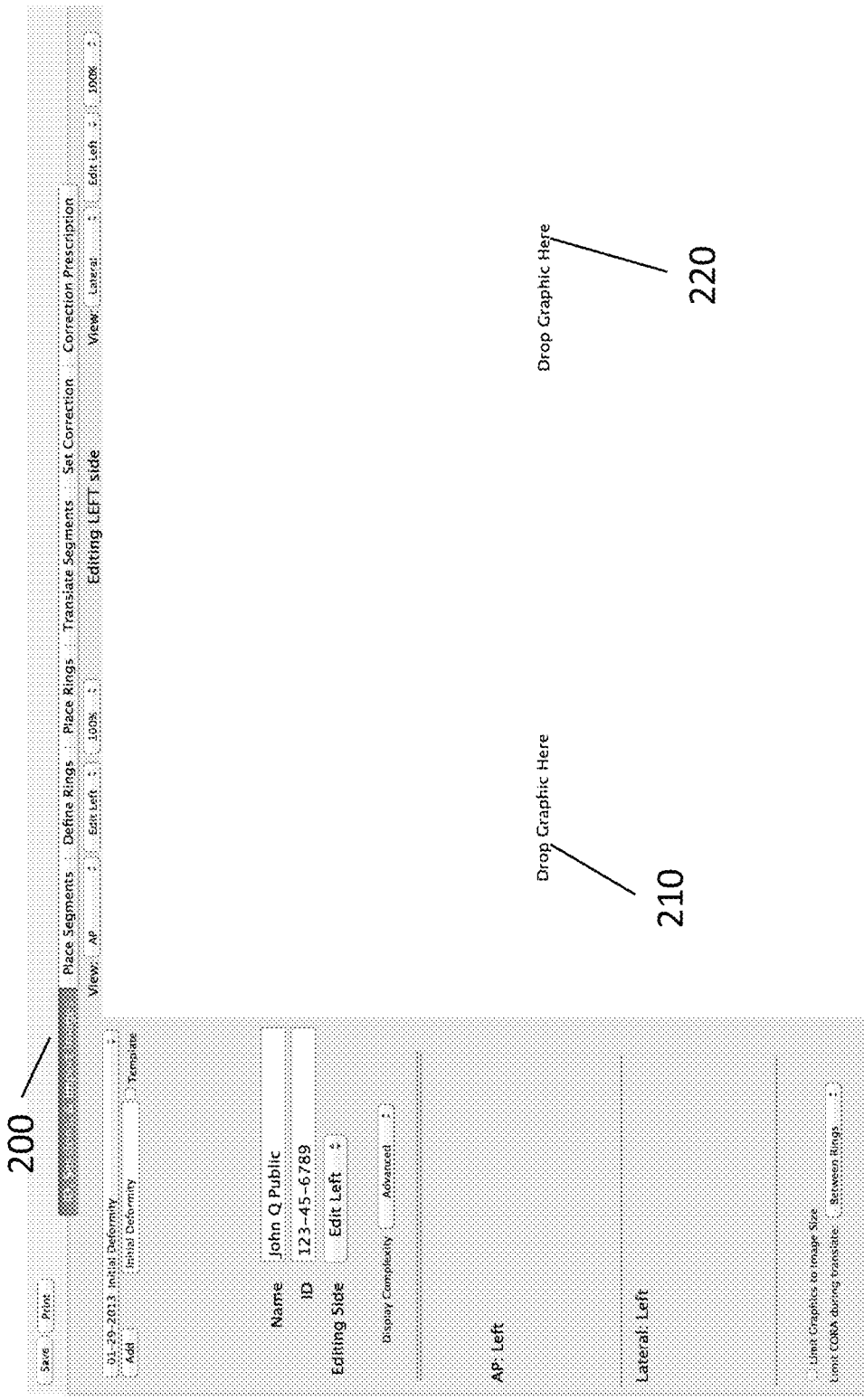
FIG. 4 shows a screen shot of the graphical user interface of the image drag and drop function of the "ID, SESSIONS, & IMPORT IMAGES" tab, according to some embodiments of the present invention.

FIG. 4 shows a screen shot of the graphical user interface of an image drag and drop function of the "ID, SESSIONS, & IMPORT IMAGES" tab 200. This tab allows drag and drop placement of two digital medical images onto the editing screen. In some embodiments, the system's graphical display comprises at least two digital medical images, each image displaying a view from a different angle of a patient's anatomical structure. Customarily, a healthcare professional will take two radiographs of the patient's anatomical structure, e.g. a bone with deformities. The radiographs of the patient's anatomical structure may show either simply the bone with deformities in isolation, or the bone with deformities following osteotomy in conjunction with an external fixator (with rings and struts) affixed to the bone. Generally one image is anterior-posterior (AP, or XY plane), while the other image, 90 degrees rotated relative to the first, is medial-lateral (lateral, ZY plane). Two radiographs of the patient's anatomical structure may be turned into digital medical images and imported into the system. Note that the XY and ZY planes need not be perfectly orthogonal in real 3D space if the two radiographs are not perfectly orthogonal. Below, the term XYZ space refers to the real 3D space while the XY and ZY planes respectively refer to the AP and lateral image planes as determined by the angle of the radiographs as they are taken relative the patient's anatomic structure.

As shown in FIG. 4, prompts 210, 220 on the editing screen direct the user to place the digital medical images. A graphic associated with prompts 210, 220 indicates a side (e.g. left side in FIG. 4) that is currently selected for editing. In some embodiments, the two digital medical images do not have to be truly orthogonal; the system may be designed to be able to compensate for different rotation angles and correct rotational deficiencies as described below, to correct for any departure from orthogonality for the orientation of the two images.

Figure 5:
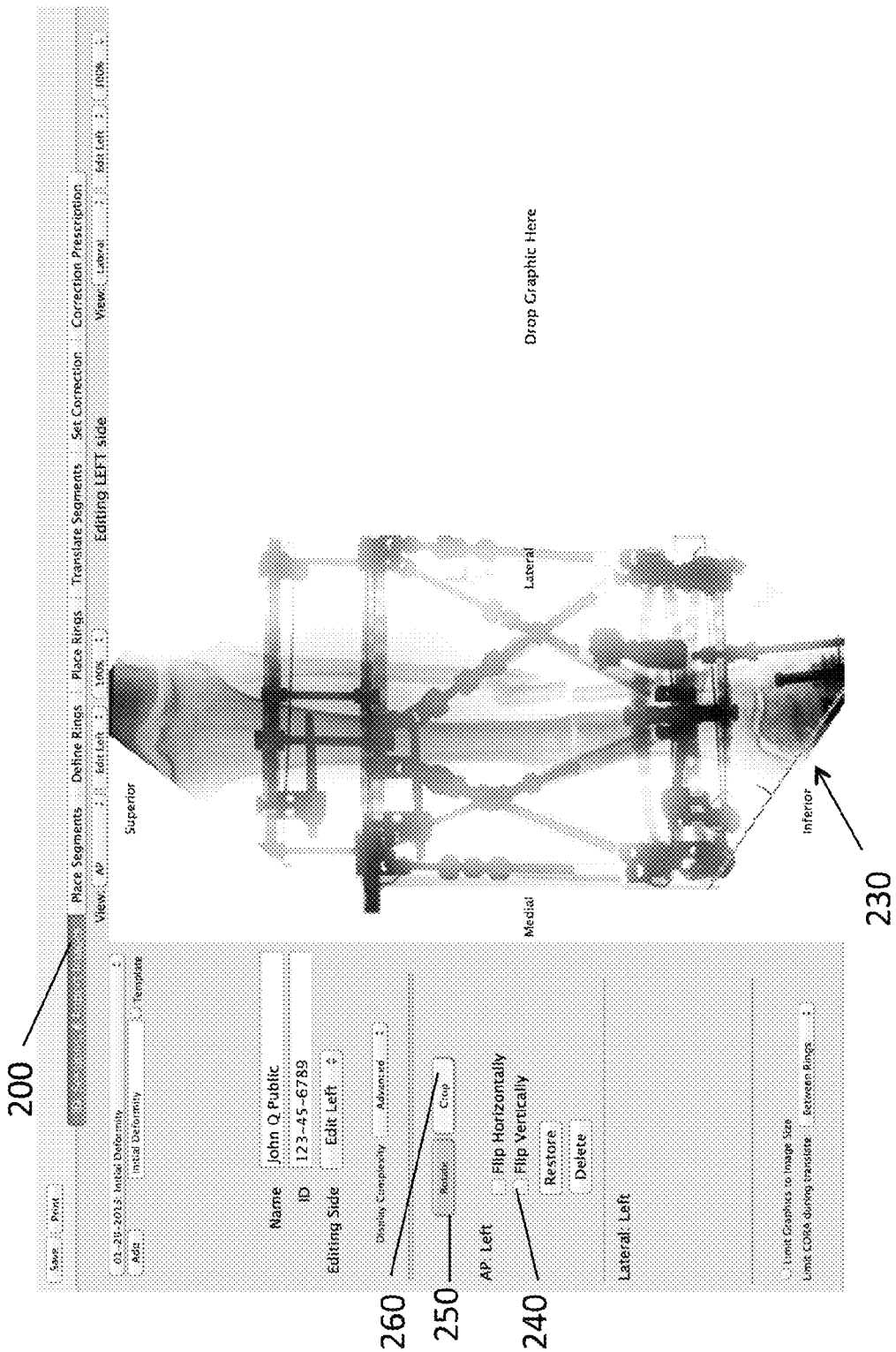
FIG. 5 shows a screen shot after a first digital medical image has been dropped, according to some embodiments of the present invention.

FIG. 5 shows a screen shot after a first digital medical image 230 has been dropped in the space defined by the prompt 210 shown in FIG. 4. Once the digital medical image is placed in its designated location, prompts for the expected orientation of the image are displayed on the left side of the screen: image manipulation tools on the left side of the screen include a flipping tool 240, a rotation tool 250, and a cropping tool 260, to optimize the representation of the image used.

Place (Set) Segments Tab

The imported digital medical images may be used to designate the position of the patient's bones to the system.

Figure 6:
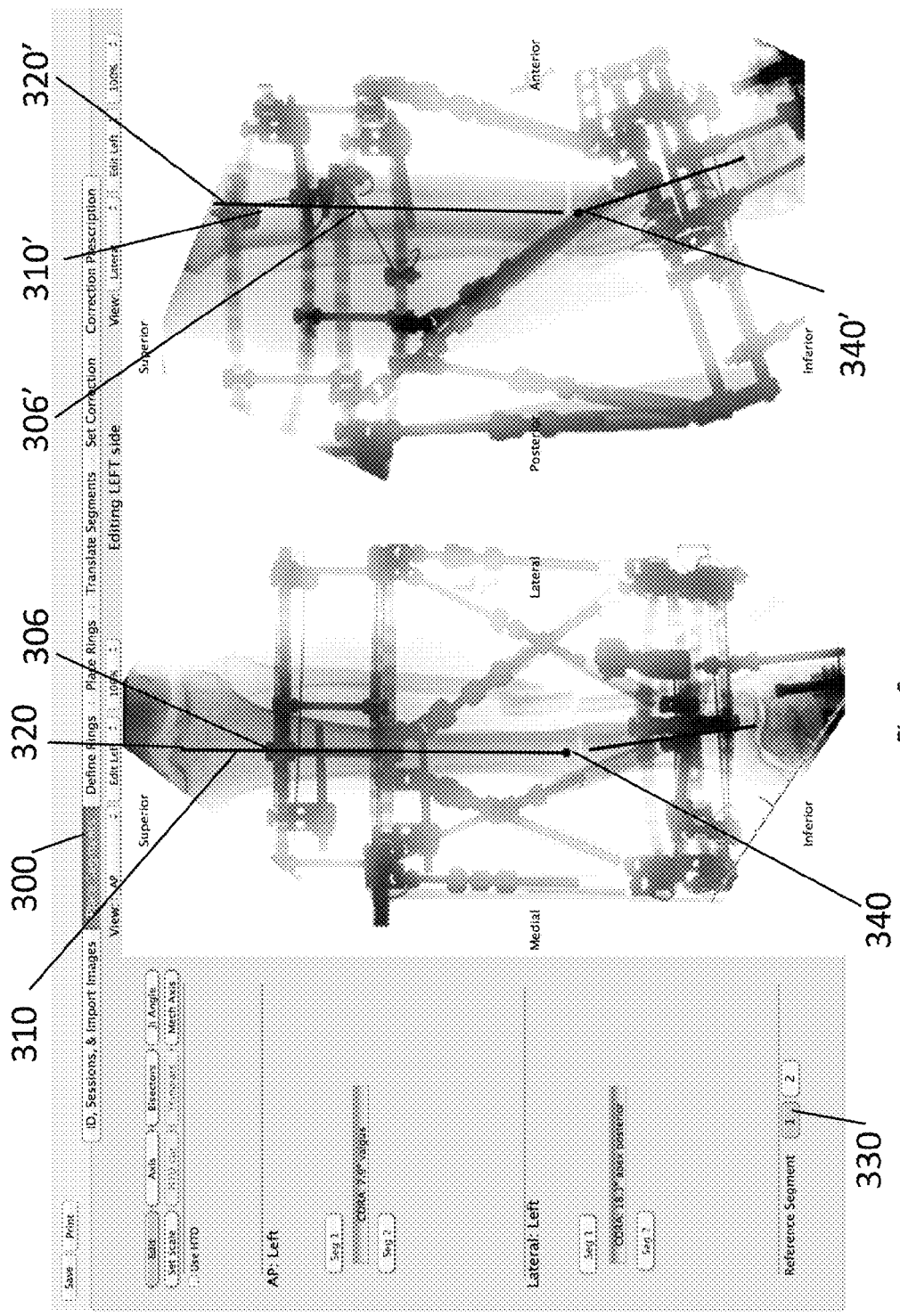
FIG. 6 shows a screen shot of the graphical user interface for defining bone segments using the "PLACE SEGMENTS" tab that defines the number and position of bone segments, according to some embodiments of the present invention.

FIG. 6 shows a screen shot of a graphical user interface for defining bone segments using the "PLACE SEGMENTS" (segment-placing) tab 300, which allows defining a number (count) and associated positions of bone segments. Segment-placing tab 300 is used to define locations/representations 306, 306' of a bone or a portion of bone, as well as the number and position of bone segments 310, 310'. As shown in FIG. 6, segments 306, 306' are defined by a user by drawing lines down the middle of corresponding bone representations. The system determines the appropriate locations of segments 306, 306' by detecting the locations of corresponding graphical user input (e.g. mouse clicks at the end points of segments 306, 306'). Corresponding segments on the AP and lateral views are color-coded to match labels associated with each view in the left image tab. Segments can be dragged by endpoints 320, 320' or by selecting an internal point along the line representing a bone.

CORA locations 340, 340' are automatically drawn and color-coded with both colors of the segments involved. CORA or center of rotational angulation is a well-defined term in deformity analysis and refers to the point around which a segment can be rotated to bring it into alignment with another segment. In the simplest form, it is the intersection of the two segments. A section 330 on the left side of the screen allows selecting a reference segment in each image; a reference segment is one whose location stays constant throughout the analysis described below, and ideally is perpendicular to the X-ray beam. Non-reference segments may be termed moving segments.

Figure 7:
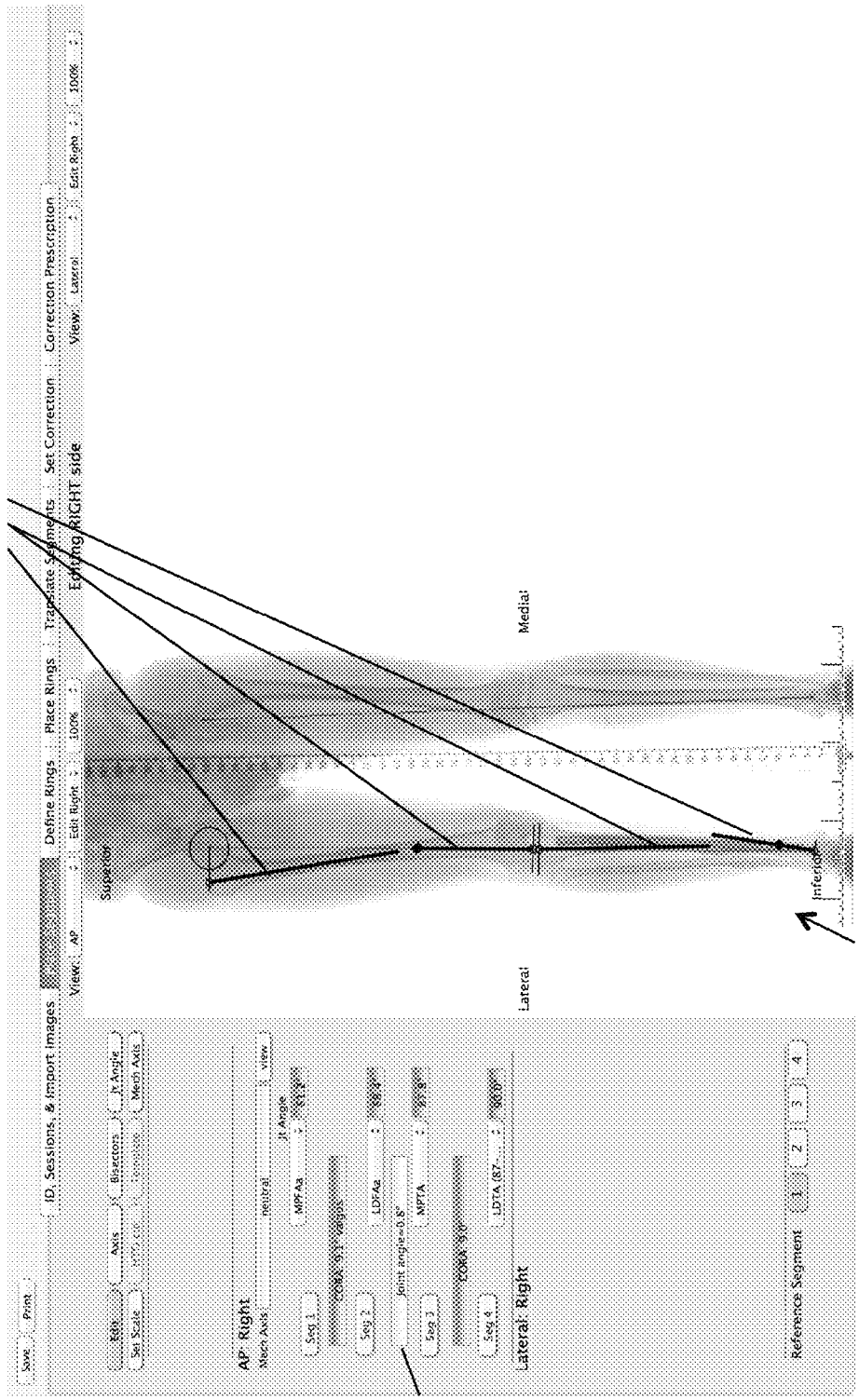
FIG. 7 shows a screen shot where multiple segments have been placed on a digital medical image, according to some embodiments of the present invention.
Figure 8:
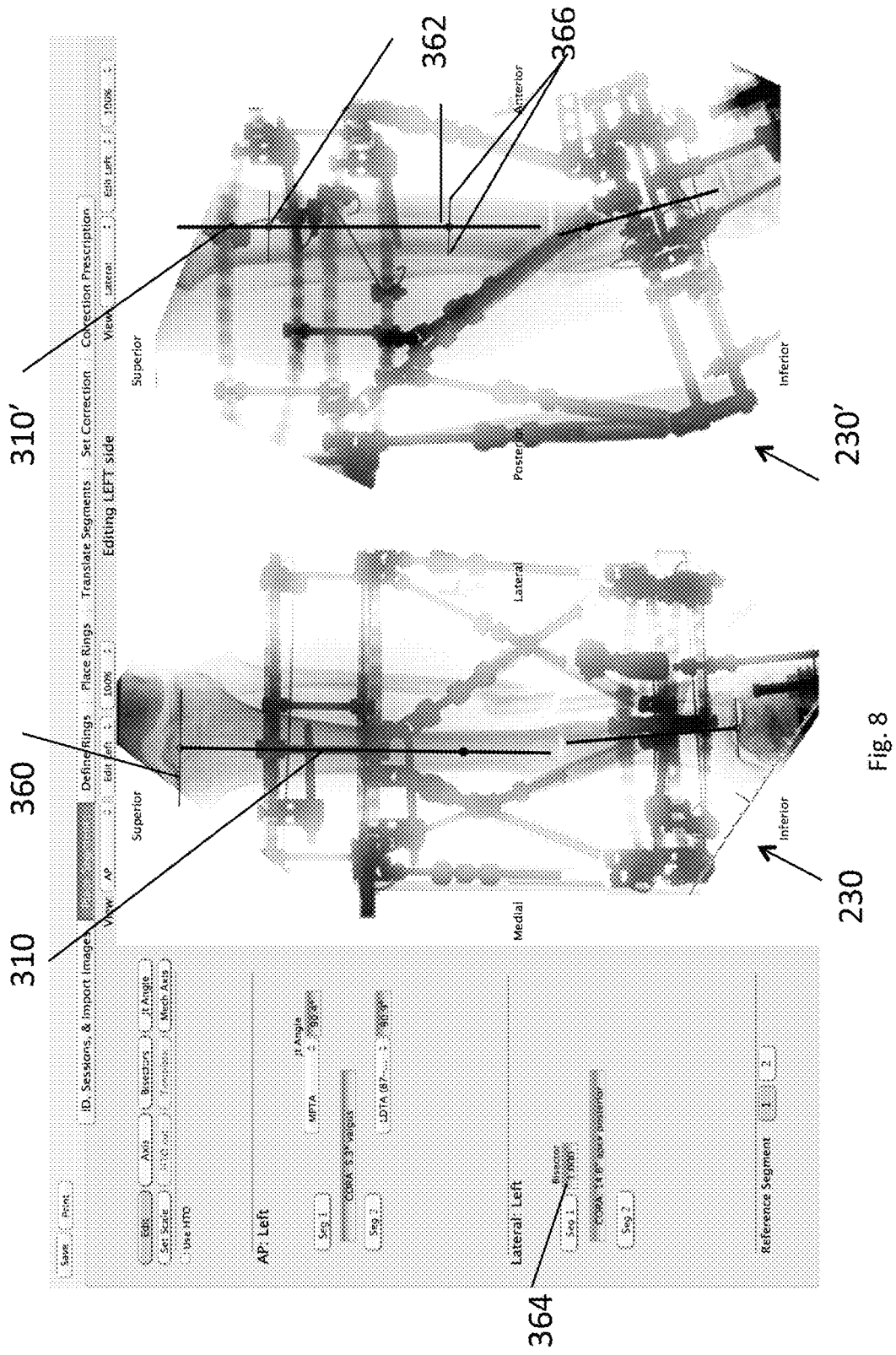
FIG. 8 shows a screen shot where joint lines and bisectors have been set for each segment, according to some embodiments of the present invention.

As shown in FIGS. 7-8, in some embodiments joint line(s) and segment bisector(s) can be placed by a user so as to help facilitate the accurate placement of segments. Segments typically intersect joint lines at defined positions and angles, as well as the midpoint of a diaphyseal bone bisector. These anatomic relationships are used by fixing the segment to the appropriate joint line or bisector point(s). Joint lines are fixed at the closest segment end-point, while segments are fixed to bisectors using a best-fit linear regression equation.

FIG. 7 shows a screen shot illustrating the placement by a user of multiple segments 310 on a digital medical image 230 according to some embodiments of the present invention. A pair of angles 350, between adjacent segments, characterize the size of the deformity to be corrected. The user may place segments 310 using a mouse or other input device, and the system's determination of the locations of segments 310 may include determining the positions of user actions that identify the endpoints of segments 310 (e.g. mouse clicks at the appropriate positions).

FIG. 8 shows a screen illustrating a user's setting of joint lines 360 and bisectors 362 for each segment 310, 310' on two digital medical images 230, 230'. Joint lines 360 help facilitate placement of segments 310, 310' by fixing each segment 310, 310' to the correct anatomic point on the corresponding joint line 360. Joint lines 360 also help demonstrate if there is a deformity close to the joint by measuring the joint line angle. Bisectors 362 are drawn by a user between boundaries of a bone's diaphysis 366 (cylindrical portion) anywhere along the bone. A segment 310 should fall on the midpoints of these bisectors and is calculated as a best-fit line between these points. Advantageously, linear regression may be used to define bisector best fit and generate a display of bisector closeness of fit ("R value"). The user can choose to lock or unlock the segment to the joint line(s) and/or bisector(s) 364 using on screen commands.

Joint lines 360 can be named based on their anatomic location, to help the system understand the relationship between segments based on anatomic location, for instance, to pre-define if a CORA should be set. Naming also allows the program to set the appropriate location on the joint line where the segment should intersect based on anatomic norms. The angle between the segment and associated joint line is displayed, and the "R" value for goodness of fit for multiple bisectors is displayed.

As noted above, CORA or center of rotational angulation is a well-defined term in deformity analysis and refers to the point around which a segment can be rotated to bring it into alignment with another segment. In the simplest form, it is the intersection of the two segments. In some embodiments, the CORA for each segment pair is automatically calculated and placed on-screen. The angular difference between adjacent segments (angular deformity) is calculated and displayed. If it's inappropriate to have a CORA between segments, such as between the distal femur and proximal tibia at the knee, the CORA can be turned off. In this circumstance, if joint lines are set at these intersections, a joint angle is calculated and displayed. Defining the names of joint lines can help the program to know if it should set a CORA active or inactive based on anatomic relationships.

Figure 60:
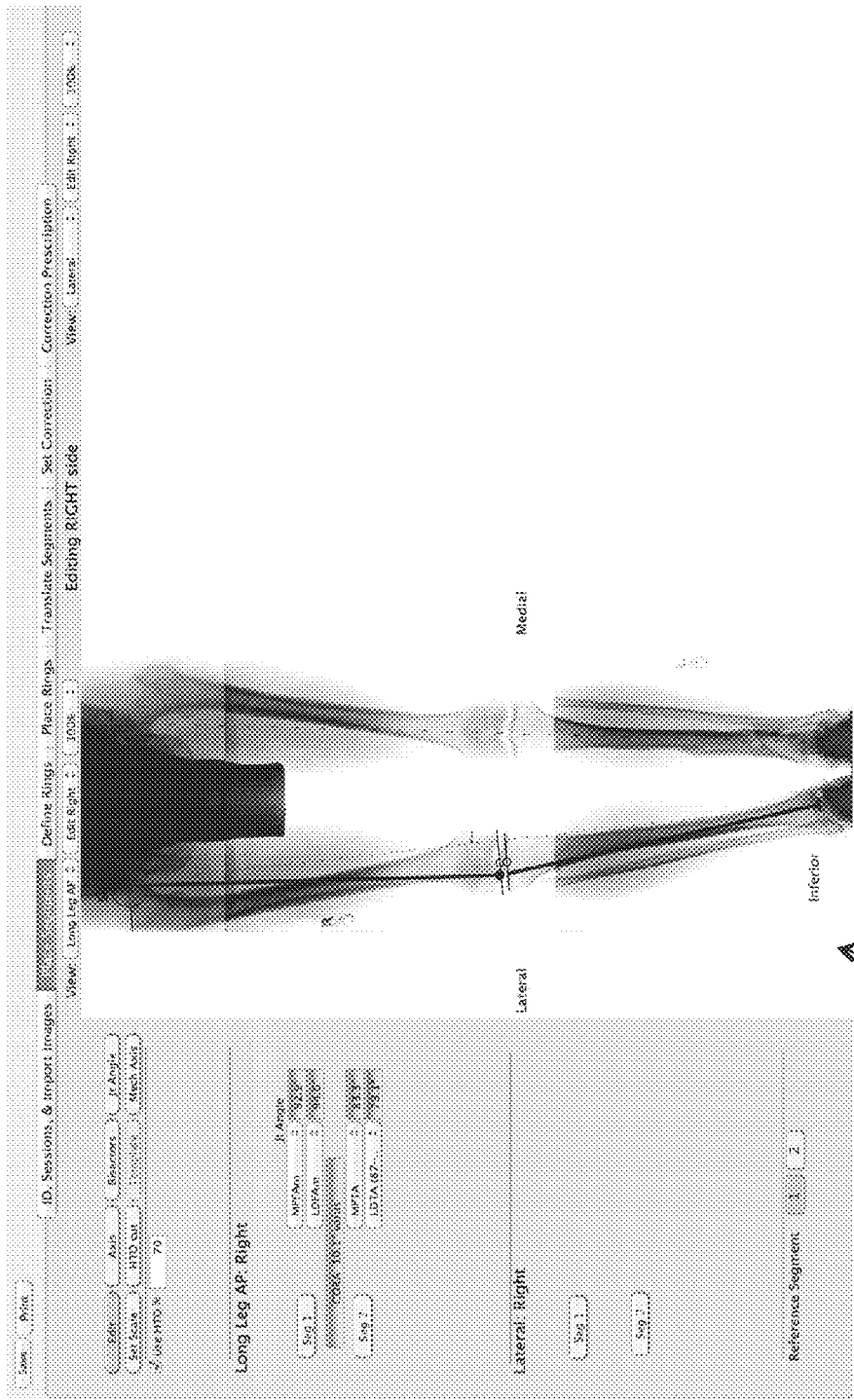
FIG. 60 shows an exemplary screenshot for high tibial osteotomy correction, according to some embodiments of the present invention.

For example, long leg hip to ankle digital medical images can be analyzed in real time to assist with calculation of high tibial osteotomy correction. This starts with the definition of the femur and tibia segments and the proximal tibia joint line as defined above. Next the user can define the goal location for lower extremity mechanical axis after correction as a real time moving point along the tibial joint line with percentage of total joint line length calculated and displayed. Finally, the user can select an osteotomy location for opening or closing wedge osteotomy and the program will calculate the size of the wedge to be inserted or removed. FIG. 60 shows an exemplary screenshot for high tibial osteotomy correction 1300.

Long leg hip to ankle digital medical images can be analyzed in real time to assist with calculation of distal femoral osteotomy correction (not shown). This starts with the definition of the femur and tibia segments and the distal femur joint line as defined above. Next the user can define the goal location for lower extremity mechanical axis after correction as a real time moving point along the femoral joint line with percentage of total joint line length calculated and displayed. Finally, the user can select an osteotomy location for opening or closing wedge osteotomy and the program will calculate the size of the wedge to be inserted or removed.

Figure 9:
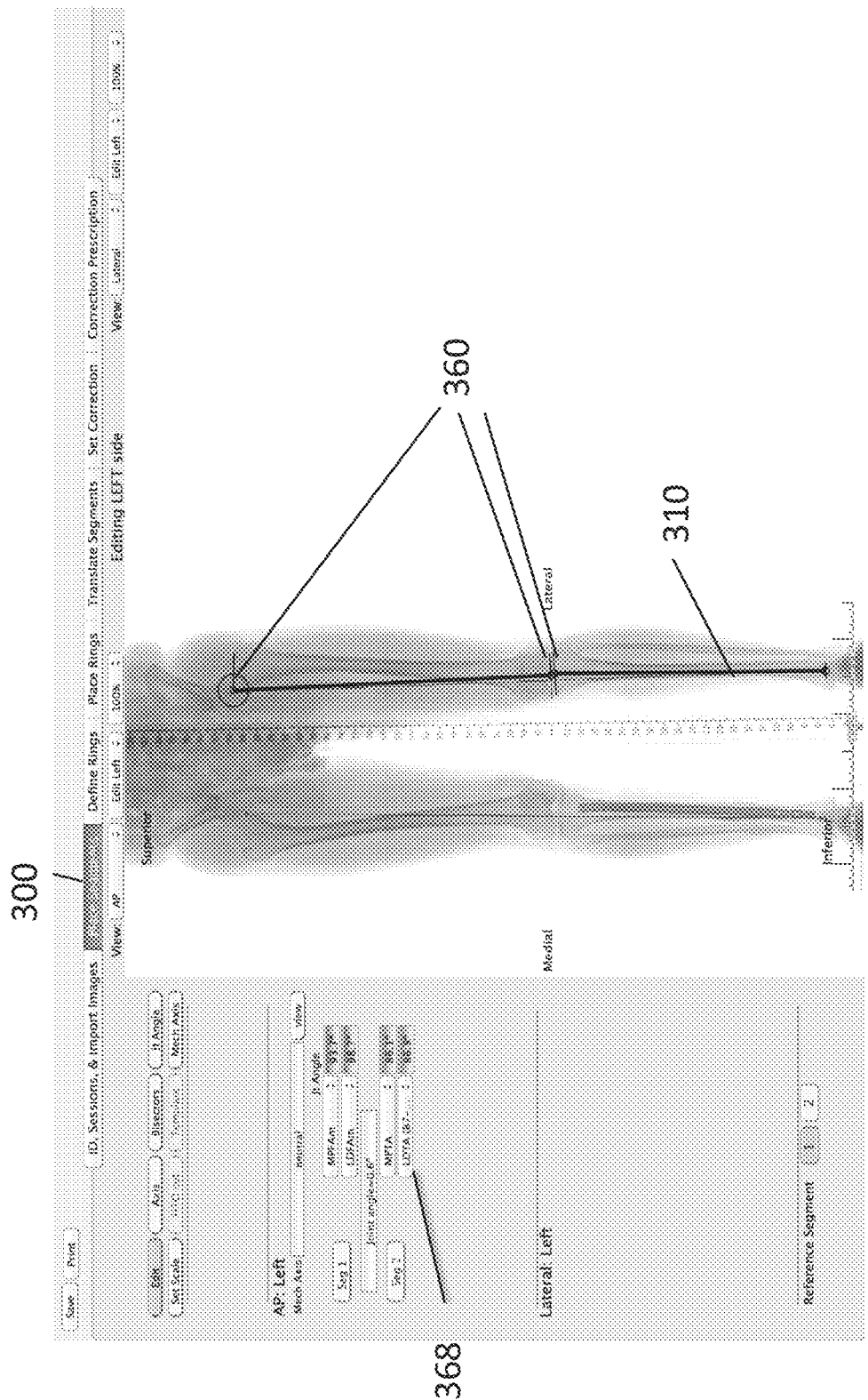
FIG. 9 shows a screen shot where multiple joint lines can be defined for each segment, according to some embodiments of the present invention.

FIG. 9 shows a screen shot illustrating a user's defining multiple joint lines 360, for each segment 310. If a segment comprises an entire bone, it may be more appropriate to have a joint line at each the end of the segment. The system also displays population norms 368 for joint line to segment angles. It highlights when joint line to segment angles are not within anatomic norms to draw attention to the user that a deformity exists close to the joint.

Figure 10:
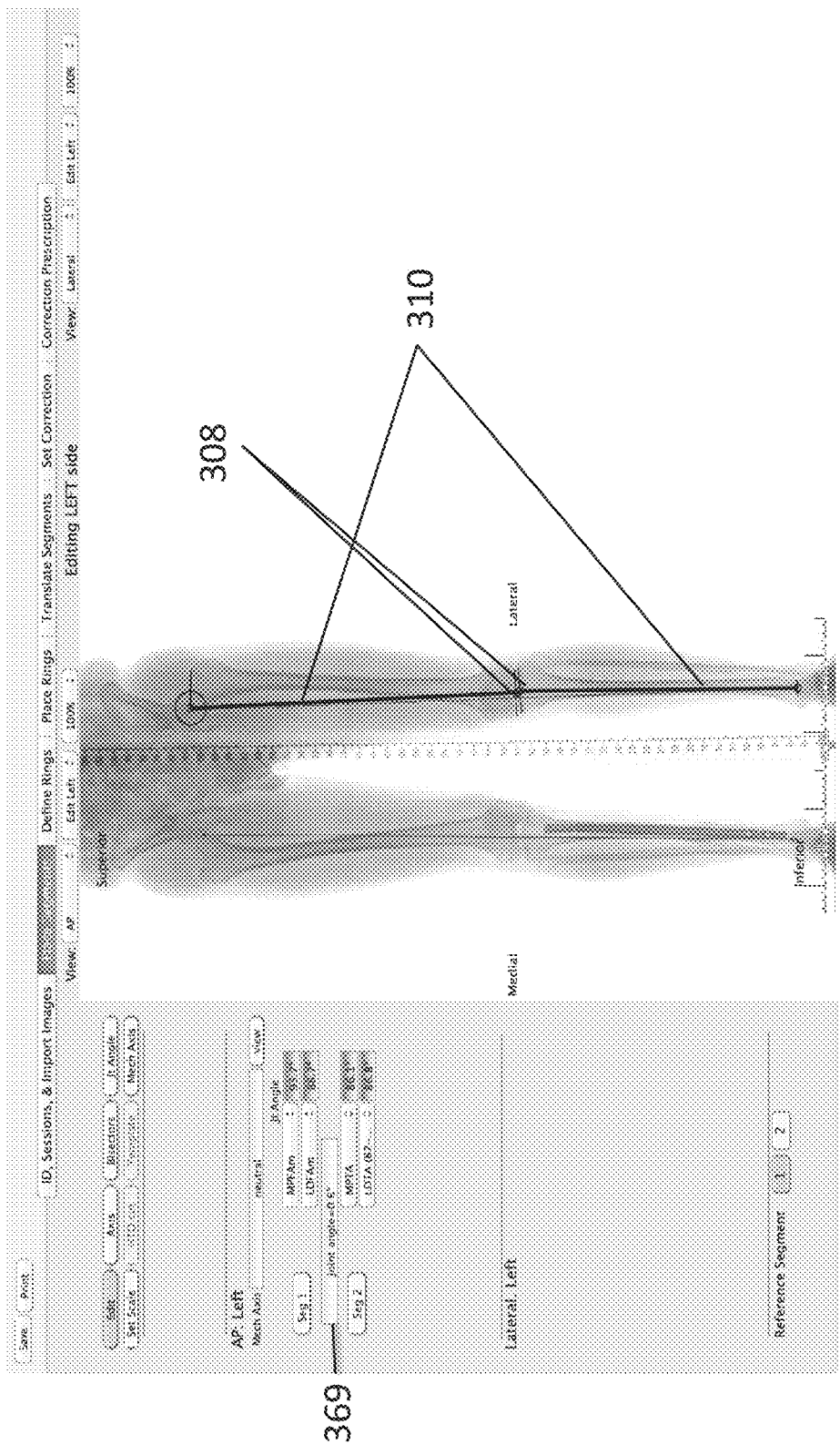
FIG. 10 shows a screen shot where segments are on different sides of a joint, according to some embodiments of the present invention.

FIG. 10 shows a screen shot where segments 310 are on different sides of a joint 308, the concept of CORA is not valid, so the CORA can be turned off, shown at 369. If joint lines 360 are defined for these segments on each side of a joint, a joint angle is calculated. The joint angle measures the congruency of reduction of the joint (i.e., it should be close to 0°).

A first level of error correction may be done at this point. In real life two segments represent the same anatomic structure, and this knowledge can be used to perform a first step in error correction. We call this rotating for reference. The x-ray beam should be perpendicular to a reference segment when images are taken. A reference segment is predefined by the user and stays constant throughout the correction analysis. As previously stated, moving segments are segments that are not the reference segment.

Figure 11:
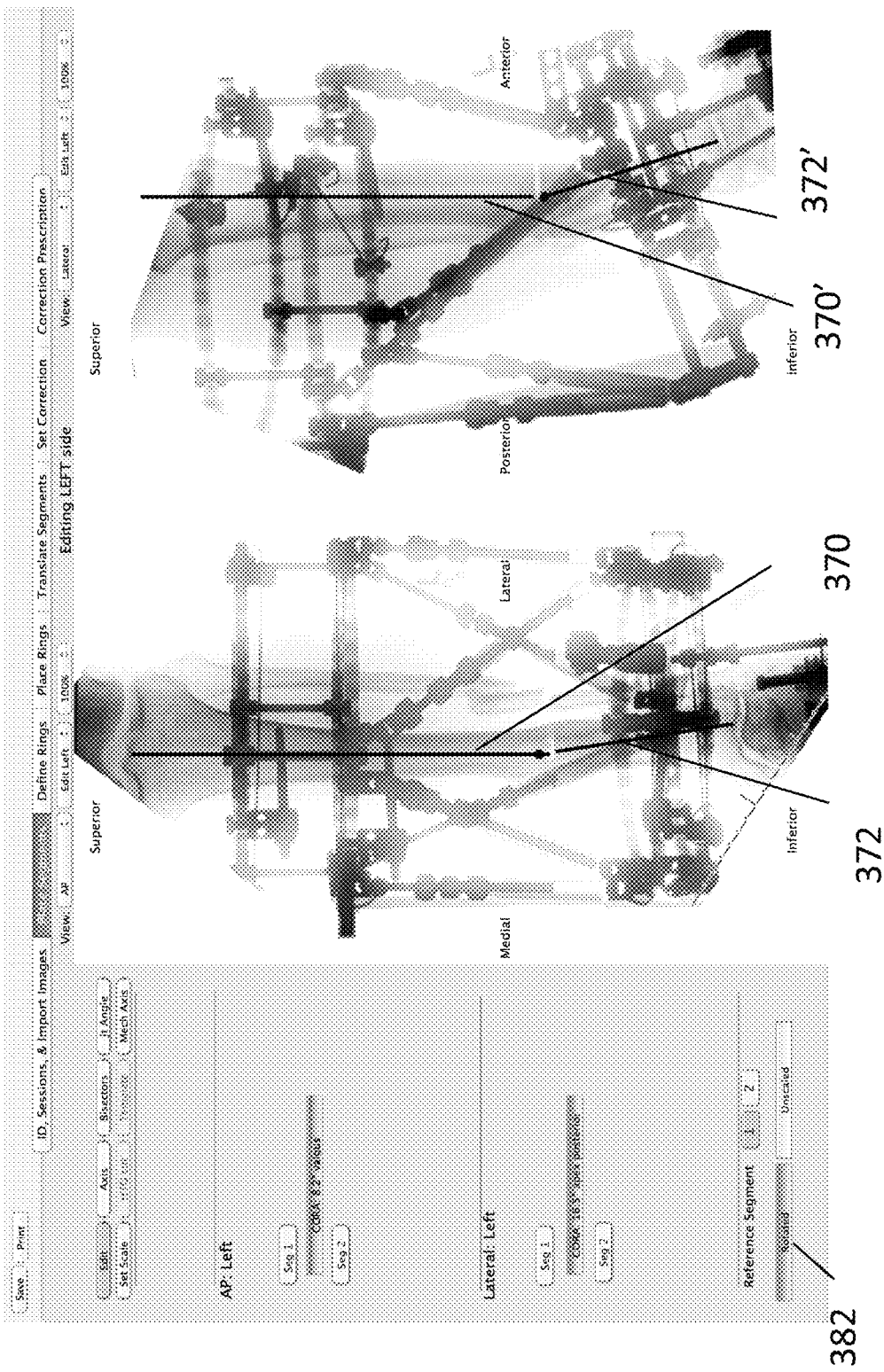
FIGS. 11A-B show screen shots that illustrating the concept of rotating for reference, according to some embodiments of the present invention.
Figure 11:
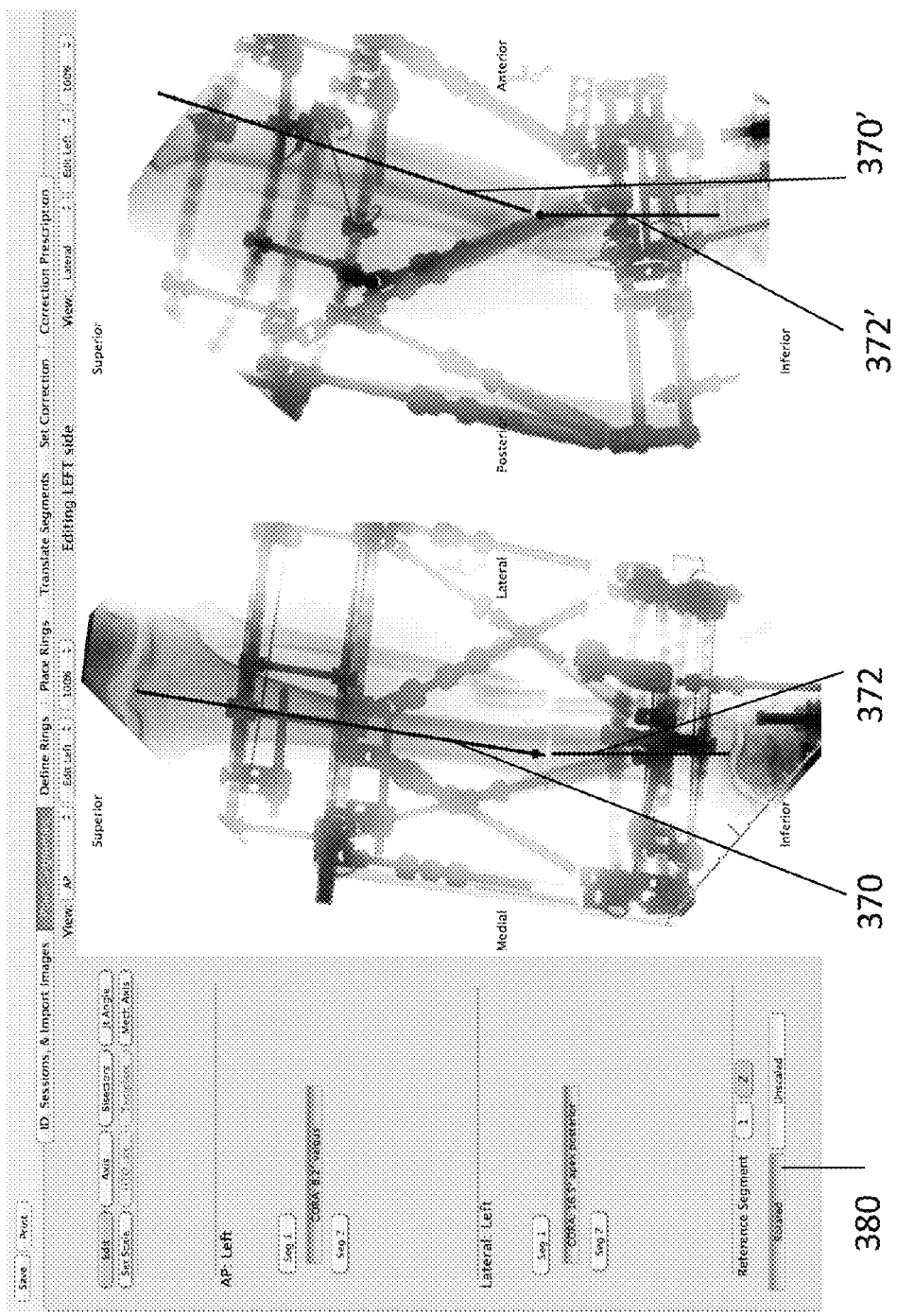

FIGS. 11A-B show screen shots illustrating the concept of rotating for reference. In FIG. 11A, the reference segment has been set to segment 1, shown at 370, 370'. Changing to segment 2, shown at 372, 372' as in FIG. 11A, rotates the images so segment 2 is parallel and vertical in both AP and lateral plane images. Finally, the visual rotation of the image can be turned on (shown at 380 in FIG. 11A) or off (shown at 382 in FIG. 11B). The visual rotation can be turned on or off by the user, though behind the scenes, the program continues to correct for the rotation for reference.

Define Rings Tab

In some embodiments, once the location of the segments has been finalized, the next step involves graphically representing the external fixator superimposed on a graphical display of at least one digital medical image. An external fixator comprises at least two rings interconnected by a plurality of struts. The system uses a tiltable ellipse to represent a ring of an external fixator attachable to the patient's anatomical structure, in this case a patient's bone(s). In one embodiment the system may receive ring identification user input identifying at least two points defining the tiltable ellipse. The digital medical image may show an external fixator, which may appear as already attached the patient's bone. In such an embodiment, a user may manipulate a synthetic fixator representation to match the position of the real fixator in the digital medical image, in order to determine the 3D position of the real fixator from the screen position(s) of the synthetic fixator elements. In an alternative embodiment, the digital medical image may show only the patient's bone(s). In such an embodiment, a synthetic fixator representation may be superimposed on the digital medical image to represent a desired/simulated positioning of a potential real fixator. In some embodiments, a display of a tiltable ellipse superimposed on a graphical display of at least one digital medical image, in this case a patient's radiograph that has been digitized, is generated using user-controllable DEFINE RINGS and PLACE RINGS tabs, as described below.

Figure 12:
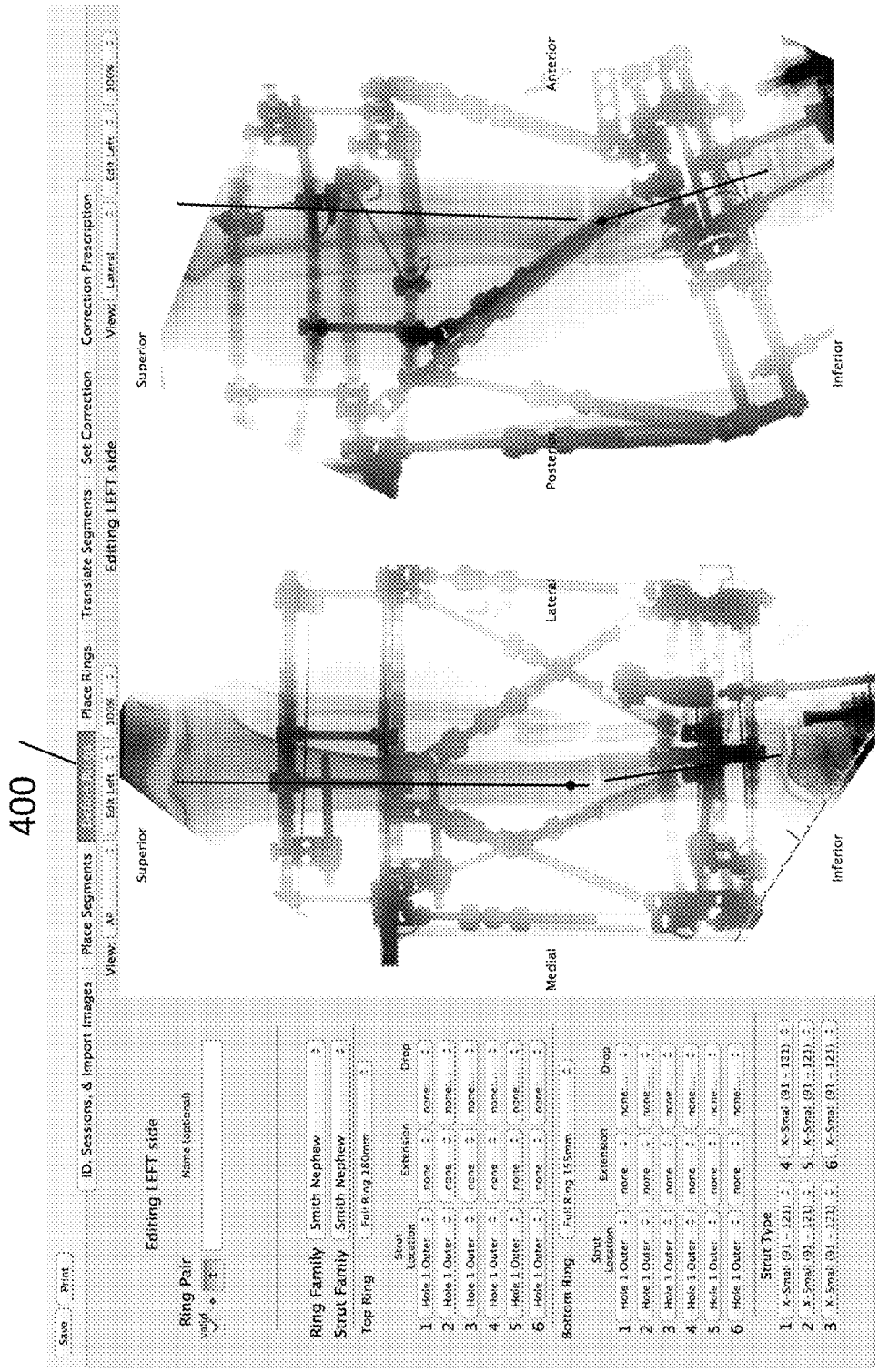
FIG. 12 shows a screen shot of the "DEFINE RINGS" tab, according to some embodiments of the present invention.

FIG. 12 shows a screen shot of a "DEFINE RINGS" tab 400. The user of the system starts by entering the type and size of ring information for each ring-pair. A graphical user interface may be used as well to click on a schematic of a ring to define where the struts are attached. In one embodiment, the brand and model of each ring may be entered, and preexisting ring/strut size information retrieved according to the entered brand and model.

Figure 13:
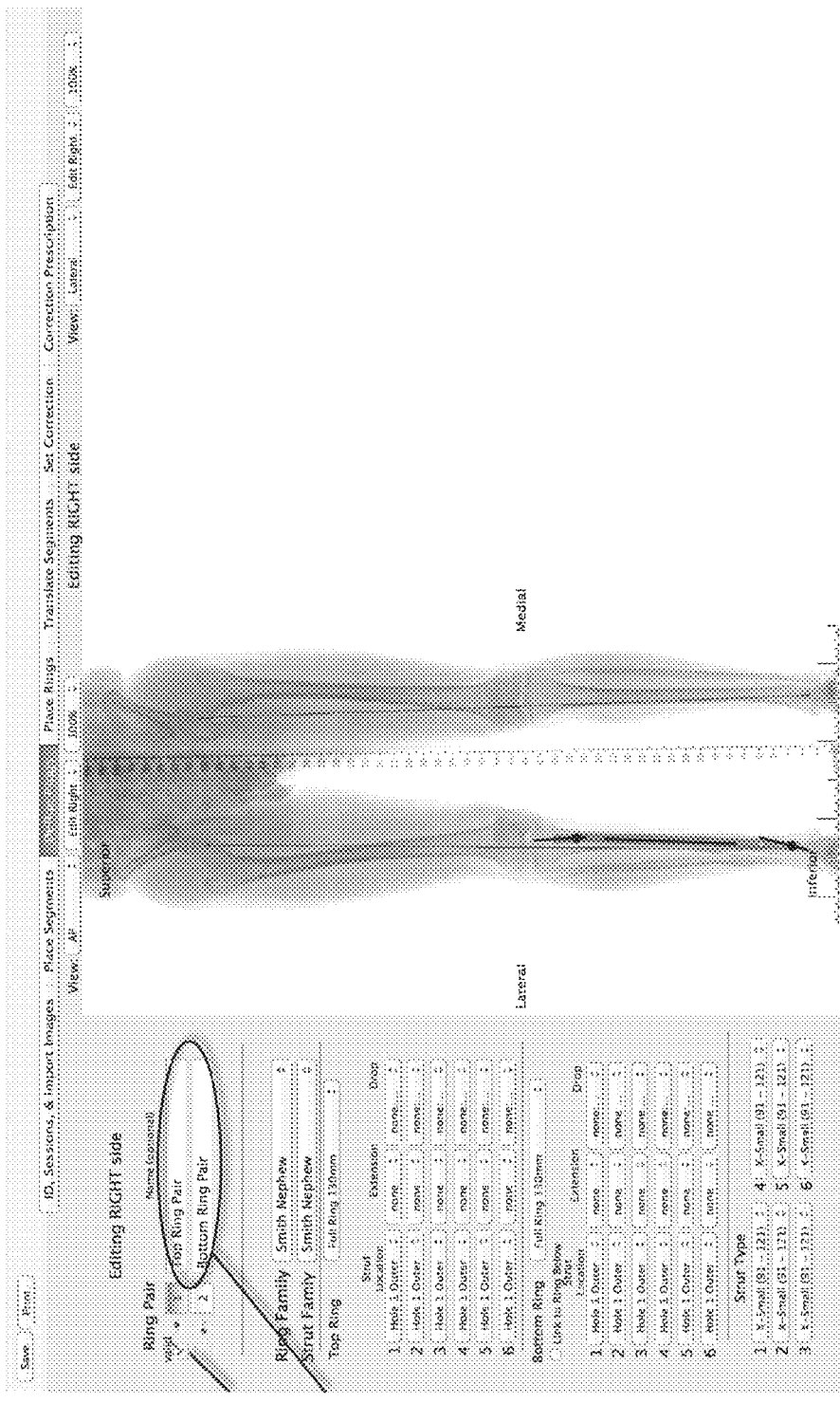
FIG. 13 shows a screen shot of the DEFINE RINGS tab where multiple ring-pairs have been defined, according to some embodiments of the present invention.
Figure 14A:
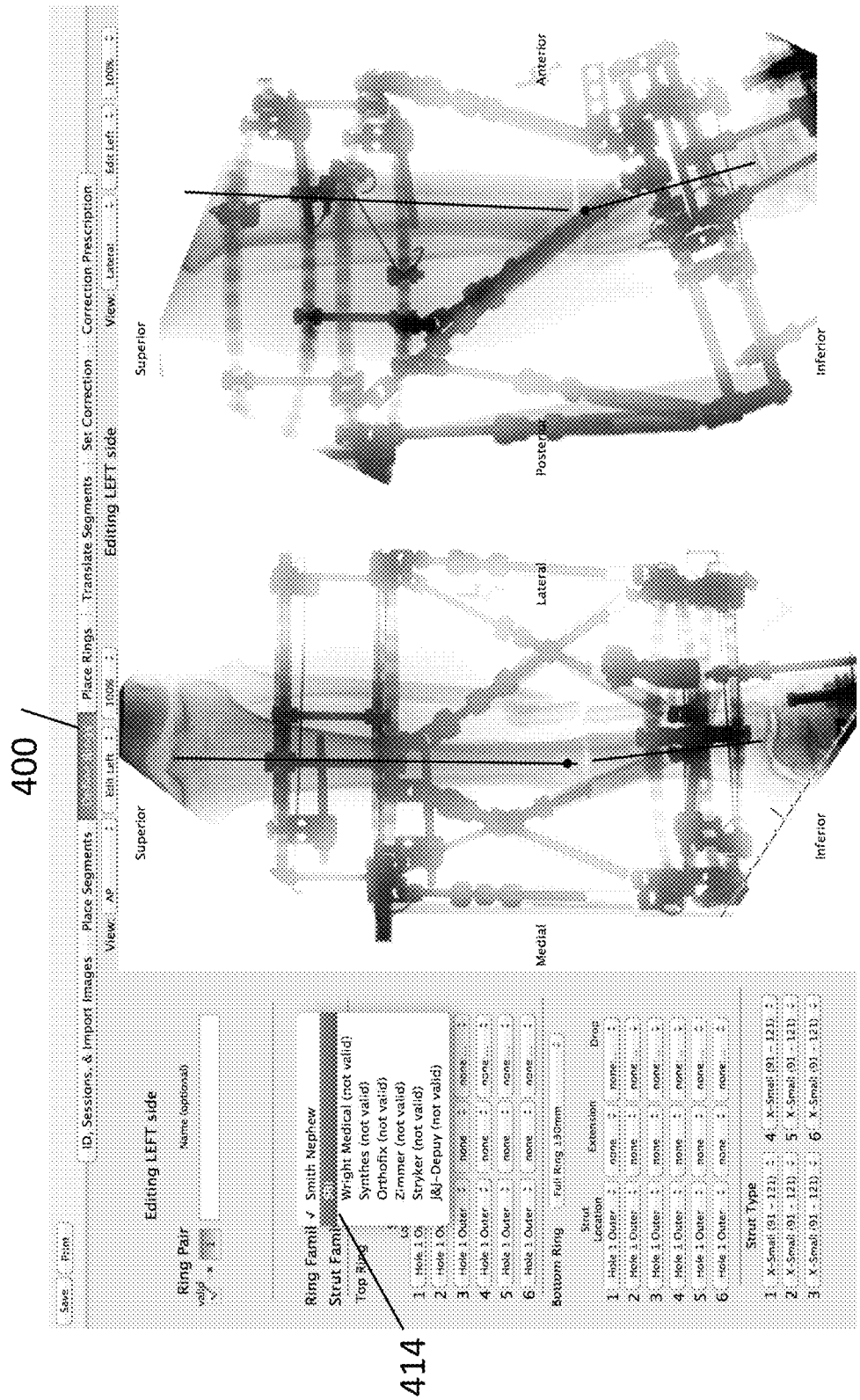
FIGS. 14A-14B show screen shots of the DEFINE RINGS tab where the user has defined the ring geometry for the top and bottom ring of a ring pair by selecting the type and size of rings being used, according to some embodiments of the present invention.
Figure 14:
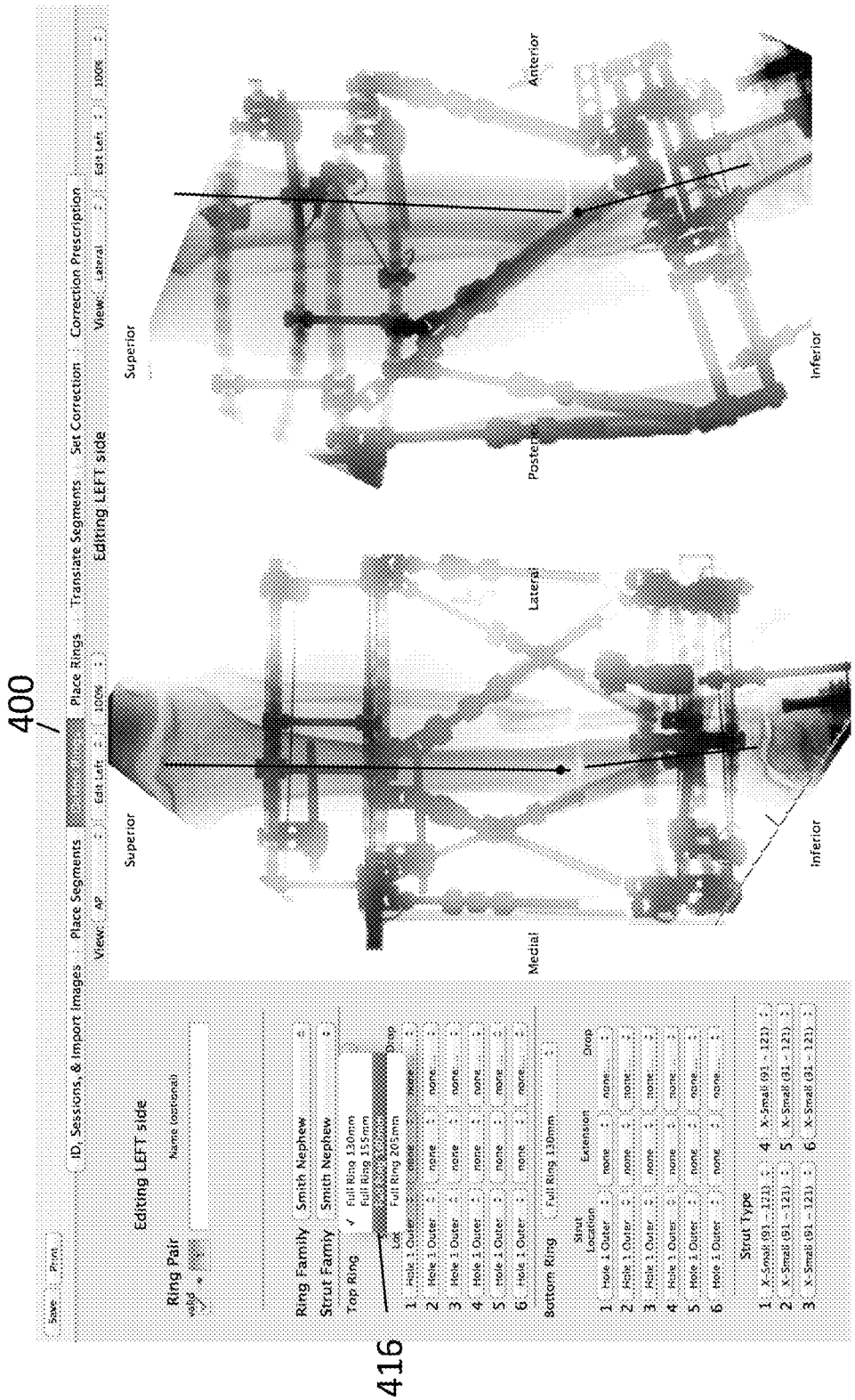

FIG. 13 shows a screen shot of a DEFINE RINGS tab 400 where multiple ring-pairs 410 have been defined. In this case, the user selects which ring pair they are currently defining. A check box 412 reminds the user if a ring-pair has been defined. FIGS. 14A-14B show screen shots of the DEFINE RINGS tab 400 where the user has defined the ring geometry for the top and bottom ring of a ring pair by selecting the type 414 and size 416 of rings being used.

Figure 15:
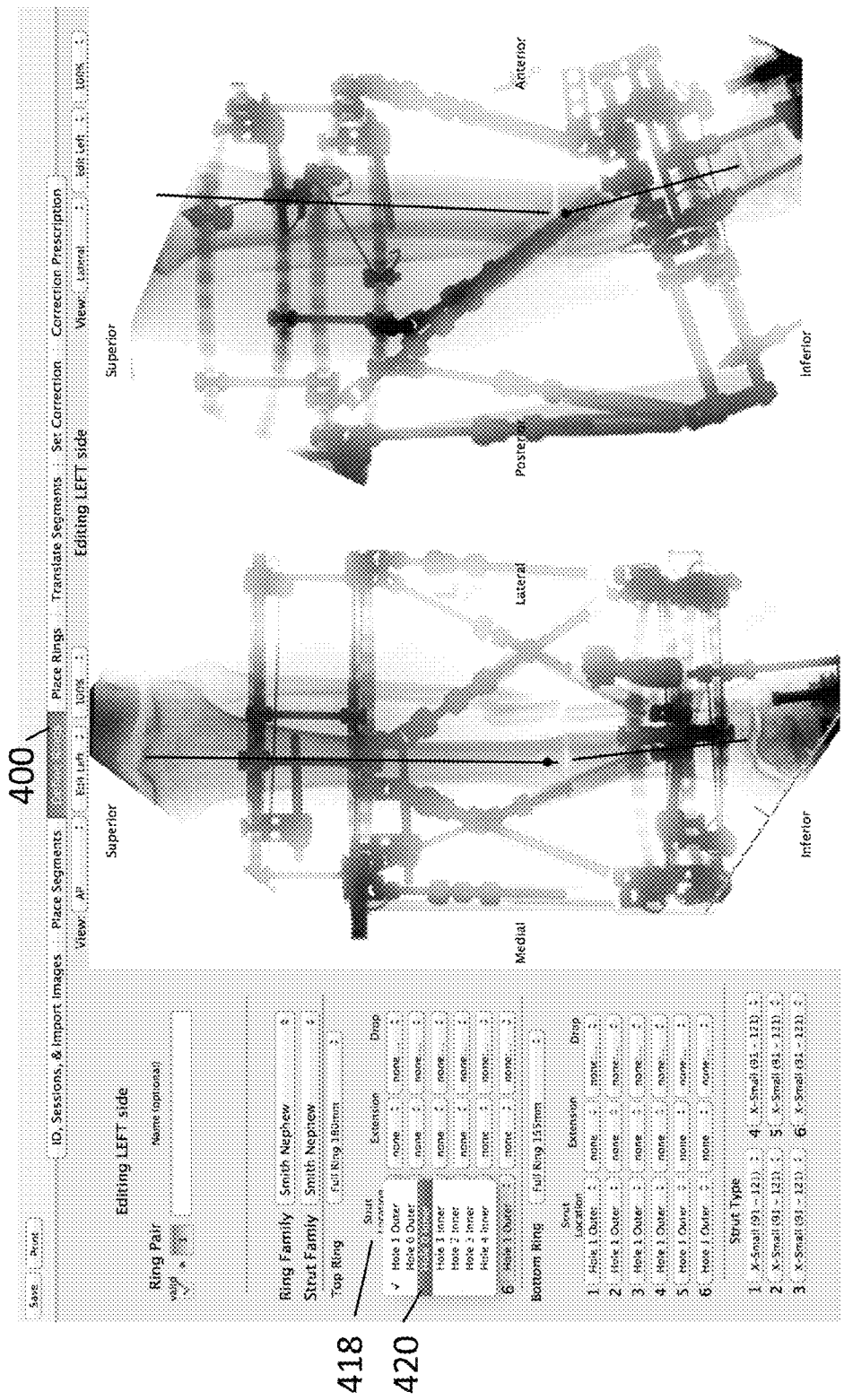
FIG. 15 shows a screen shot of the DEFINE RINGS tab where the user is selecting the attachment point for each strut, according to some embodiments of the present invention.

After the system generates the graphical representation of the ring(s), e.g. the ellipse, strut attachment points may be selected by a user. FIG. 15 shows a screen shot of the DEFINE RINGS tab 400 where the user is selecting an attachment point 418 for each strut. The user has the flexibility to use any ring holes 420 to attach the ring to the bone, and still be able to attach a strut to the ring and make the calculations described below. In some embodiments, by selecting an attachment point for each strut, the user may define a strut angle and strut radius.

Figure 16:
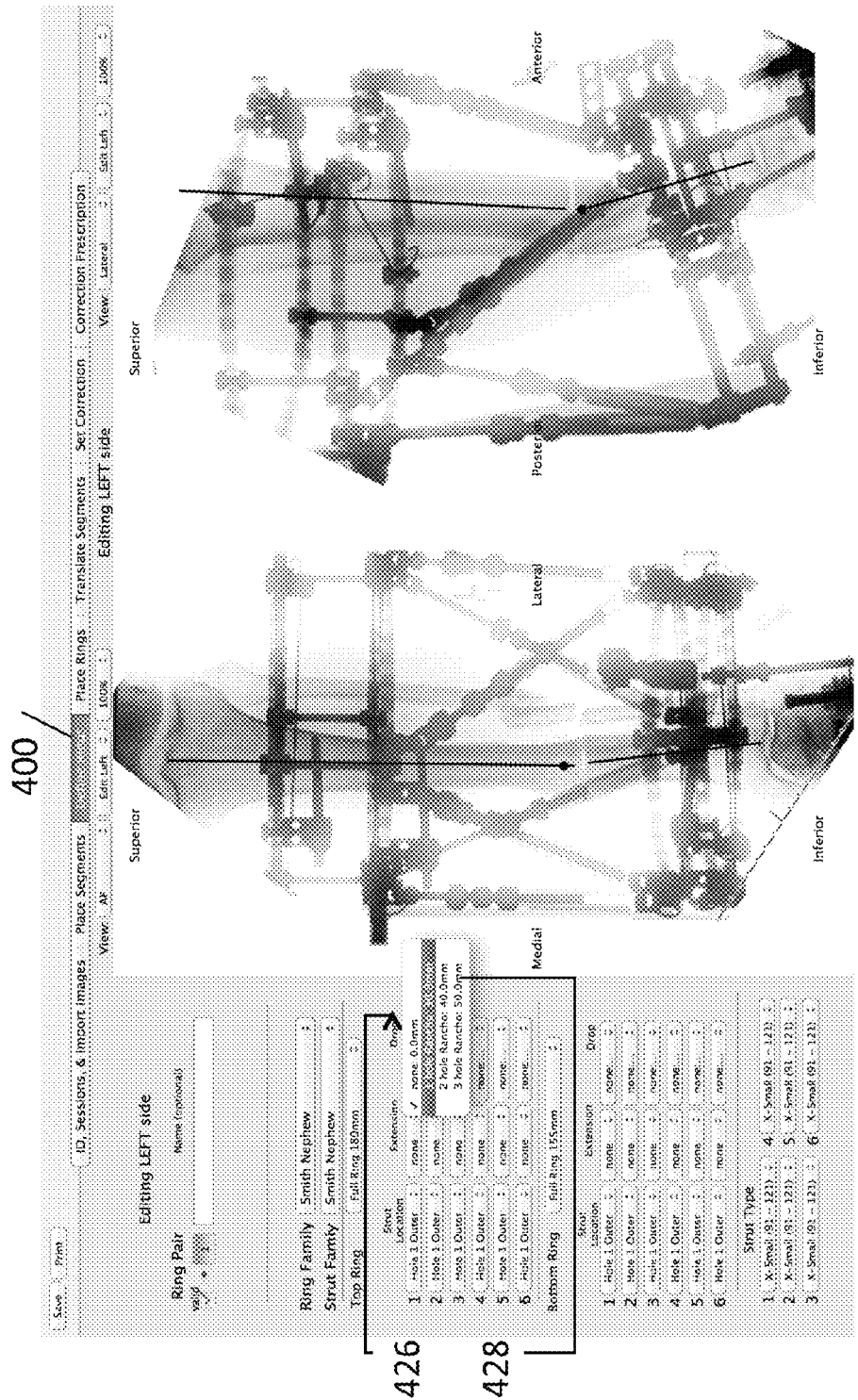
FIG. 16 shows a screen shot of the DEFINE RINGS tab in which the user has chosen to attach the strut to the ring by way of an intermediary piece of hardware, in this case, a ring drop, according to some embodiments of the present invention.

FIG. 16 shows a screen shot of a DEFINE RINGS tab 400 in which the user has chosen to attach a strut to the ring by way of an intermediary piece of hardware, in this case, a ring drop 426. Using the ring drop 426 allows dropping the strut for a predefined distance from the ring. It allows the user to move struts out of the way of other hardware to prevent the struts hitting fixed structures as the rings/struts move during correction. The length of ring drop 426 defines the strut drop length 428.

Figure 17:
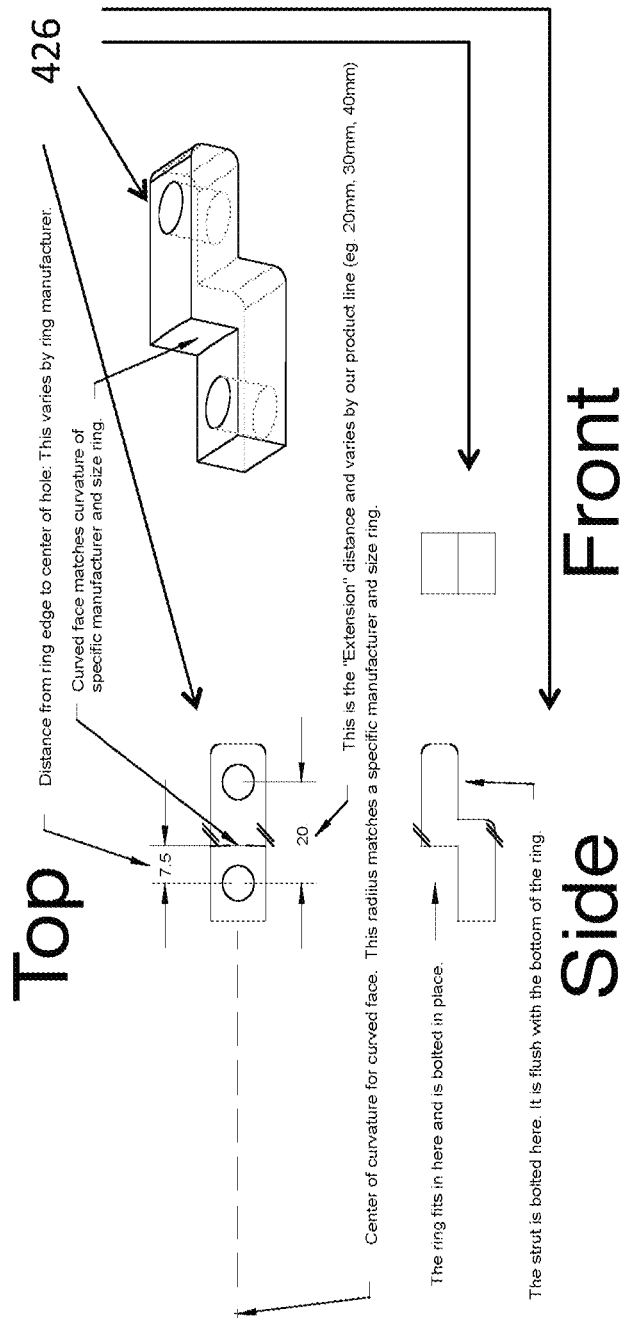
FIG. 17 is a schematic drawing showing a top, perspective, front and side views of a ring drop used to attach a strut to the ring, according to some embodiments of the present invention.

FIG. 17 is a schematic drawing showing a top, perspective, front and side views of a ring extender 426 used to attach a strut to a ring according to some embodiments of the present invention. This separate hardware allows the user to attach the strut to a ring at any point on the ring by extending the strut radius from a given ring position, and could have a built-in ring drop as well. Variations in the products could alter the strut angle as well.

Place Rings Tab

Although a ring-pair is commonly a set of two rings connected by six struts that connect two segments, other alternative ring and strut combinations may also be used. The ring-pair enables one segment to be moved relative to another to facilitate a correction. By changing the length of each strut according to a prescription calculated in the following tabs, the rings can be manipulated in space and the corresponding segments manipulated in the patient. To make these calculations, the program uses its knowledge of the 3D shape of the ring. The calculations described below are generally applicable to any ring, or really any shaped structure. Such calculations may rely on three-dimensional measurements of ring/structure sizes pre-entered into the program's database. The user chooses the ring type and size to let the program know which ring data to use for its calculations.

Figure 18:
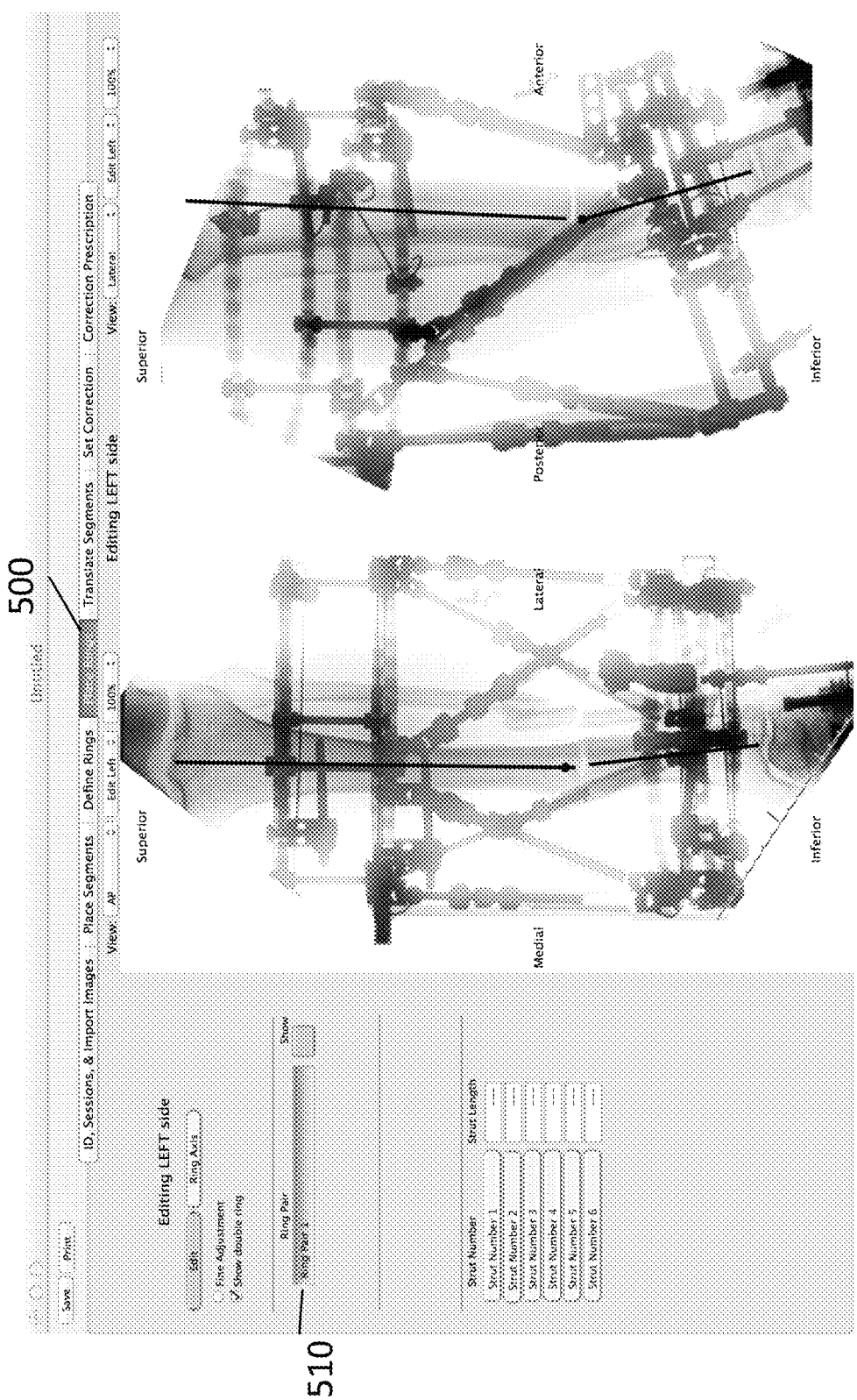
FIG. 18 shows a screen shot of the "PLACE RINGS" tab, according to some embodiments of the present invention.

FIG. 18 shows a screen shot of a "PLACE RINGS" tab 500 that allows the user to define the location of the external fixator ring(s) relative to surrounding anatomic structures; the ring pair being placed is chosen from a drop-down menu 510.

Figure 19:
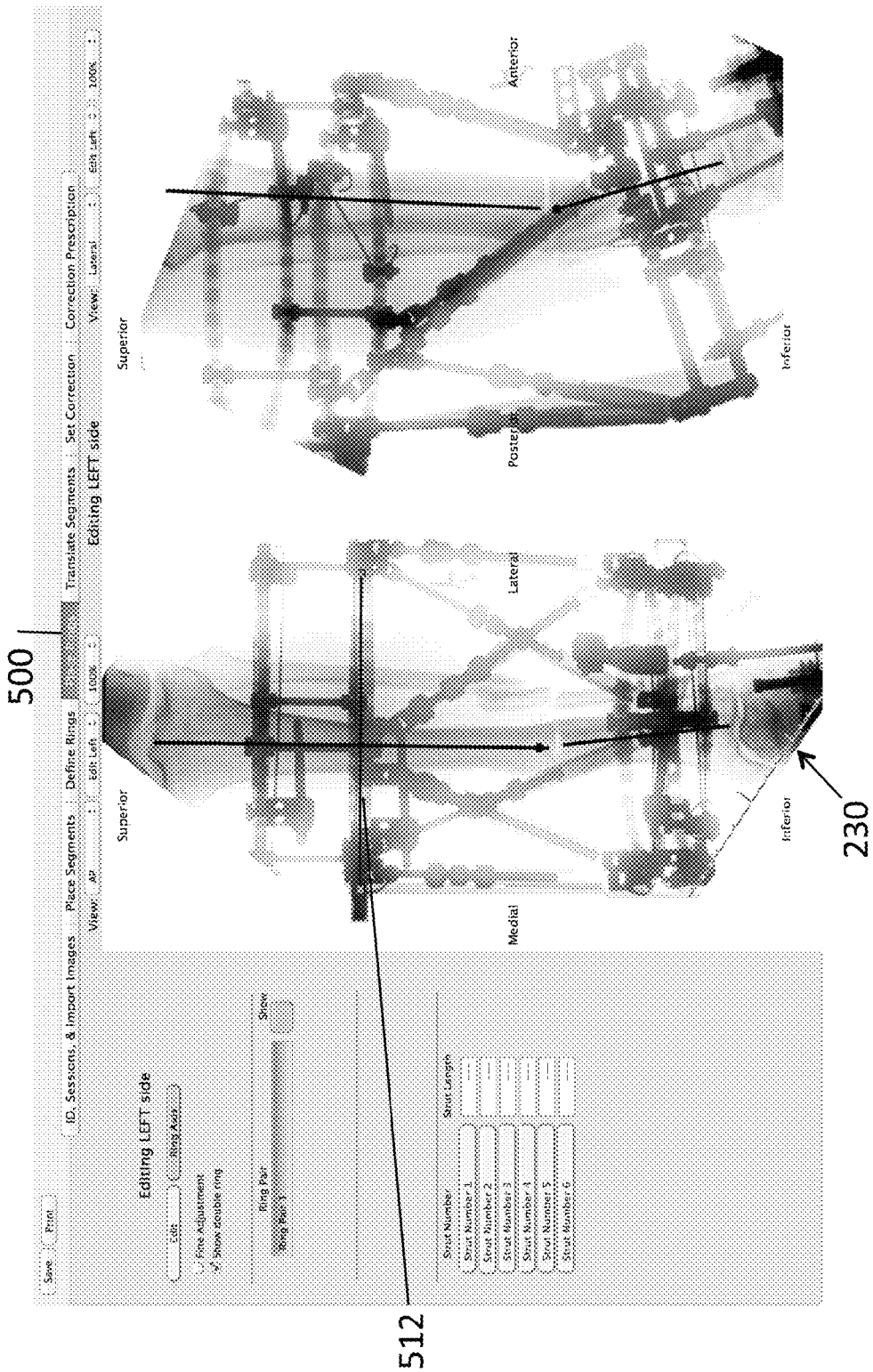
FIG. 19 shows a screen shot of the PLACE RINGS tab where a ring bisector is drawn on the AP view of the digital medical image, according to some embodiments of the present invention.

In some embodiments, a user begins by drawing a ring bisector for each ring. FIG. 19 shows a screen shot of the PLACE RINGS tab 500 where a ring bisector 512 is drawn on the AP view of the digital medical image 230. The ring bisector is constant despite changes in x-ray beam position and therefore allows for accurate ring position definition. The program then uses an ellipse to represent the graphical display of the ring on the AP and lateral digital medical images. The ellipse is represented by a center, an "a" or long axis length, a "b" or short axis length, and a slope. The center, "a" axis length, and slope are set by drawing the ring bisector.

Figure 47A:
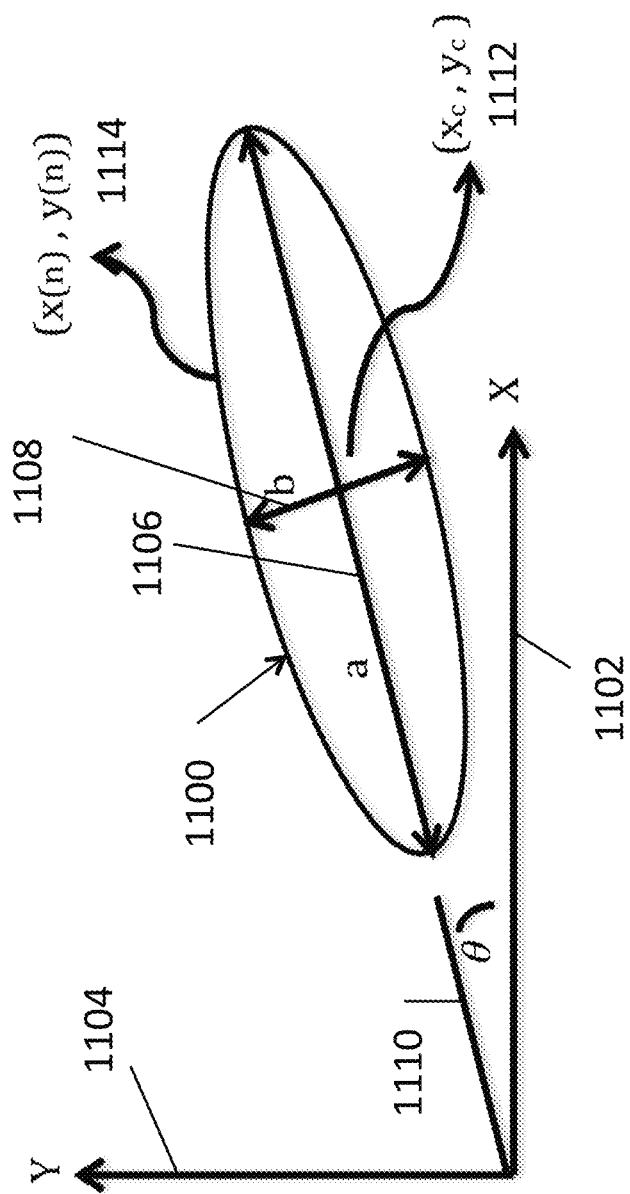
FIGS. 47A-B illustrate a tilted ellipse in a 2D (X, Y) plane, according to some embodiments of the present invention.
Figure 47B:
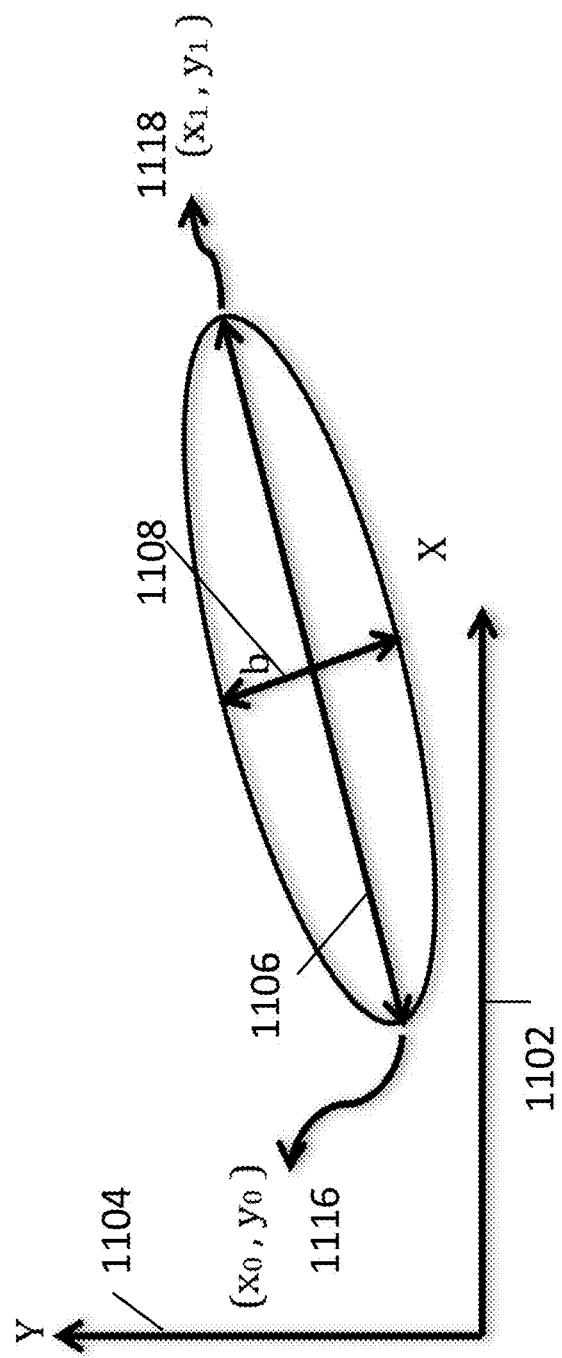

In some embodiments, a tilted ellipse representing a ring is generated using a set of mathematical formulas described below. FIGS. 47A-B illustrate a tilted ellipse 1100 in a 2D (X,Y) plane, where the X-axis 1102 is shown perpendicular to the Y-axis 1104. The two axes of the ellipse are represented by the "long" axis of length 2*a 1106 referred to as "a" axis and the "short" axis of length 2*b 1108 referred to as "b" axis. An angle θ, shown at 1110, represents the angle between the "a" axis 1106 and the X-axis 1102. When θ=0 the ellipse's "a" axis is parallel to X-axis and the "b" axis is parallel to Y-axis. Each point in this 2D plane is represented by a pair of numbers; they are the coordinates of the point. Significant points on the ellipse include: the center of the ellipse with coordinates $(x_c, y_c)$ 1112; a point on the ellipse with coordinates (x(n), y(n)) 1114 (where "n" is an angle, expressed in radians, ranging from 0 to $2\pi$); the points ($x_0$, $y_0$) 1116 and ($x_1$, $y_1$) 1118 are the endpoints of the "a" axis (the "long" axis).

The x and y coordinates of a point on a tilted ellipse in a 2D plane may be expressed as:

$$x(n)=x_c+a\cdot\cos n\cdot\cos \theta - b\cdot\sin n\cdot\sin \theta \quad (1)$$

$$y(n)=y_c+a\cdot\cos n\cdot\sin \theta + b\cdot\sin n\cdot\cos \theta \quad (2)$$

The coordinates (x(n), y(n)) 1114 of a point on the ellipse may be calculated as functions of the following parameters: the center of the ellipse ($x_c$, $y_c$) 1112, the values of "a" 1106 and "b" 1108, the angle n 1118 and the angle $\theta$ 1110. The ellipse may be translated by adding/subtracting horizontal and vertical translation extents to the center coordinates ($x_c$, $y_c$). Rotational transformations are described in detail below.

Figure 20:
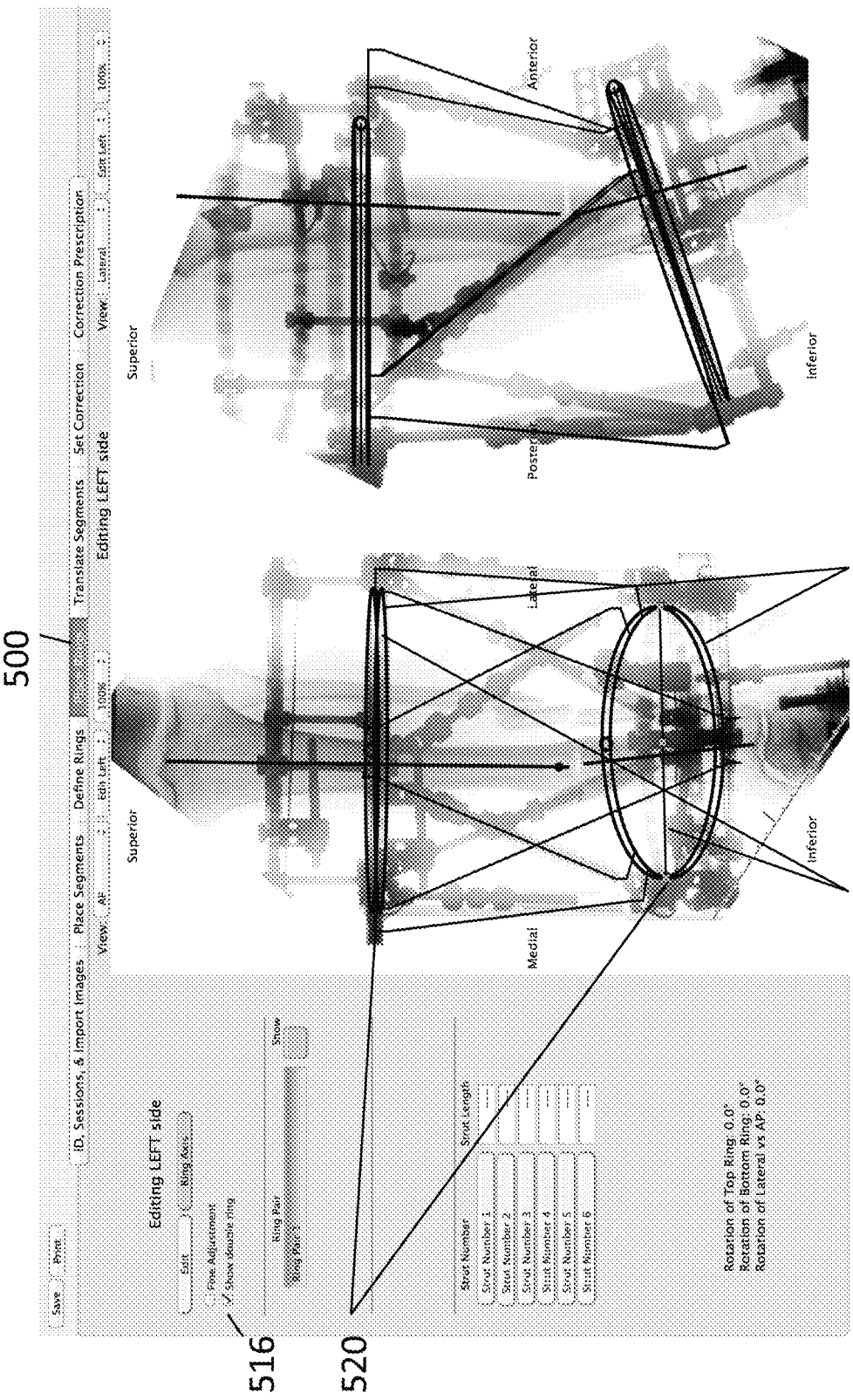
FIG. 20 shows a screen shot of the PLACE RINGS tab where, after placing four ring bisector axes (AP & lateral, top & bottom), the program places an initial set of rings, according to some embodiments of the present invention.
Figure 21:
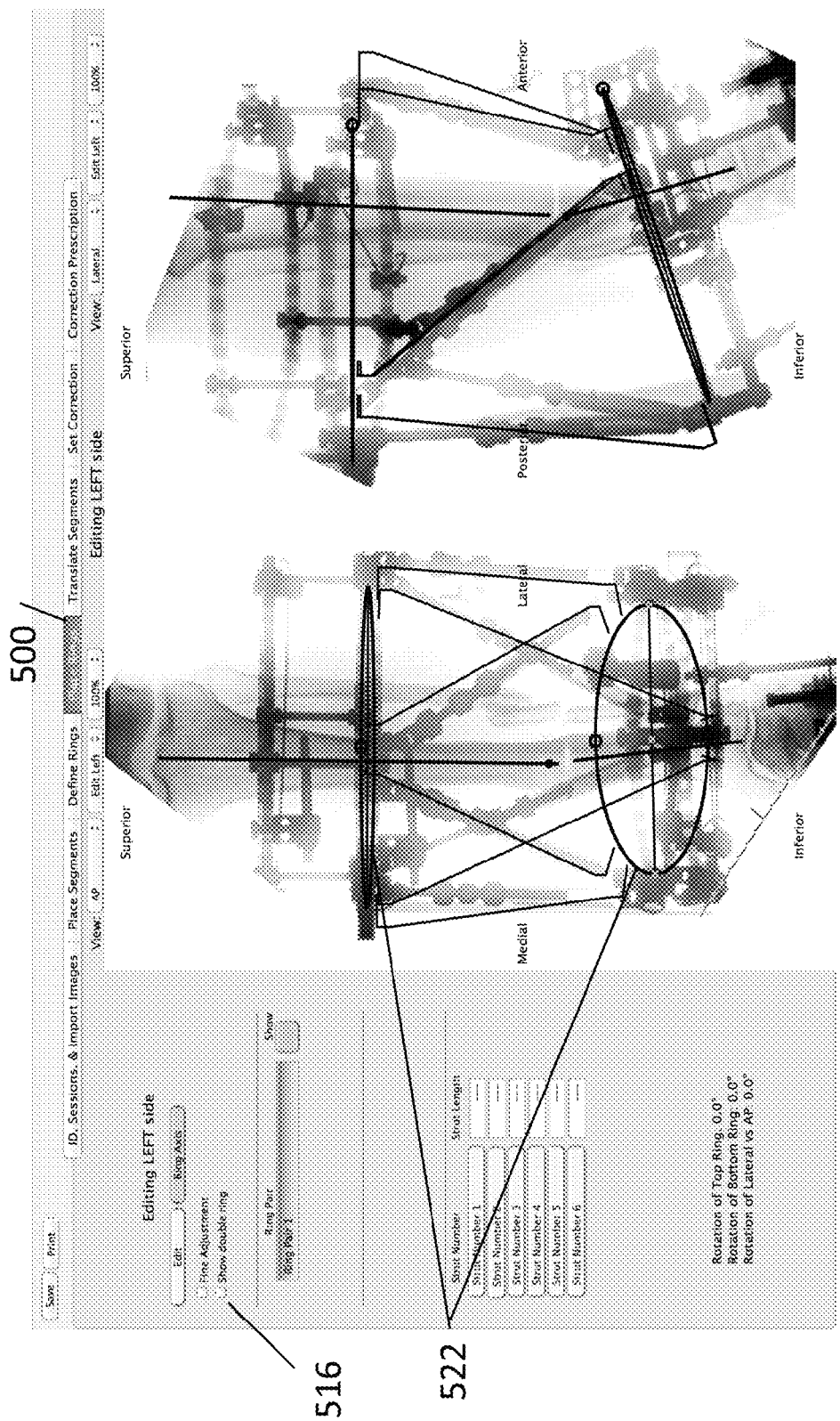
FIG. 21 shows a screen shot of the PLACE RINGS tab of a display of the ring as a single ellipse, according to some embodiments of the present invention.

FIG. 20 shows a screen shot of the PLACE RINGS tab 500 where, after placing four ring bisector axes 512 (AP & lateral, top & bottom), the program places an initial set of rings. At this stage, the program can also scale the images, segments, and rings relative to each other, as shown at 516. The rings 514 are displayed as double ellipses 520 showing the true height of the ring. FIG. 21 shows a screen shot of the PLACE RINGS tab 500 of a display of the ring as a single ellipse 522.

In some embodiments, once the top and bottom ring centers are defined in both the AP and lateral planes, the image, segments, and ring parameters can be scaled. Scaling corrects for differences in the ratio of distance from the x-ray source to anatomic structure and distance from anatomic structure to x-ray plate. This ratio will magnify or shrink the AP view relative to the lateral view. Calculating the scale factor for the AP and lateral planes corrects for this magnification. Scaling can be based on any structure that is known to be the same on the AP and lateral views. These include the distance between joint line centers of the same bone segment (when defined) or ring centers (when defined). Alternatively, size markers included when the digital medical image was taken may be used by the program to determine magnification and scaling.

The "b" axis length may be defined as a ring spread. The ideal or expected ring spread is the spread that would be seen if the x-ray source were an infinite number of parallel beams. However, x-rays are sources are point based, which causes parallax in the ring projection based on where the point source is relative to the ring. This makes the ring spread bigger or smaller even though the actual ring position hasn't changed.

In some embodiments, a user is able manipulate the spread to match what is seen on the screen (view ring spread). The user may need to adjust the ring bisector as the view ring spread is set. This is a form of error correction for x-ray beam position.

Figure 22:
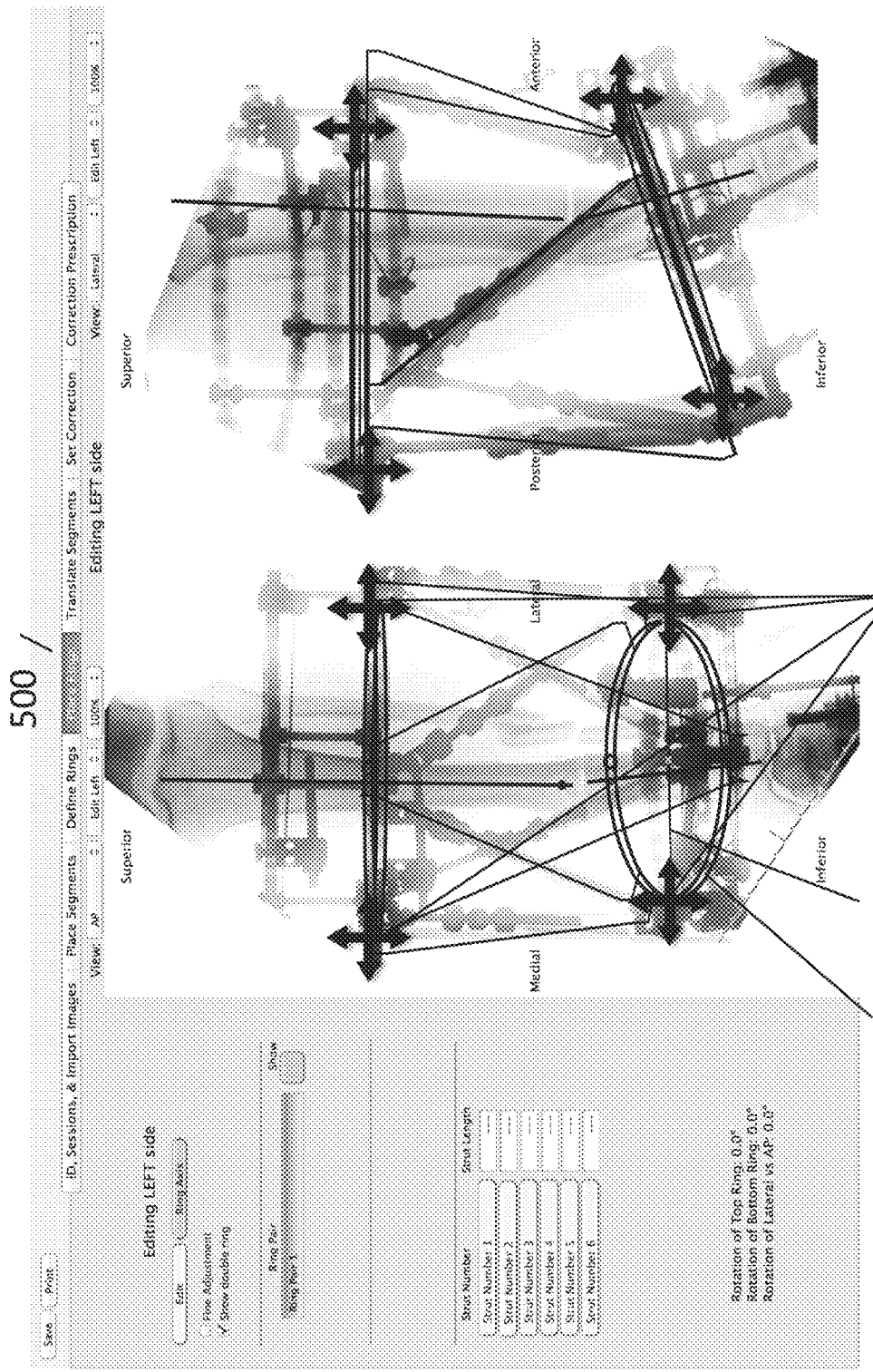
FIG. 22 shows a screen shot of the PLACE RINGS tab where the width and position of the rings are adjusted by manipulating ring axes, according to some embodiments of the present invention.

FIG. 22 shows a screen shot of a PLACE RINGS tab 500 where the width and position of the rings 514 are adjusted by manipulating ring axes 512. This is done by manipulating handles 524 on the ring bisector axes 512 or by separate controls.

Figure 23:
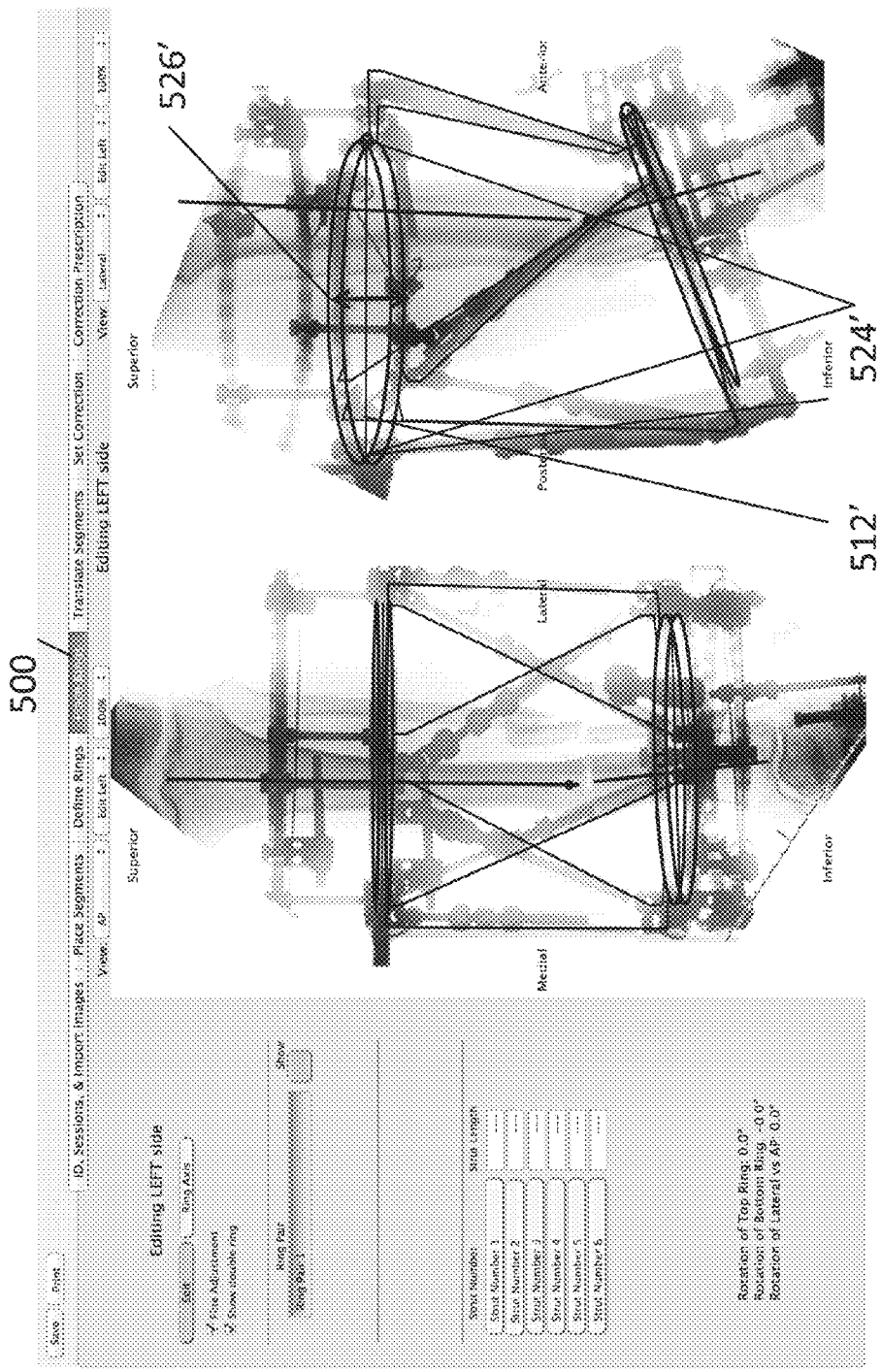
FIG. 23 is a screen shot of the PLACE RINGS tab showing adjustment of the ring "b" or short axis to match the ring position on screen, according to some embodiments of the present invention.

FIG. 23 is a screen shot of a PLACE RINGS tab 500 showing adjustment of the ring "b" or short axis 526' to match the ring position on screen. This can be done by manipulating handles 524' on the ring bisector 512' or by separate controls.

In some embodiments, as illustrated in FIG. 47B, the movement of the endpoints ($x_0$, $y_0$) 1116 and ($x_1$, $y_1$) 1118 of the "a" axis adjusts ($x_c$, $y_c$) 1108, $\theta$ (not shown), and the "a" axis 1106 length as follows:

$$x_c=(x0+x1)/2 \quad (3)$$

$$y_c=(y0+y1)/2 \quad (4)$$

$$a=\text{sqrt}((x1-x0)^2+(y1-y0)^2)/2 \quad (5)$$

$$\theta=\tan-1((y1-y0)/(x1-x0)) \quad (6)$$

Figure 48A:
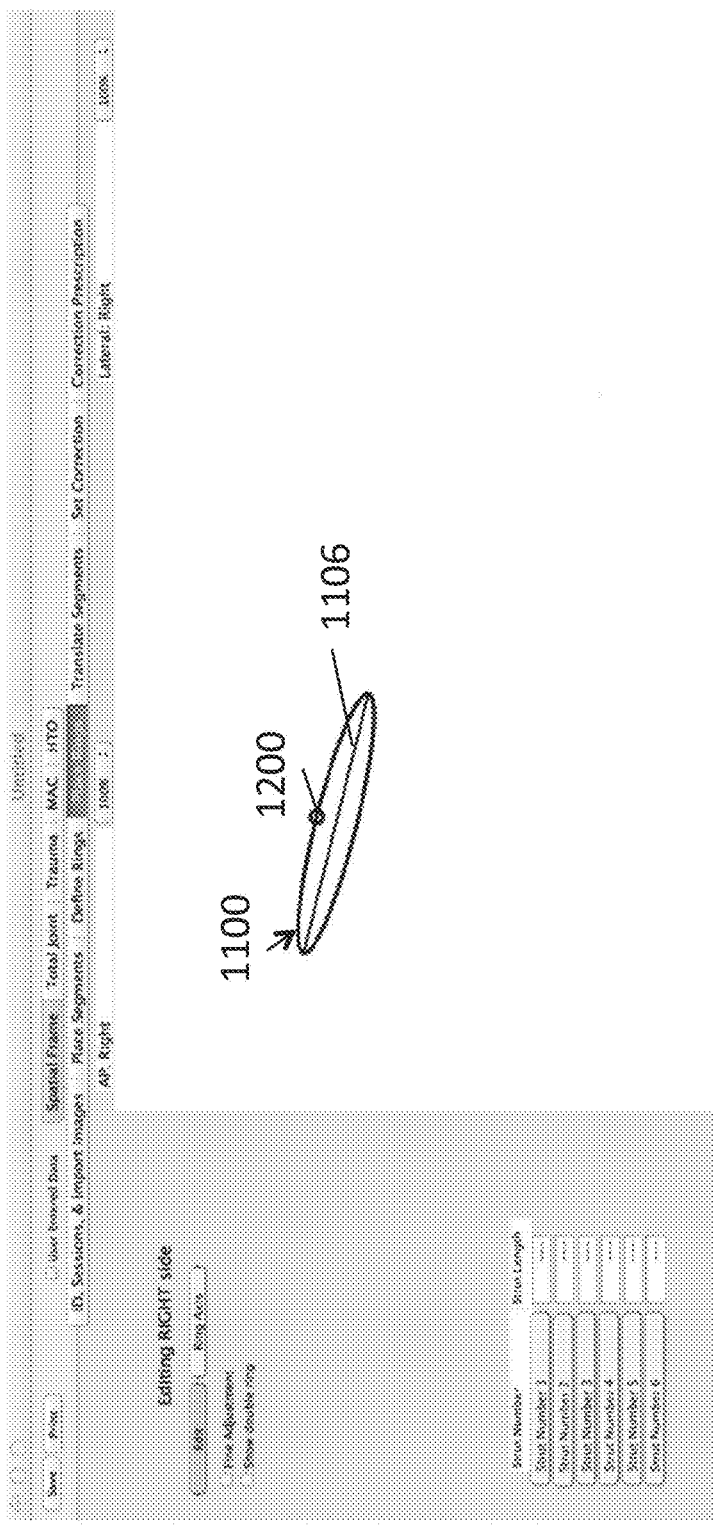
FIGS. 48A-B show an exemplary embodiment of an ellipse, with an "a" axis, and an adjustment handle, where the ellipse may be dragged by its "a" axis endpoints, according to some embodiments of the present invention.
Figure 48B:
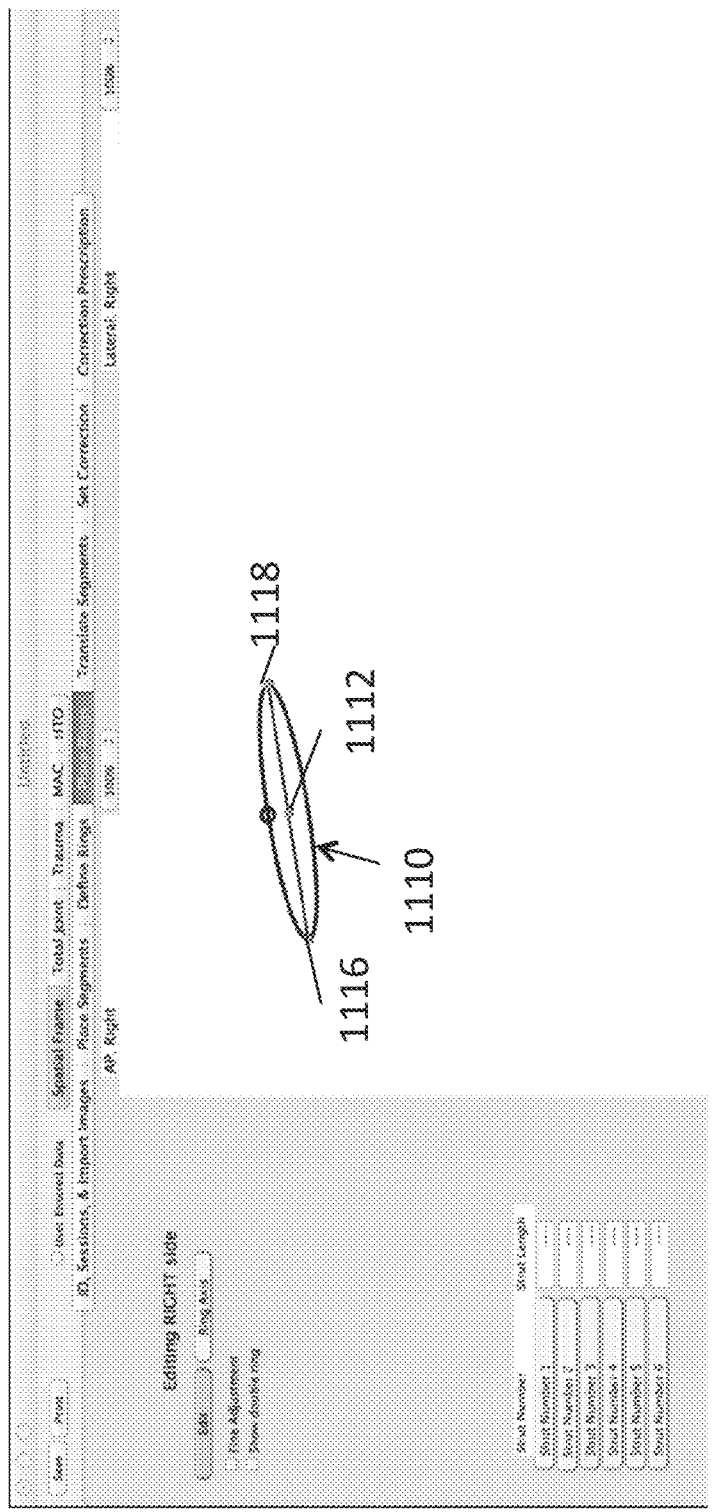

FIG. 48A shows an exemplary embodiment of an ellipse 1100, with an "a" axis 1106, and an adjustment handle 1200. As shown in FIG. 48B, the ellipse 1100 may be dragged by its "a" axis endpoints 1116, 1118.

Once a ring has been defined, in the PLACE RING tab the system receives ring rotation user input controlling an axial rotation and an azimuthal rotation of the graphical representation of the ring superimposed on the at least one digital medical image. In some embodiments, a user can control the axial and azimuthal rotations of each of two rings (top & bottom) individually. Individual ring rotation capabilities account for the possibility that a ring may be fixed to a bone segment in a rotated position (ring mounting rotation), either volitionally or because of error inherent in the mounting procedure.

Figure 24:
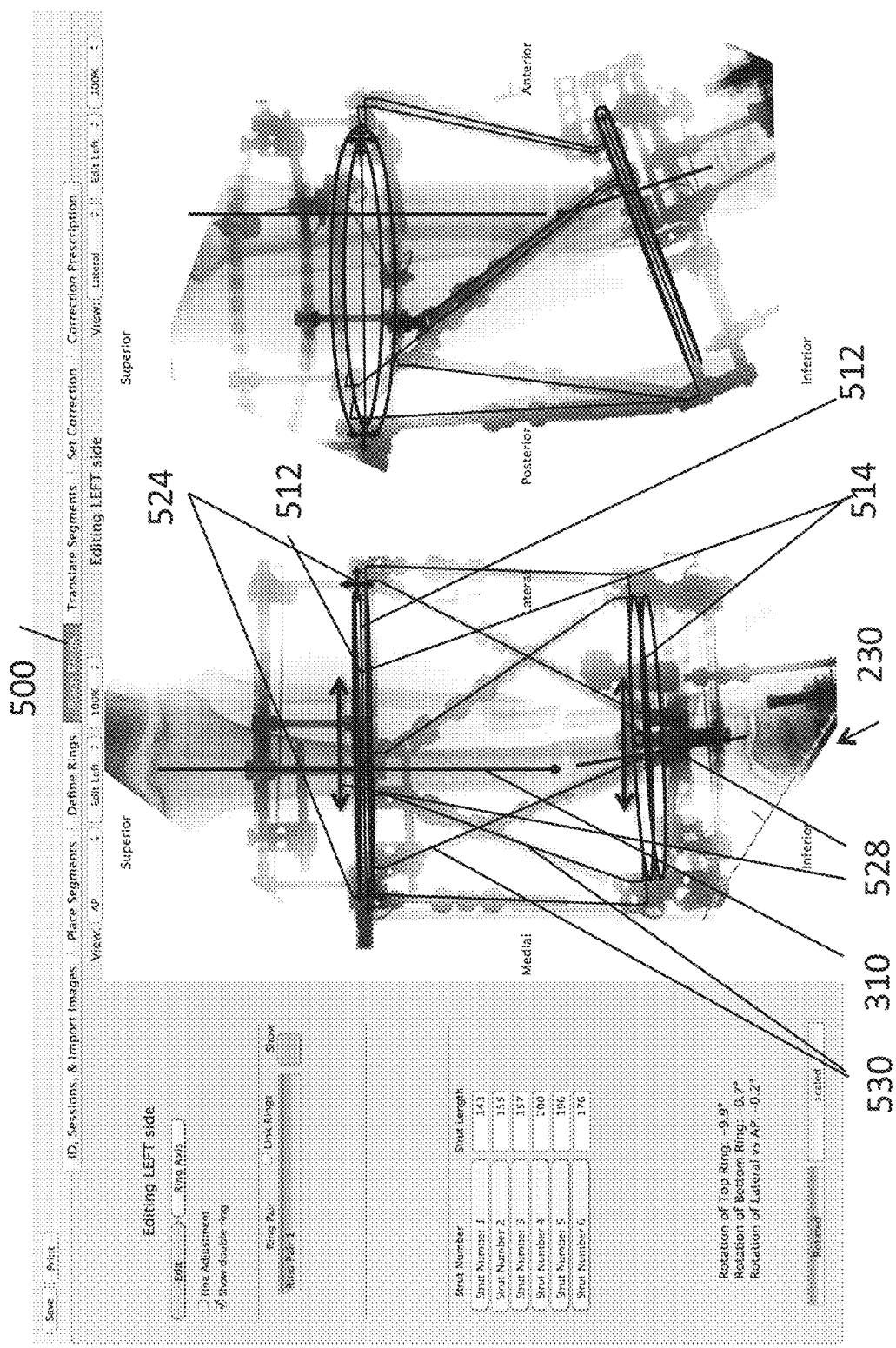
FIG. 24 shows a screen shot of the PLACE RINGS tab of a user adjusting the ring rotation, according to some embodiments of the present invention.

FIG. 24 shows a screen shot of a PLACE RINGS tab 500, illustrating a user's adjusting a ring rotation, as marked by the arrows 528. First the orientations of the top and bottom rings 514 are adjusted relative to the segment 310. This is best done by comparing the strut position 530 of the AP view 230. Both the AP and lateral views rings change as the ring rotation is manipulated here (compare with FIG. 23). A user can rotate a ring by manipulating handles 524 on the ring bisector 512, on the ring itself, or by separate controls.

Figure 49A:
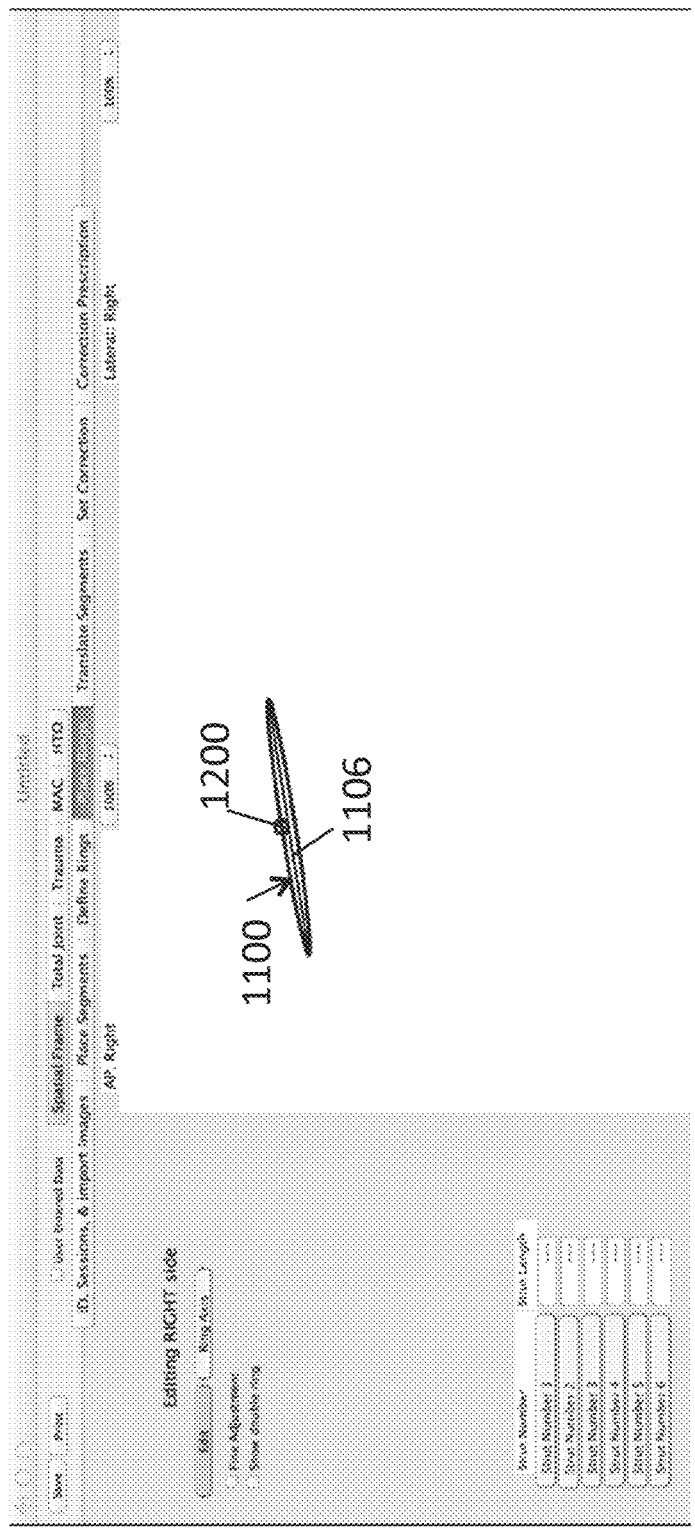
FIGS. 49A-B, show one type "axial rotation", for example a rotation of the display of the ring around the "a" axis is accomplished by changing the length of the "b" axis, according to some embodiments of the present invention.
Figure 49B:
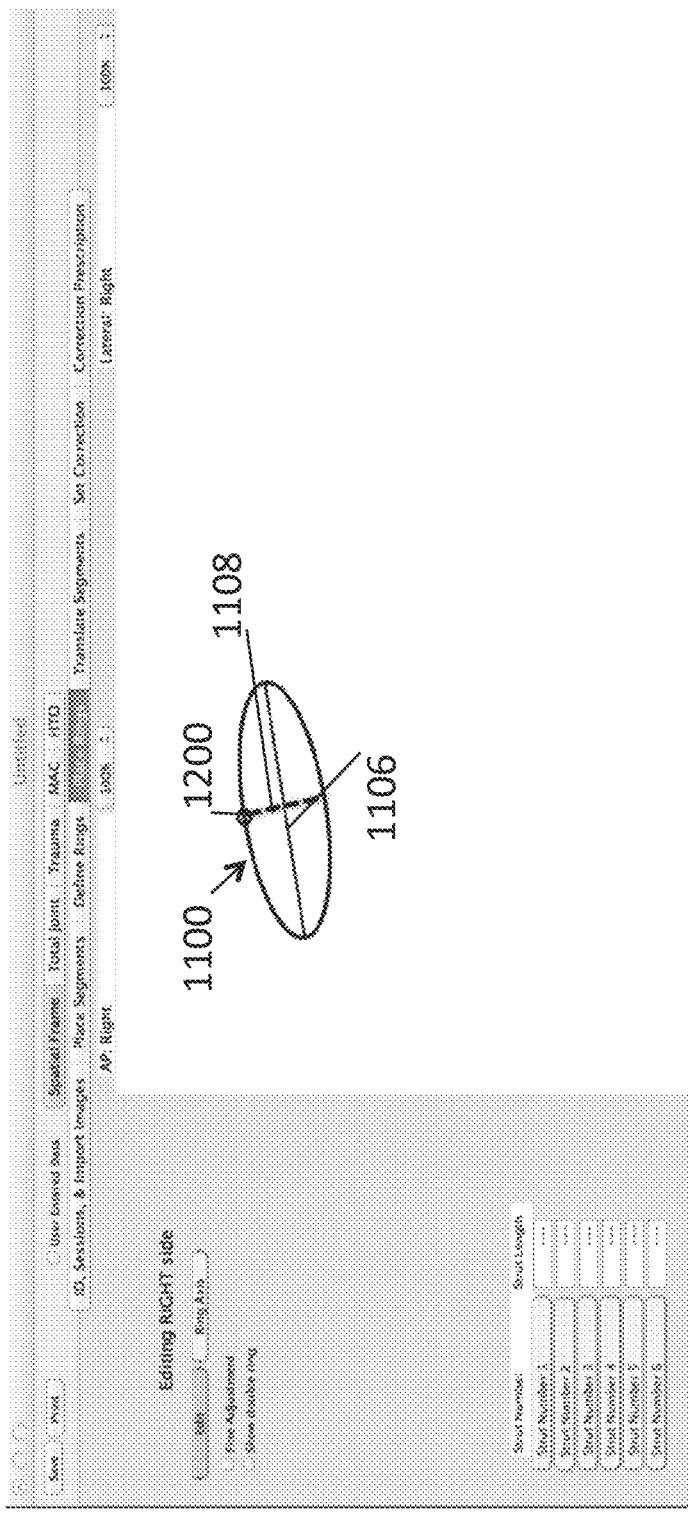
Figure 51A:
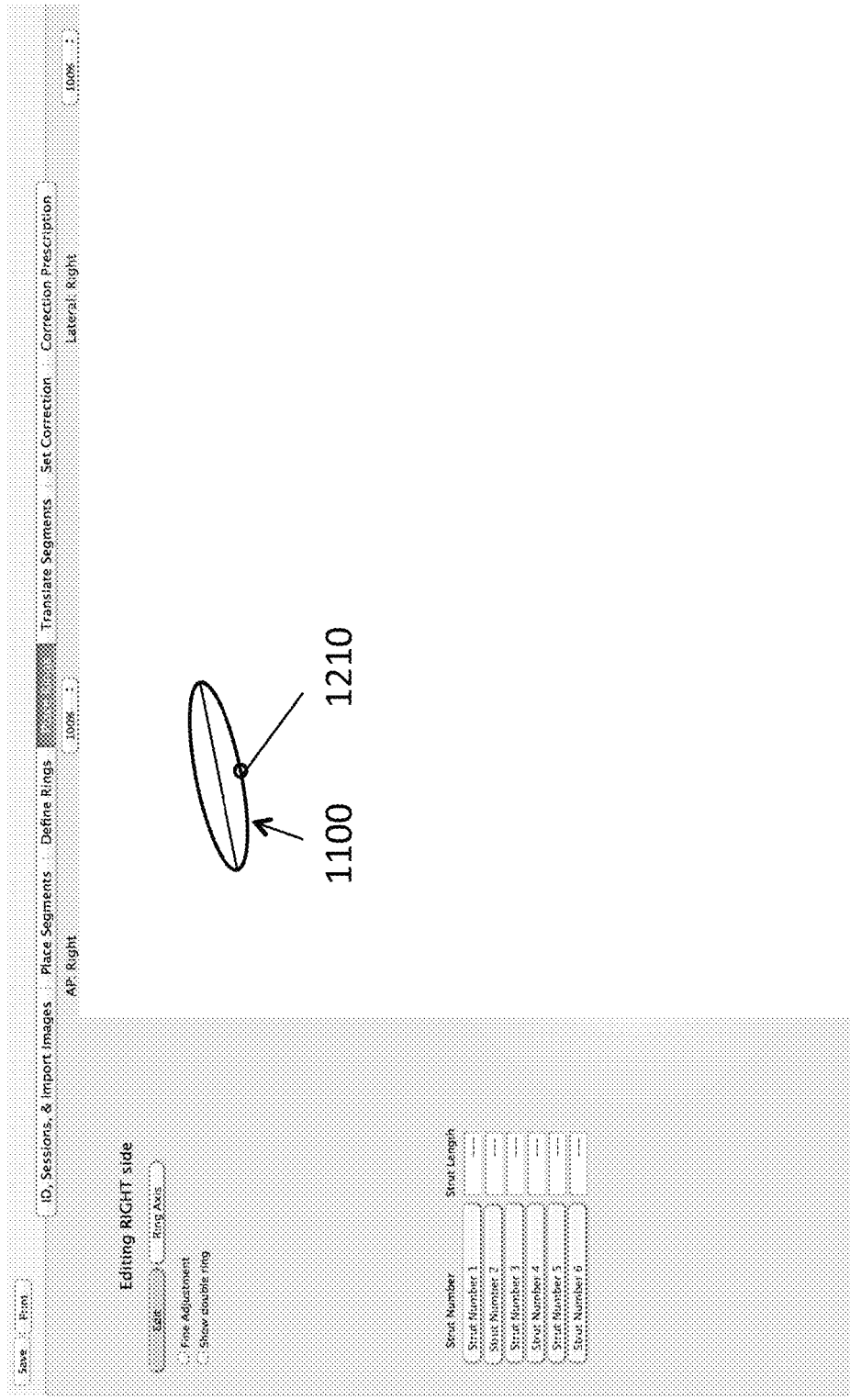
FIGS. 51A-B show screenshots of a rotation of the top ring around the "a" axis, accomplished by changing the length of the "b" axis, according to some embodiments of the present invention.
Figure 51B:
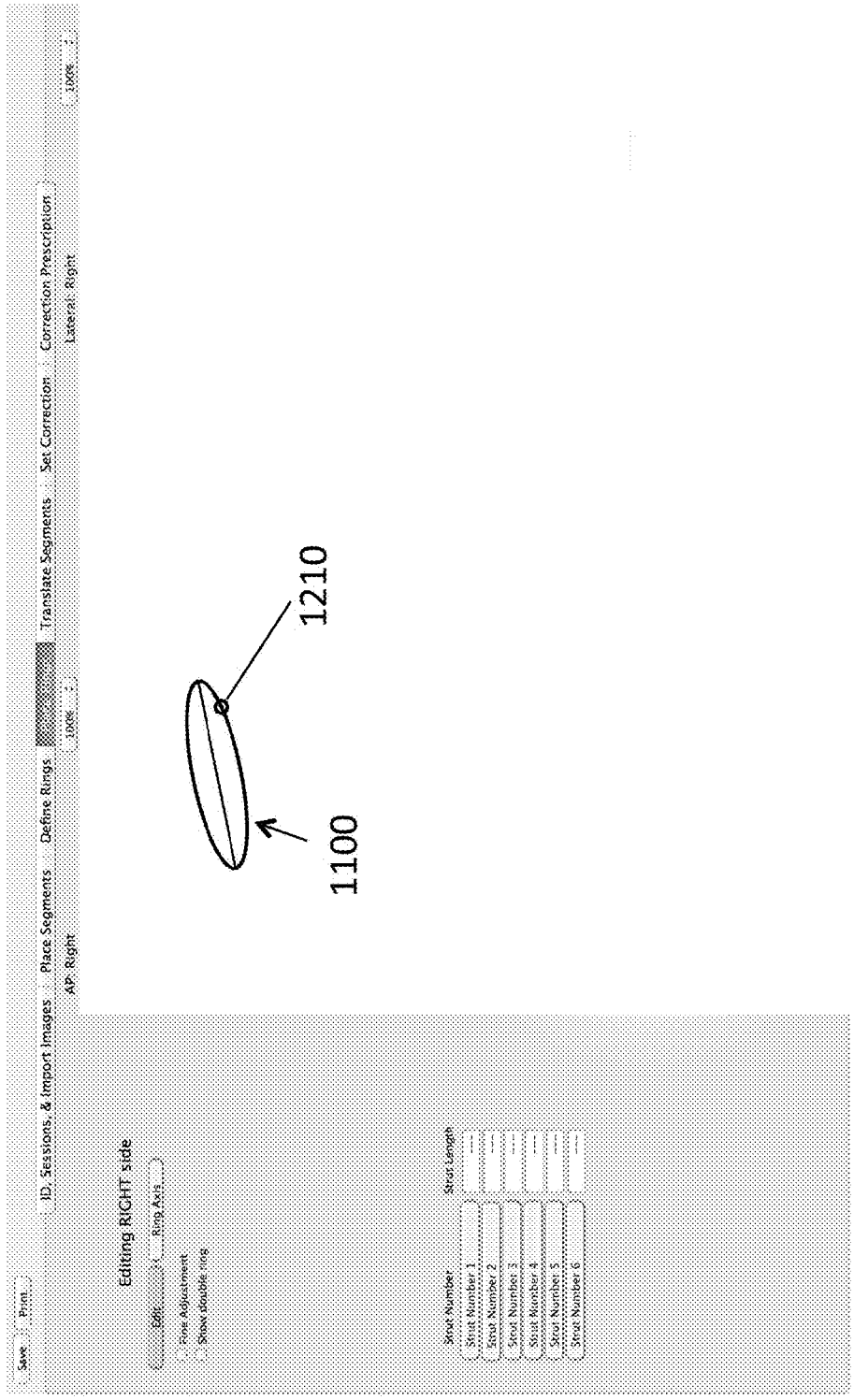

In some embodiments, as shown in FIGS. 49A-B, one type of "axial rotation", for example a rotation of the display of the ring around the "a" axis 1106 is accomplished by changing the length of the "b" axis 1108. In some embodiments, a user drags an adjustment handle 1200 (FIG. 49B) up & down to increase or decrease the "b" axis length (which reflects an axial rotation of the corresponding ring 3D position). FIGS. 51A-B illustrate examples of ring rotations showing rotational reference 1120 in two different locations, but where the ring 1100 looks the same.

Figure 47C:
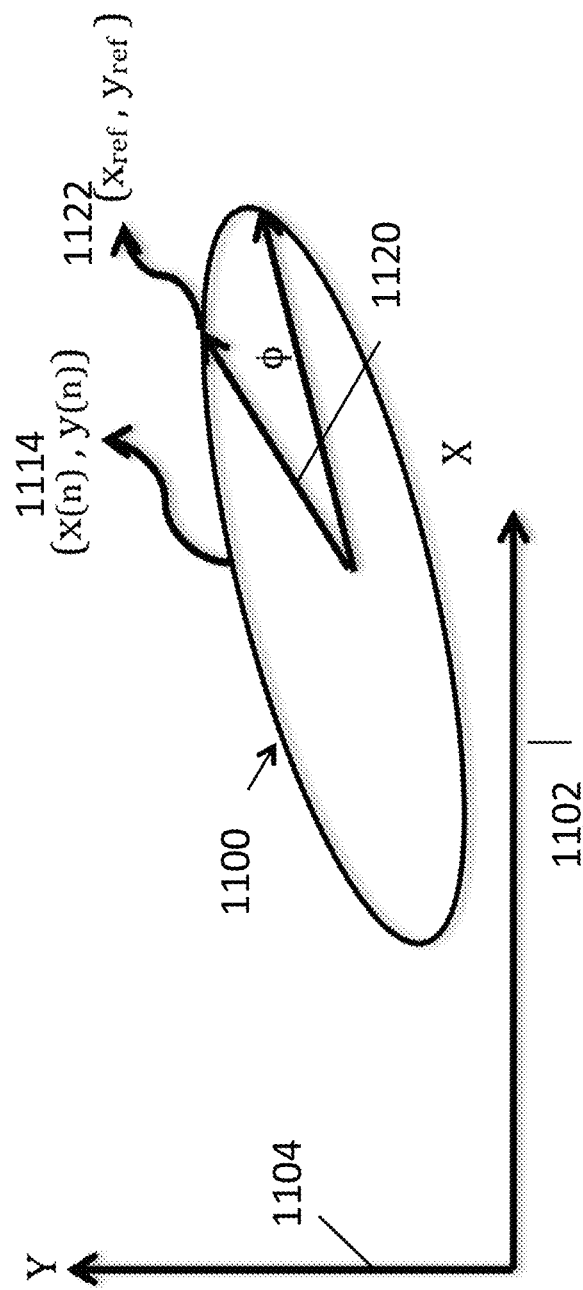
FIG. 47C illustrates an example of a ring's azimuthal rotation, where a fixed point on the ring is defined as an azimuthal rotational reference point, according to some embodiments of the present invention.
Figures 47D, 47E:
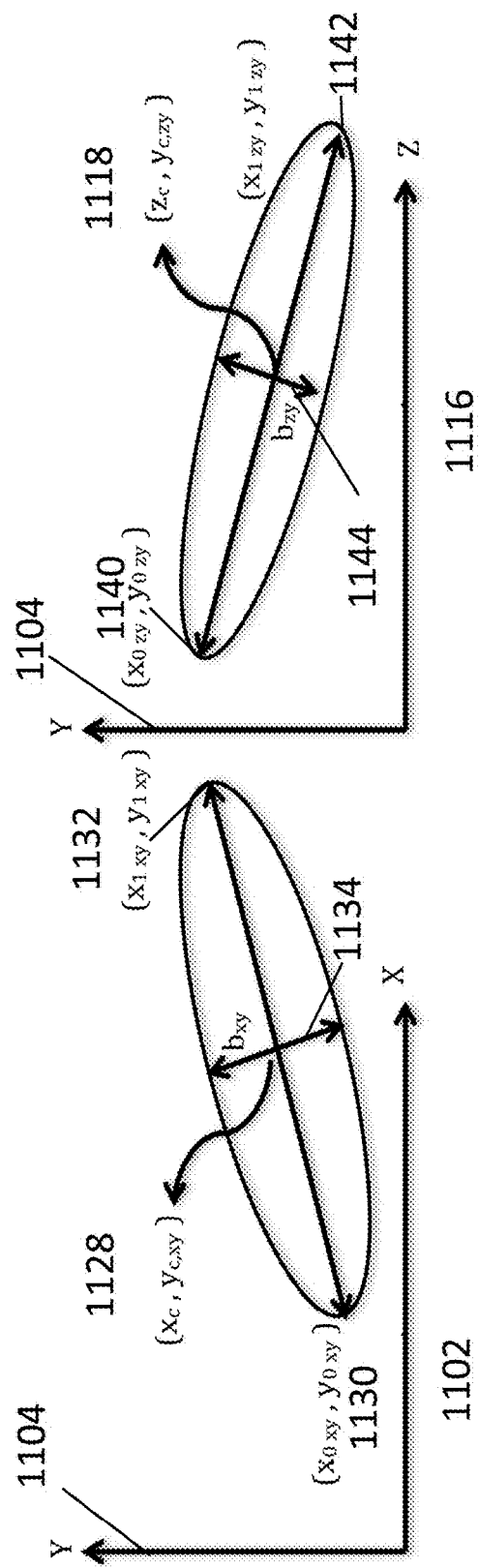
FIGS. 47D-E illustrate two orthogonal planes, XY and ZY, according to some embodiments of the present invention.

"Azimuthal rotation" of a 3D ring is rotation of the ring around an axis through its center point and perpendicular to a plane defined by the ring. As shown in FIG. 47C, to keep track of a ring's azimuthal rotation, a separate angular measure is maintained, the azimuthal ring rotation, or $\phi$, shown at 1120, and a fixed point on the ring is defined as an azimuthal rotational reference point ($x_{ref}$, $y_{ref}$) 1122.

Figure 50A:
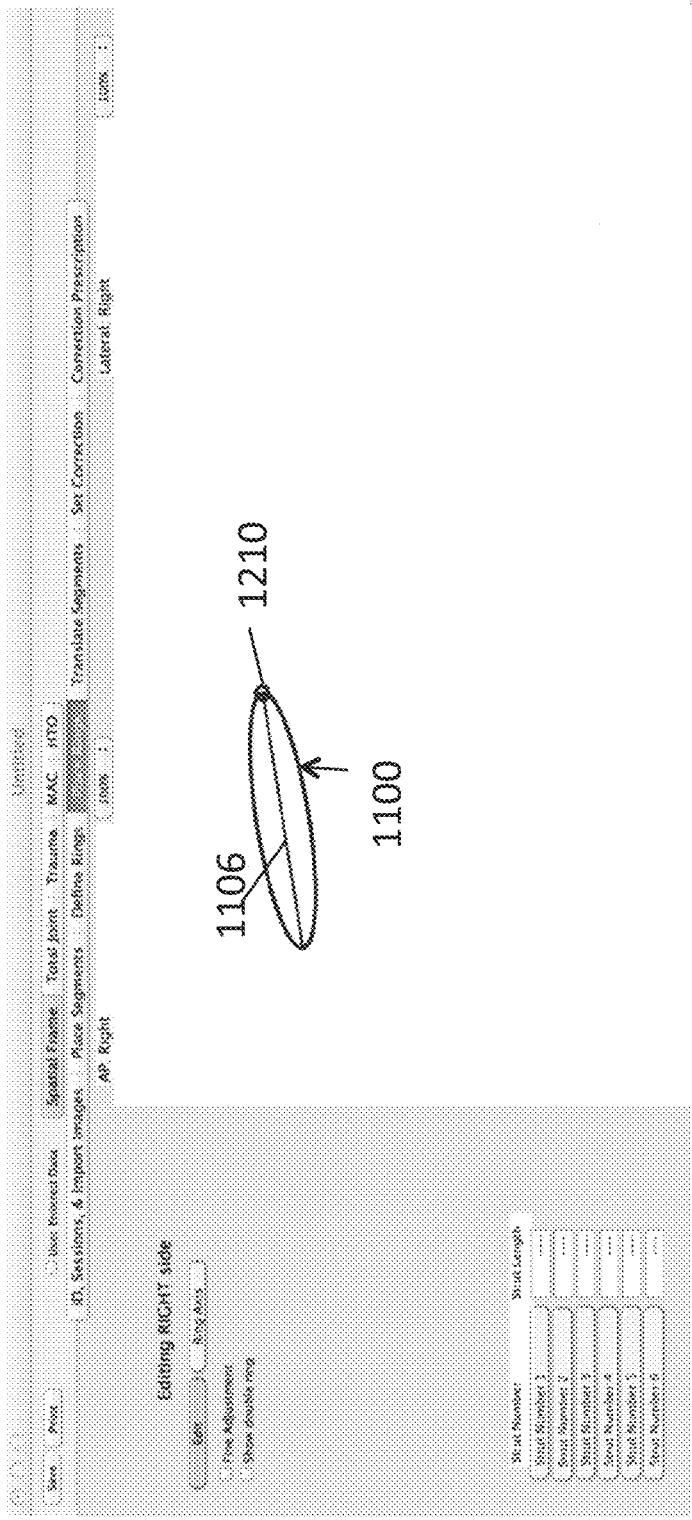
FIGS. 50A-B show that changing φ need not change the appearance of a ring without azimuthal features (i.e. a plain ring), according to some embodiments of the present invention.
Figure 50B:
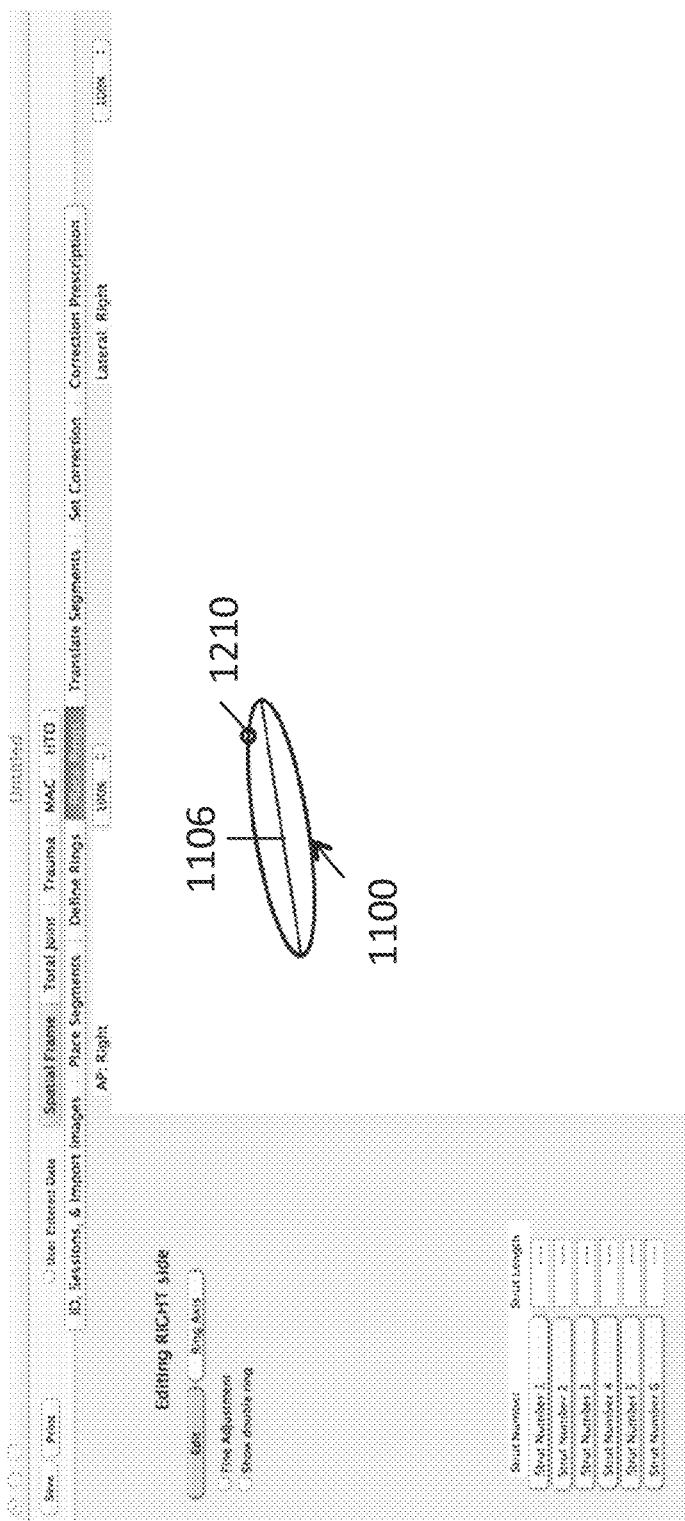

FIGS. 50A-B show that changing $\phi$ need not change the appearance of a ring 1000 without azimuthal features (i.e. a plain ring). However, azimuthal rotation will move a rotational reference point 1210 around the ring. The x and y coordinates of a given point on the ring may be expressed, relative to the reference point, as:

$$x(n)=x_c+a\cdot\cos(n-\varnothing)\cdot\cos \theta - b\cdot\sin(n-\varnothing)\cdot\sin \theta \quad (7)$$

$$y(n)=y_c+a\cdot\cos(n-\varnothing)\cdot\sin \theta + b\cdot\sin(n-\varnothing)\cdot\cos \theta \quad (8)$$

Known points on the ring, such as strut fixation points, can be defined by their azimuthal rotation relative to the rotation reference point. Strut position user input may identify 3D positions for the plurality of struts on the external fixator. For example, to find a point at 0.1 radians along the ring relative to the rotation reference point, the value n=0.1 is entered into the equations above. Once strut position user input has identified the 3D position of each strut of the external fixator has been identified, then the ring rotation user input may control an axial rotation and an azimuthal rotation of a graphical representation of the plurality of struts superimposed on the digital medical image.

In some embodiments the system receives ring rotation user input controlling the axial rotation and the azimuthal rotation of the graphical representation of the ring superimposed on a first digital medical image of the at least two digital medical images according to ring rotation user input entered along a second digital medical image of the at least two digital medical images. In some embodiments, rotation of two rings (top & bottom) is corrected concurrently in either the AP or lateral x-ray view. Such concurrent rotation accounts for errors introduced if the anatomic segments are rotated relative to the true AP and lateral planes when x-rays are taken (ring x-ray rotation). The user may adjust the ring bisector as the ring x-ray rotation is set, as a form of error correction for x-ray beam position.

Figure 25:
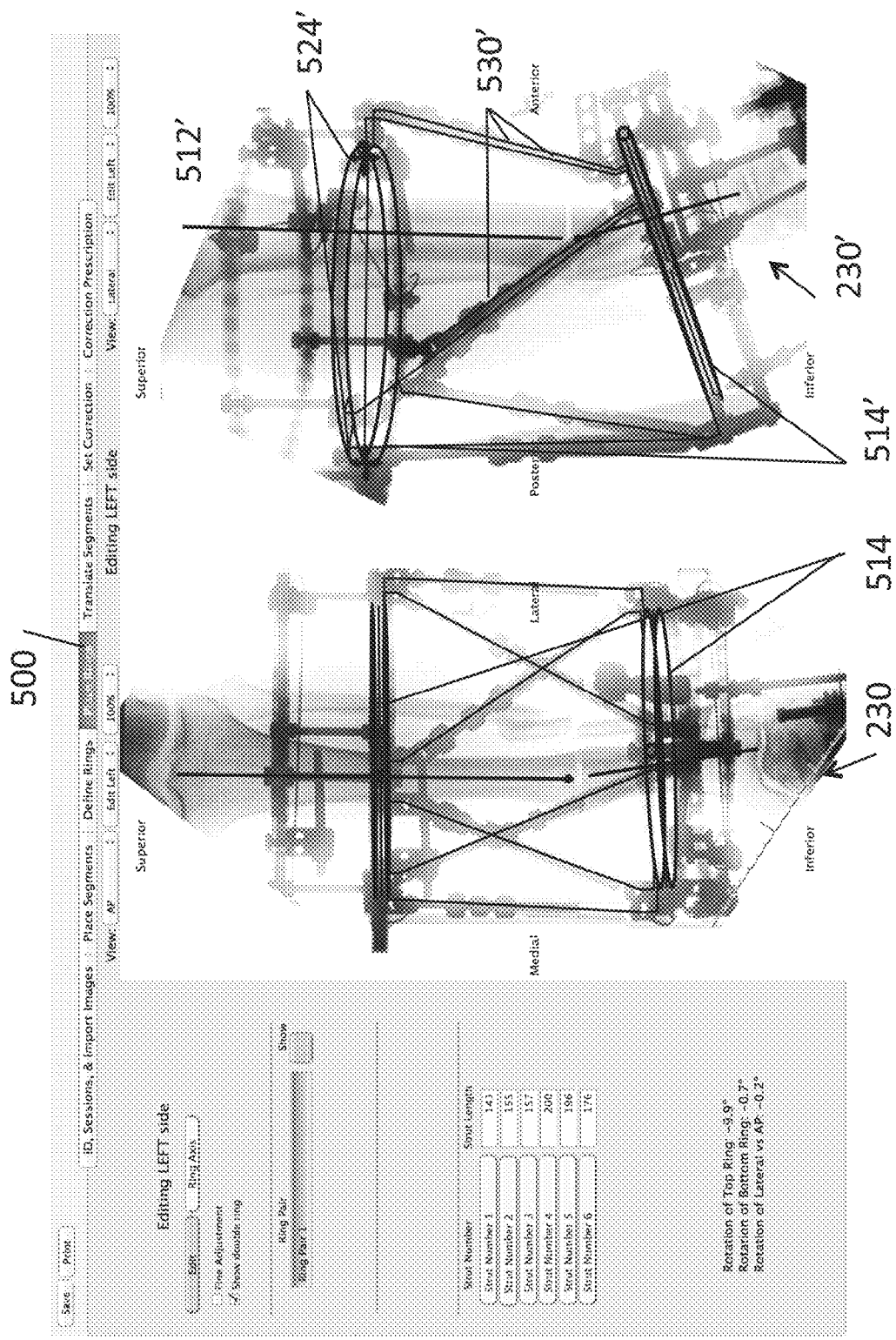
FIG. 25 is a screen shot of the PLACE RINGS tab of a user adjusting the ring rotation of the lateral view relative to the AP view, according to some embodiments of the present invention.

FIG. 25 is a screen shot of a PLACE RINGS tab 500 illustrating a user's adjusting the ring rotation of a lateral view 230' relative to an AP view 230. The rotation can be understood by comparing the strut positions 530' in the lateral view 230'. Both the top and bottom rings 514' of the lateral image change as the ring rotation is manipulated. The ring can be rotated by a user by manipulating handles 524' on the ring bisector 512', on the ring itself 514', or by separate controls.

Figure 55:
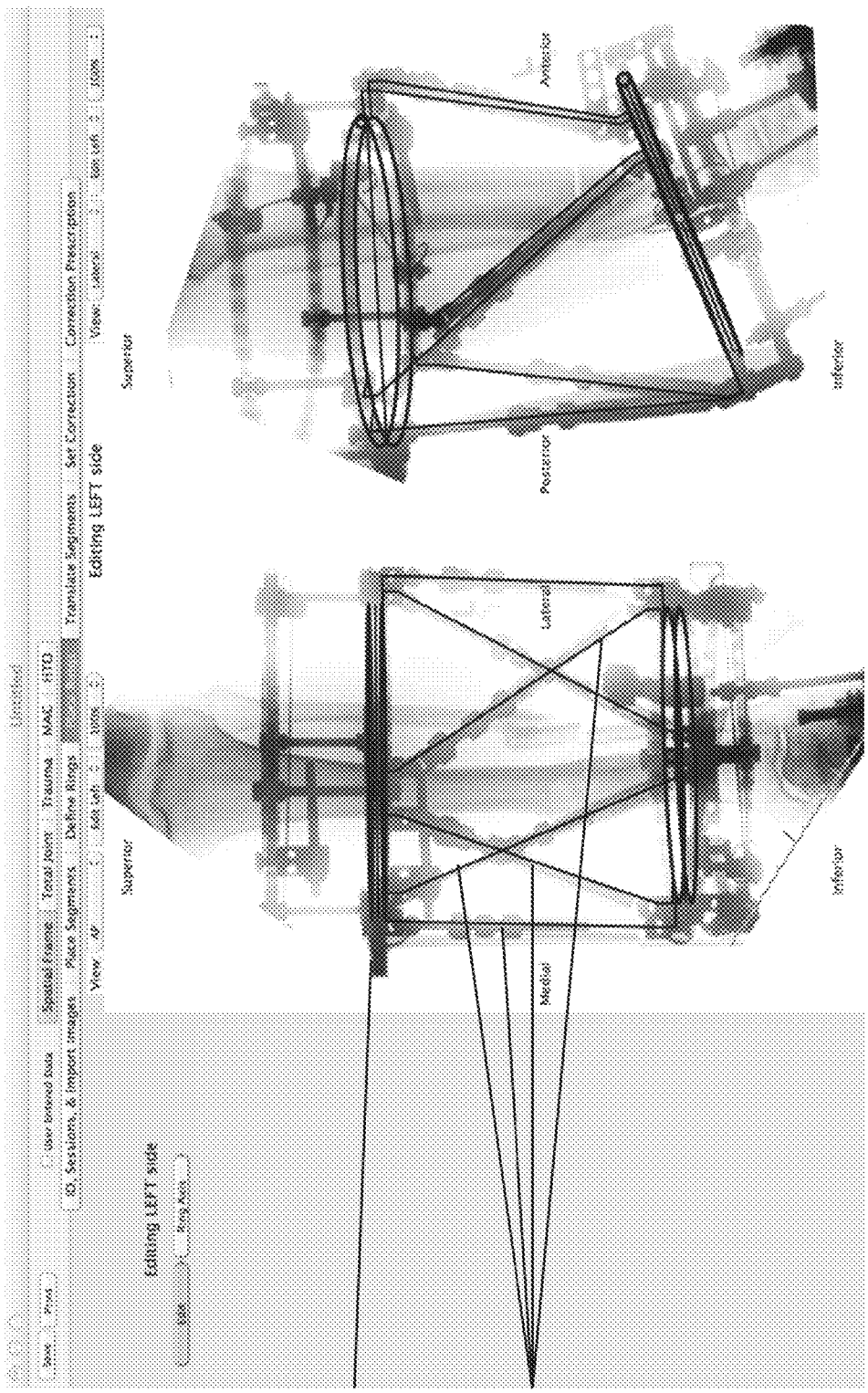
FIGS. 55-56 show screen shots illustrating an exaggerated rotation of the top ring, according to some embodiments of the present invention.
Figure 56:
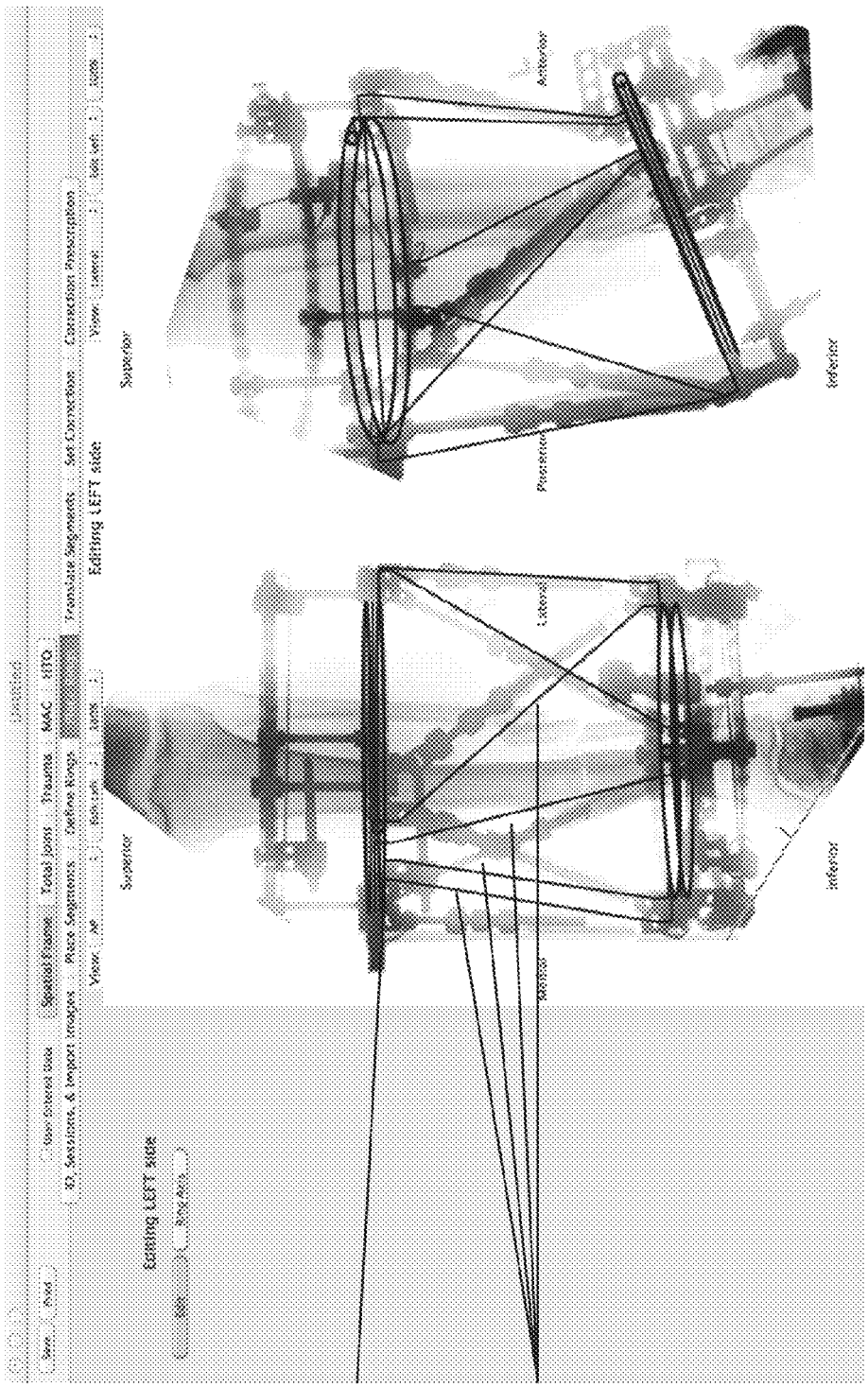

In some embodiments, changing the azimuthal rotation of a ring in one plane can be used to set azimuthal rotation of a ring in another plane. For example, when rotating a ring in the XY plane, a similar rotation can be made on the corresponding ring in the ZY plane. This has the effect of rotating the "true" ring relative to the anatomic structure in both the XY and ZY planes. FIGS. 55-56 show screen shots illustrating an exaggerated rotation of the top ring 514. Notice the change in position of the struts 530.

Changing the azimuthal rotation of a ring in one plane can also be used to set the azimuthal rotation of another ring in the same plane. Such coupled rotations can serve two purposes. First, coupled rotation can allow the "linking" of two rings. In practice, two or more separate pairs of rings and struts can be applied to anatomic structures on the same body part, and the bottom ring of one ring pair can be physically attached to the top ring of another ring pair. These "linked" rings can be rotated together such that when the azimuthal rotation of one ring is changed, the azimuthal rotation of the "linked" ring is also changed.

Figure 57:
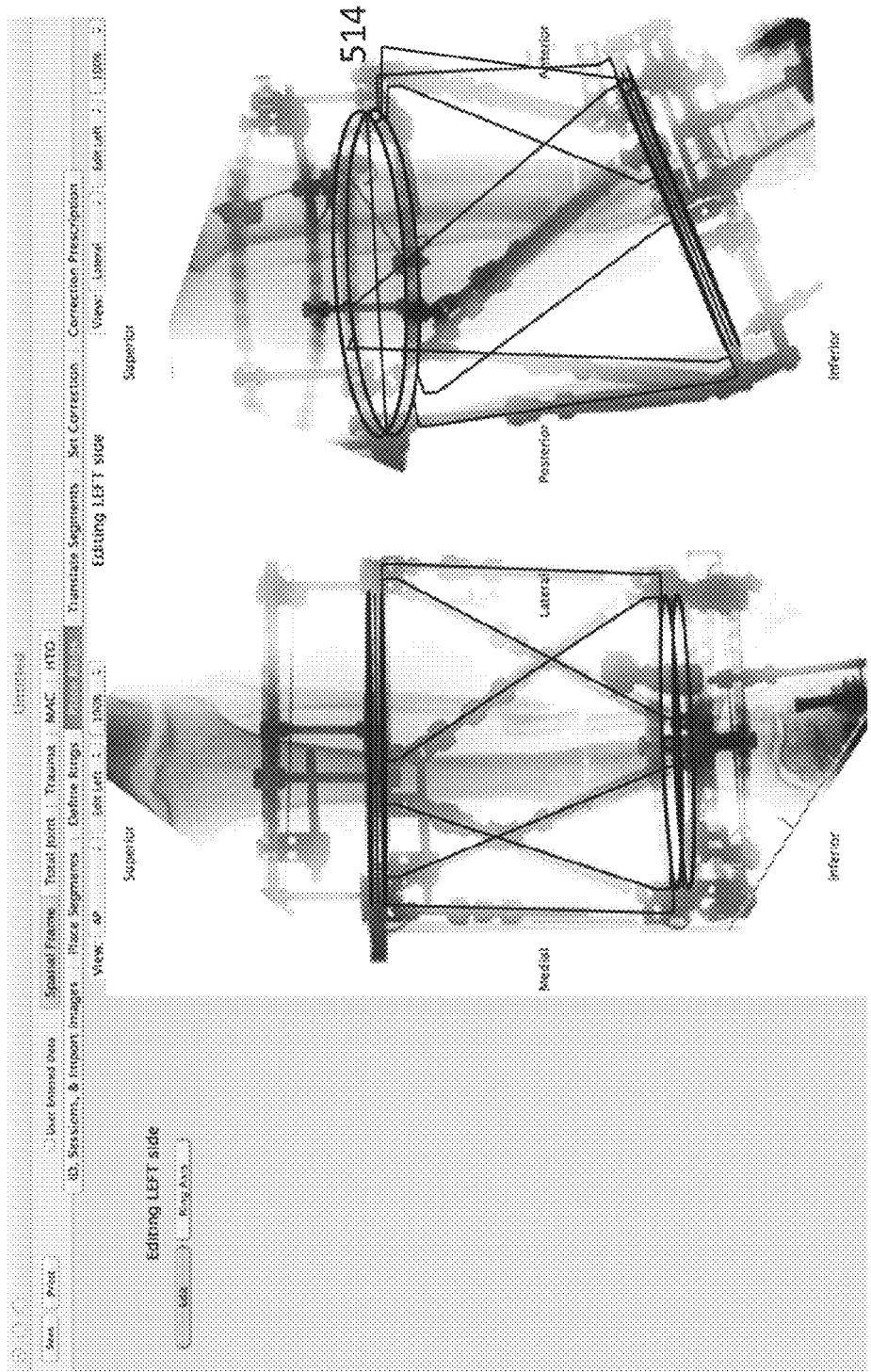
FIG. 57 shows a screen shot illustrating an example of a rotation of both rings on the lateral image, according to some embodiments of the present invention.

Second, the azimuthal rotation of a ring in one plane setting the azimuthal rotation of another ring in the same plane can be used to adjust for error introduced by the plane not being orthogonal to a reference plane when radiographs are taken. When initially set, the azimuthal rotation of the second plane is set 90° to the first assuming that the two planes are orthogonal. By rotating both rings of a ring pair in the second plane, the user sets the azimuthal rotation of both rings as if the azimuthal rotation the second plane was not taken orthogonal to the first plane. FIG. 57 shows a screen shot illustrating an example of a rotation of both rings 514' on the lateral image 230', as compared to FIG. 56.

After desired ring parameters are defined by the user (e.g. ring bisector, view ring spread, ring mounting rotation, ring x-ray rotation), in some embodiments a number of calculations are made to minimize error in the ring definition process.

In some embodiments, a first calculation generates an averaged ring. If a ring is a circle in 3D, the bisector (a measure of the circle's diameter) should be the same on AP and lateral views. To minimize variation in the user entered ring parameters, the ring "a" axis lengths may be averaged between AP and lateral views.

A second calculation generates an expected ring spread. The expected ring spread is the ring spread that would occur if the x-ray beam were "ideal", that is if it were an infinite number of parallel beams rather than a point based beam source. The expected ring spread may be calculated from the ring bisector of the opposite radiographic image.

A third calculation generates a corrected, rotated ring. Such a ring rotation corrects the ring parameters and segment position for variation in ring x-ray rotation from true orthogonal planes. The ring bisector and expected ring spread may be recalculated for the already averaged ring parameters. The segment angulation may also be corrected since the true deformity size will be different if the x-ray image planes are not orthogonal.

A fourth calculation sets the ring in the AP and lateral views. In some embodiments, the ring may be represented as a single ellipse based on the ring view parameters above, or a double ellipse using the additional knowledge of ring thickness set when the user chooses a ring during ring definition.

A fifth calculation defines a number of strut points. The system receives strut position user input identifying 3D positions for the plurality of struts of the external fixator on the at least one digital medical image. Once strut position user input has identified the 3D position of each strut of the external fixator, then the ring rotation user input may control an axial rotation and an azimuthal rotation of a graphical representation of the plurality of struts superimposed on the digital medical image. Strut positions relative to the ring position may have been defined prior to controlling the ring rotations. Once the true 3D ring position in space has been calculated, strut end points in space may be calculated from the known strut angle on the ring, strut radius, and strut drop distance. The ring plane (the 3D plane in which the ring lies) is calculated, and may be represented as a bisector to the ring plane and the position of the master point on the plane. The strut positions in space are calculated in the ring plane using the strut angle and strut radius by a simple polar coordinate calculation. The drop strut position is calculated by moving the ring plane up or down along the plane bisector. The strut positions in the AP and lateral views as well as positions that describe the "look" of an actual strut (strut view points) are also calculated in a similar fashion.

A sixth calculation generates a strut distance in pixels for each strut, which may be simply a three dimensional distance between points.

A seventh calculation generates a pixel scale factor (mm/pixel), which converts a distance in scaled pixels to a distance in millimeters. A pixel scale factor can be calculated from the known ring diameter (mm)÷averaged ring bisector "a" length (pixels), the average of the true strut lengths (mm)÷strut distance in pixels (pixels), or from a known size marker on the original radiograph. The true strut lengths may be entered by the user as read from the actual hardware.

An eighth calculation generates a strut scale factor (unitless) for each individual strut. This is the true strut length (mm)÷(strut distance in pixels (pixels)*pixel scale factor) for each individual strut. The strut scale factor can be used in a final correction for each strut, to correct for any remaining error involved with the definition of ring positions or x-ray beam position. For example, this type of error may occur if the x-ray beam is not orthogonal to the reference segment. The strut scale factor ensures that the initial strut lengths calculated in the correction tab will match the initial true strut lengths.

In some embodiments, the user can template a ring pair by placing a theoretical ring pair on an image. Strut change minimization calculations can be made to show the user the ideal ring placement to minimize the number of strut changes (strut replacements) that are needed during a correction.

In some embodiments, special hardware is used to facilitate proper identification of ring positioning using digital imaging. A wide variety of shapes may be used with the common purpose of marking a spot on the external fixator ring that is easily identifiable on both the AP and lateral images. Such marking facilitates setting of proper view ring spread, ring mounting rotation, and ring x-ray rotation.

In some embodiments, having received axial and azimuthal rotation user input, the system calculates a 3D-position of each ring of the external fixator relative to the anatomic structure on each of the at least two digital medical images according to the ring rotation user input. The first step in determining a 3D ring's position based on the ring's projection in two planes is to rotate the (graphics in the) two planes so their Y-axes are parallel. During the act of shooting a radiograph, a rotational artifact can be introduced when changing between imaging planes. To correct for this artifact, the images may be rotated based on the user's definition of a reference bone segment on the image in each plane.

An actual ring in 3D is represented as corresponding ellipses in 2-D planes. FIGS. 49D-E illustrate two orthogonal planes, XY and ZY. In practice these planes do not have to be perfectly orthogonal. These two planes share a common Y-axis 1104. FIG. 49D shows the YX plane, with X-axis 1102, ellipse center ($x_c$, $y_{c,xy}$) 1128, ellipse endpoints ($x_{0,xy}$, $y_{0,xy}$) 1130 and ($x_{1,xy}$, $y_{1,xy}$) 1132, and short axis $b_{xy}$ 1134. FIG. 49E shows the ZY plane with Z-axis 1116, ellipse center ($z_c$, $y_{c,zy}$) 1118, ellipse endpoints on the long axis ($z_{0,zy}$, $y_{0,zy}$) 1140 and ($z_{1,zy}$, $y_{1,zy}$) 1142, and short axis $b_{zy}$ 1144.

Figures 47F, 47G:
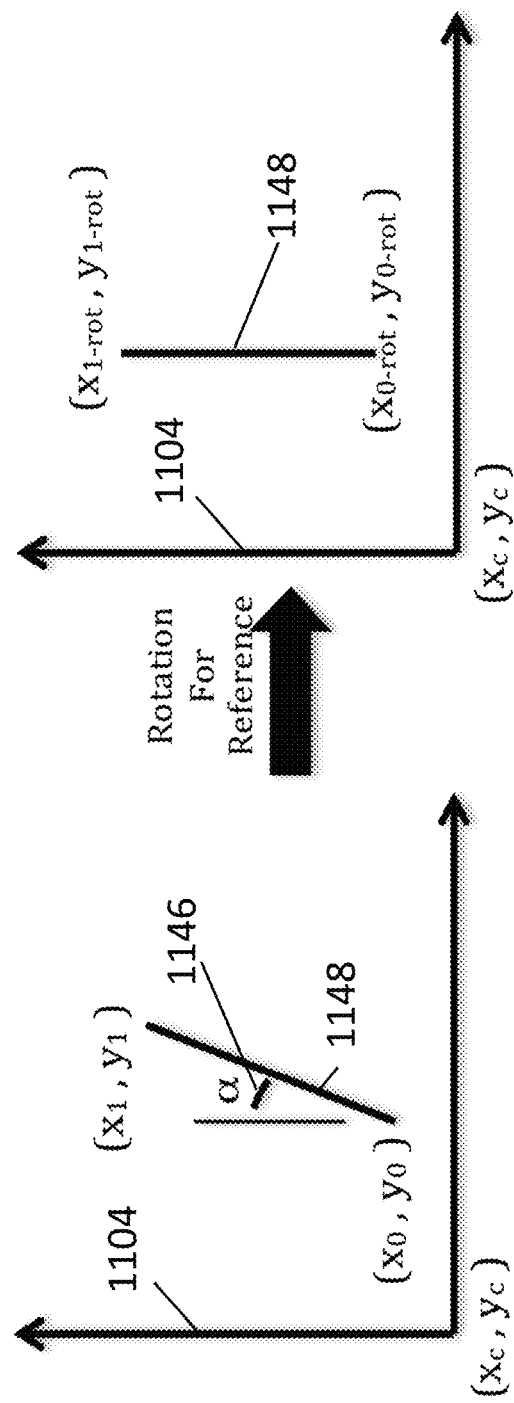
FIGS. 47F-G illustrate the rotation of a segment, to bring it parallel to the Y-axis, according to some embodiments of the present invention.
Figure 52:
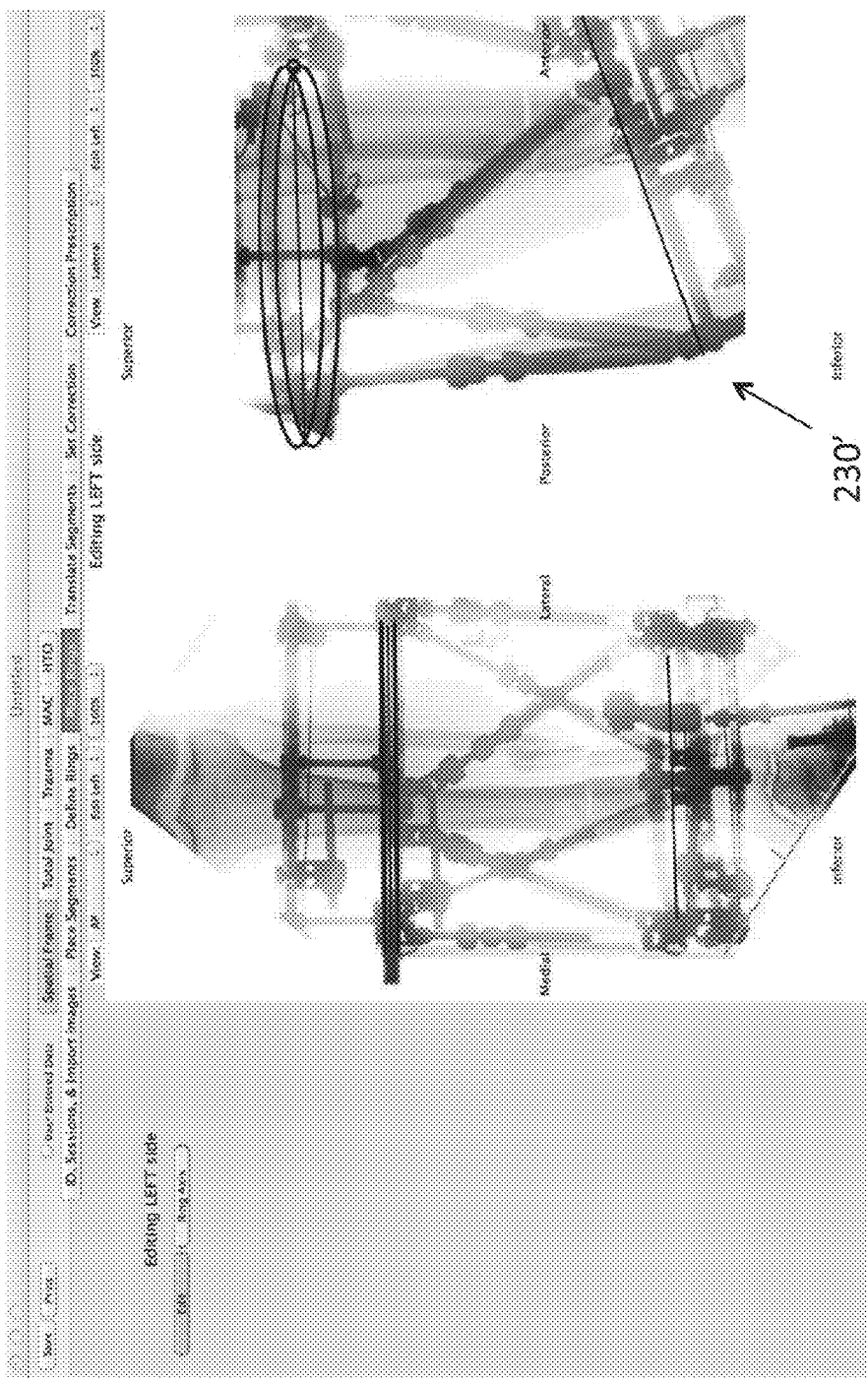
FIG. 52 illustrates an image rotated for reference, according to some embodiments of the present invention.

At the time of shooting the radiograph, the reference bone segment is the segment perpendicular to the x-ray beams. Since the reference bone segments represent the same straight line in each plane, rotating each image so the reference bone segment is parallel to the Y-axis, and parallel to each other, removes any artifact introduced by rotation of the radiograph. FIG. 52 illustrates an image rotated for reference. FIGS. 47F-G illustrate the rotation of a segment 1148, to bring it parallel to the Y-axis 1104.

Figure 53:
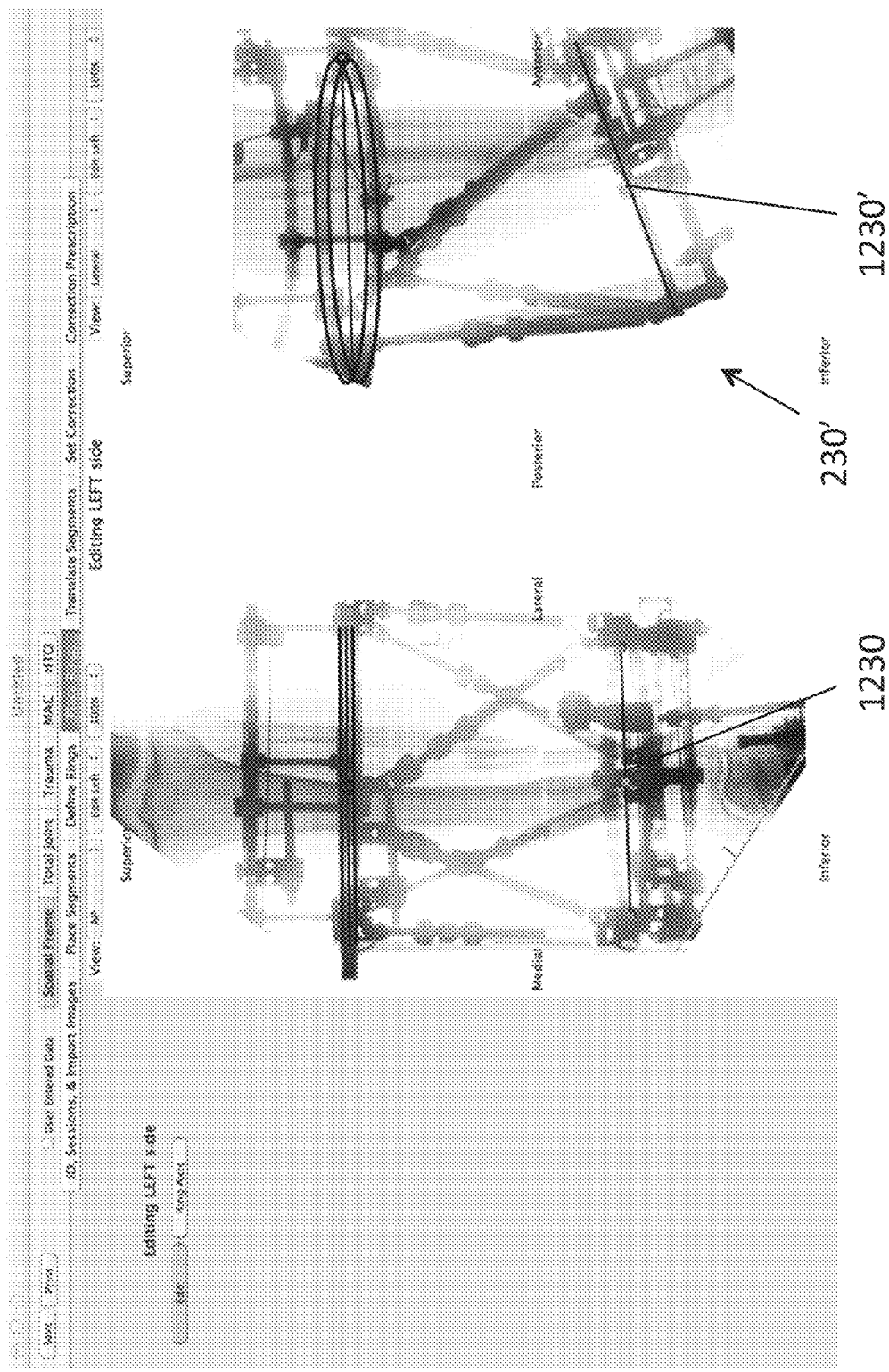
FIG. 53 shows a screen shot where the Y-axis values of the two center points are equal according to some embodiments of the present invention.

In some embodiments, the AP and lateral images are scaled relative to each other and translated along the Y-axis to match corresponding anatomic structures. During the act of shooting a radiograph, a scaling artifact can be introduced based on the distance from the x-ray source to the anatomic segment, and the distance from the anatomic segment to the x-ray cassette (or digital collector). To correct for this artifact, each subsequent image is scaled relative to the first. FIGS. 52-53 show screen shot of a lateral image 230' that has been scaled, as shown in FIG. 53. A scaling factor can be determined from the imaged size of objects of known real size (e.g. length). A number of structures of known size present on each image may be used to generate a scaling factor, including: the length of a single ring's "a" axis, the distance between the center points of two rings' "a" axes, the distance between the center points of two joint-lines; or the length of a sizing marker of known length present on the images.

Matching each image's Y axis set point ($y_{set}$) may be achieved by identifying a point on each image that represents the same structure A number of identifiable structures present on each image can be used for y-axis set point matching, including the center point of a single ring's "a" axis and the center point of a joint-line.

A scale factor (sf) for image i relative to image 0 based on a known fixed distance (d) may be defined as:

$$sf_i = \frac{d_0}{d_i} \tag{9}$$

and a point (xp, yp) in image i is scaled to match scaling and Y-axis translation (matching fixed point (x0, y0) to a given $y_{set}$) as:

$$x_{n\text{-}scaled} = x_{0\text{-}rotated} + (x_{n\text{-}rotated} - x_{0\text{-}rotated}) \cdot sf_i \tag{10}$$

$$y_{n\text{-}scaled} = y_{0\text{-}rotated} + (y_{n\text{-}rotated} - y_{0\text{-}rotated}) \cdot sf_i + (y_{set} - y_{0\text{-}rotated}) \tag{11}$$

Once scaling is complete, a conversion factor can be determined between a distance in the image and an actual distance based on a number of methods, including: the length of a single ring's "a" axis and the known diameter of the ring it represents, the length in three dimensions of a strut and the known length of the strut it represents; and/or the length of a sizing marker of known length present on the images.

Scaling and rotating for reference can also be applied in reverse for display purposes. That is, many of the calculations described below occur in the rotated for reference and scaled XYZ space, while we may want to display the un-scaled and un-rotated values on the screen. The above formulas can be applied in reverse to calculate screen data from rotated for reference and scaled data.

Once the images are rotated for the reference segment and scaled, further corrections can help convert the two 2D ellipse representations of a ring into a 3D representation. First, as described above, the XY ad ZY plane's elliptical representation of the ring's center point y values are equal: yc,xy=yc,zy. This can be done because the real life ring's center point in the XYZ space will match the center point in both the XY (xc, yc, xy) and ZY (zc, yc, zy) planes. So the center point of the ring can be represented by the three dimensional point (xc, yc, zc). As shown in FIG. 53, the Y-axis values of center points 1230, 1230' are equal.

The next adjustment corrects for parallax artifact introduced when point source x-ray beams are used. To understand this artifact, consider the difference in radiographs of a ring taken with the x-ray beam directed perfectly parallel to the ring versus a beam translated away from the parallel position. The first radiograph will display the ring as a line, while the second will display the ring as an ellipse. They are the same ring in space, but they appear differently on the radiograph depending on where the point-source x-ray beam is positioned.

Figure 54A:
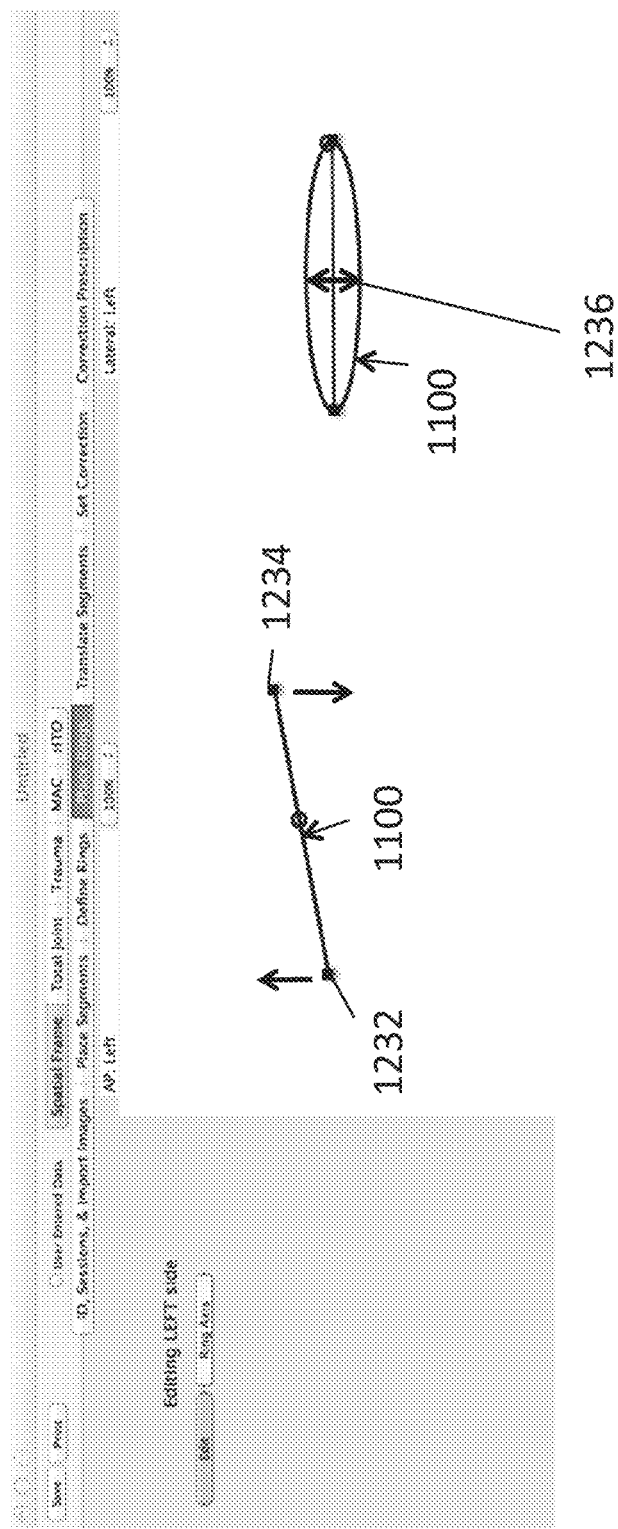
FIGS. 54A-B illustrate a correction of the parallax effect in the lateral view of an ellipse, according to some embodiments of the present invention.
Figure 54B:
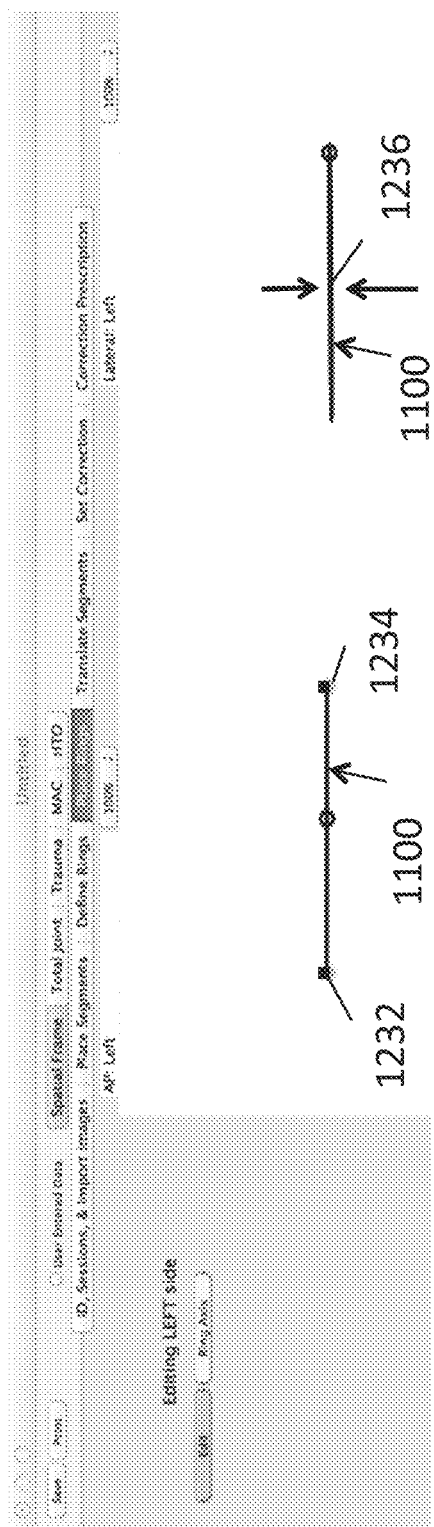

The information in the (near) orthogonal planes is used to correct for this parallax effect. Ideal "b" axes in the XY and ZY planes are based on the Y axis height of the "a" axis in the ZY and XY planes respectively: bxy–ideal=abs(y1zy–y0zy)/2; bzy–ideal=abs(y1xy–y0xy)/2. FIGS. 54A-B illustrate a correction of the parallax effect in the lateral view of an ellipse. As the user adjusts the "a" axis endpoints 1232, 1234, the corresponding "b" axis 1236 in the opposite plane is adjusted. The user can further adjust the "b" axis length, as described above when discussion axial ring rotation, to help match the graphical ellipse representation of a ring to the ring on the radiograph. However, when calculating the true position of the ring in 3D space, the user added "b" axis adjustments are discarded and the "ideal" b axis length is used.

Finally, a 3D representation of the ring can be defined as the center point (xc, yc, zc), in a plane defined by the "a" axes in the XY and ZY planes, with diameter a-averaged= $(a_{xy\text{-}scaled}+a_{zy\text{-}scaled})/2$.

Conversion between the 3D XYZ space and the orthogonal image planes can be made using the center point of the ring as P1, the end-point of the "a" axis in the XY plane as P2, and the end-point of the "a" axis in the ZY plane as P3, following the techniques defined below. A ring's plane can also be represented as a 3D vector ($V_{orthogonal}$) perpendicular to the ring originating from the ring's center point. This can be calculated based on the cross product of two 3D vectors, one from the center point to one end of the "a" axis in the XY plane, and one from the center point to one end of the "a" axis in the ZY plane.

$$\vec{V}_{xy}=(x_c,y_c,z_c)\rightarrow(x_{1xy},y_{1xy},z_c) \quad (12)$$

$$\vec{V}_{zy}=(x_c,y_c,z_c)\rightarrow(x_c,y_{1zy},z_{1zy}) \quad (13)$$

$$\vec{V}_{orthogonal}=\vec{V}_{xy}\times\vec{V}_{zy}(\text{vector cross-product}) \quad (14)$$

In the more general sense, a plane is defined as based on three 3D points $$P1=(x1,y1,z1), P2=(x2,y2,z2); \text{ and } P3=(x3,y3,z3) \quad (15)$$

Some intermediate values are also defined, including:

$$d12=\text{sqrt}((x2-x1)^2+(y2-y1)^2+(z2-z1)^2) \quad (16)$$

$$d23=\text{sqrt}((x3-x2)^2+(y3-y2)^2+(z3-z2)^2) \quad (17)$$

$$d13=\text{sqrt}((x3-x1)^2+(y3-y1)^2+(z3-z1)^2) \quad (18)$$

$$\text{temp1}=(d13*d13+d12*d12-d23*d23)/(2*d12) \quad (19)$$

$$\text{temp2}=\text{sqrt}(d13*d13-a*a) \quad (20)$$

Point P1 is mapped to the origin of the 2D plane (P1→ (0,0)); Point P2 is mapped to a distance d12 along the 2D plane's X axis (P2→(0,d12)); Point P3 is mapped to an intermediate point based on the calculations above (P3→ (temp1, temp2));

Nine plane definition parameters are defined based on the above formulas so that we can calculate a 3D point P0=(x0, y0, z0) based on a 2D point in the defined plane (i,j) such that:

$$x0=c1*i+c2*j+c3; y0=c4*i+c5*j+c6; z0=c7*i+c8*j+c9 \quad (21)$$

$$c1=(x2-x1)/d12 \quad (22)$$

$$c2=(x3-c1*\text{temp1}-c3)/\text{temp2} \quad (23)$$

$$c3=x1 \quad (24)$$

$$c4=(y2-y1)/d12 \quad (25)$$

$$c5=(y3-c4*\text{temp1}-c6)/\text{temp2} \quad (26)$$

$$c6=y1 \quad (27)$$

$$c7=(z2-z1)/d12 \quad (28)$$

$$c8=(z3-c7*\text{temp1}-c9)/\text{temp2} \quad (29)$$

$$c9=z1 \quad (30)$$

A plane can also be defined based a 3D vector ($V_{orthogonal}$) to the 2D plane, and a separate point (P2=(x2,y2,z2)) in 3D space that lies in the 2D plane. The origin of the 2D plane P1=(x1,y1,z1) is defined as the closest point of P2 on $V_{orthogonal}$. A 3D vector ($V_{1-2}$) is defined from P2 to P1. We define a 3D vector ($V_{1-3}$) parallel to the cross-product of $V_{orthogonal}$ and $V_{1-2}$, starting at P1 with length of ½ the length of $V_{1-2}$. P3=(x3,y3,z3) is defined as the endpoint of $V_{1-3}$. The plane based on points P1, P2, P3 is defined as above.

Figure 26:
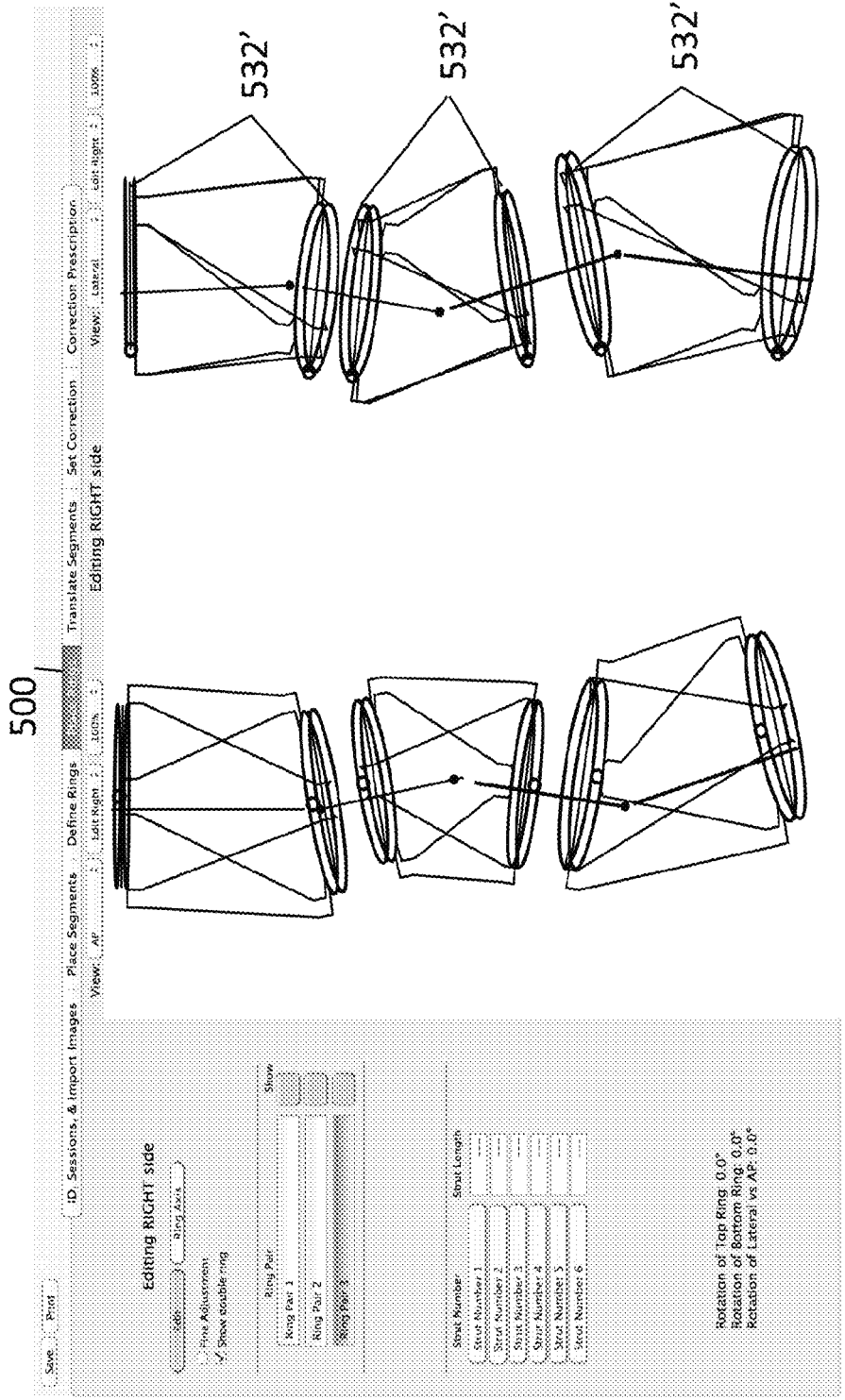
FIG. 26 is a screen shot of the PLACE RINGS tab showing rotations involving multiple ring pairs, according to some embodiments of the present invention.
Figure 27A:
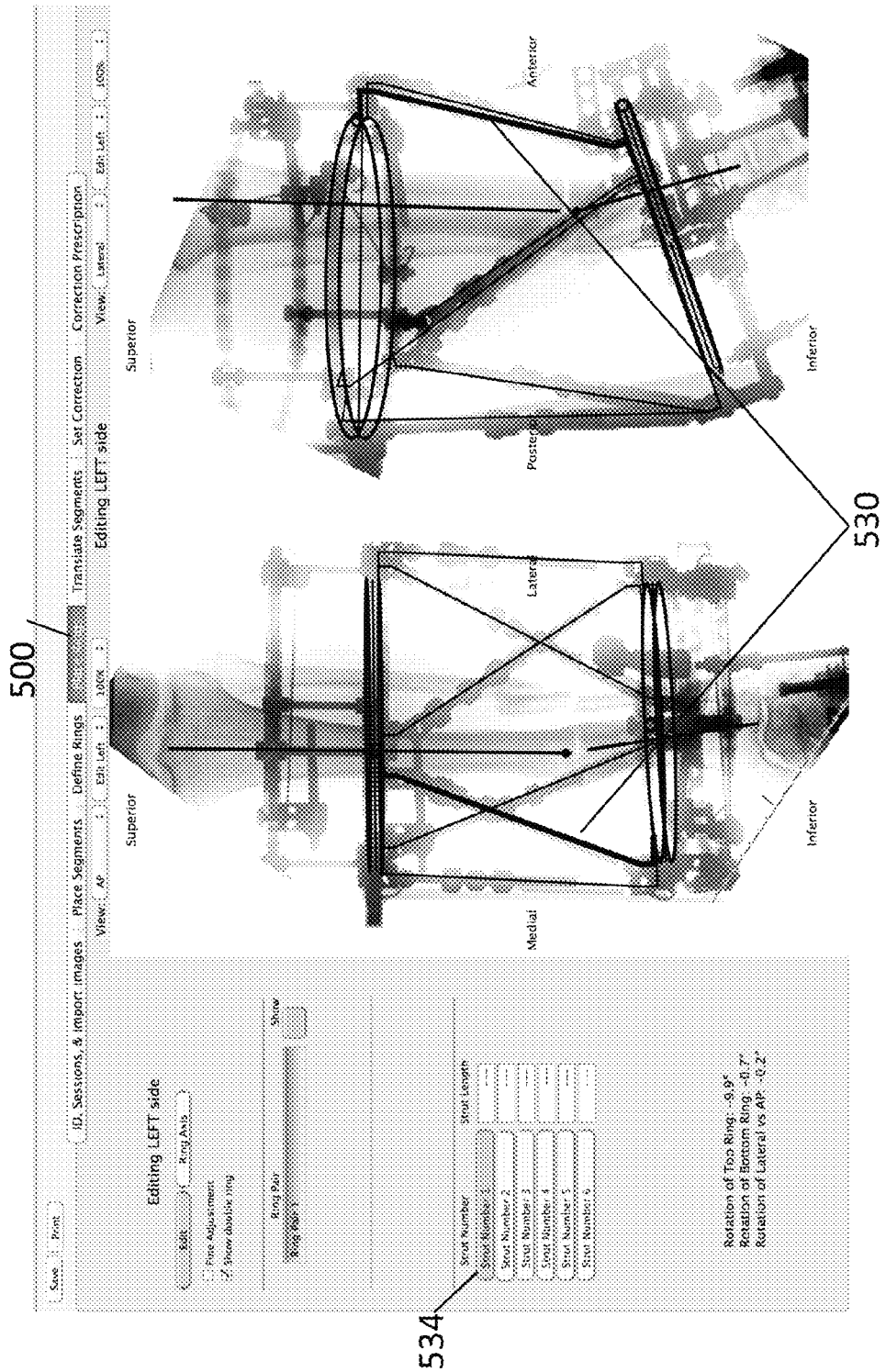
FIGS. 27A-27F show screen shots of a user highlighting each strut by number to assist with ring identification, according to some embodiments of the present invention.
Figure 27:
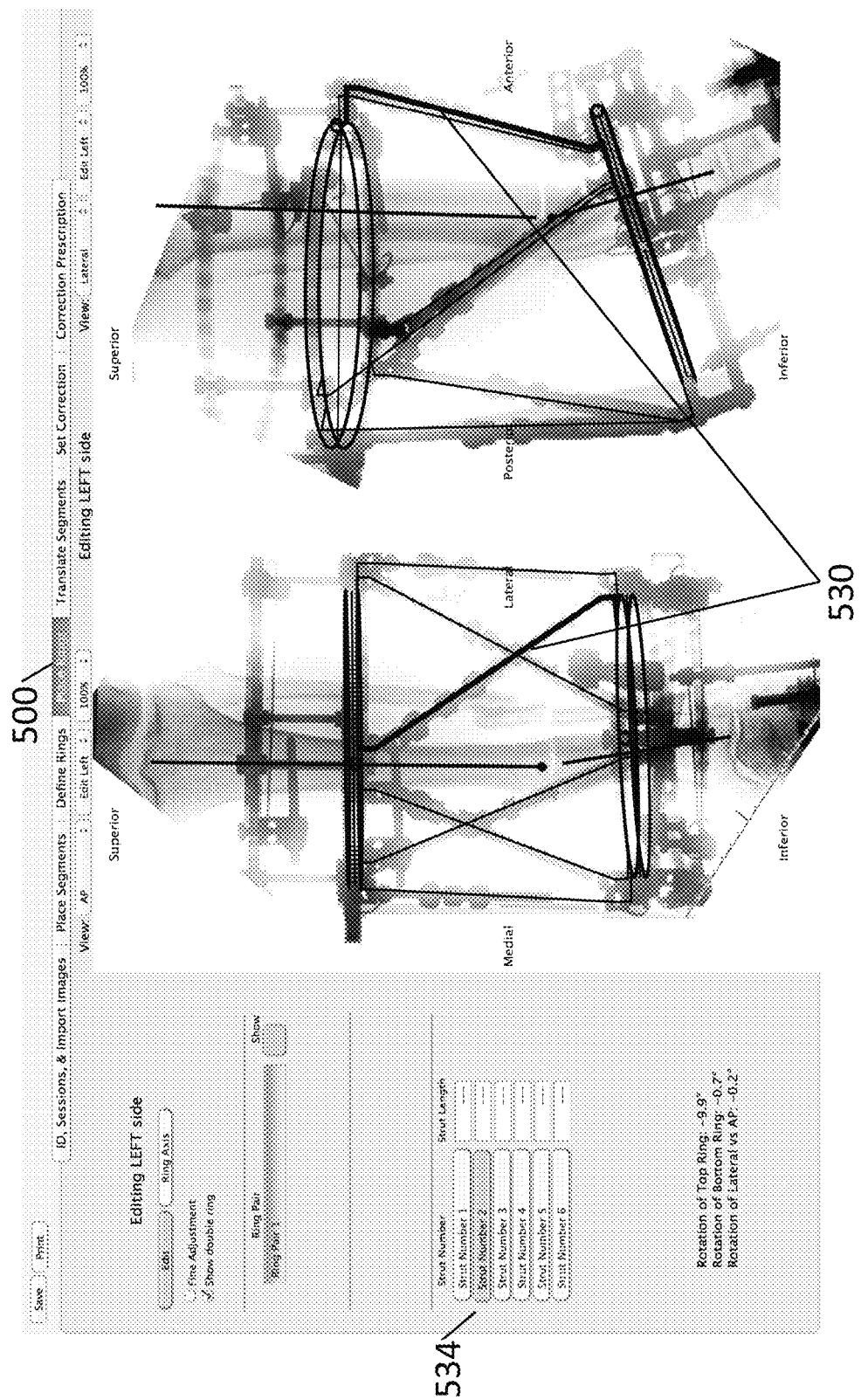
Figure 27:
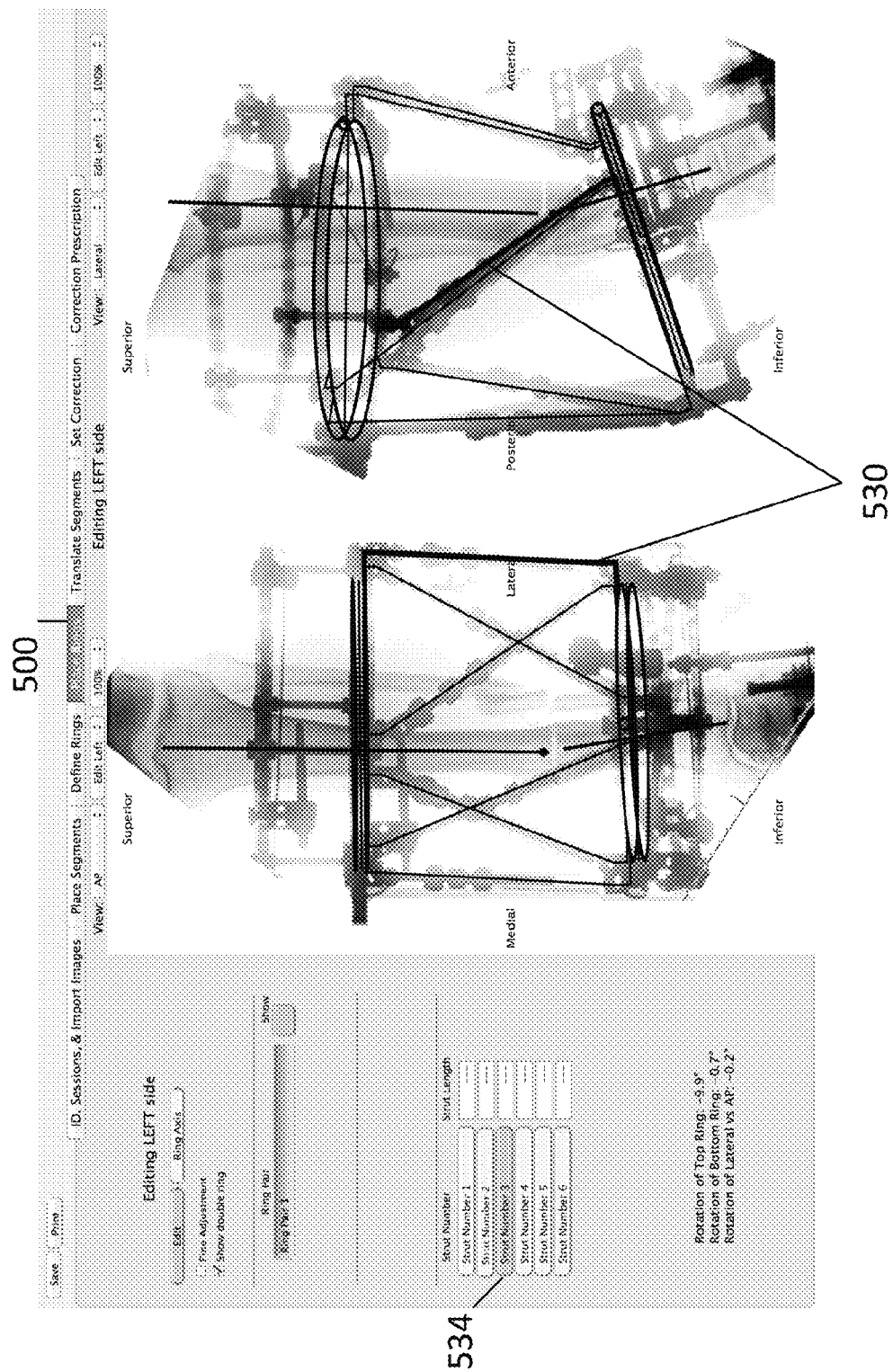
Figure 27:
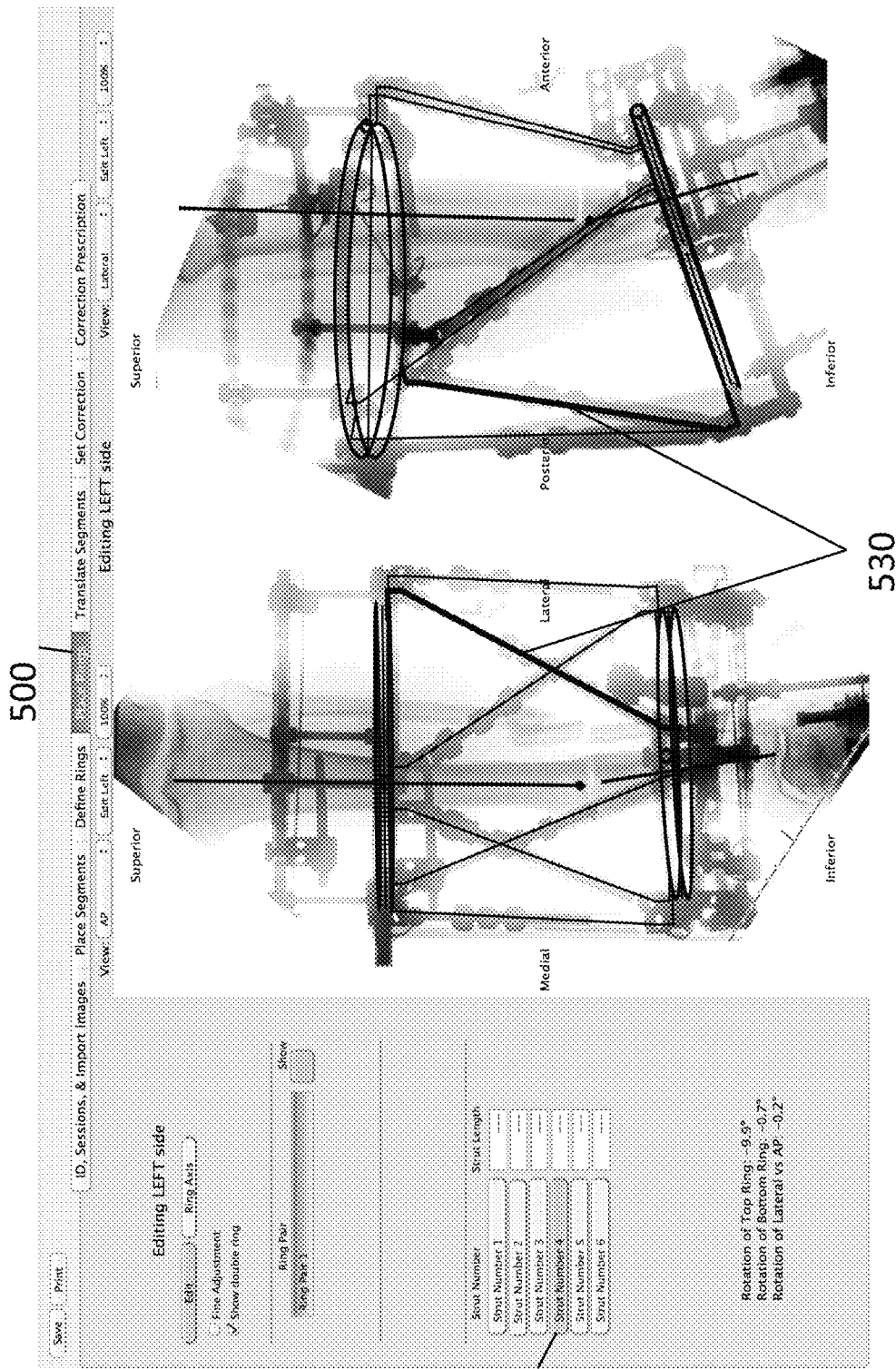
Figure 27:
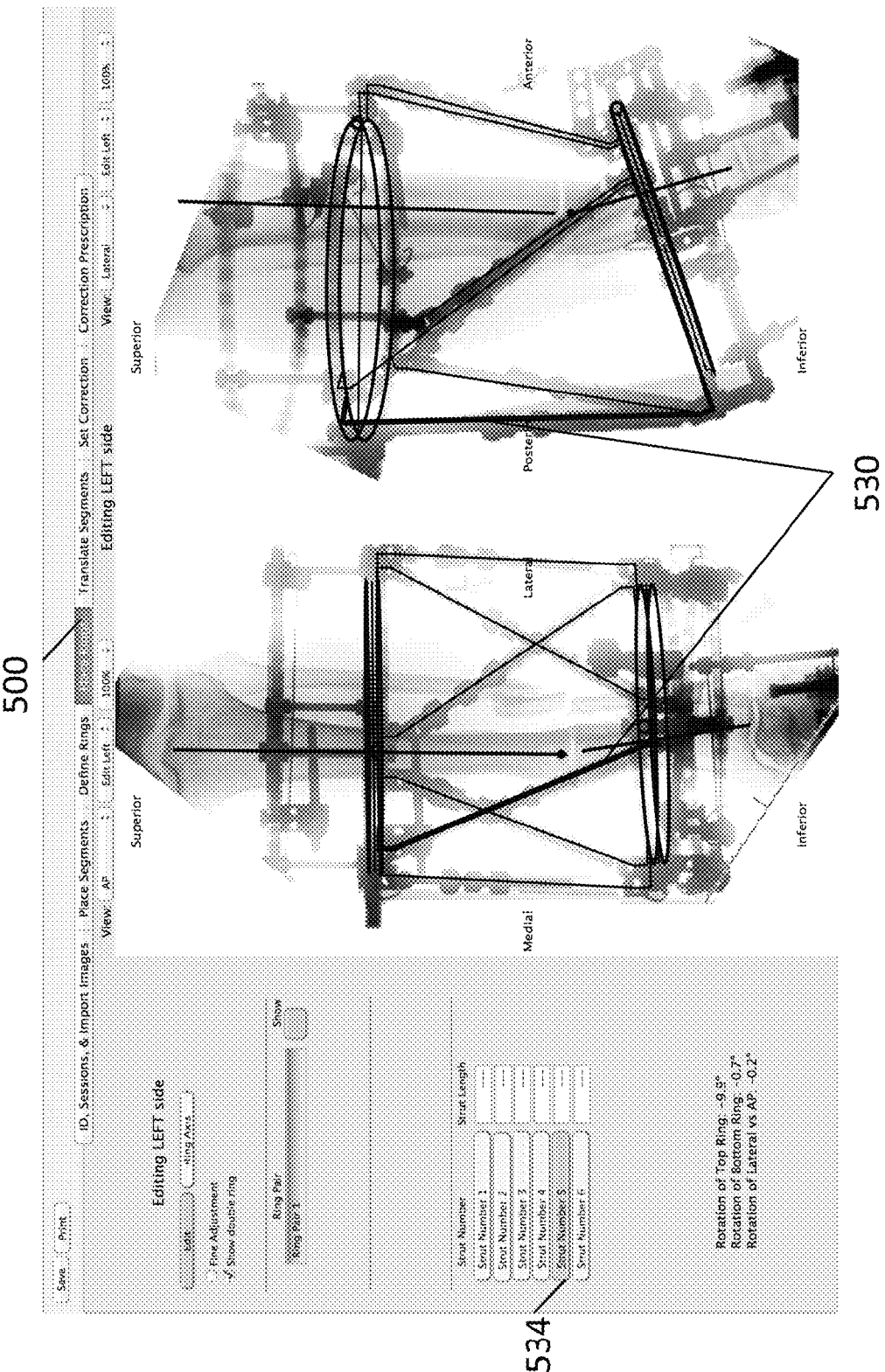
Figure 27:
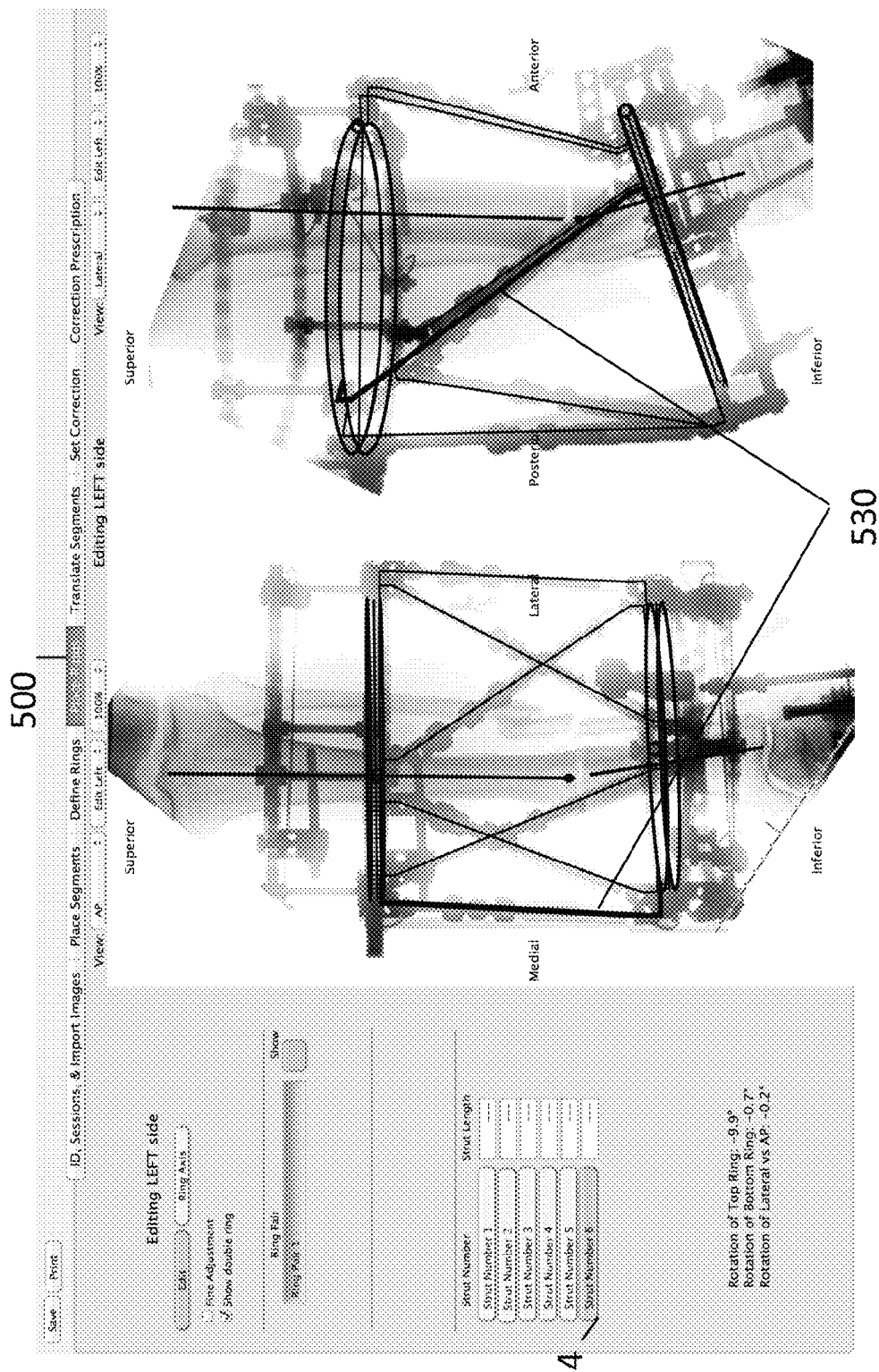

In response to receiving the ring rotation user input, the system generates a display of the resulting graphical representation of the ring superimposed on the at least one digital medical image. FIG. 26 is a screen shot of the PLACE RINGS tab 500 showing rotations involving multiple ring pairs 532'. FIGS. 27A-27F show screen shots of a user highlighting each strut 530 by number 534 to assist with ring identification.

Figure 28:
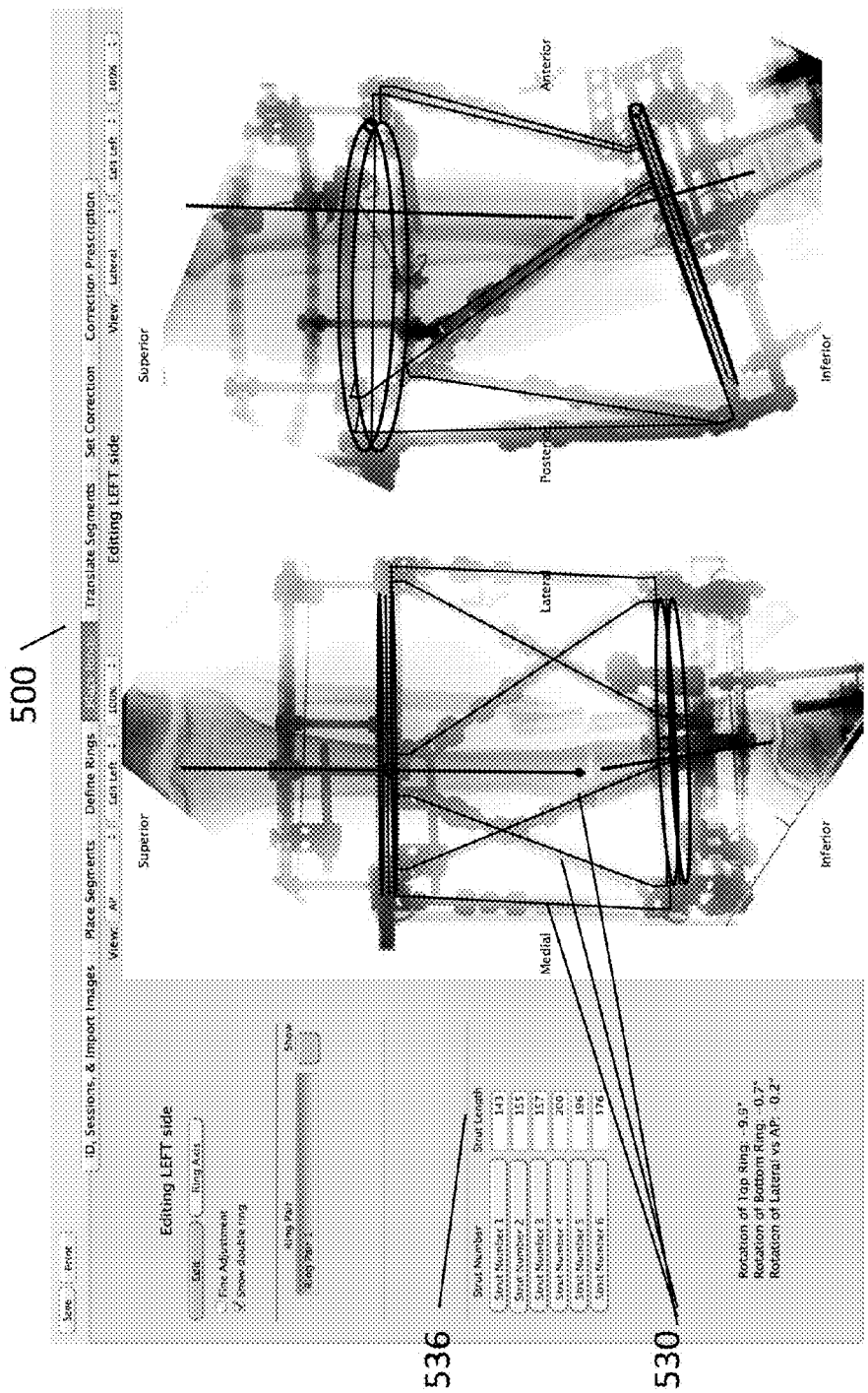
FIG. 28 is a screen shot of the PLACE RINGS tab showing a user entering true strut lengths taken from the actual struts, according to some embodiments of the present invention.
Figure 29:
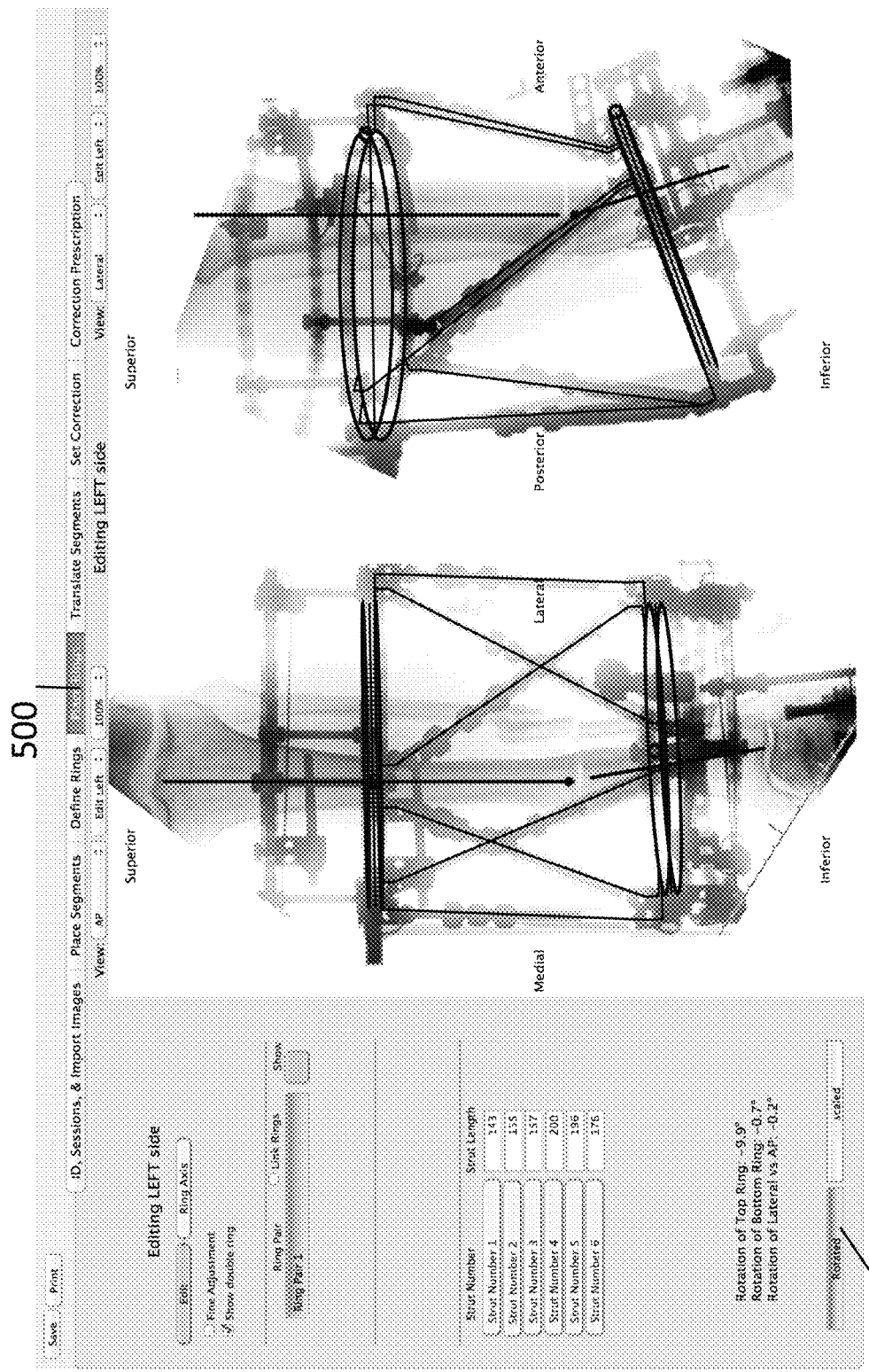
FIG. 29 shows a screen shot of the PLACE RINGS tab where user can choose to view the images with or without rotation for reference and/or scaling, according to some embodiments of the present invention.

FIG. 28 is a screen shot of the PLACE RINGS tab 500 showing a user entering true strut lengths 536 taken from the actual struts 530. This aids in calculating one or more scaling factors. As shown in FIG. 29, the user can choose to view the images with or without rotation for reference and/or scaling 538.

In some embodiments, the location of strut attachments on the ring—defined by the manufacturer and selected by the user—in the 2D ring plane (the major plane of the ring), can be used to convert this information to the position of struts in the XY and ZY planes. For each strut attachment point, the radius from the ring's center point to the strut attachment point ($\text{strut}_{radius}(n)$), and the angle from the ring's rotational reference point to the attachment point ($\text{strut}_{angle}(n)$) are both known. Additional devices may be attached to the ring to further modify the strut attachment point, which will in turn modify ($\text{strut}_{radius}(n)$) and ($\text{strut}_{angle}(n)$). To find the display parameters for the strut attachment point, we can calculate:

$$x_{strut}(n)=x_c+\text{strut}_{radius}(n)\cdot 2\cdot \cos(n-\text{strut}_{angle}(n))\cdot\cos\theta-b\cdot\sin(n-\text{strut}_{angle}(n))\cdot\sin\theta \quad (31)$$

$$y_{strut}(n)=y_c+\text{strut}_{radius}(n)\cdot 2\cdot \cos(n-\text{strut}_{angle}(n))\cdot\sin\theta+b\cdot\sin(n-\text{strut}_{angle}(n))\cdot\cos\theta \quad (32)$$

Struts may also have a portion directed perpendicular to the ring ($\text{strut}_{drop}(n)$) from the strut attachment point. This includes a portion of the strut itself that is fixed perpendicular to a ring as well as half of the ring thickness itself. Additional devices may be attached to the ring to further modify the drop length, which will in turn modify ($\text{strut}_{drop}(n)$). One way to calculate the displayed portion of this dropped segment involves using the cosine of the ratio of the ring's "b" axis to the "a" axis. This displayed portion of the drop length is then drawn perpendicular to the "a" axis to obtain $x_{strut\text{-}drop}(n)$:

$$\text{strut}_{drop\text{-}xy}(n) = \cos\frac{b_{xy}}{a_{xy}} \cdot \text{strut}_{drop\text{-}xy}(n) \quad (33)$$

Another way to calculate the dropped portion of the strut is to calculate a 3D vector orthogonal to the major plane of the ring starting from the ring's center point (xc, yc, zc) as described above. Translation of the ring's center point along this 3D orthogonal to the ring plane followed by recalculating the strut attachment point, as described above, using the translated ring reveals the $\text{strut}_{drop}$ point.

As shown in FIG. 55, a complete strut on the display can be drawn between the corresponding calculated strut$_{drop}$ points between two rings in each of the XY and ZY planes.

The strut length can be calculated between corresponding calculated strut$_{drop}$ positions between two rings in the XYZ space using a standard formula for distance between two points where x1, y1, z1 are the drop point on ring 1, and x0,y0,z0 are the drop points on ring 0:

$$Strut_{length}(n) = \sqrt{\begin{array}{c}(x1_{drop}(n) - x0_{drop}(n))^2 + (y1_{drop}(n) - y0_{drop}(n))^2 + \\ (z1_{drop}(n) - z0_{drop}(n))^2\end{array}} \quad (34)$$

Figure 30:
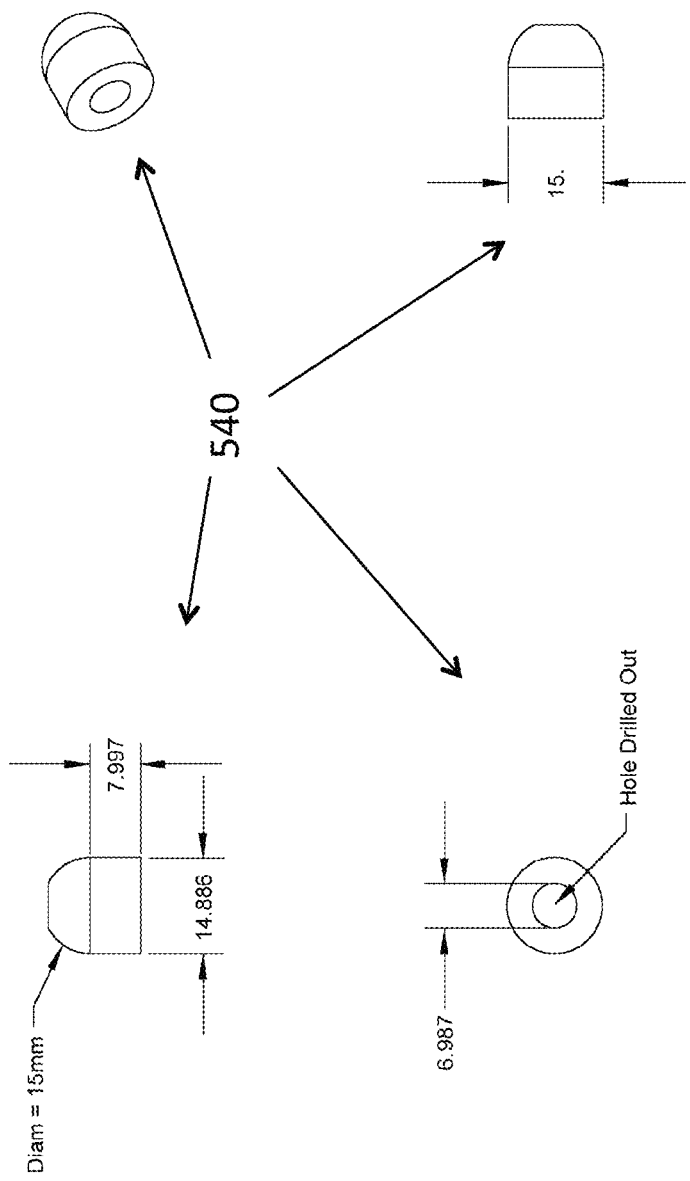
FIG. 30 shows a schematic drawing of various views of a model of a ring marker, according to some embodiments of the present invention.

FIG. 30 shows a schematic drawing of various views of a model of a ring marker 540 hardware that may be placed on a ring to facilitates proper identification of ring positioning when using digital imaging. A wide variety of shapes may be used with the common purpose of marking a spot on the external fixator ring that is easily identifiable on both the AP and lateral images. This facilitates setting of proper view ring spread, ring mounting rotation, and ring x-ray rotation as described above. Shown here is just one of a variety of shapes that may be used for this purpose.

Translate Segments Tab

Figure 31:
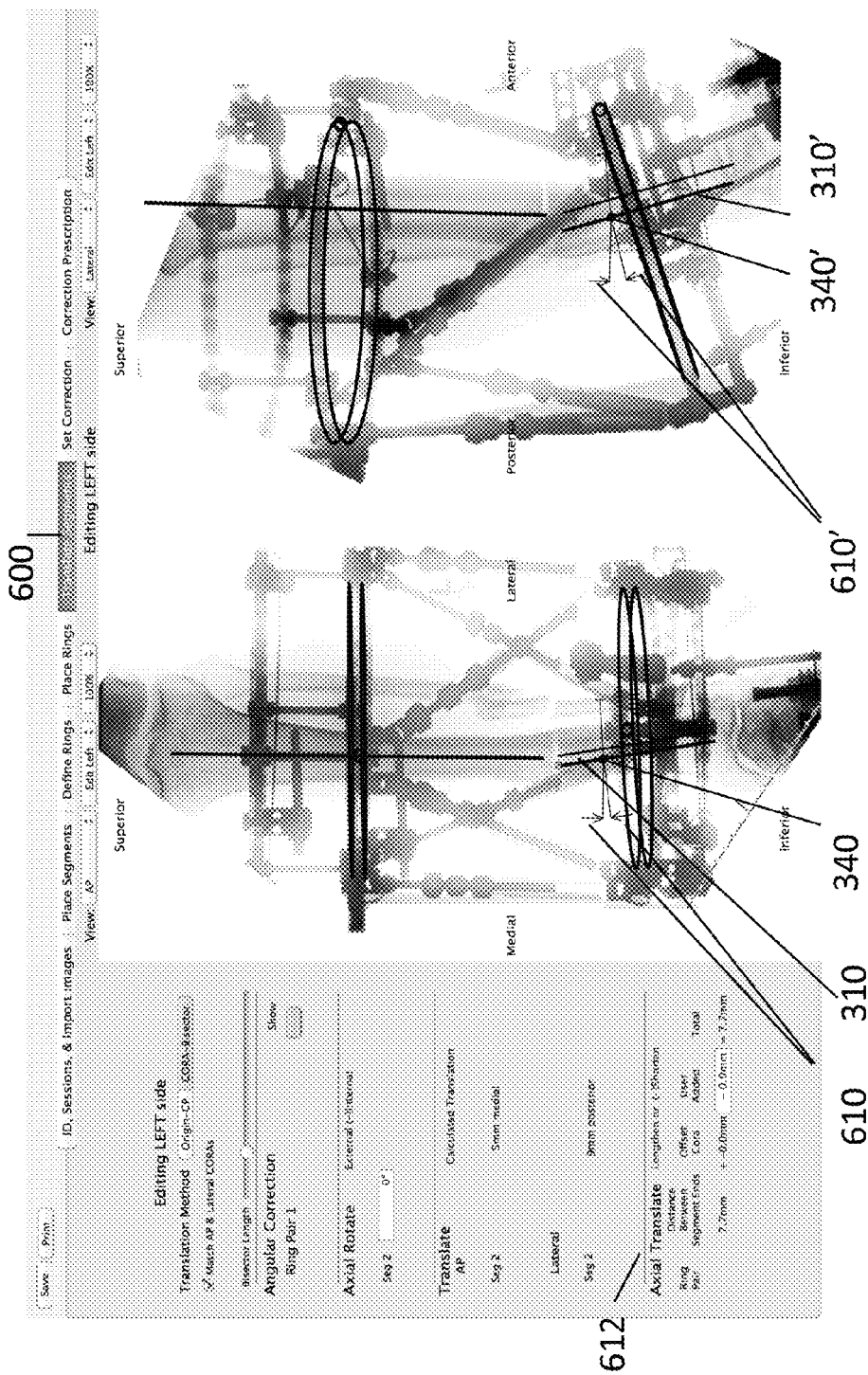
FIG. 31 shows a screen shot of the "TRANSLATE SEGMENTS" tab, according to some embodiments of the present invention.

FIG. 31 shows a screen shot of the "TRANSLATE SEGMENTS" tab 600 that allows the user to translate non-reference segments relative to the reference segment to define the translational deformity. In addition to the angular deformity described above, there can be translational deformity. Translational deformity is when one segment is translated relative to another. For example, imagine the situation where adjacent segment are parallel to each other but one is shifted relative to the other one. Since they never intersect, there is no CORA and no angular deformity. In this circumstance the deformity is purely translational. More commonly, there will be a component of angulation and translation in a deformity. The program calculates and updates a new CORA based on the translated segments and updates the display in real time.

The second aspect of this tab is the ability to translate the CORA. A translated CORA still is a point around which rotation will correct the angular deformity but is moved away from the intersection of the two segments. The translated CORA can be any point along the geometric bisector of the larger angle made by the two segments. Translating a CORA will either lengthen (distract) or shorten (compress) the moving segment relative to the reference segment depending on which direction the translated CORA is moved. The size of the lengthening or shortening is calculated and displayed on screen graphically and numerically in real time for easy user reference.

The third aspect available that the user can also choose to match the vertical position of the AP and lateral view CORAs (match CORAs). In this circumstance, the program will calculate the segment translation in one plane as the user translates the segment in the other plane.

Finally, the user can choose to define translation by marking start and end points on either segment of the deformity. With this concept, the user defines a point on or near the reference segment (start point) and a point on or near the moving segment (end point) that is supposed to end up at the start point as the correction is made. The amount of translation and updated CORA and moving segment are calculated and displayed in real time.

Figure 32:
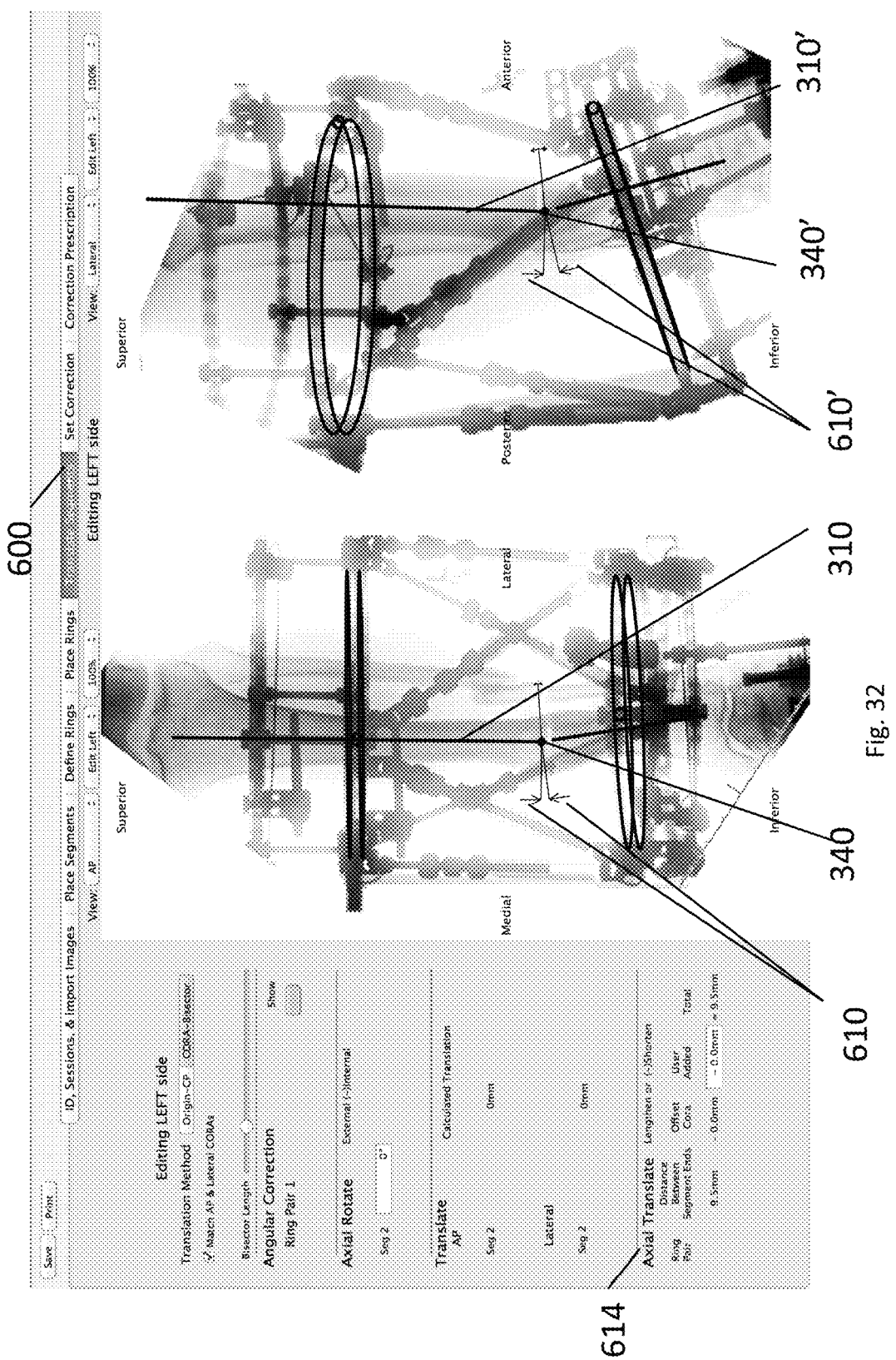
FIG. 32 shows a screen shot of the TRANSLATE SEGMENTS tab where the AP segment is being translated medially, according to some embodiments of the present invention.

As seen in FIG. 31, the segments 310, 310' are displayed with associated CORA 340, 340'. The arrows on the transverse lines 610, 610' show the size of the lengthening or shortening that will occur at points away from the CORA. FIG. 32 shows a screen shot of the AP segment 310 being translated medially. Of note is the new segment position 310 and updated CORA position 614, as compared to the CORA position 612 in FIG. 31.

Figure 33:
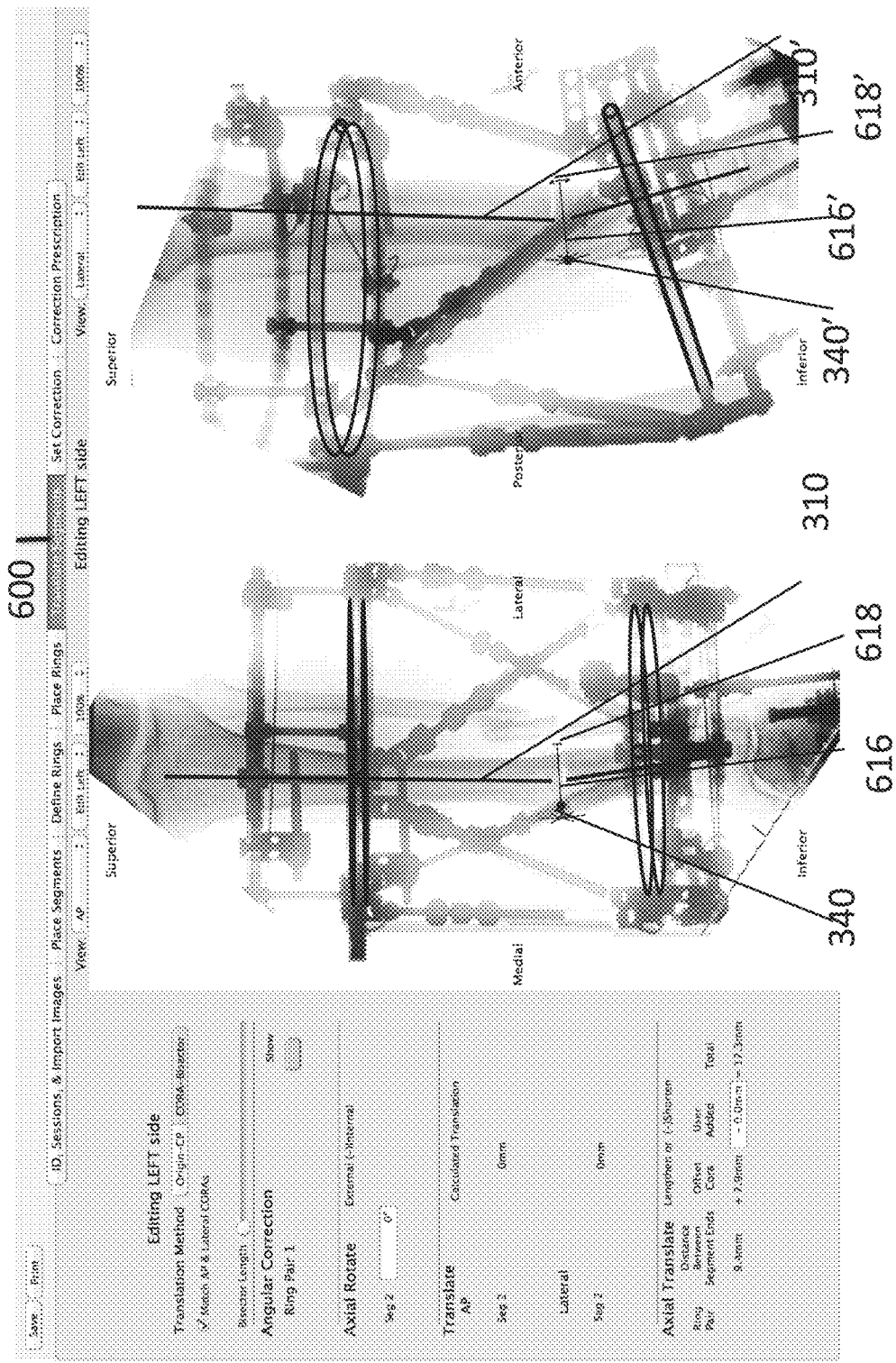
FIG. 33 is a screen shot of the TRANSLATE SEGMENTS tab showing a user moving the CORAs, according to some embodiments of the present invention.

FIG. 33 is a screen shot of the "TRANSLATE SEGMENTS" tab 600 showing a user moving the CORAs 340. Here both the AP 340 and lateral CORA 340' have been moved to the apex side of the deformity, away from the center line of the bone. This prevents impinging (binding) of bone segments 310, 310' during the correction. It is equivalent to correcting the angular deformity around the non-translated CORA and adding a small amount of lengthening. The amount of lengthening is shown by the lines 616, 616' and arrows 618, 618'.

Figure 34:
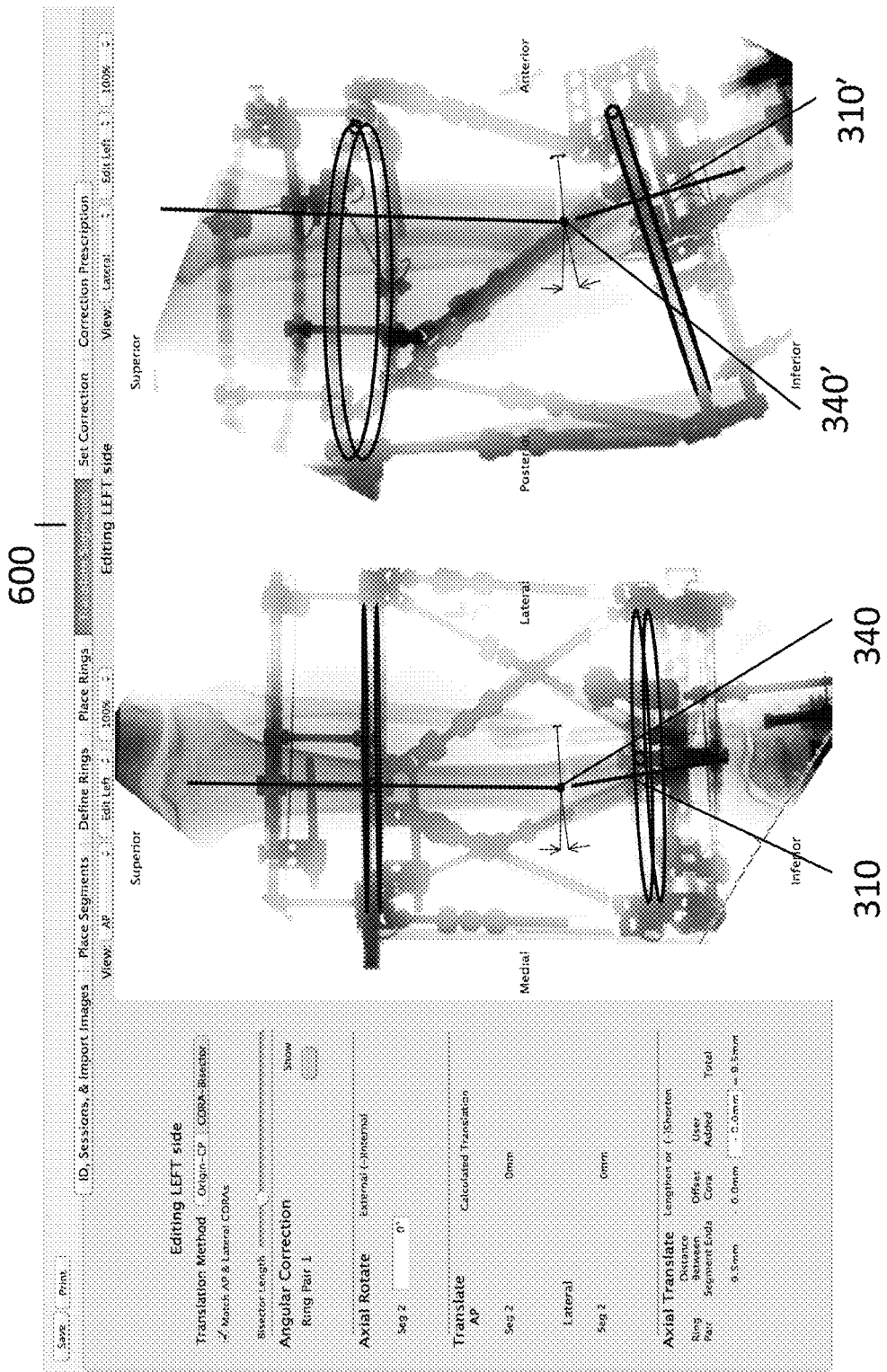
FIG. 34 shows a screen shot of the TRANSLATE SEGMENTS tab where the vertical positions of the CORAs are matched, according to some embodiments of the present invention.

FIG. 34 shows a screen shot of the TRANSLATE SEGMENTS tab 600 where the vertical positions of the CORAs 340, 340' are matched. In this case, when the user translates a segment 310 in one view it is translated in the other view by an amount to keep the CORAs matched.

Figure 35A:
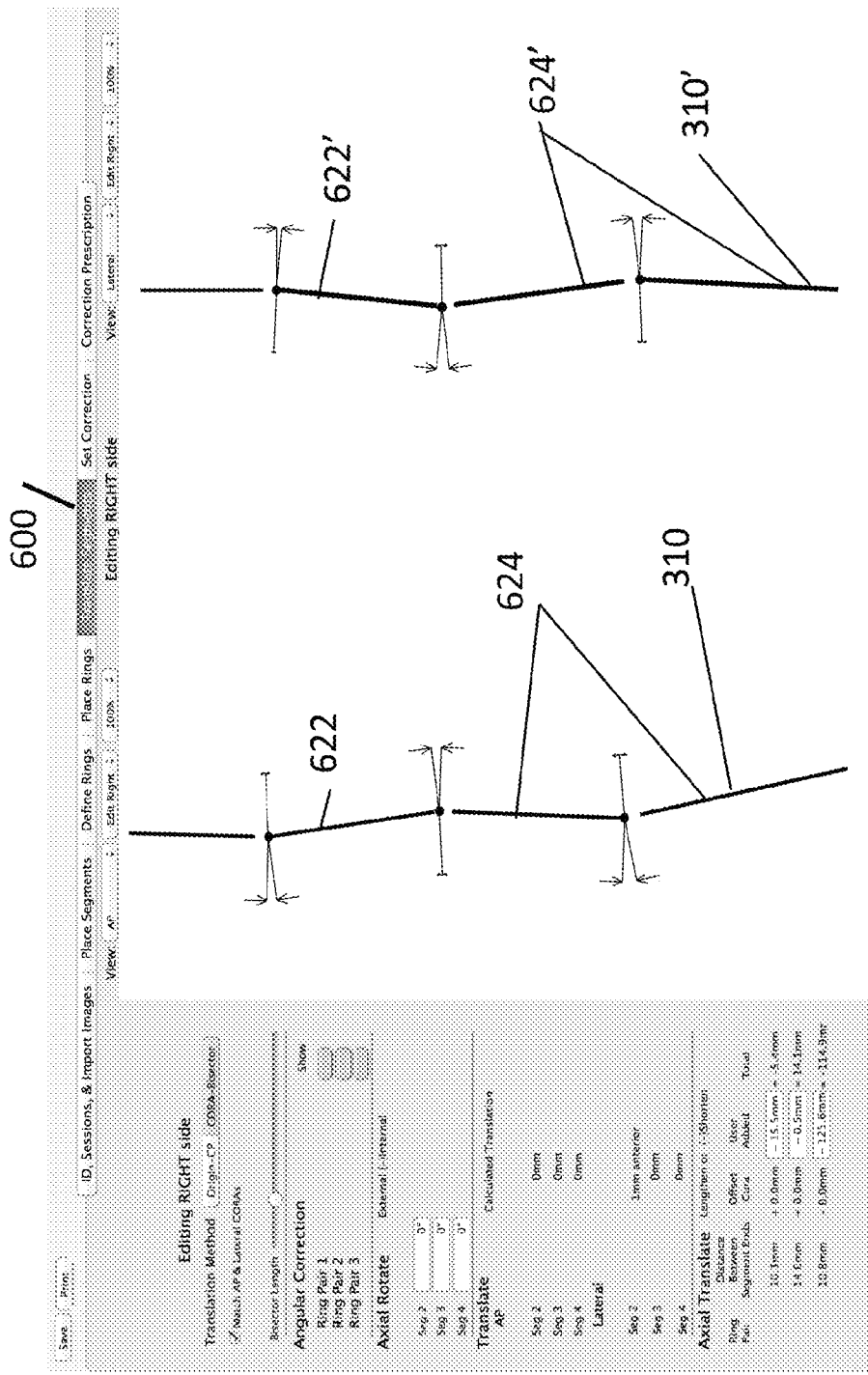
FIGS. 35A-35B show screen shots of multiple segments being translated, according to some embodiments of the present invention.
Figure 35B:
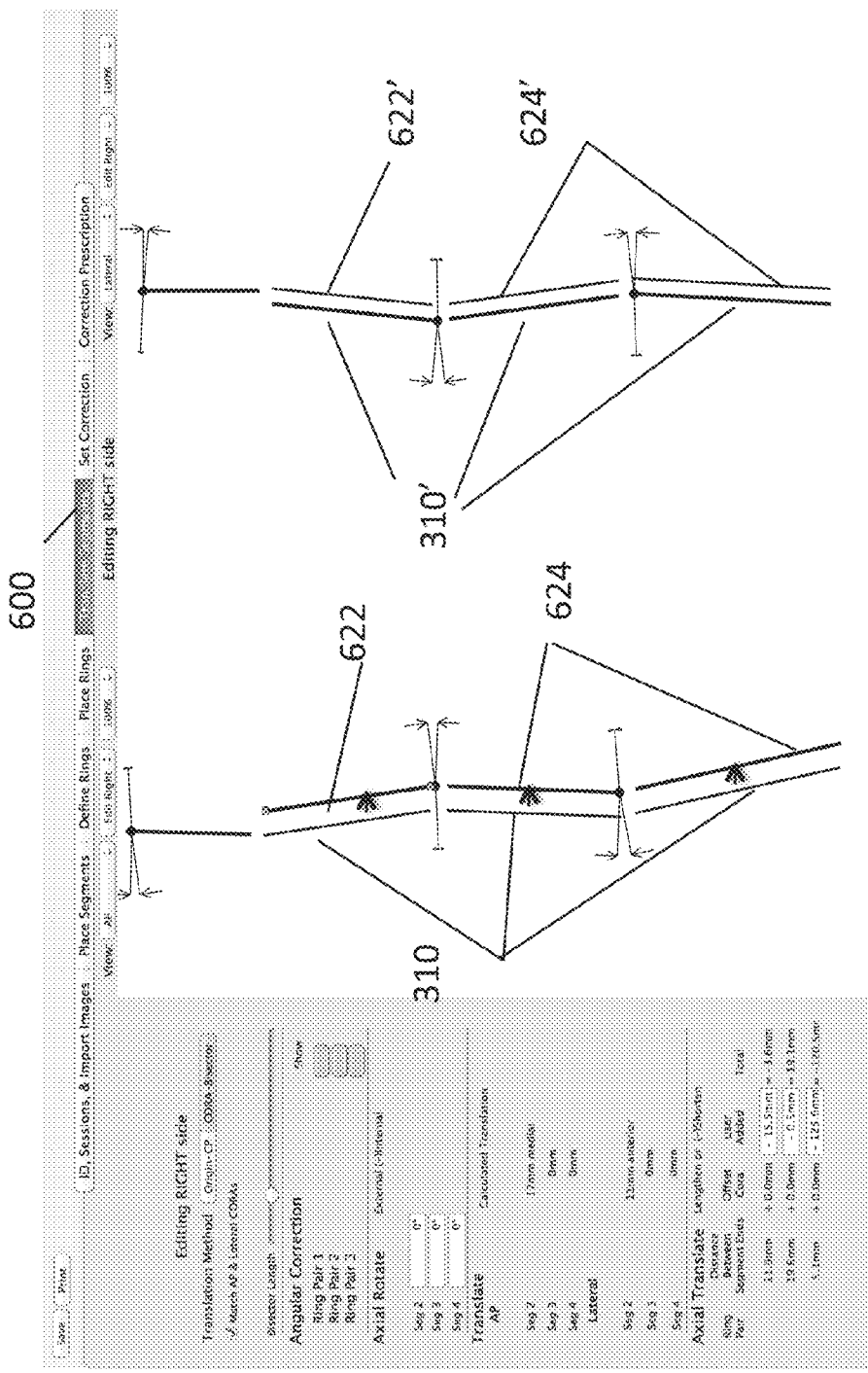

FIGS. 35A-35B show screen shots of multiple segments 310, 310' being translated. When a segment 622, 622' is translated, all the segments below 624, 624' (or above for those above the reference segment) are translated as well. This keeps the net translation for these other segments at zero.

Figure 36:
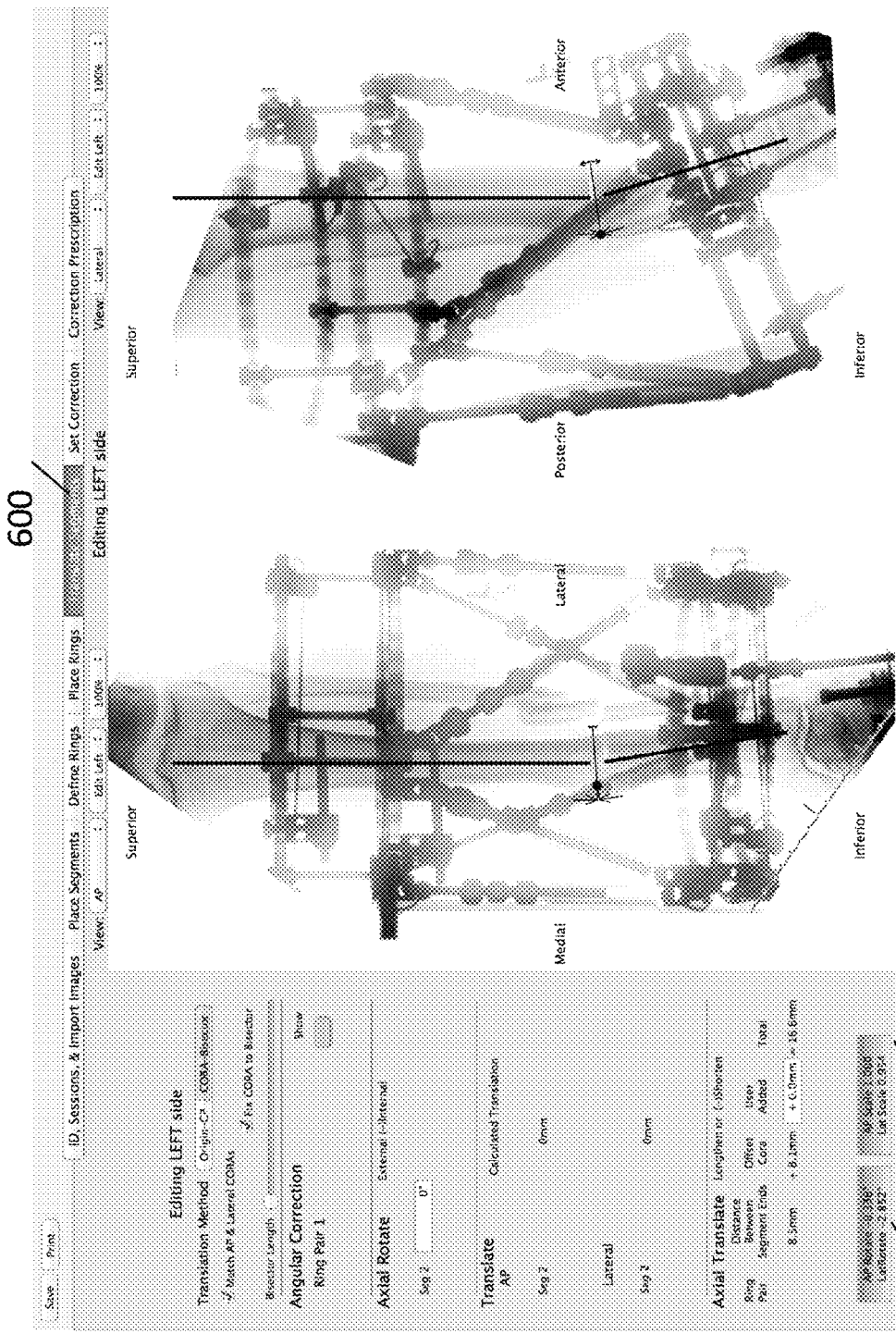
FIG. 36 is a screen shot of the TRANSLATE SEGMENTS tab showing how images may be viewed with or without rotation for reference and/or scaling, according to some embodiments of the present invention.

FIG. 36 is a screen shot of the TRANSLATE SEGMENTS tab 600 showing how images may be viewed with or without rotation 626 for reference and/or scaling 628.

In some embodiments, a 3D point can be manipulated based on rotation and translation in each of the 3 planes defined by XYZ space: rotation$_{xy}$, rotation$_{zy}$, rotation$_{xz}$, translation$_{xy}$, translation$_{zy}$, translation$_{xz}$.

Rotation of a point P1(x1,y1,z1) in the xy plane of XYZ space around a defined point P0(x0,y0,z0) starts by setting a vector in the xy plane $V_{0-1}$=(x0,y0)→(x1,y1) in the xy plane with polar coordinates "radius" and "angle to the x axis" starting at point P0. In this description the xy plane refers to a real plane in XYZ space and may be distinct from the XY plane (AP plane) defined by the radiographic images.

$$\vec{V}_{0-1,radius} = \sqrt{(x_1 - x_0)^2 + (y_1 - y_0)^2} \quad (35)$$

$$\vec{V}_{0-1,angle} = \tan^{-1}\left(\frac{y_1 - y_0}{x_1 - x_0}\right) \quad (36)$$

The rotation then occurs by adding the desired rotation to the angular component of $V_{0-1}$ to get $V'_{0-1}$.

$$\vec{V'}_{0-1,angle} = \vec{V}_{0-1,angle} + \text{rotation}_{xy} \quad (37)$$

Standard conversions can then be used to calculate P'1 (x'1,y'1,z1) from the end point of $V_{0-1}$.

$$x'_1 = \vec{V'}_{0-1,radius} \cdot \cos \vec{V'}_{0-1,angle} + x_0 \quad (38)$$

$$y'_1 = \vec{V'}_{0-1,radius} \cdot \cos \vec{V'}_{0-1,angle} + y_0 \quad (39)$$

Rotation of a point P1(x1,y1,z1) in the zy plane of XYZ space around a defined point P0(x0,y0,z0) starts by setting a vector in the zy plane $V_{0-1}$=(z0,y0)→(z1,y1) in the zy plane with polar coordinates "radius" and "angle to the Z axis" starting at point P0. In this description the zy plane refers to a real plane in XYZ space and may be distinct from the ZY plane (lateral plane) defined by the radiographic images.

$$\vec{V}_{0-1,radius} = \sqrt{(z_1 - z_0)^2 + (y_1 - y_0)^2} \quad (40)$$

$$\vec{V}_{0-1,angle} = \tan^{-1}\left(\frac{y_1 - y_0}{z_1 - z_0}\right) \quad (41)$$

The rotation then occurs by adding the desired rotation to the angular component of $V_{0-1}$ to get $V'_{0-1}$.

$$\vec{V}'_{0-1,angle} = \vec{V}_{0-1,angle} + \text{rotation}_{zy} \quad (42)$$

Standard conversions can then be used to calculate P'1 (x1,y'1,z'1) from the end point of $V_{0-1}$.

$$z'_1 = \vec{V}_{0-1,radius} \cdot \cos \vec{V}'_{0-1,angle} + z_0 \quad (43)$$

$$y'_1 = \vec{V}_{0-1,radius} \cdot \sin \vec{V}'_{0-1,angle} + y_0 \quad (44)$$

Rotation of a point P1=(x1,y1,z1) in the xz plane of XYZ space is a special case of rotation of a point around a fixed 3D vector (V0), where V0 is the y-axis. In the general case, we define the plane of rotation using V0 and the point to correct (P1) as described in the plane definition section above for plane definition using an orthogonal vector and point. The origin of the 2D plane is the intersection of V0 and the 2D correction plane. In the 2D correction plane, this intersection is defined as point $P0_{converted}$=(i0,j0). A 2D vector V0-1 is defined starting from $P0_{converted}$ and extending to the point P1 as represented in the new 2D plane ($P1_{converted}$=(i1,j1)).

$$\vec{V}_{0-1,radius} = \sqrt{(i_1 - i_0)^2 + (j_1 - j_0)^2} \quad (45)$$

$$\vec{V}_{0-1,angle} = \tan^{-1}\left(\frac{j_1 - j_0}{i_1 - i_0}\right) \quad (46)$$

The rotational correction is added to the polar form of vector V1 to find V'1, whose end-point is $P'1_{converted}$=(i'1, j'1).

$$i'_1 = \vec{V}_{0-1,radius} \cdot \cos(\vec{V}'_{0-1,angle} + i_0) \quad (47)$$

$$j'_1 = \vec{V}_{0-1,radius} \cdot \sin(\vec{V}'_{0-1,angle} + j_0) \quad (48)$$

This $P1'_{converted}$ is converted back to 3D space as described above in the plane definition section to find P'1=(x'1,y'1,z'1).

Translation of a point P0(x0,y0,z0) along the x-axis by x units, along the y-axis by y units, and along the z-axis by z units is accomplished by adding values x, y, and z to the components of P0 to get P'0.

$$P'_{0,x} = x0 + x \quad (49)$$

$$P'_{0,y} = y0 + y \quad (50)$$

$$P'_{0,z} = z0 + z \quad (51)$$

Translation may be made perpendicular to a line in the xy, zy, or xz planes by calculating the appropriate x, y, and z components required to accommodate such a translation.

It should be noted that if multiple corrections are made, they should be made sequentially so that changes accumulate. For instance, adding the results of rotating in xy plane and the zy planes will not give the same result as rotating in the xy plane, then rotating the result of the first rotation in the zy plane.

Figure 37A:
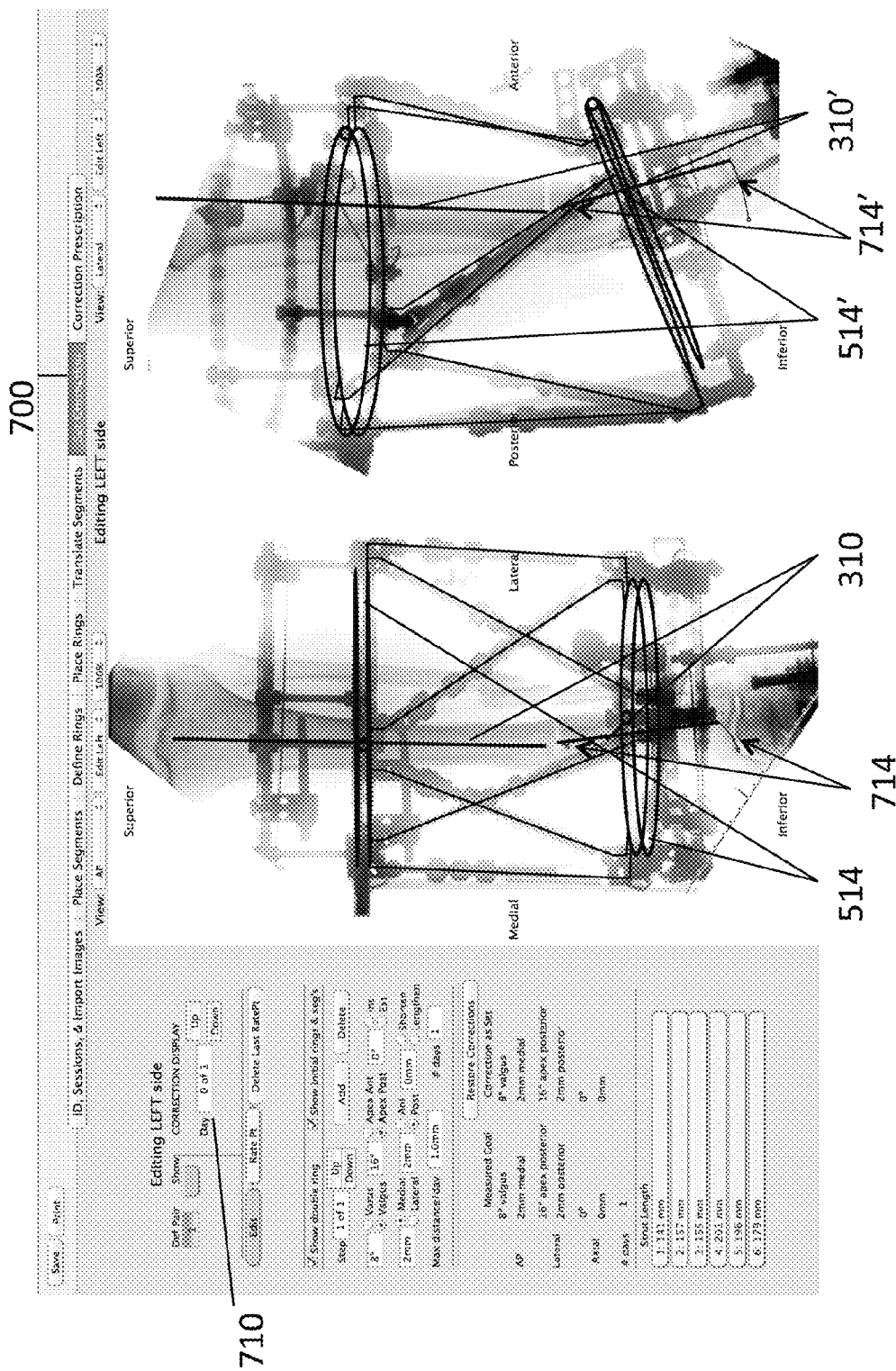
FIGS. 37A-37B show screen shots of the "SET CORRECTION" tab, according to some embodiments of the present invention.
Figure 37B:
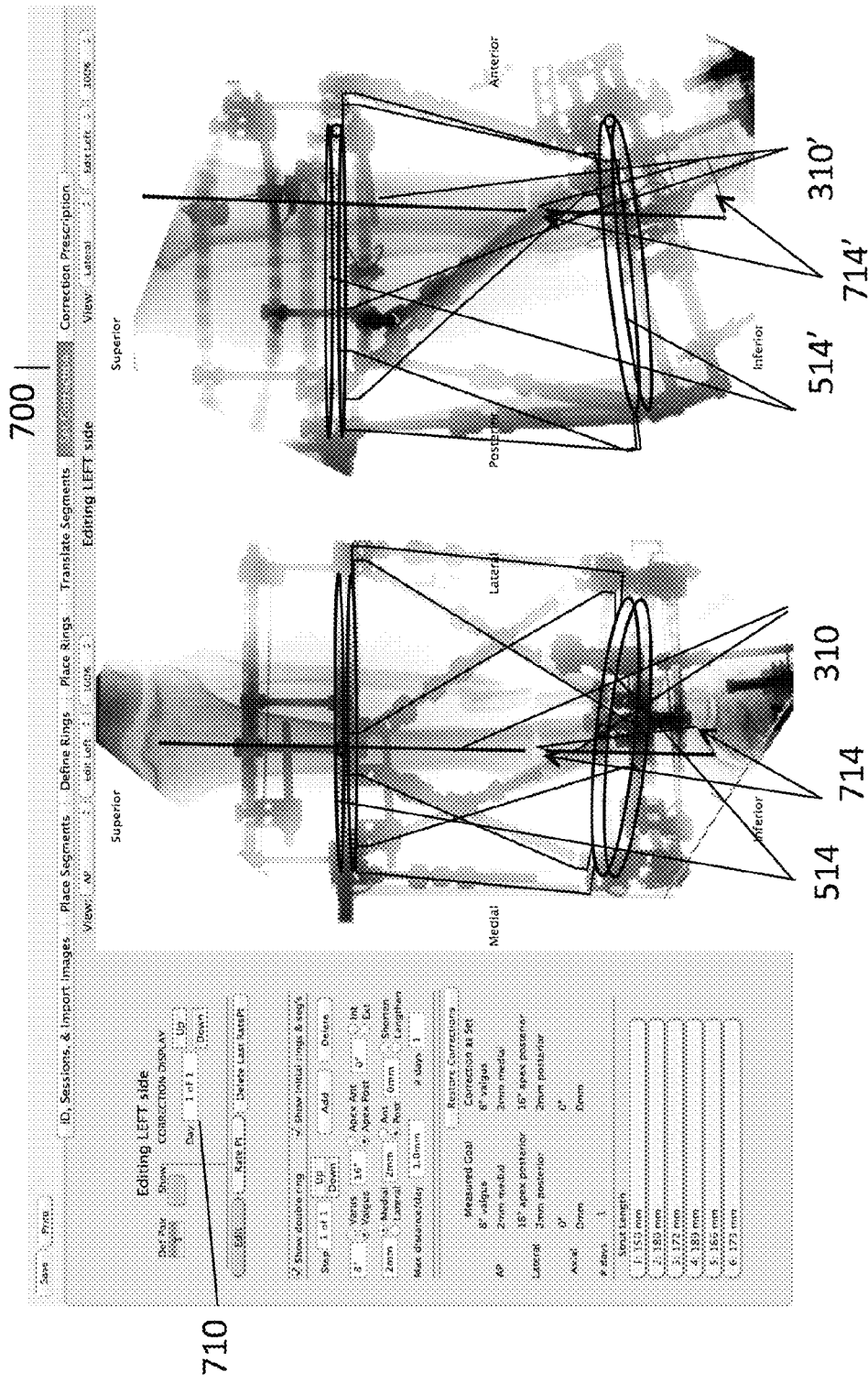

FIGS. 37A-37B shows screen shots of the "SET CORRECTION" tab 700. This tab displays the correction of segments and rings described in the preceding tabs and allows the user to customize the correction.

The correction algorithm is designed to allow independent correction of angular deformity in three planes and translational deformity in three planes. The underlying concept is the ability to calculate a correction path for any point in space based on the deformity parameters described in the preceding tabs.

The user can graphically define one or many 3D biological rate-limiting points for a bone deformity correction treatment to be performed using the external fixator; and, based upon this information, the system will calculate at least one of a 3D bone correction speed and a number of days for the bone deformity correction treatment, and/or generate a bone deformity correction plan specifying for each strut a daily sequence of strut lengths to be used in the bone deformity correction treatment.

These are points that will determine over how many days a correction will take place. By calculating a correction path rate for each 3D biological rate-limiting point (in 3D), using a large number of data points, an estimate of the true rate point correction path curve is made and the true rate point correction path length can be calculated. Dividing this number by the user defined 3D bone correction speed (mm/day) returns the number of days for the bone deformity correction.

Once the number of days for the correction is known, the final correction path for segment endpoints and ring axis points can be calculated. These correction paths are divided into the number of correction days and filled in between correction days to make the curves look smoother in the on screen views. Final strut lengths are calculated from the corrected ring axis points.

The rate point(s) can be moved on the graphical user interface and corresponding true rate point correction path, correction days, and final segment and ring corrections are calculated and displayed in real time.

The user can manipulate the correction parameters in a number of ways. Corrections can be broken up into multiple steps. In each correction step, the user can individually set each parameter (of the six correction parameters) as well as the correction rate and/or the correction days. In this way the actual correction is customizable. For instance, a small distraction can be set initially to disengage bone fragments prior to correction, or compression can be applied after correction.

The user can graphically define where a "cut" would be made on the image. The program then will move the portion of the image to be corrected with the segments/rings (partial image correction). This would show the user what the actual corrected image would look like.

An alternative is to define the segments displayed as parallel lines marking the width of the bone.

Set Correction Tab

FIGS. 37A-37B are screen shots of the SET CORRECTION tab 700 showing the initial correction screen showing the state of the segments 310, 310' and rings 514, 514' initially (correction day 0) 710 and finally (correction day 1) 712. The path of the correction of the ends of the moving segment are shown by the arrows 714, 714'.

Figure 38:
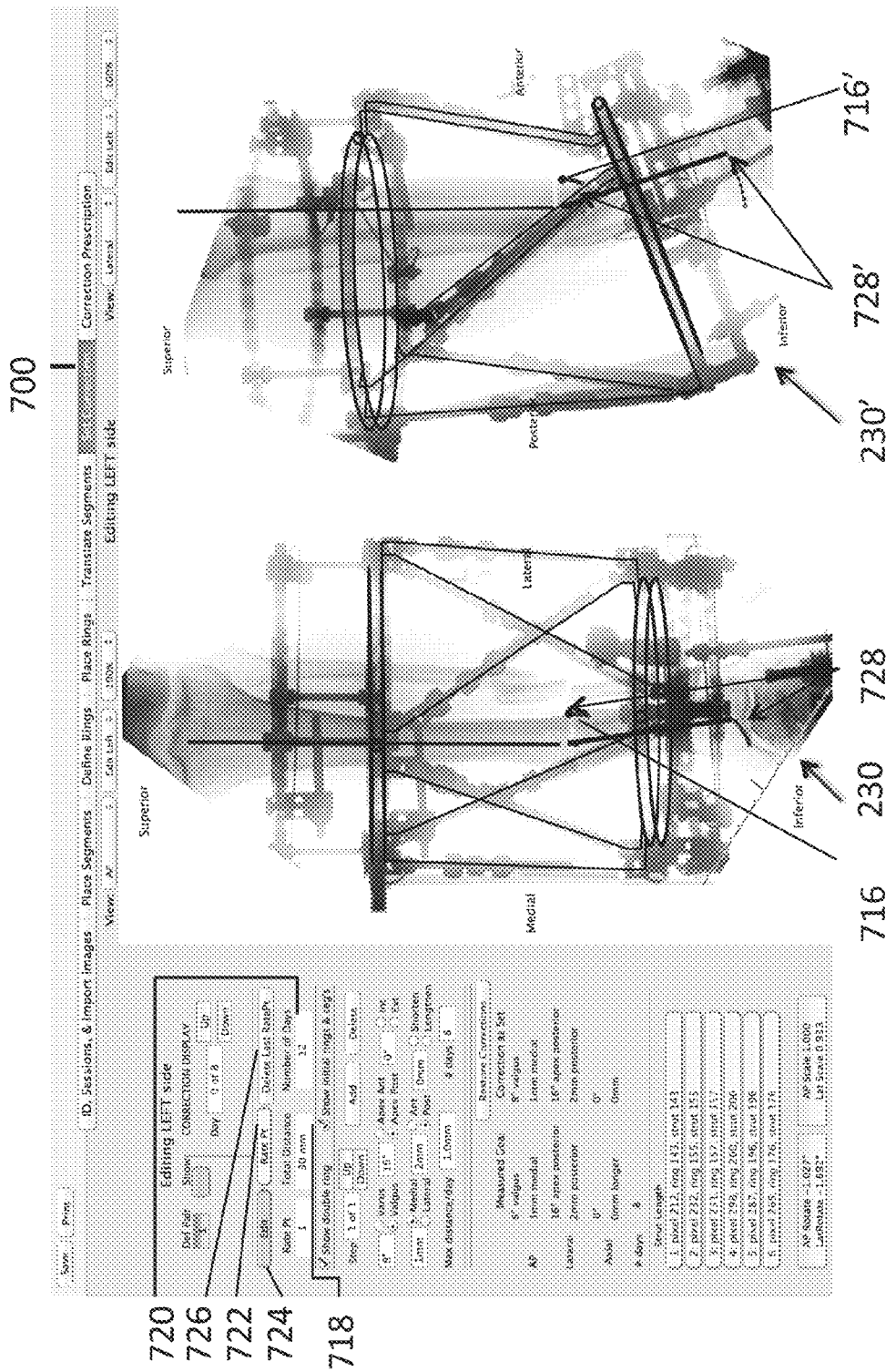
FIG. 38 shows a screen shot of the SET CORRECTION tab where a rate point has been added and can be moved by the user, according to some embodiments of the present invention.
Figure 39A:
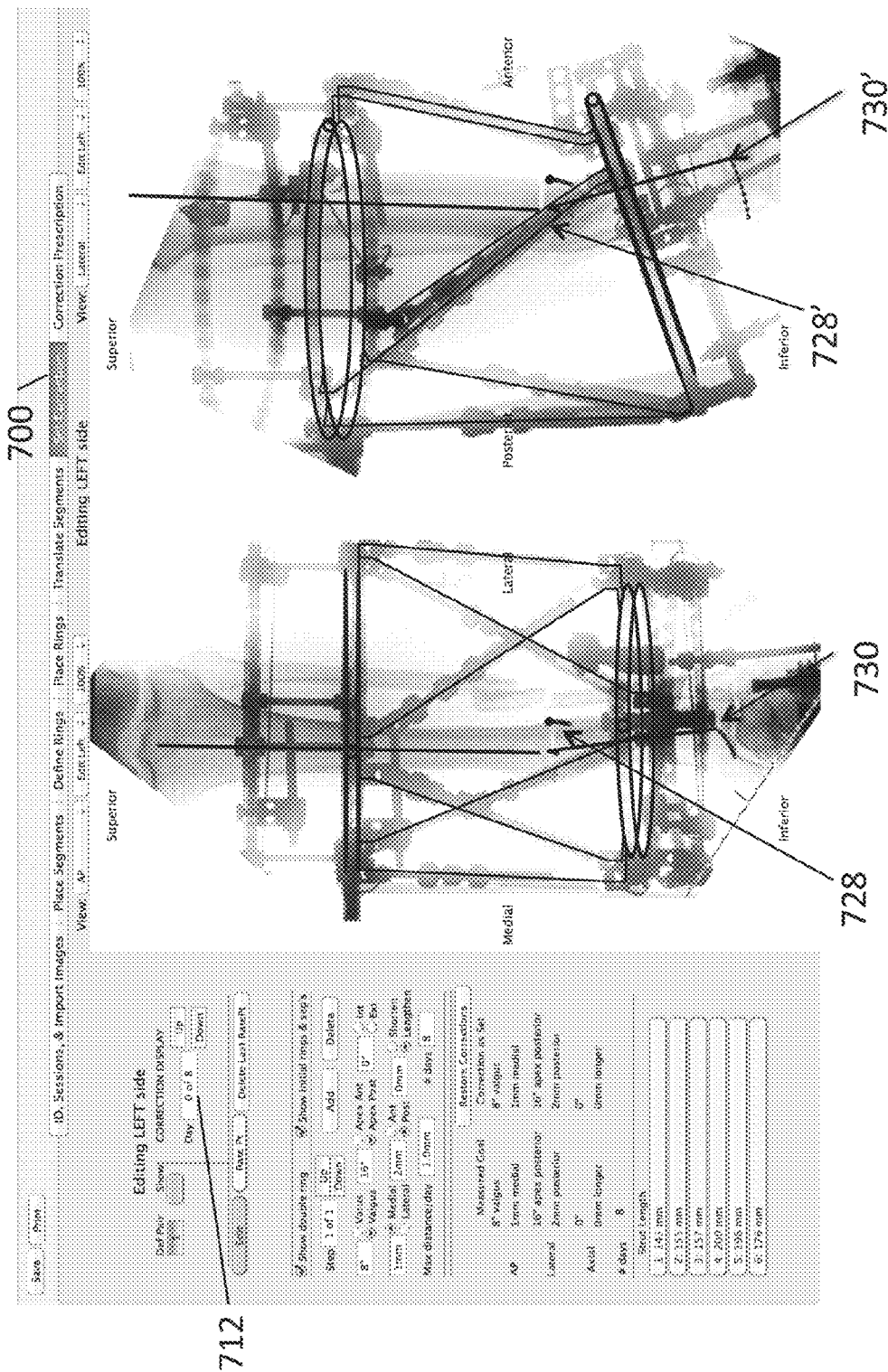
FIGS. 39A-39E show screen shots of the SET CORRECTION tab of corrections shown on day 0, 2, 4, 6, and 8 respectively, according to some embodiments of the present invention.
Figure 39B:
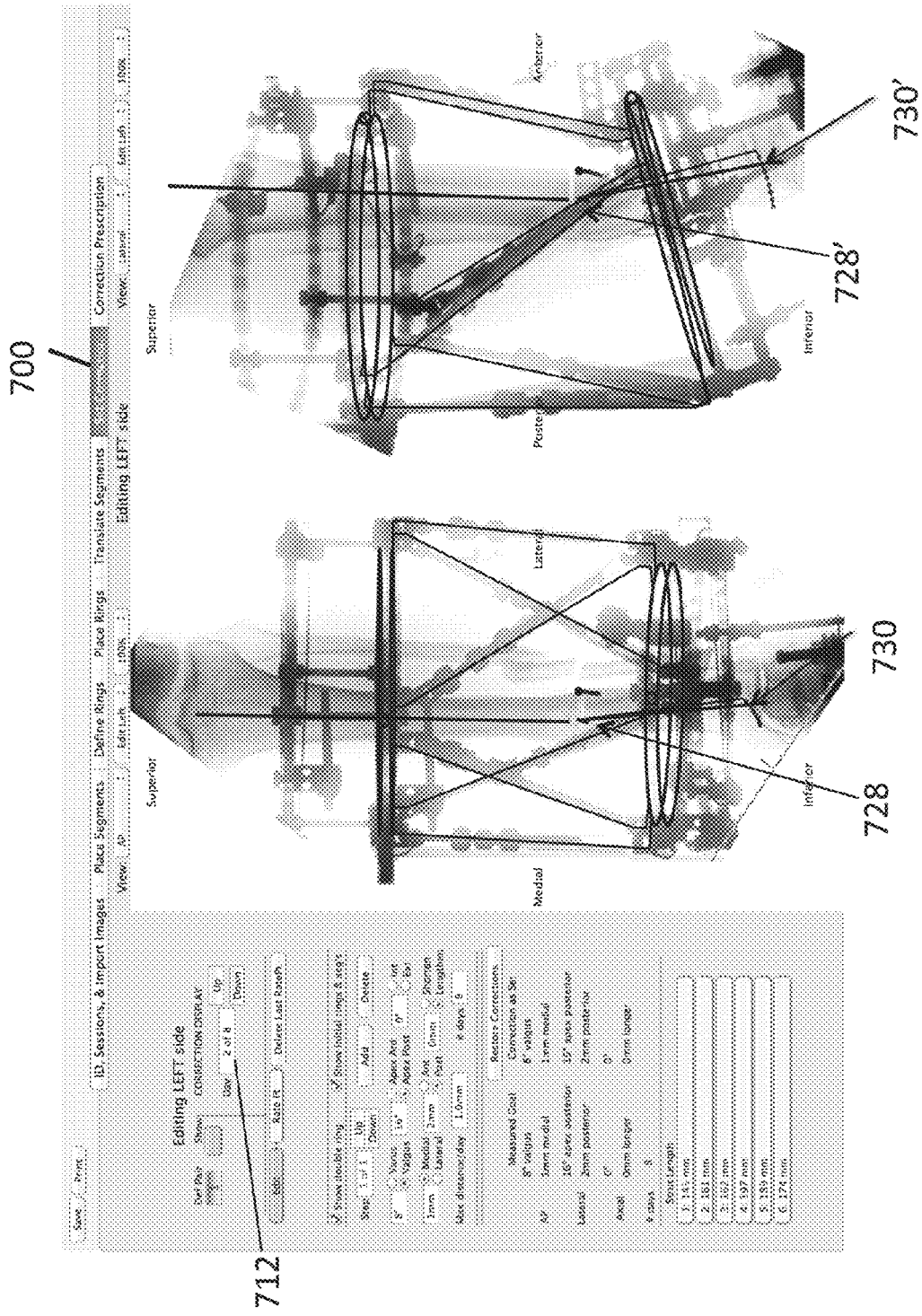
Figure 39C:
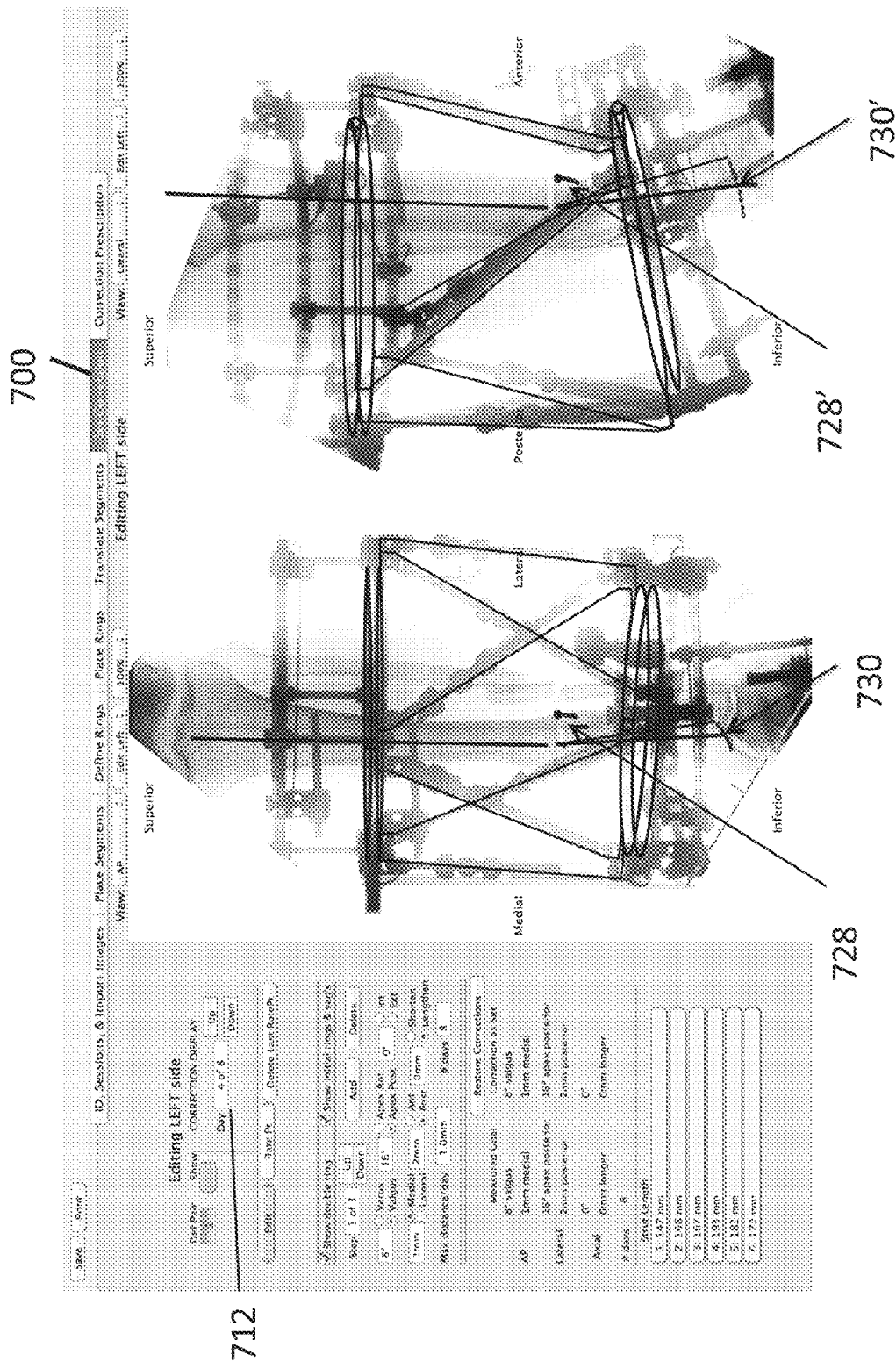
Figure 39D:
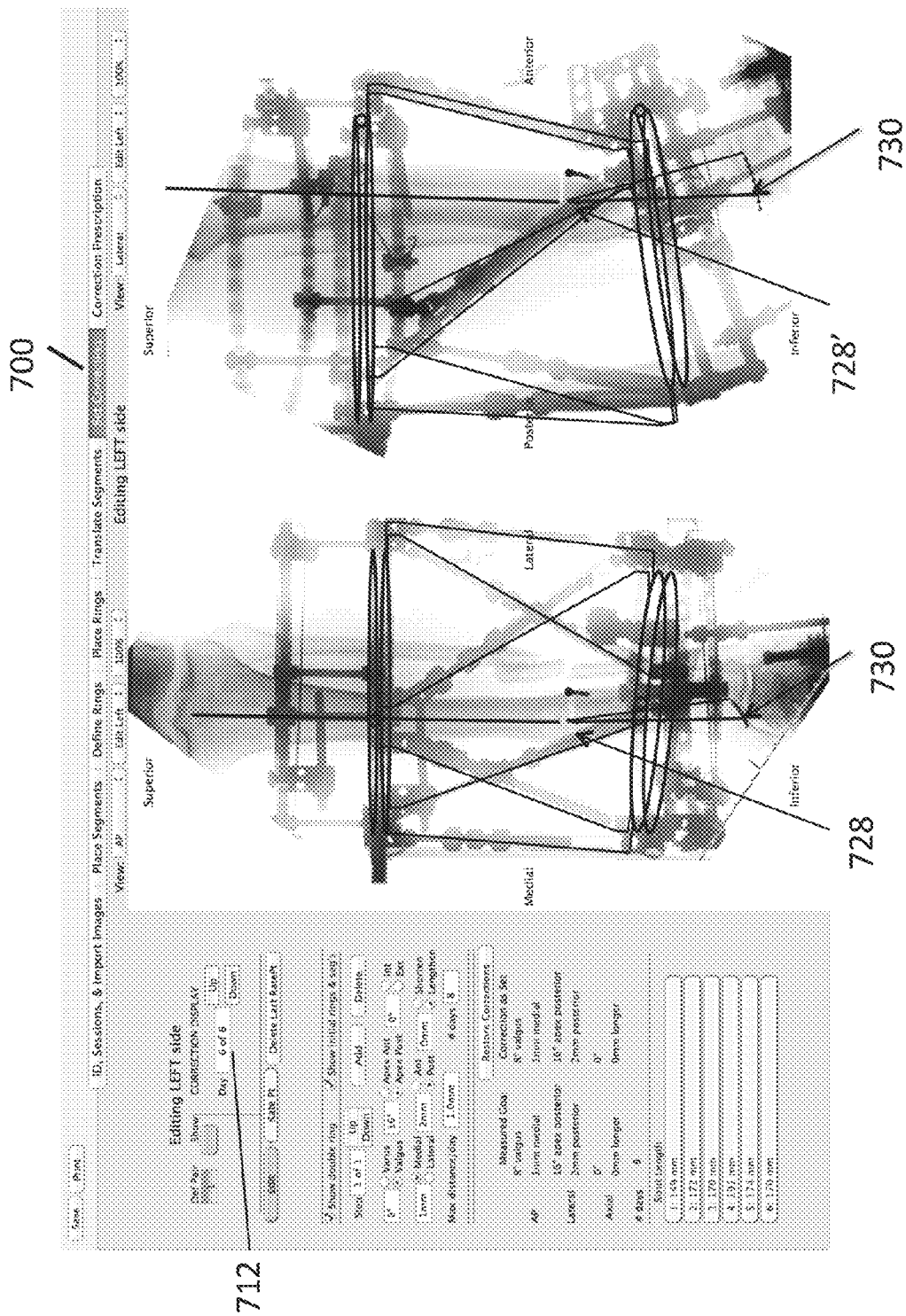
Figure 39E:
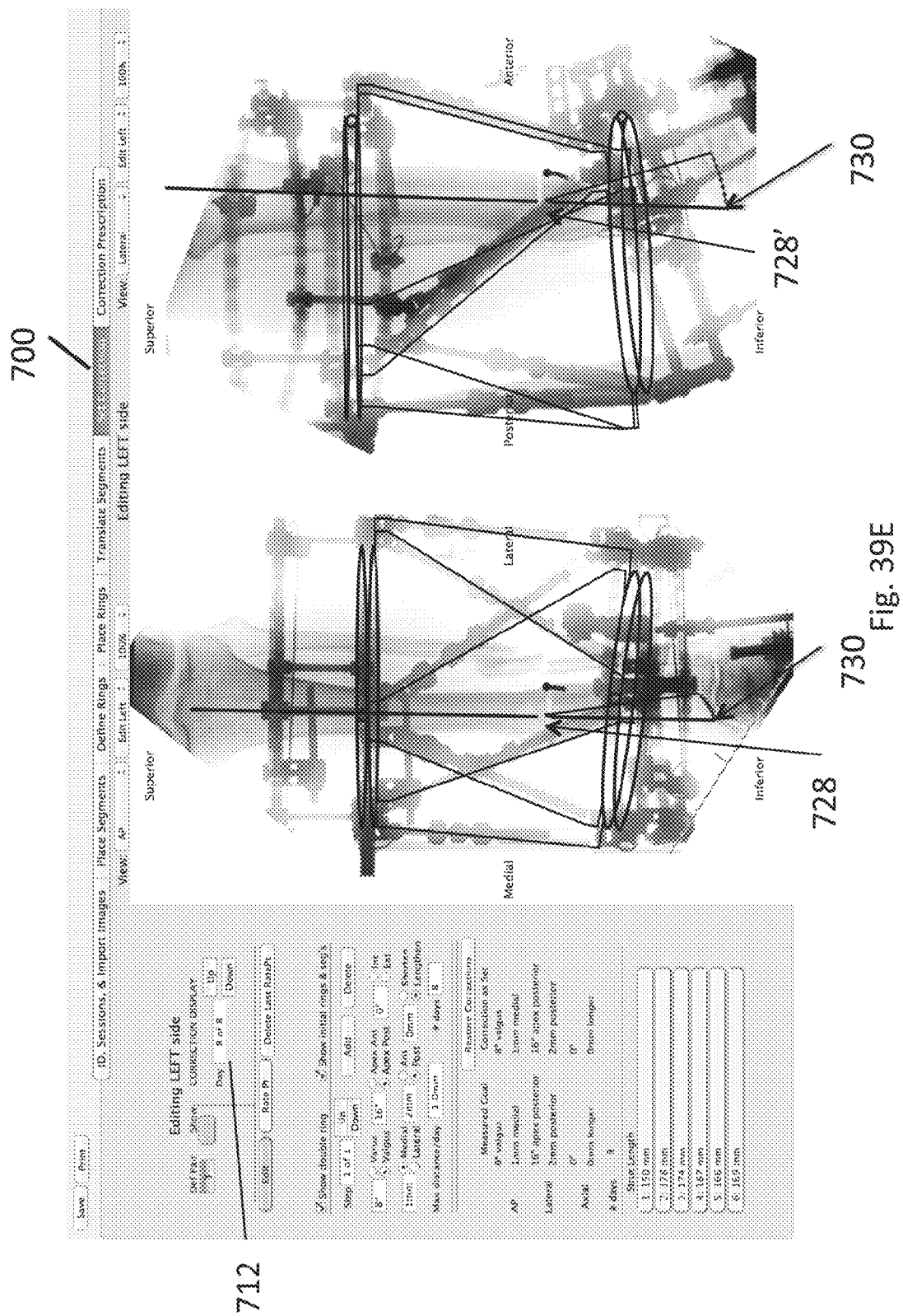

FIG. 38 shows a screen shot of the SET CORRECTION tab 700 where a rate point 716, 716' has been added and can be moved by the user. Rate points can be added 722, edited 724, and deleted 726. The rate point is a three dimensional entity and has a representation in both the AP and lateral planes of the digital medical images 230, 230'. The program calculates the true rate point correction path length 718 and then calculates the number of correction days 720 based on the correction rate (maximum distance/day). The rate point correction path 728 is shown. Rate points are identified by color with the deformity pair for which they are set.

FIGS. 39A-39E show screen shots of the SET CORRECTION tab 700 of corrections shown for days 0, 2, 4, 6, 8 on the correction display 712. Note the correction path 728, 728' and gradual correction of segments and rings. The user can scroll up and down the correction day number to see the effect of correction visually, shown by 730, 730'.

Figure 40:
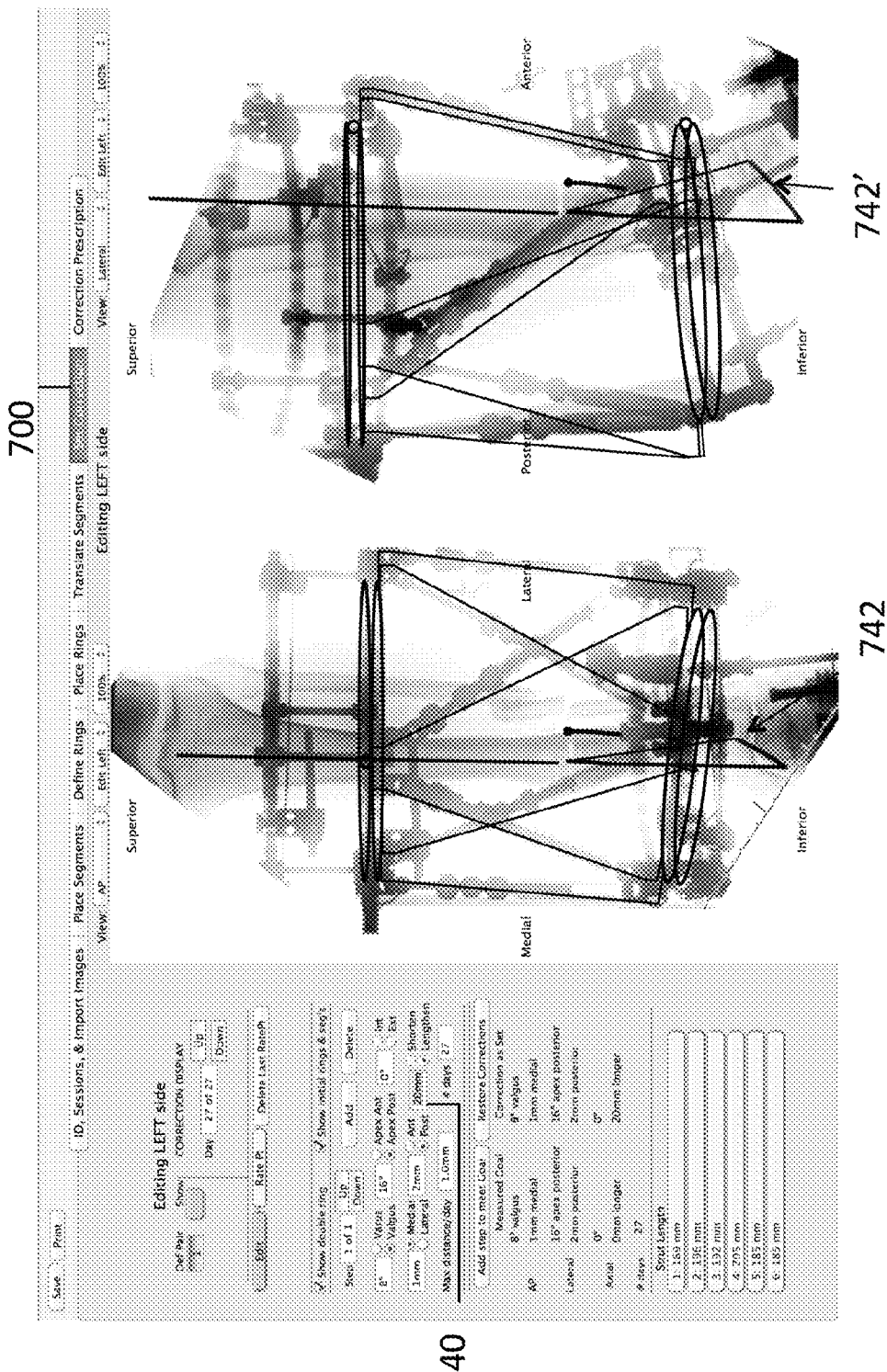
FIG. 40 shows a screen shot of the SET CORRECTION tab where a user is adjusting components of the correction individually, according to some embodiments of the present invention.

FIG. 40 shows a screen shot of the SET CORRECTION tab 700 where a user is adjusting components of the correction individually. Here the user has added 20 mm of length to the correction 740. Compared to FIG. 29, the correction paths 742, 742' are changed. The final result is similar to FIG. 29D except lengthened longitudinally.

Figure 41A:
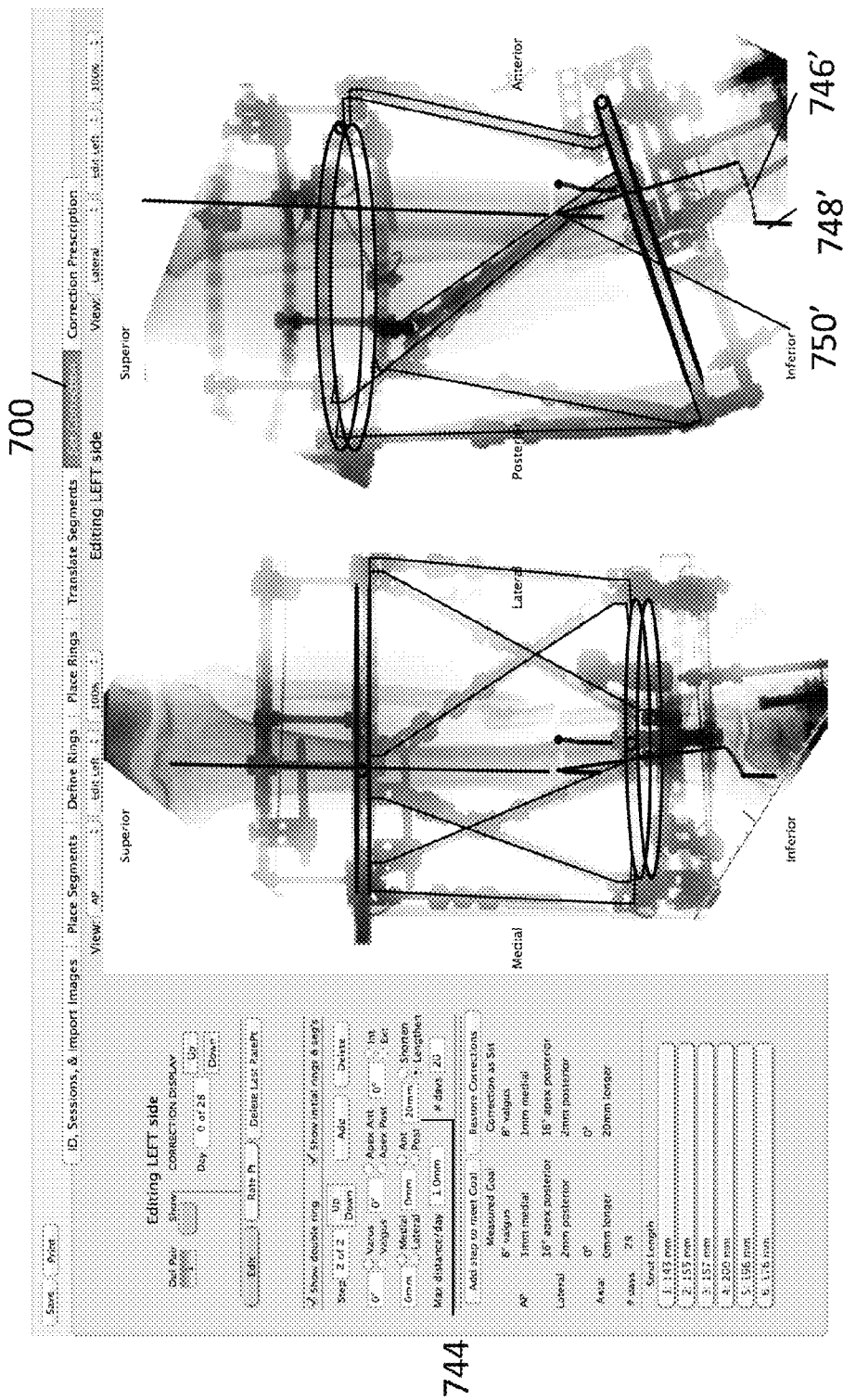
FIGS. 41A-41C show screen shots of a two-step correction on days 0, 8, and 28, respectively, according to some embodiments of the present invention.
Figure 41:
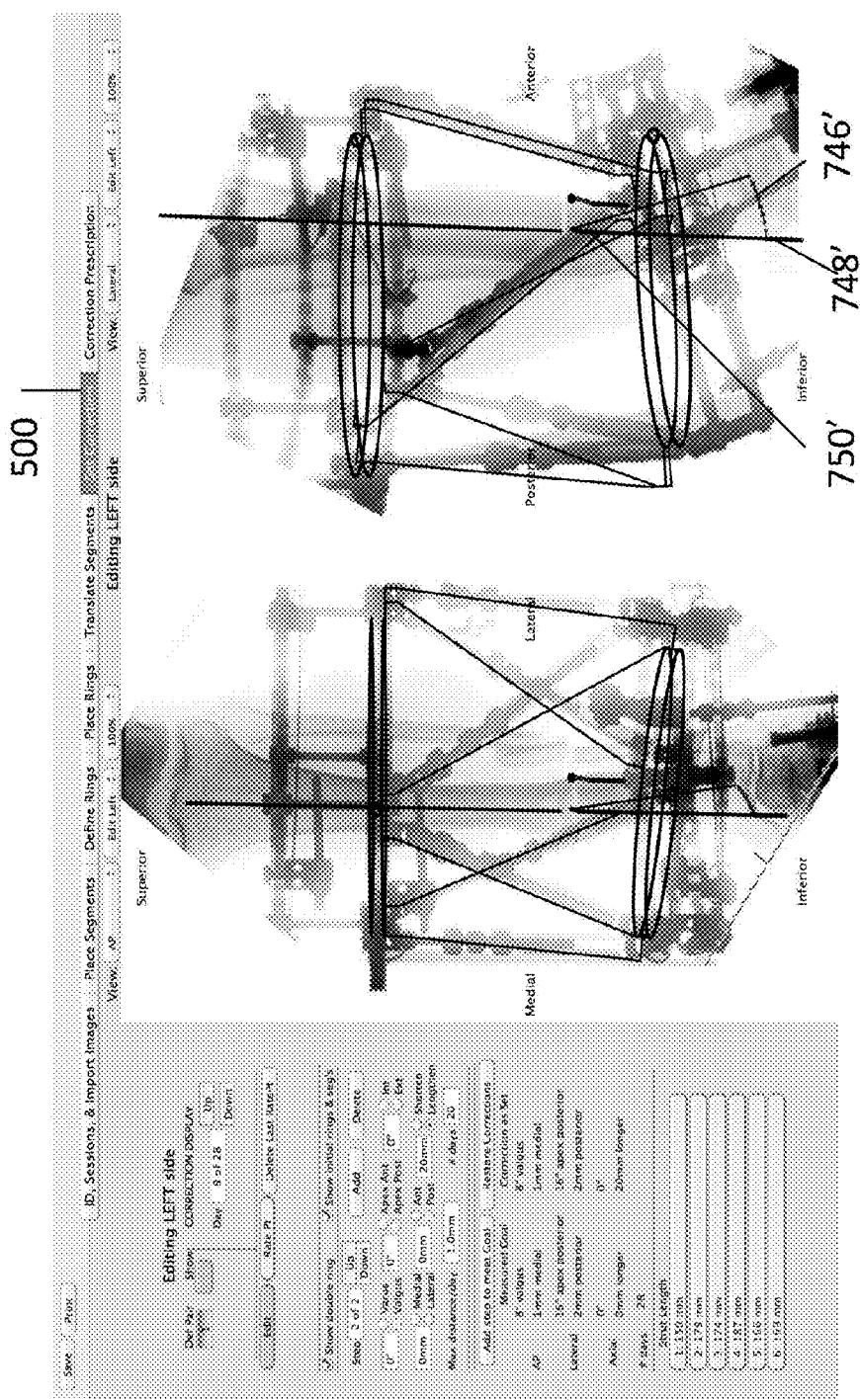
Figure 41C:
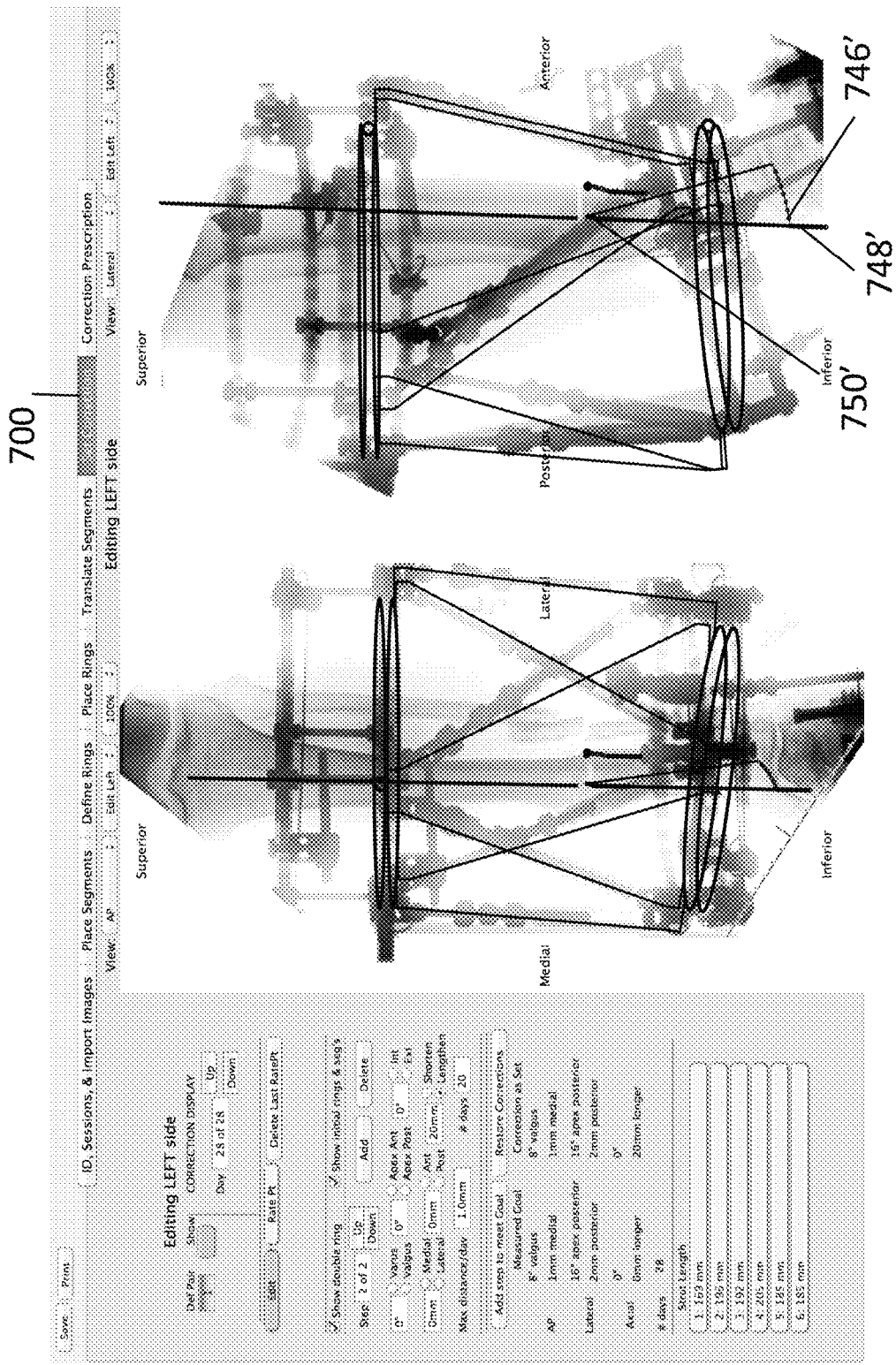

FIGS. 41A-41C show screen shots of a two-step correction on days 0, 8, and 28, respectively. In FIG. 41A step 1 of 2 is the initial correction calculated based on deformity parameters. Step 2 of 2 (shown here) adds 20 mm of length 744. Notice on the rate paths that initially the correction is angular (curved portion) 746' and then there is a linear translation (straight portion) 748'. In FIG. 41B on day 8 of 28 of the same two-step correction, the angular correction is complete 746' and the linear translation 748' is about to begin. Notice the segment endpoint position 750' on the correction path. In FIG. 41C on day 28 of 28, the moving segment endpoint 750' and ring 514' have been translated distally (linearly). The end result is the same as in FIG. 40.

Figure 42A:
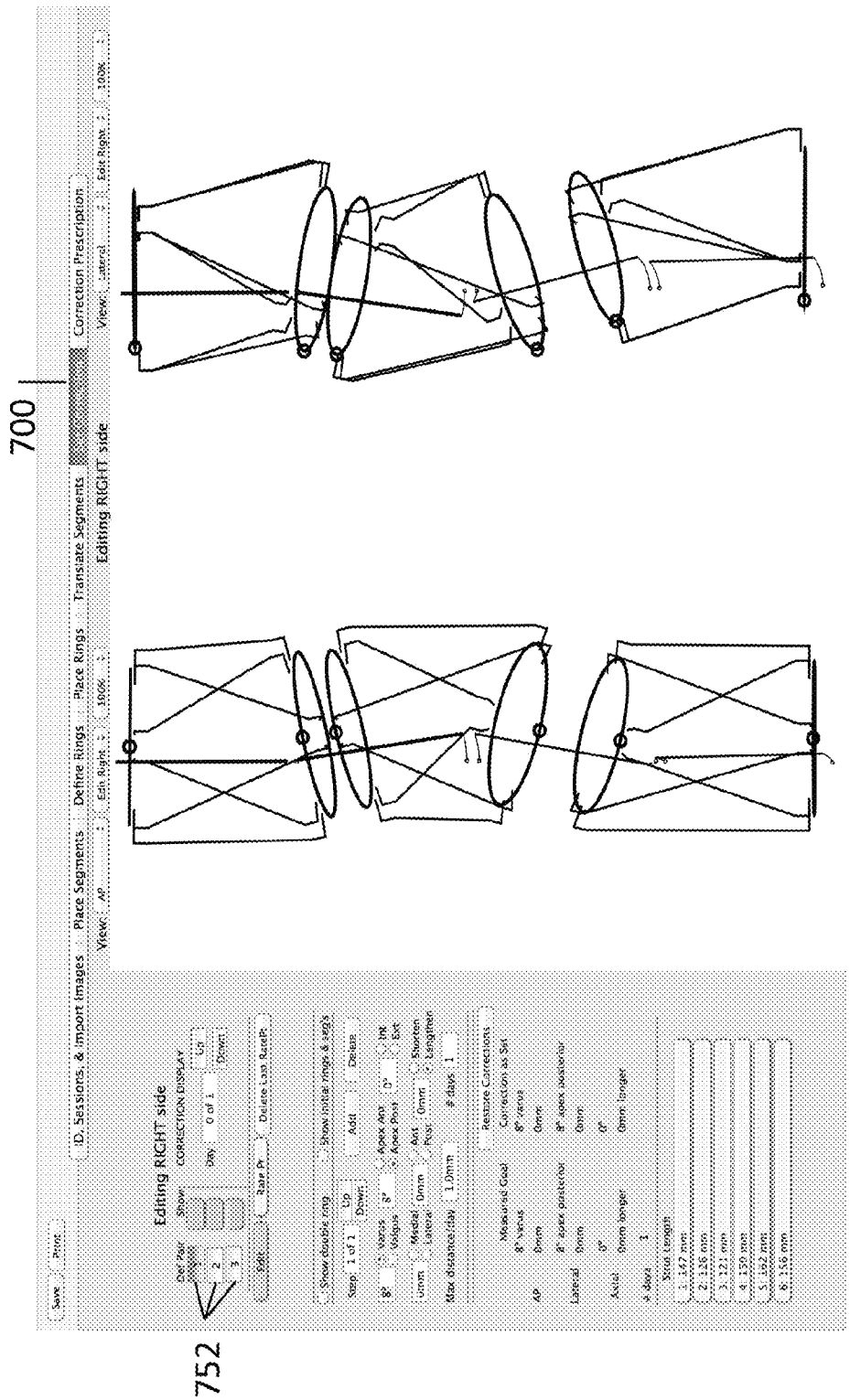
FIGS. 42A-42B show screen shots of the SET CORRECTION tab where corrections applied to multiple deformity pairs, according to some embodiments of the present invention.
Figure 42B:
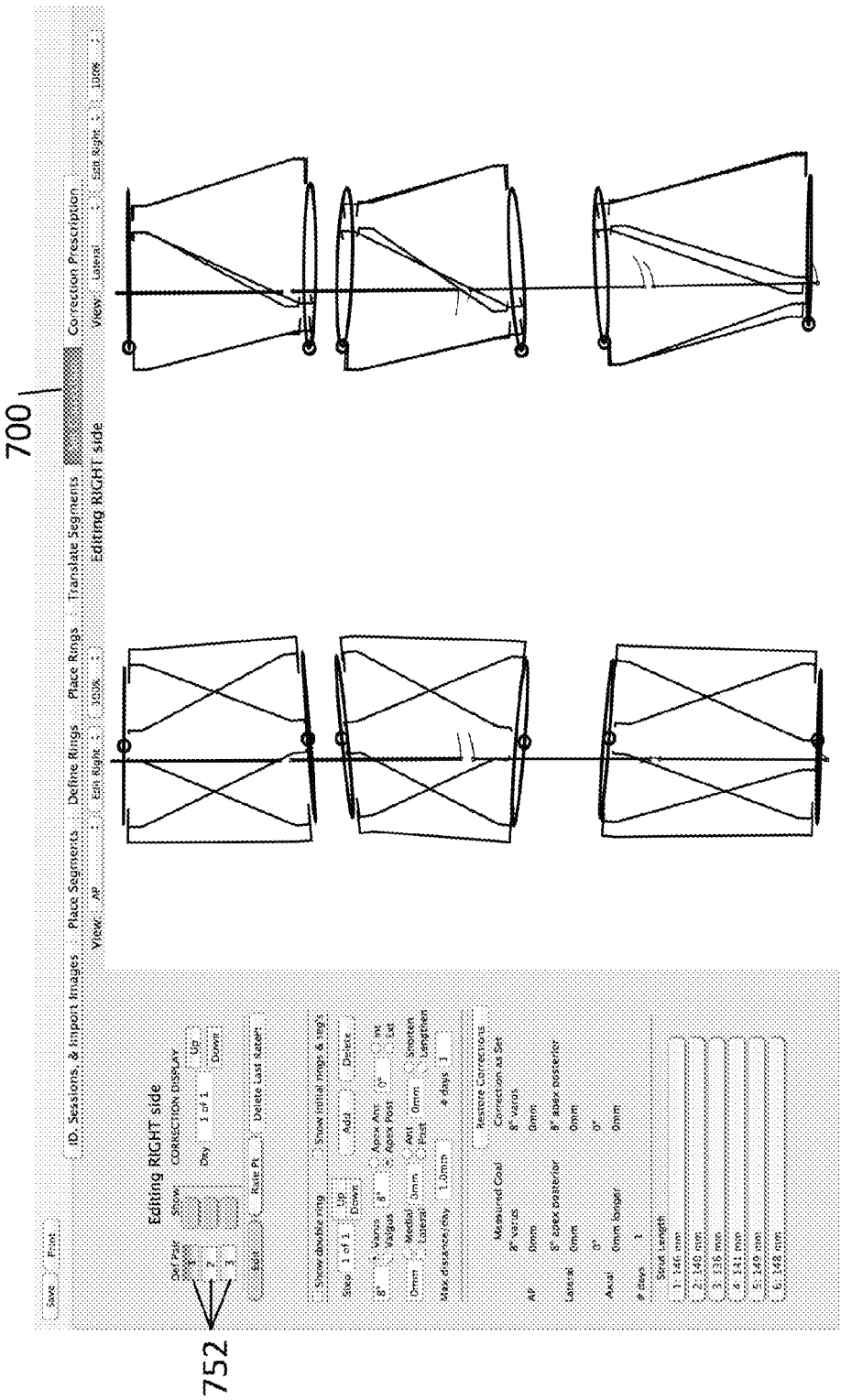
Figure 43:
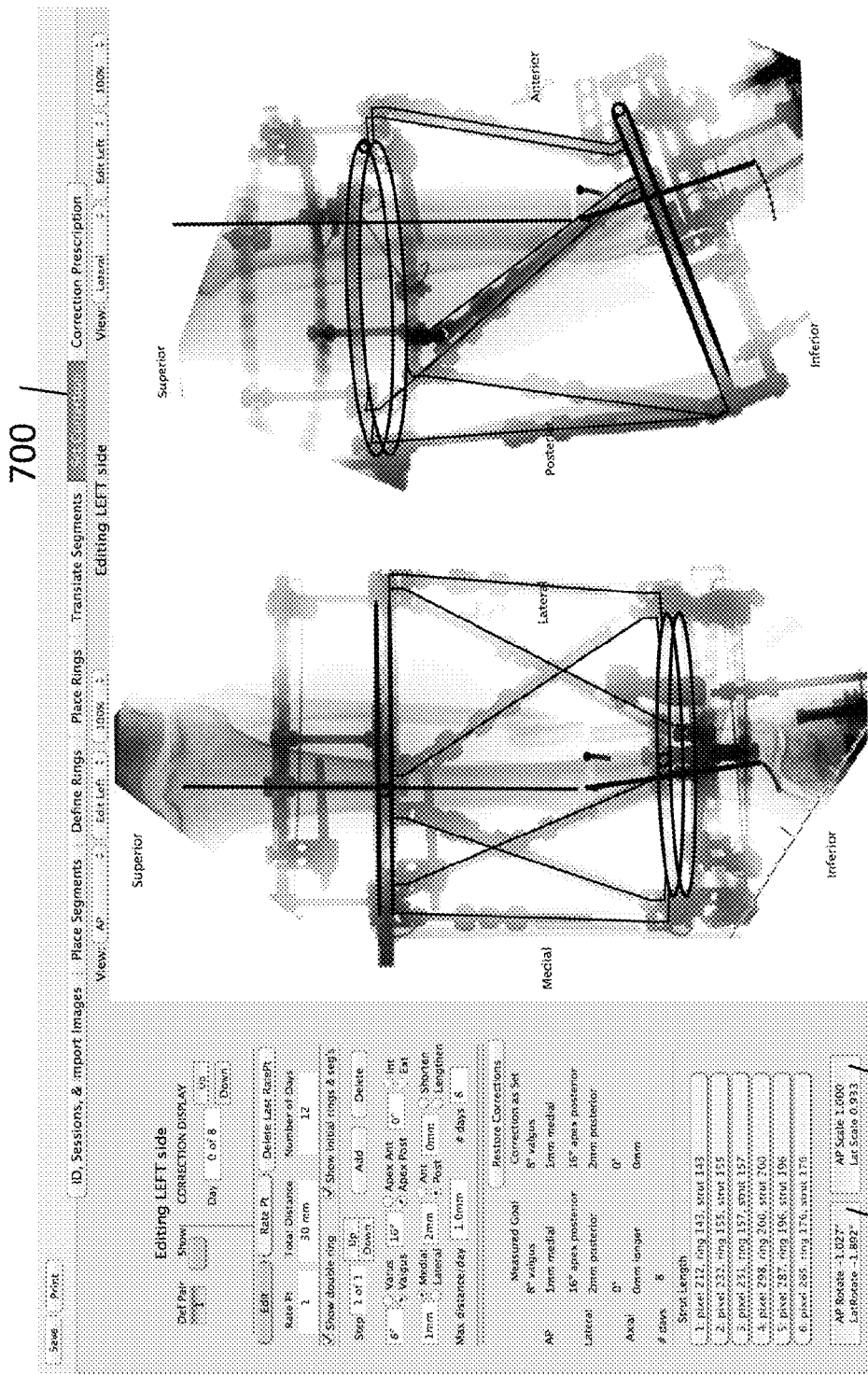
FIG. 43 is a screen shot showing a user's ability to view images with or without rotation for reference and/or scaling, according to some embodiments of the present invention.

FIGS. 42A-42B show screen shots of the SET CORRECTION tab 700 where corrections applied to multiple deformity pairs 752. FIG. 43 is a screen shot showing a user's ability to view images with or without rotation for reference 754 and/or scaling 756.

Figure 58A:
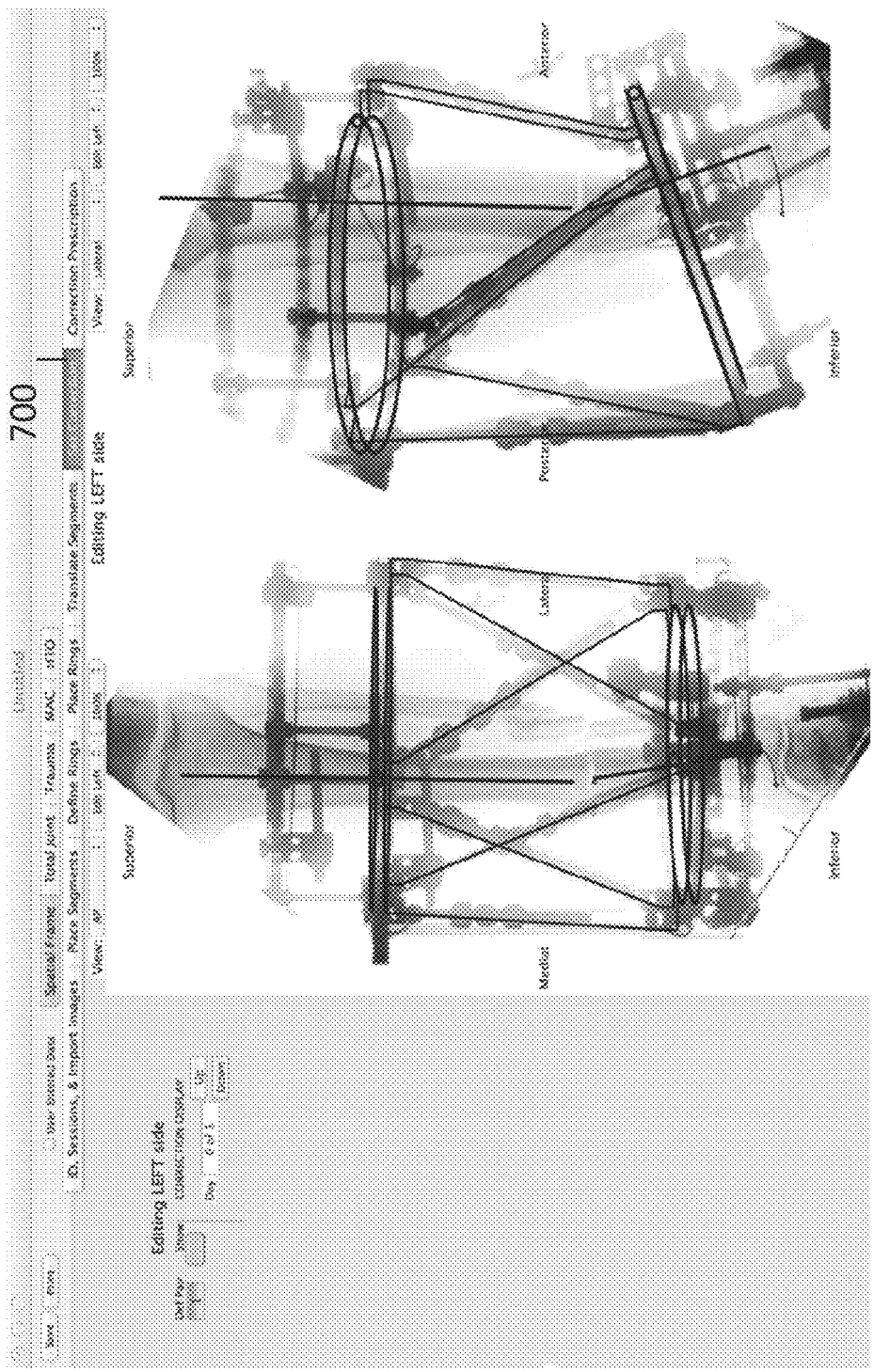
FIGS. 58A-B show screenshots of the SET CORRECTION tab on days 0 and 1 of a correction, according to some embodiments of the present invention.
Figure 58B:
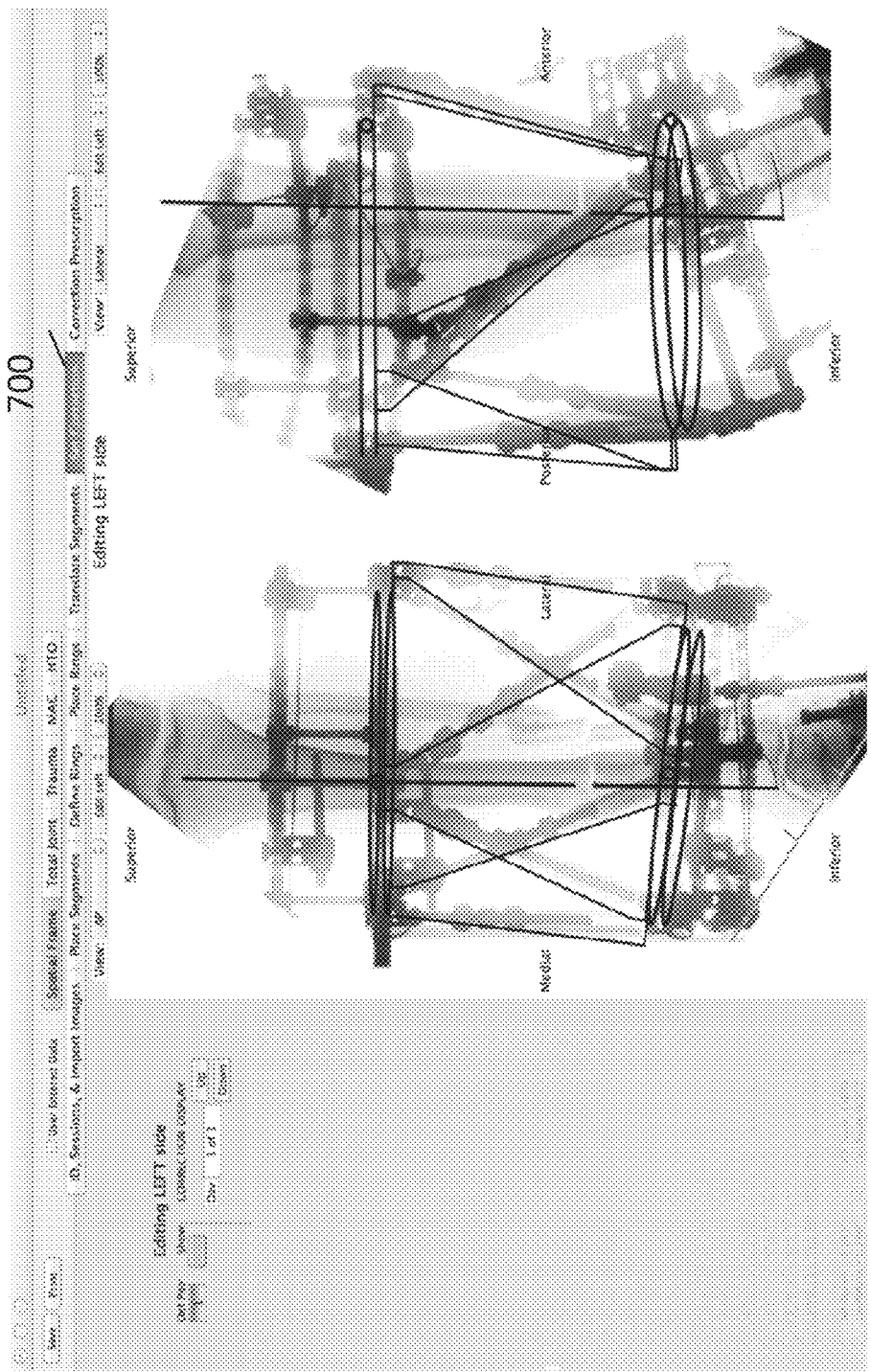

In some embodiments, the manipulation (rotation with three degrees of freedom and translation in three planes) of a 3D representation of a ring, as described in the sections above, is made by manipulating the end-points of the orthogonal vector ($V_{orthogonal}$) that defines the 2D major plane of the ring. Manipulation of these endpoints can be performed, as described above. We may also manipulate the 3D ring rotation reference point ($P_{ref}$) to keep track of ring azimuthal rotation during manipulation. The methods described above are used to manipulate the end-points of $V_{orthogonal}$ to find $V'_{orthogonal}$ and to manipulate $P_{ref}$ to find $P'_{ref}$. Next, we define the plane of the ring after manipulation using $V'_{orthogonal}$ and $P'_{ref}$ as described in the plane definition section above. Orthogonal vectors ($V'_{xy\text{-}ringplane}$ and $V'_{zy\text{-}ringplane}$) along the long axes of the ring are defined in the plane of the ring using: the ring's center point ($P'_{c\text{-}ringplane}$), which is defined during ring plane calculation; the manipulated and converted ring rotation reference point in the plane of the ring ($P'_{ref\text{-}ringplane}$); and the ring azimuthal rotation angle. Finally, converting from the plane of the ring back to 3D space, as described in the plane definition section above, returns vectors representing the axes of the ring in the xy and zy planes of 3D space $V'_{xy}$ and $V'_{zy}$. Converting $P'_{ref\text{-}ringplane}$ from the plane of the ring back to 3D space returns the manipulated reference point ($P'_{ref}$). With this information, all the points of the ring can be constructed as described above. FIGS. 58A-B show screenshots of the SET CORRECTION tab 700 on days 0 and 1 of a correction.

Figure 59A:
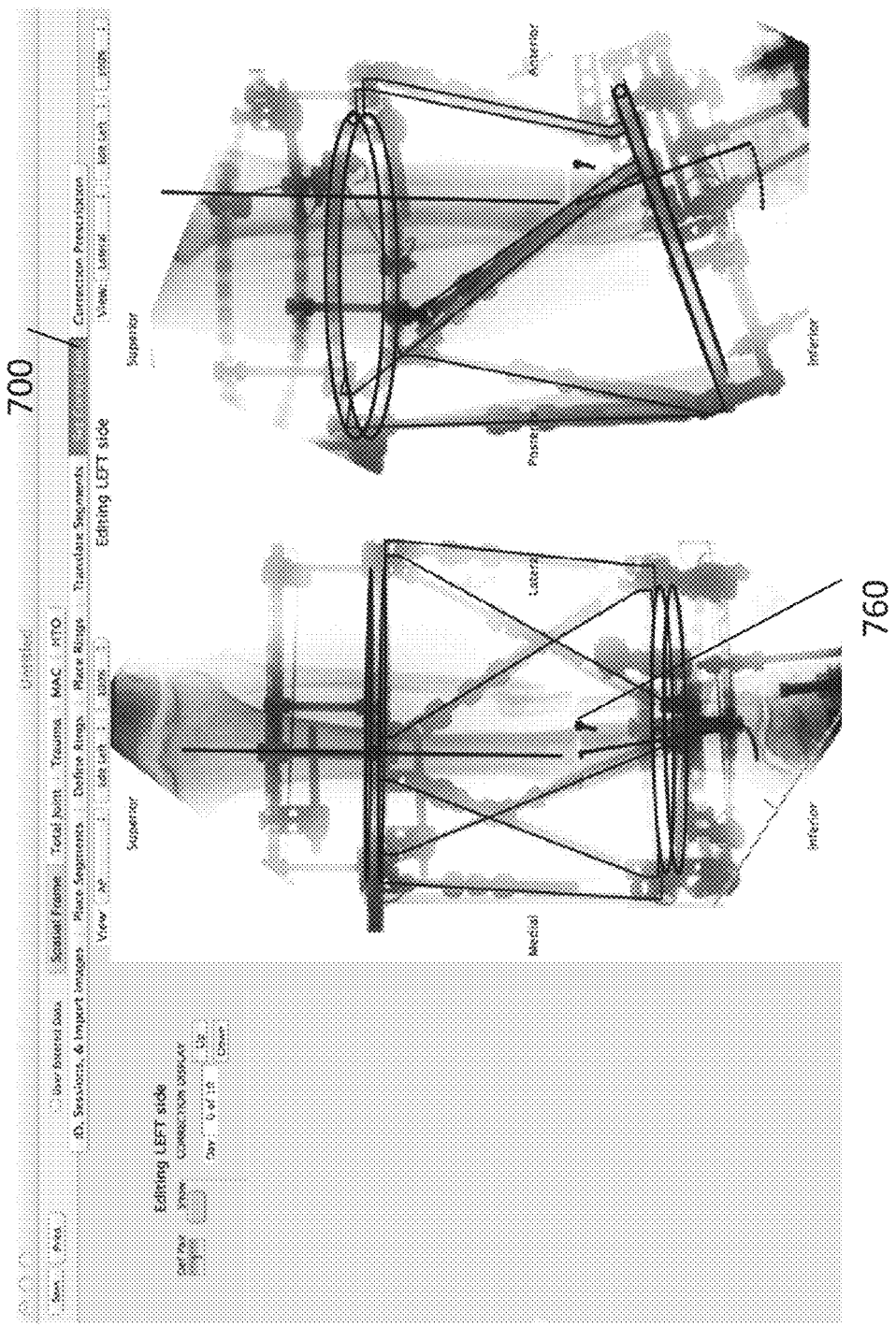
FIGS. 59A-F show screen shots of a manipulation with a rate point on days 0, 2, 4, 6, and 8 of 8, according to some embodiments of the present invention.
Figure 59B:
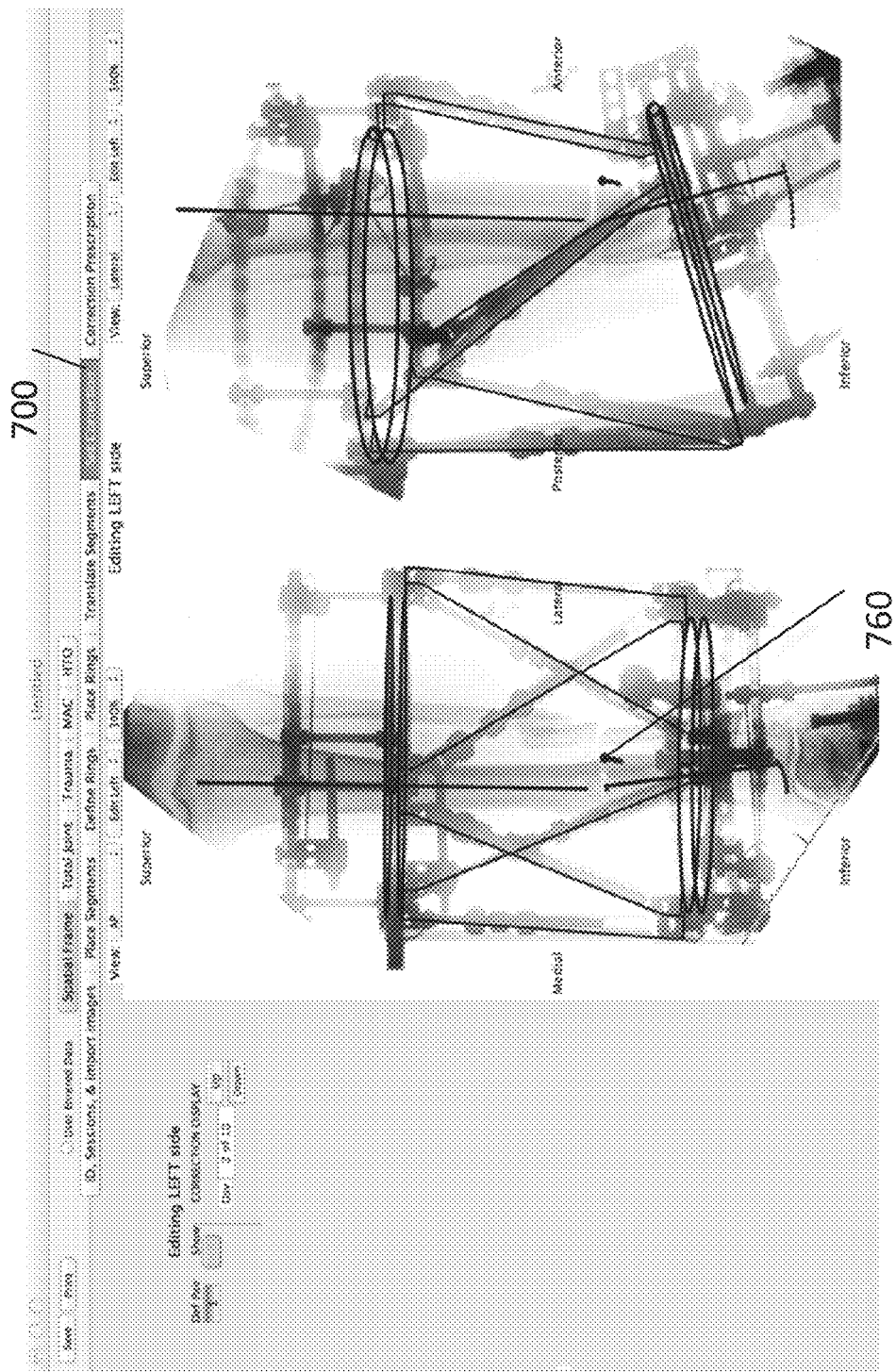
Figure 59C:
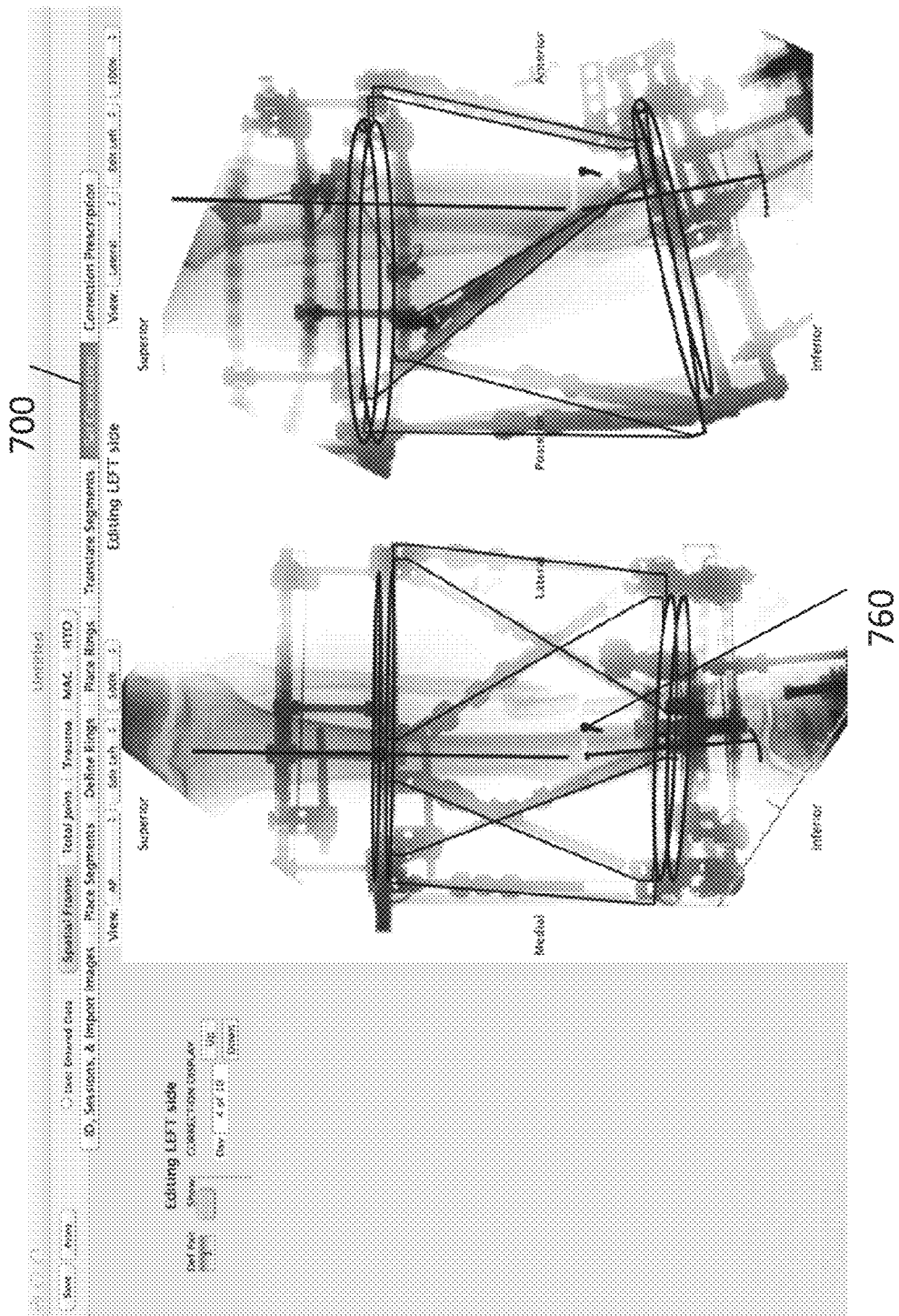
Figure 59D:
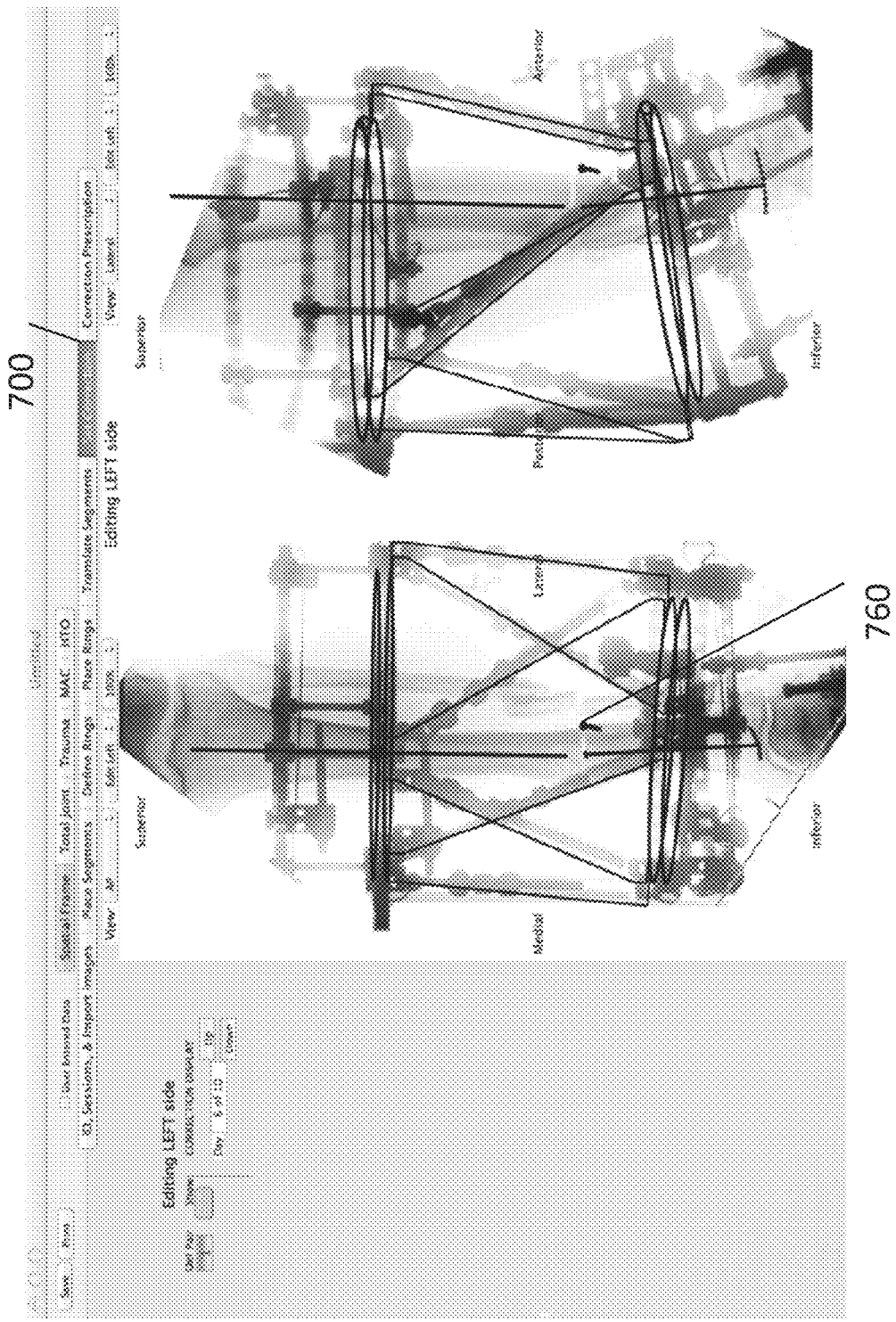
Figure 59E:
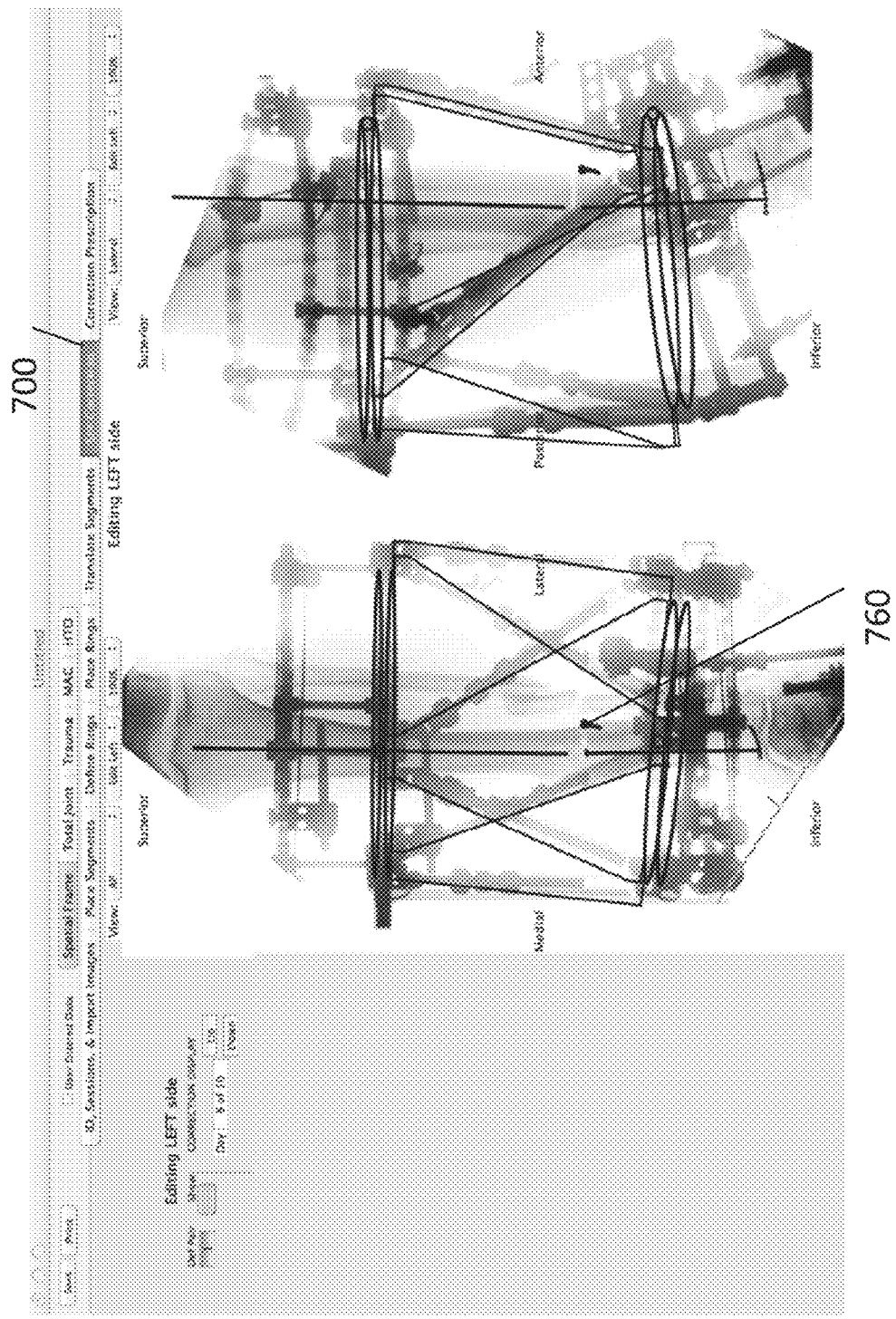
Figure 59F:
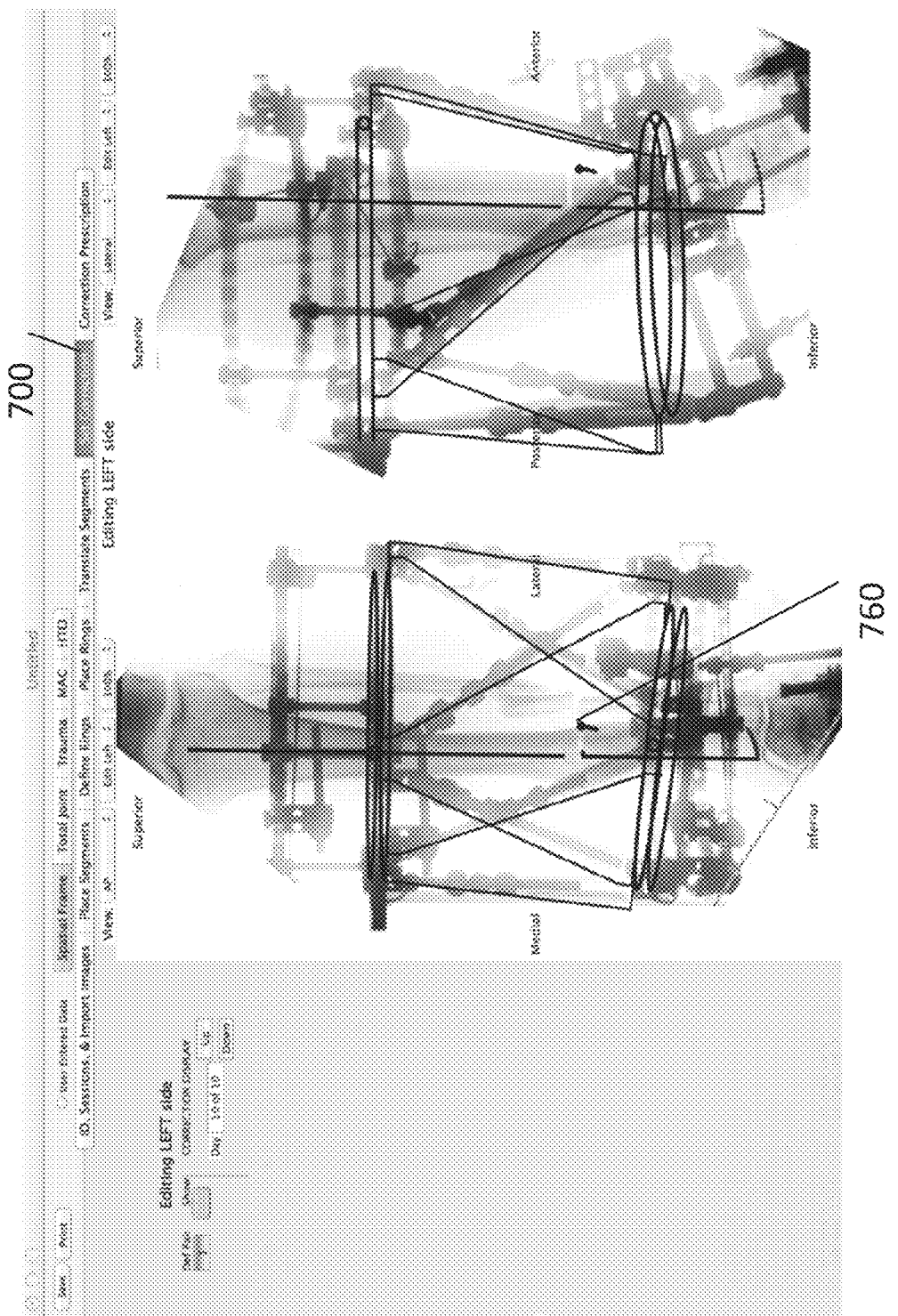

In order to determine the number of days over which a ring manipulation is to occur, we can define one or more rate-points on the rotated for reference and scaled images in two or more planes ($RP(n)=(x_n, y_n, z_n)$). FIG. 59A shows a screen shot of the SET CORRECTION tab 700 of a manipulation with a rate point 760 on day 0 of 10. The rate point is manipulated by rotating in three planes and translating in three planes as defined above. Each of the six parameters of the total manipulation ranging over a large number (e.g. x=0 to 1000) are divided, such that each rotational and translational manipulation parameter at sub-manipulation x is multiplied by x/1000. Next the system calculates each of these sub-manipulations to find $RP'(n,x)=(x'_{n,x}, y'_{n,x}, z'_{n,x})$. Finally, an approximation of the distance over which $RP(n)$ moves over the entire correction is calculated:

$$\text{distance}(n) = \sum_{x=0}^{999} \sqrt{(x'_{n,x} - x'_{n,x+1})^2 + (y'_{n,x} - y'_{n,x+1})^2 + (z'_{n,x} - z'_{n,x+1})^2} \quad (52)$$

The system can calculate the number of days required to complete a manipulation by dividing the user defined manipulation rate (rate(n)) for a given rate point (rate(n));

$$\text{number\_of\_days}(n) = \frac{\text{distance}(n)}{\text{rate}(n)} \quad (53)$$

Alternatively, if the user defines the number of days (number_of_days(n)), the rate of manipulation can be determined:

$$\text{rate}(n) = \frac{\text{distance}(n)}{\text{number\_of\_days}(n)} \quad (54)$$

Finally, the total number of days for a given manipulation is chosen as the maximum value of number_of_days(n) for the number (n) of defined rate points.

Once the number of days (number_of_days) over which a ring manipulation will occur is known, the manipulation of the ring for each day is defined by dividing each of three rotational and three translational components of the total ring manipulation desired by the number_of_days and calculating the sub-manipulations of the ring for each day, as described in the section on manipulation of ring parameters above. In response to the bone correction data user input, the system can generate a graphical simulation of the bone deformity correction treatment superimposed on the at least one digital medical image. FIGS. 59A-F show screen shots of the SET CORRECTION tab 700 illustrating a manipulation with a rate point 760 on days 0, 2, 4, 6, and 8 of 8.

Correction Prescription Tab

Figure 44:
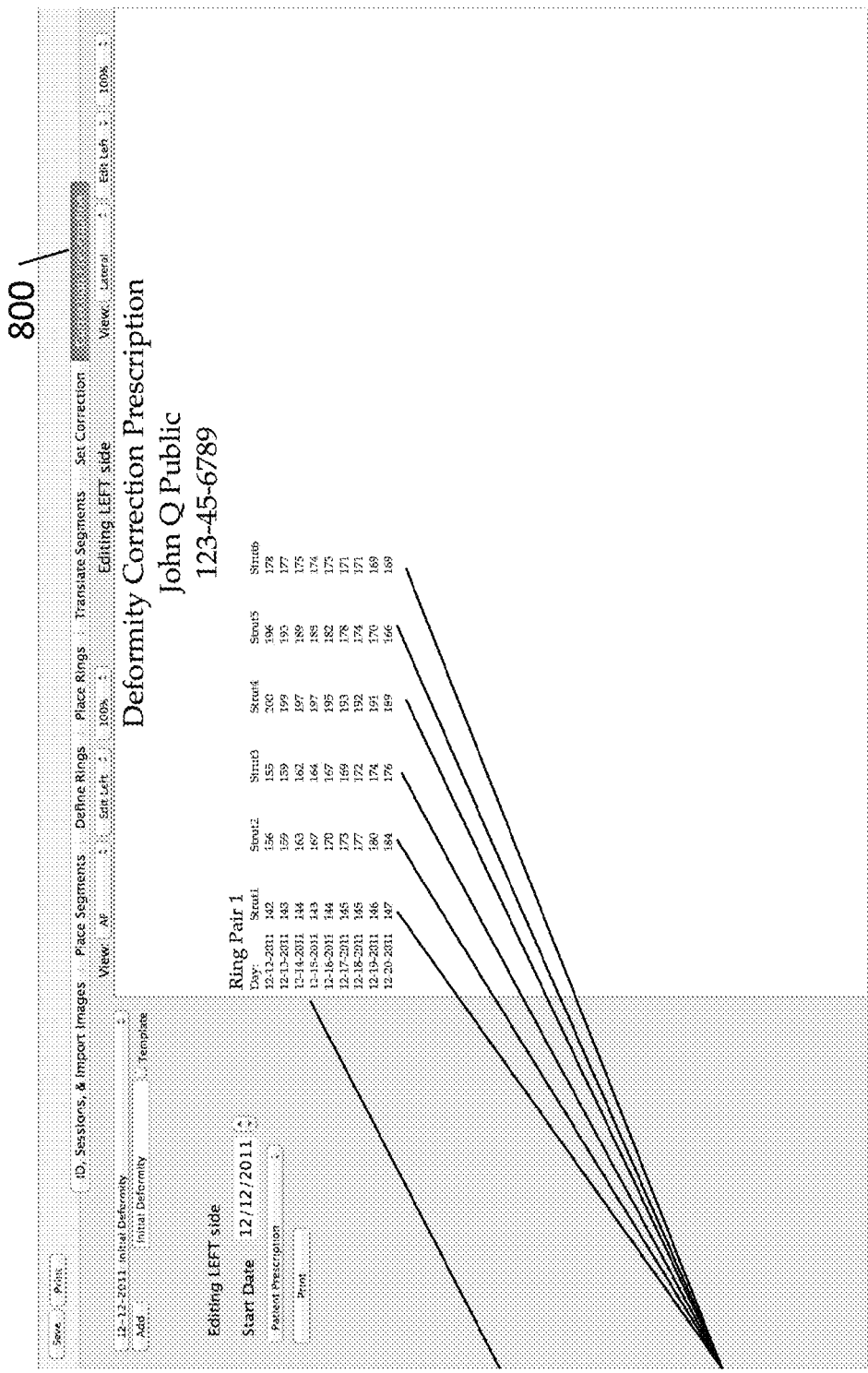
FIG. 44 shows a screen shot of the "CORRECTION PRESCRIPTION" tab, according to some embodiments of the present invention.

FIG. 44 shows a screen shot of the "CORRECTION PRESCRIPTION" tab 800. Based upon the correction data entered by the user, the system then generates a prescription in the form of a bone deformity correction plan. The CORRECTION PRESCRIPTION tab displays the prescription for performing the correction. The prescription is a list of strut lengths 810 that the patient or a healthcare professional should apply for each correction day 812. There are 6 strut lengths per day, one for each strut on the ring. A different prescription will be generated for each deformity pair. Advantageously, the system allows calculating, according to the bone correction plan, for various strut sizes corresponding numbers of strut replacements, to allow a selection of strut sizes that minimize the number of strut replacements on the external fixator (not shown).

In one embodiment, one special case involving drawing rings and struts on a display involves templating a pair of rings and set of struts to an anatomic segment, with a given ring manipulation. The goal of templating is to pre-operatively determine a set of strut lengths that fits the patient's anatomy, as well as potentially to minimize the number of times a strut has to be exchanged during the manipulation process. Real-life struts have a prescribed range over which they function. During a manipulation, the struts may have to physically be exchanged for a strut with the next longer or shorter prescribed range. In practice, the user would like to minimize the number of these strut exchanges that need to be performed.

Rings and struts can be drawn on images of anatomic segments and manipulated as described above, allowing the user to approximate the location for the rings. This defines a set of ring placement parameters such as the ring's center point ($P_c=(x_c,y_c,z_c)$), the tilt relative to the XY ($\theta_{XY}$) and ZY ($\theta_{ZY}$) planes, and the azimuthal rotation azimuthal rotation ($\phi$). Alternatively, the program can define a set of initial parameters based on the location of anatomic segments.

The program can find the position and rotation of the rings that would minimize the number of strut exchanges required by the user by varying these parameters over a defined range and figuring the number of times a strut would need to be exchanged for a given set of parameters.

For example, the program could vary $y_c$ by $\Delta y$ over a range n=–N to N (N and $\Delta y$ can be user or programmatically defined).

$$y_c(n)=y_c+n\cdot\Delta y \quad (55)$$

$$P_c(n)=(x_c,y_c(n),z_c) \quad (56)$$

The program calculates the number of strut exchanges that would be required for the given ring manipulation for the set of ring parameters defined by each n. The n value that returns the minimal number of strut exchanges is termed $n_{min}$. Finally, the ring parameters and strut lengths defined by $n=n_{min}$ are calculated and returned to the user.

This prescription for a bone deformity correction will become part of the patient record to be saved as part of the "ID, SESSIONS, & IMPORT IMAGES" tab. In the case where the patient has already undergone an osteotomy and has had an external fixator affixed to the bone, the patient may receive a hard copy, email, or other type of electronic communication of the prescription of strut lengths.

Exemplary Methods

Figure 45A:
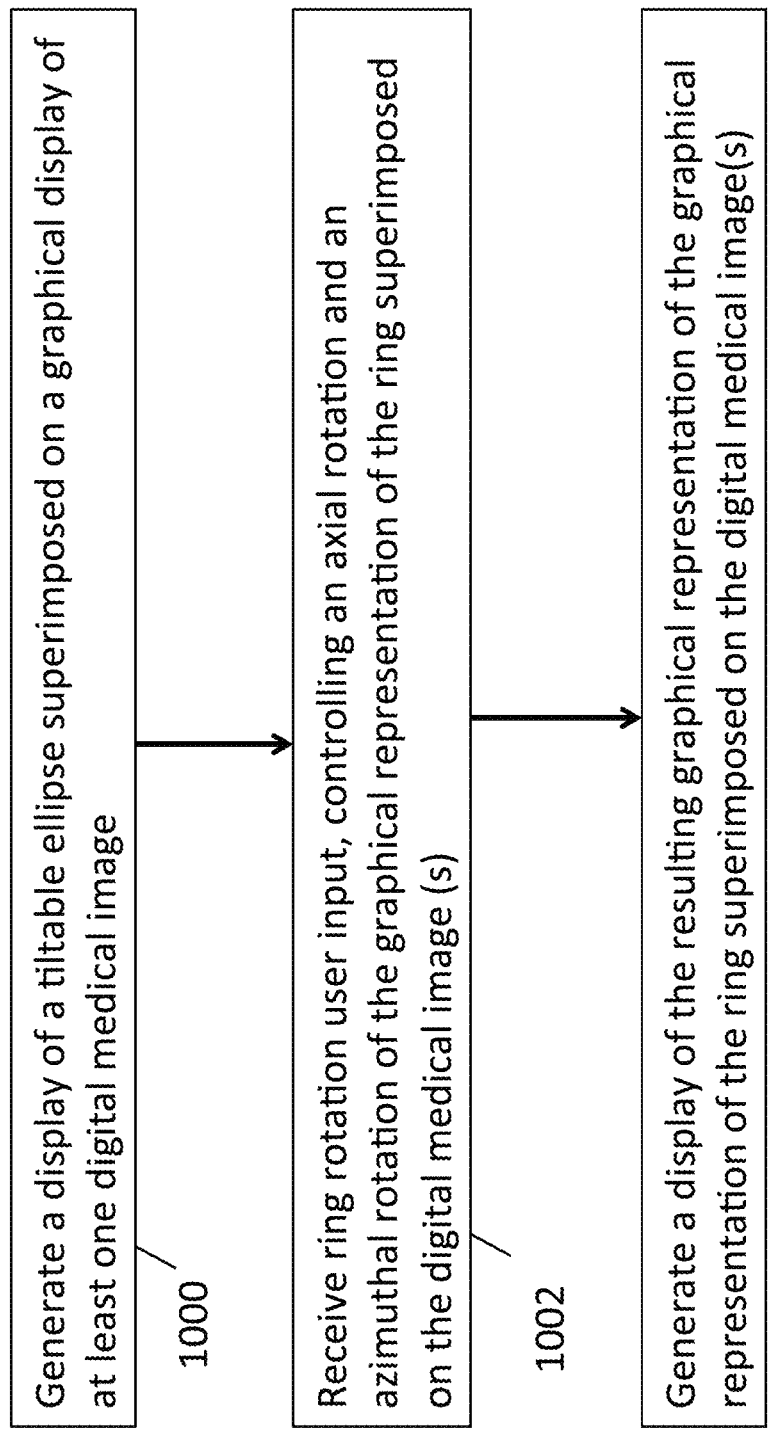
FIGS. 45A-J illustrate a computer-implemented method, along with its alternative embodiments, to generate a graphical display of a ring superimposed on a digital medical image, according to some embodiments of the present invention.

FIGS. 45A-J illustrate a computer-implemented method, along with its alternative embodiments, to generate a graphical display of a ring superimposed on a digital medical image, according to some embodiments of the present invention. As shown in FIG. 45A, the computer-implemented method includes instructions to generate a display of a tiltable ellipse superimposed on a graphical display of at least one digital medical image 1000, receive ring rotation user input controlling an axial rotation and an azimuthal rotation of the graphical representation of the ring superimposed on the digital medical image(s) 1002, and generate a display of the resulting graphical representation of the graphical representation of the ring superimposed on the digital medical image(s) 1004.

Figure 45B:
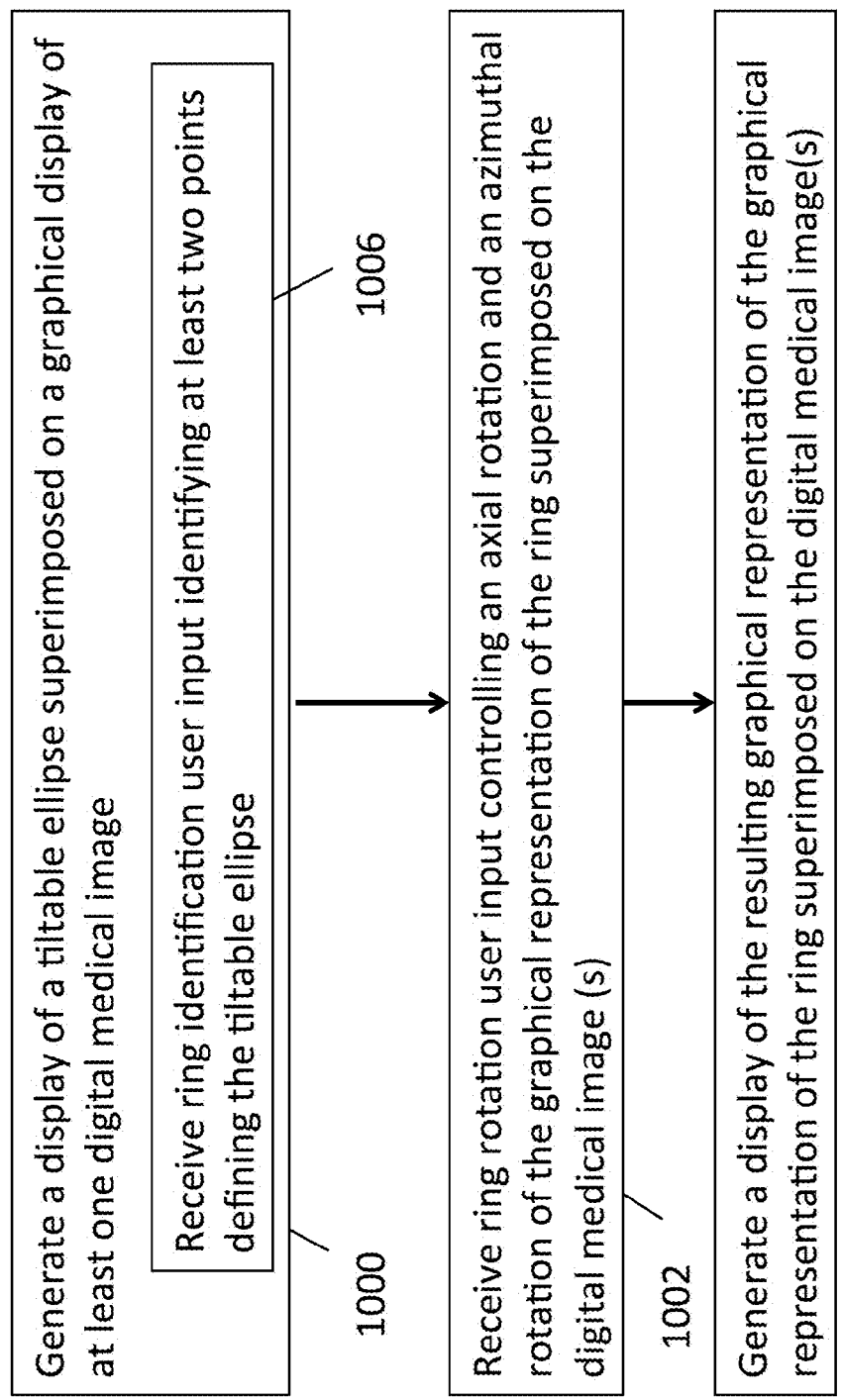
Figure 45C:
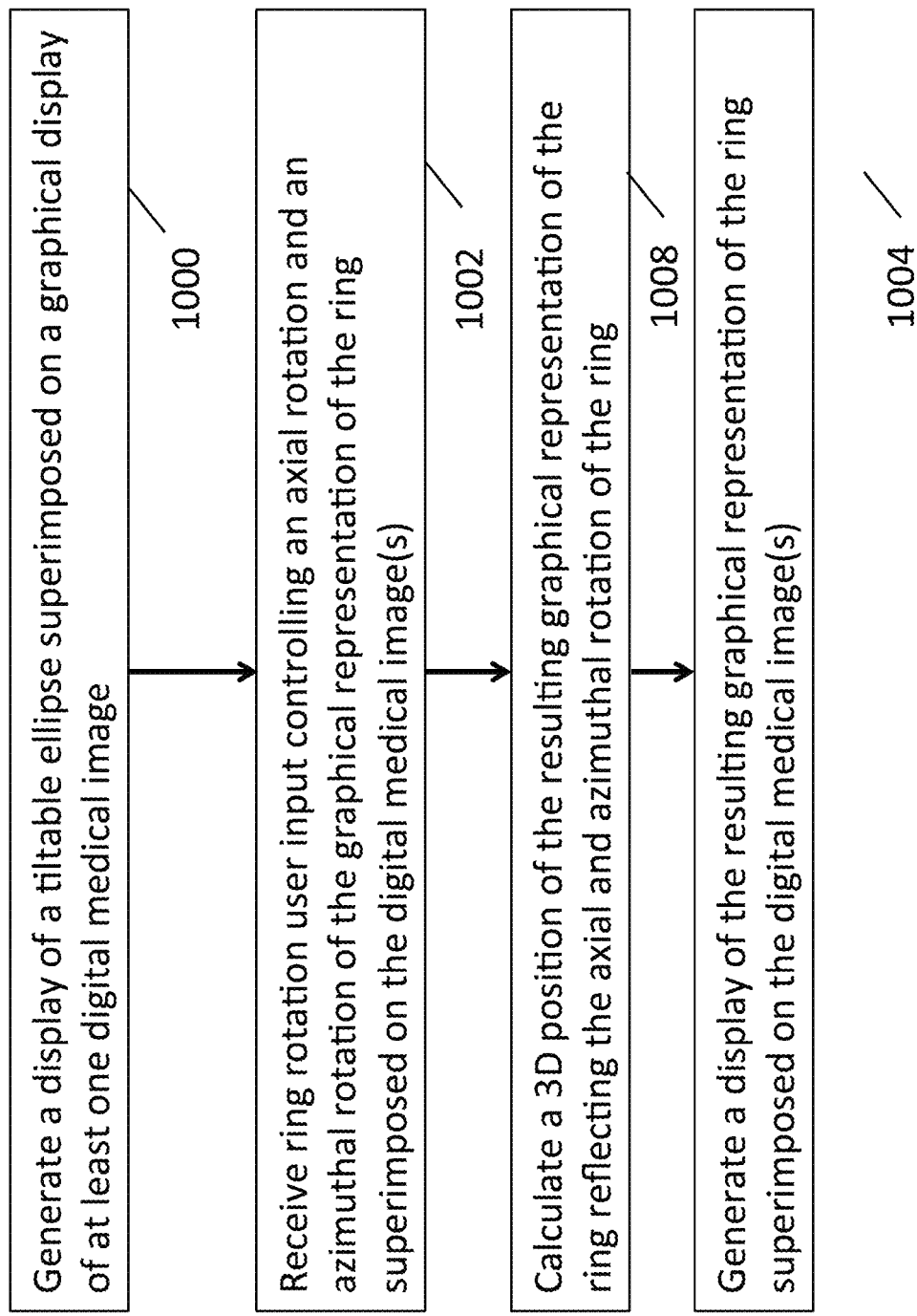
Figure 45D:
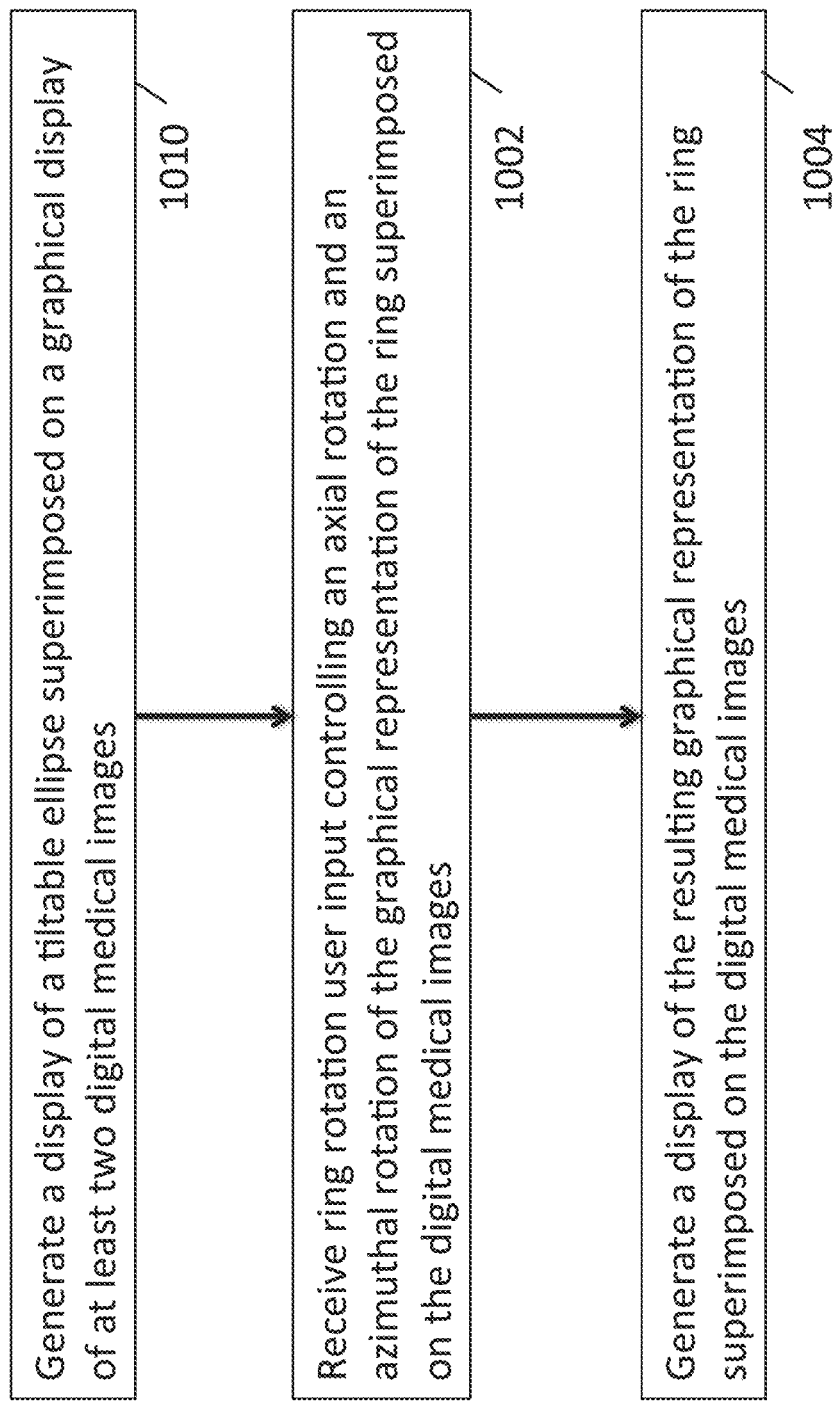

In other embodiments, the computer-implemented method further includes instructions to receive ring identification user input identifying at least two points defining the tiltable ellipse 1006, as shown in FIG. 45B, and calculate a 3D position of the resulting graphical representation of the ring reflecting the axial and azimuthal rotation of the ring 1008, as shown in FIG. 45C. In an alternative embodiment shown in FIG. 45D, the computer-implemented method further includes instructions to generate a display of a tiltable ellipse superimposed on a graphical display of at least two digital medical images 1010, receive ring rotation user input controlling an axial rotation and an azimuthal rotation of the graphical representation of the ring superimposed on the digital medical images 1002, and generate a display of the resulting graphical representation of the ring superimposed on the digital medical images 1004.

Figure 45E:
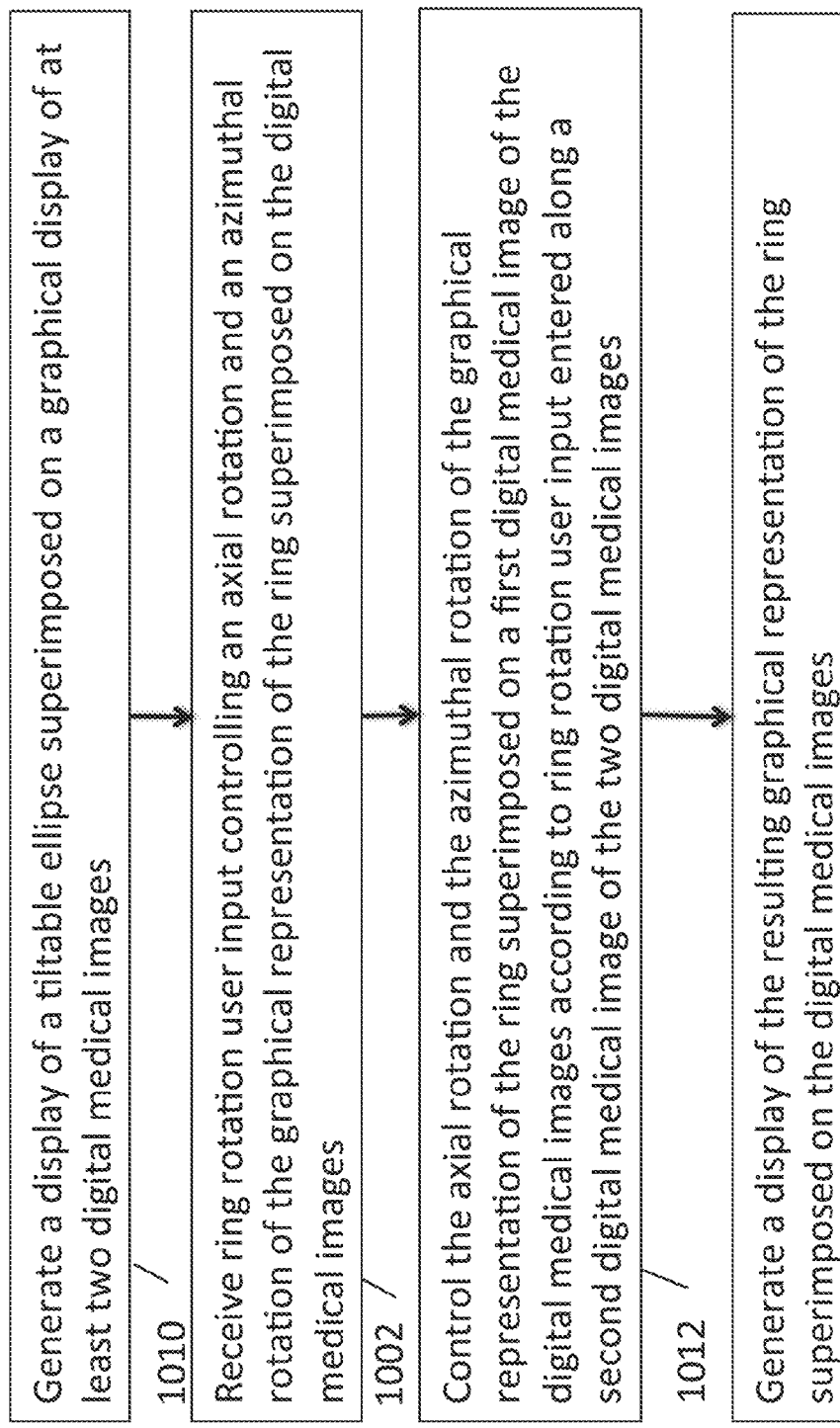
Figure 45F:
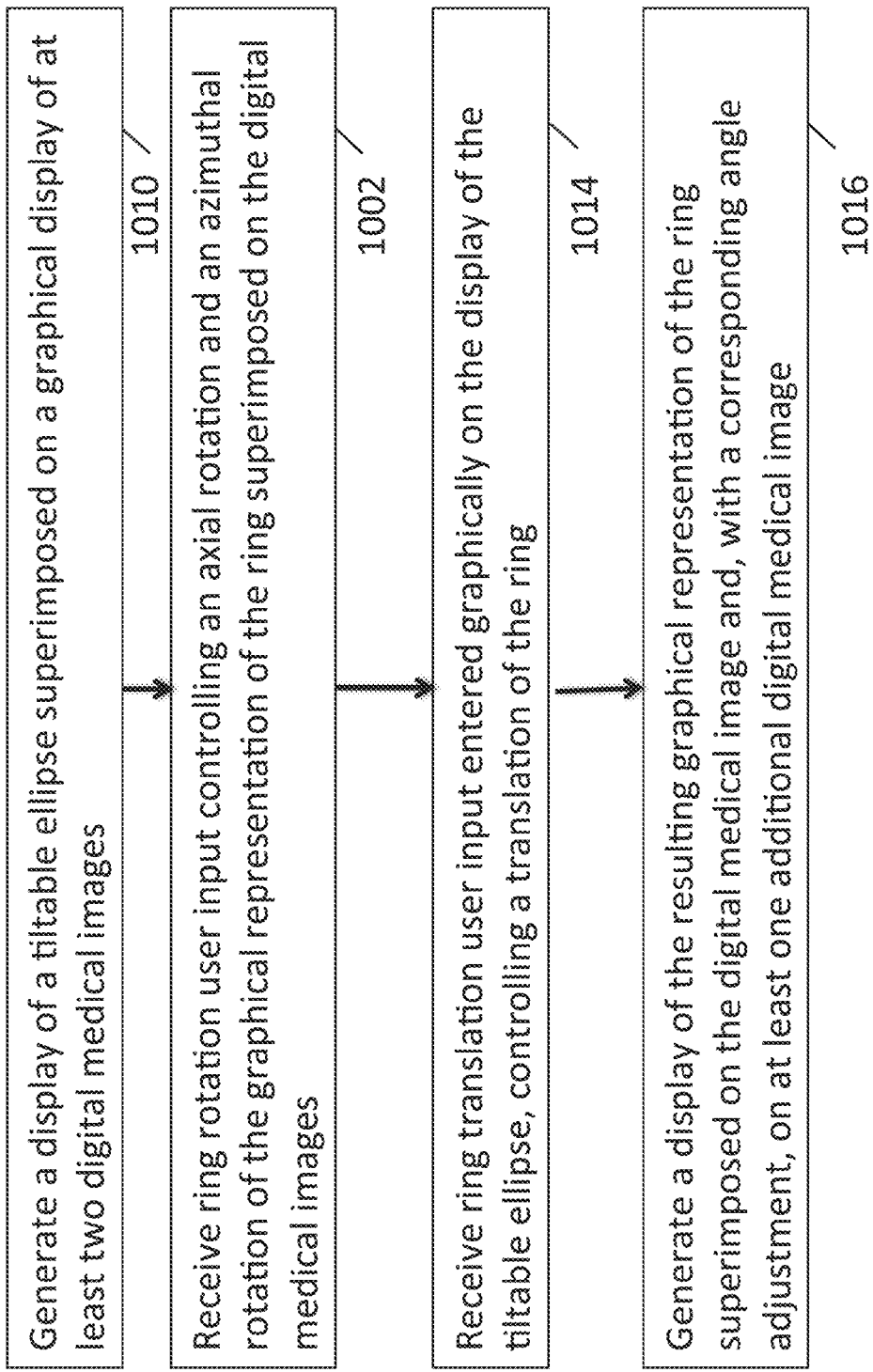
Figure 45G:
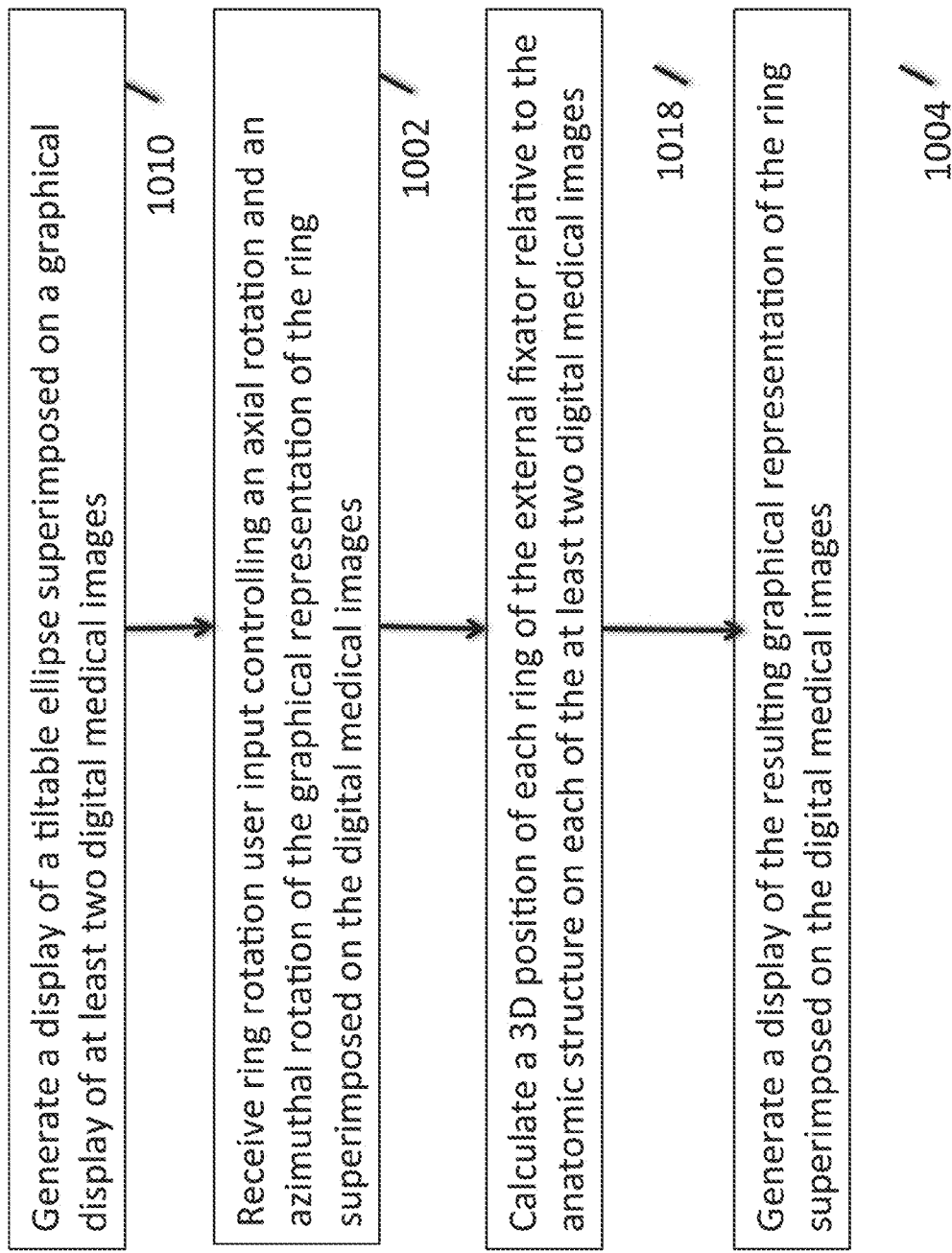
Figure 45H:
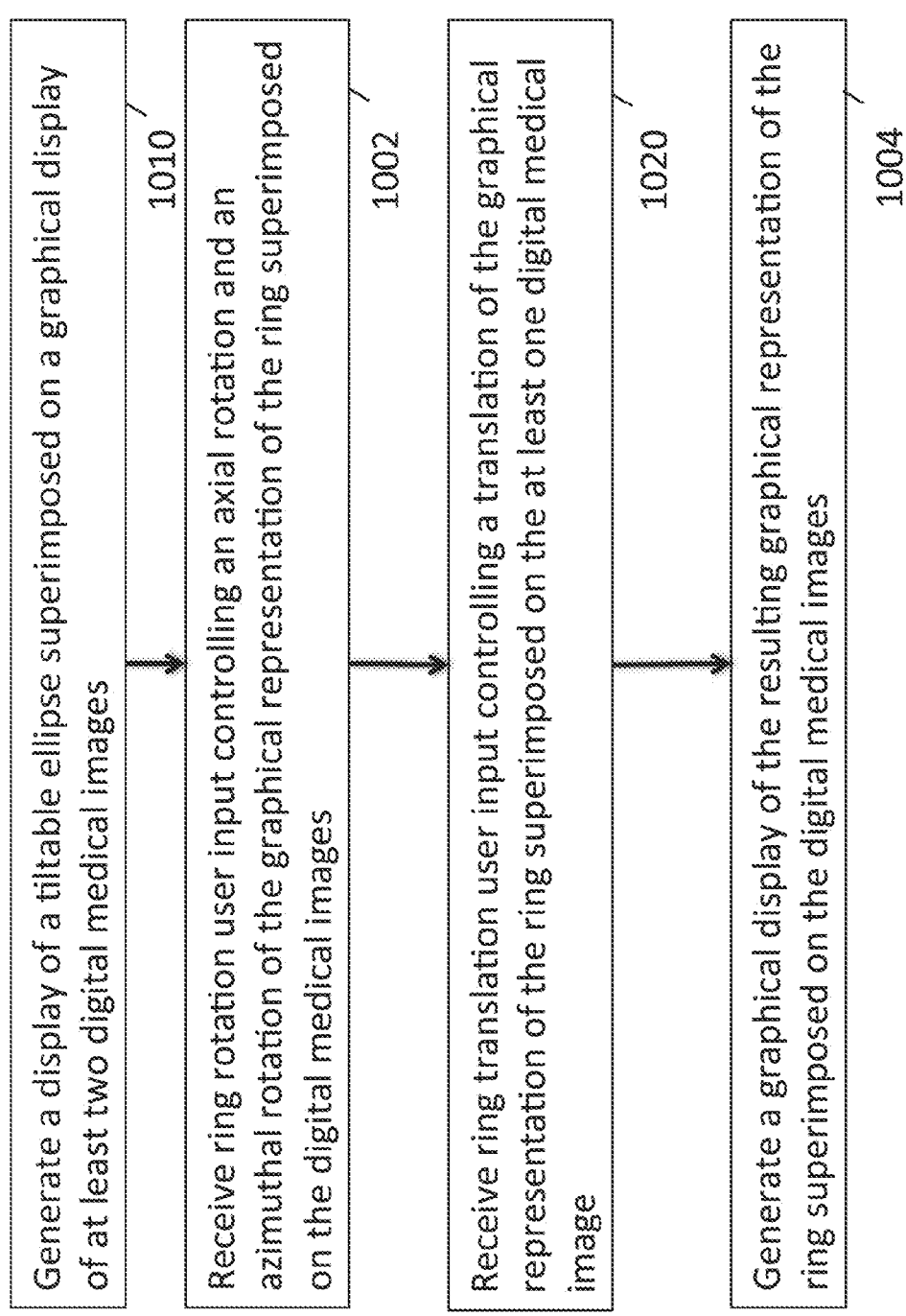
Figure 45I:
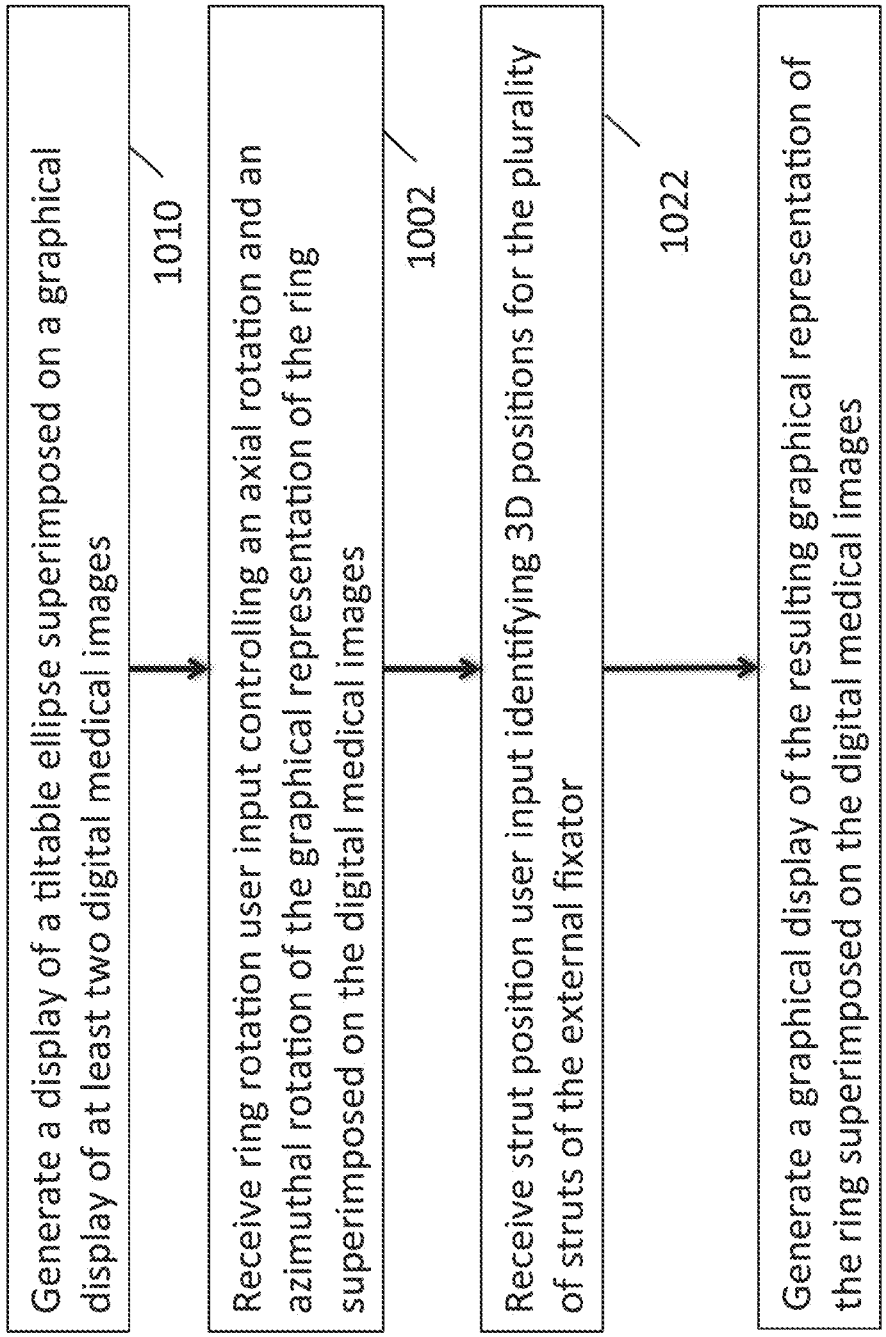
Figure 45J:
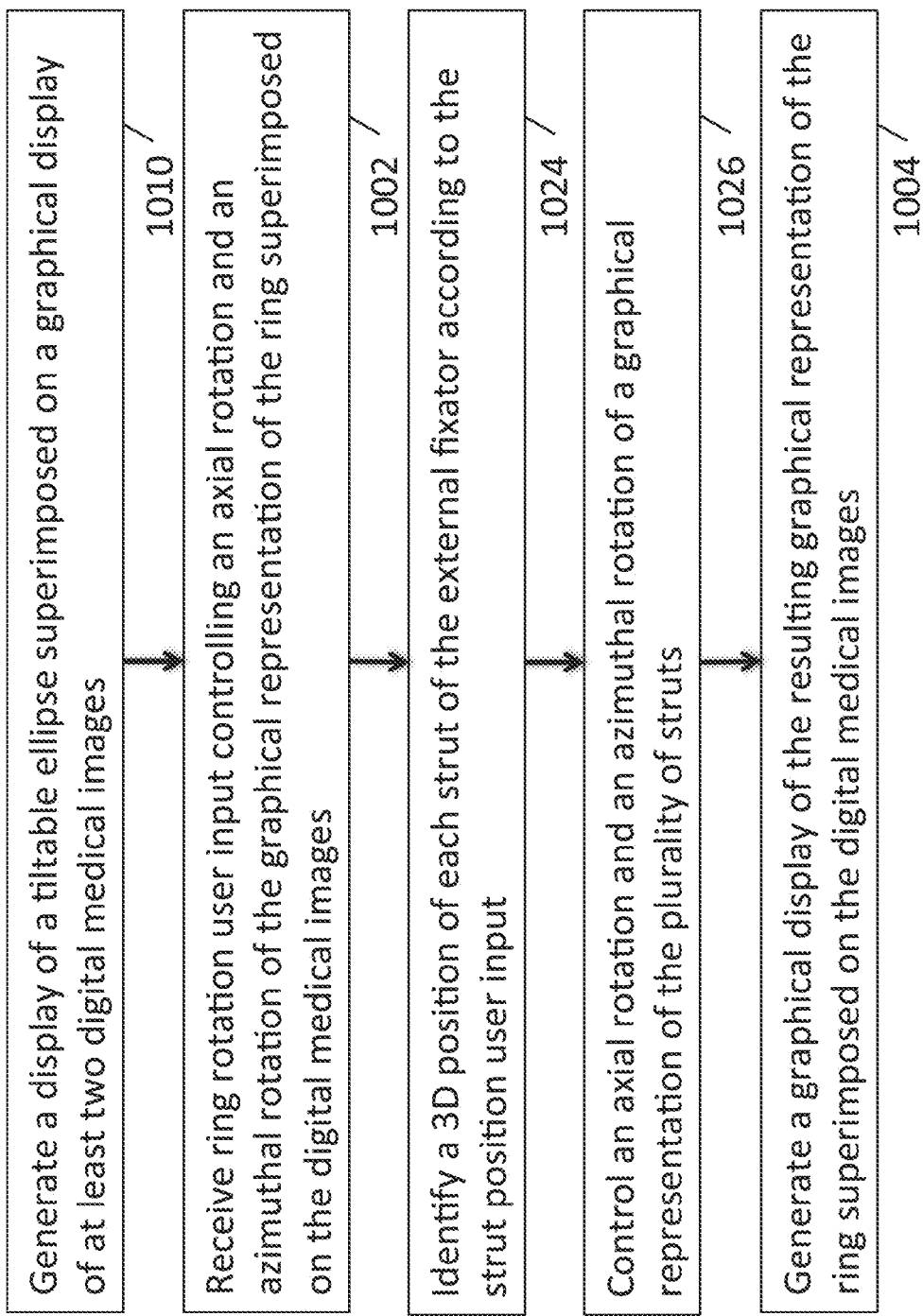

In other alternative embodiments, the computer-implemented method further includes instructions to control the axial rotation and the azimuthal rotation of the graphical representation of the ring superimposed on a first digital medical image of the digital medical images according to ring rotation user input entered along a second digital medical image of the two digital medical images 1012, as shown in FIG. 45E, receive ring translation user input entered graphically on the display of the tiltable ellipse to control a translation of the ring 1014, as shown in FIG. 45F, and calculate a 3D position of each ring of the external fixator relative to the anatomic structure on each of the digital medical images 1018, as shown in FIG. 45G. In other alternative embodiments, the computer-implemented method further includes instructions to receive ring translation user input controlling a translation of the graphical representation of the ring superimposed on the at least one digital medical image 1020, as shown in FIG. 45H, receive strut position user input identifying 3D positions for the plurality of struts of the external fixator 1022, as shown in FIG. 45I, and identify a 3D position of each strut of the external fixator according to the strut position user input 1024 and control an axial rotation and an azimuthal rotation of a graphical representation of the plurality of struts 1026, as shown in FIG. 45J.

Figure 46A:
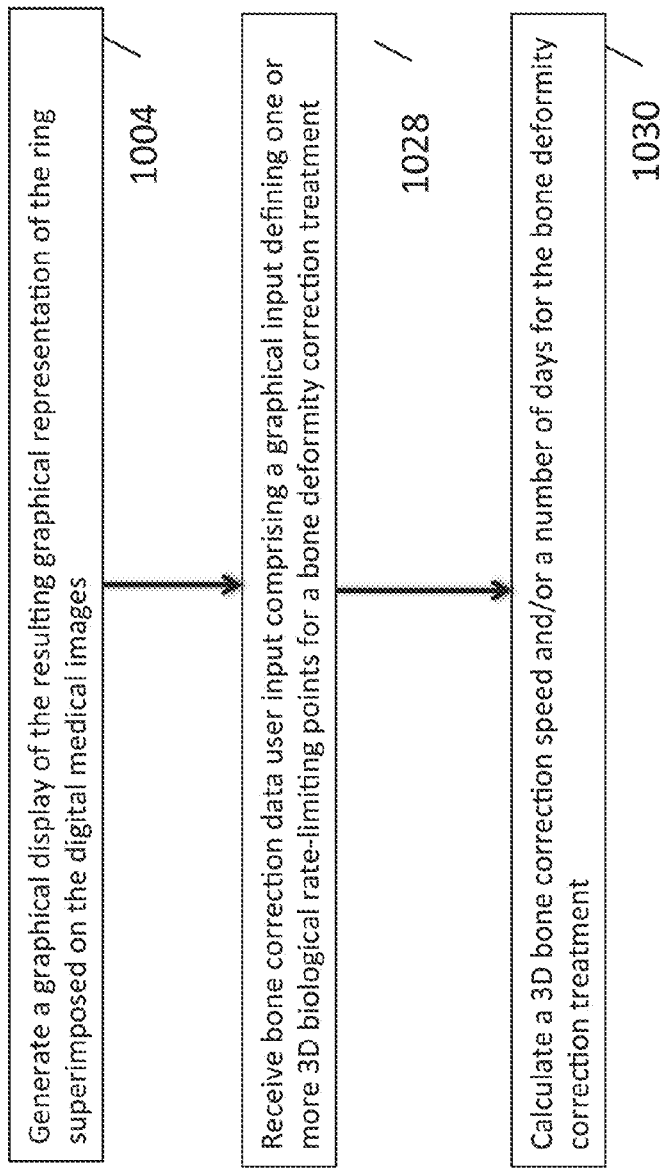
FIGS. 46A-F illustrate the method of FIG. 45J, further including various aspects involved in bone deformity treatment, according to some embodiments of the present invention.
Figure 46B:
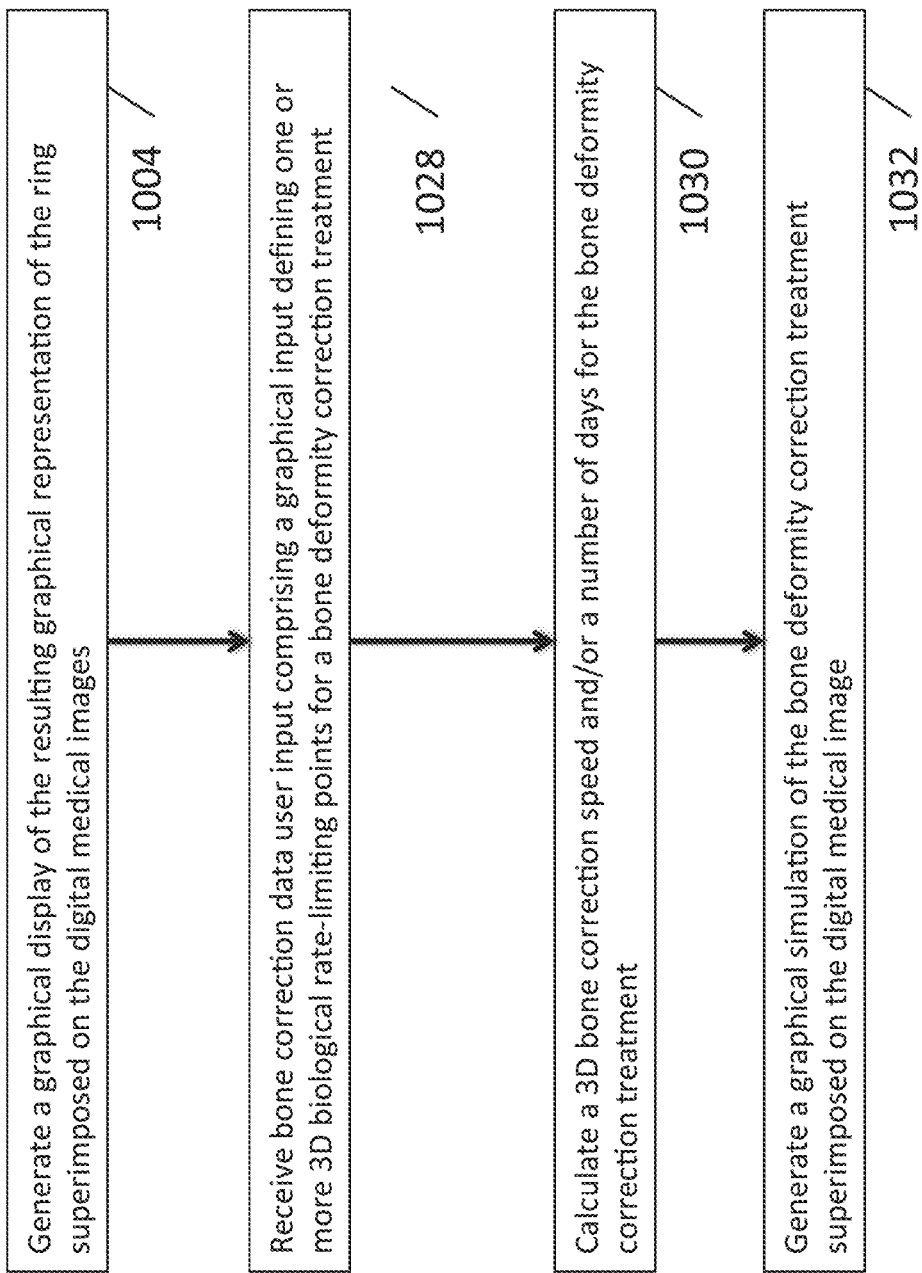
Figure 46C:
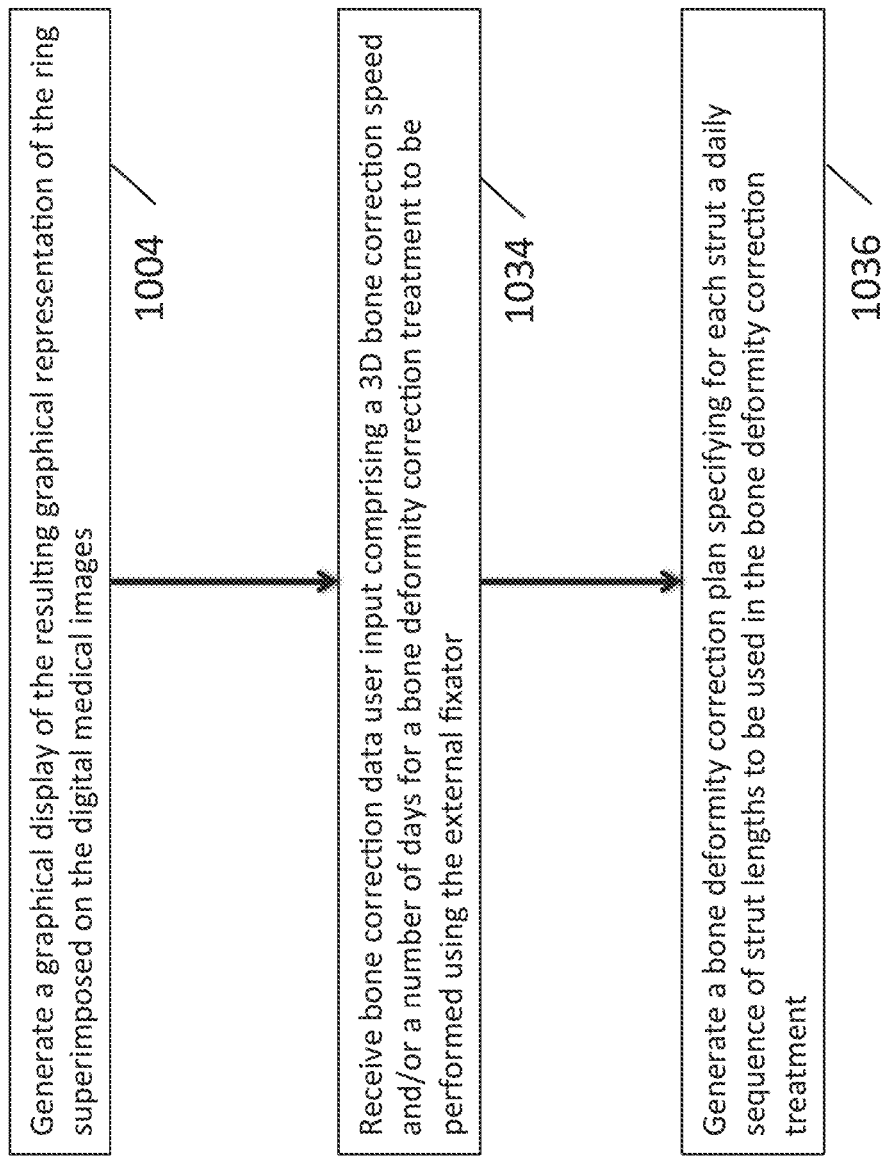

In some embodiments, generating a graphical display of the resulting graphical representation of the ring superimposed on the digital medical images 1004 further includes instructions to receive bone correction data user input comprising a graphical input defining one or more 3D biological rate-limiting points for a bone deformity correction treatment 1028 and calculate a 3D bone correction speed and/or a number of days for the bone deformity correction treatment 1030, as shown in FIG. 46A, and calculate a 3D bone correction speed and/or a number of days for the bone deformity correction treatment 1030, as shown in FIG. 46B. In some embodiments, generating a graphical display of the resulting graphical representation of the ring superimposed on the digital medical images 1004 further includes instructions to receive bone correction data user input comprising a 3D bone correction speed and/or a number of days for a bone deformity correction treatment to be performed using the external fixator 1034 and generate a bone deformity correction plan specifying for each strut a daily sequence of strut lengths to be used in the bone deformity correction treatment 1036, as shown in FIG. 46C.

Figure 46D:
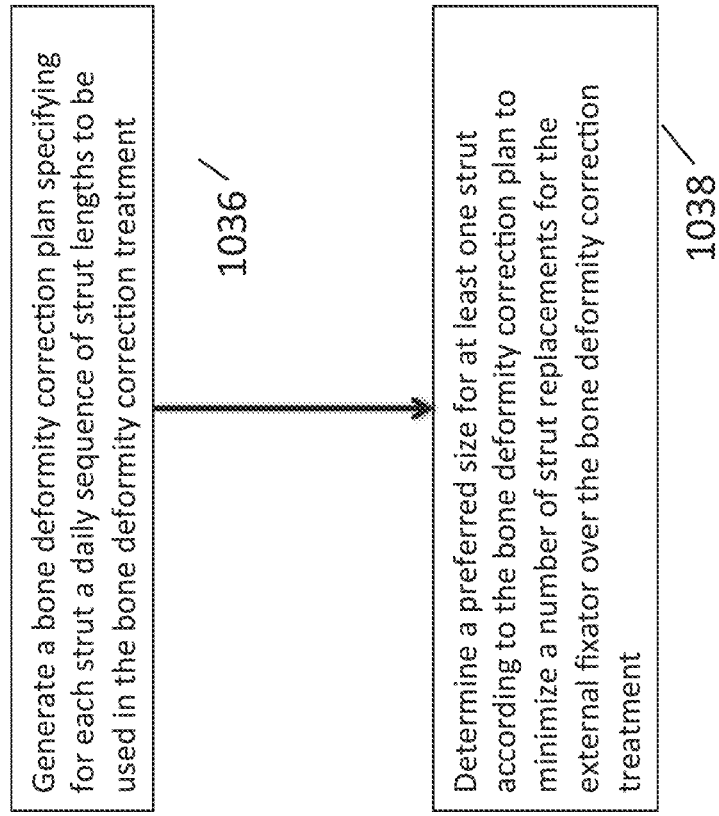
Figure 46E:
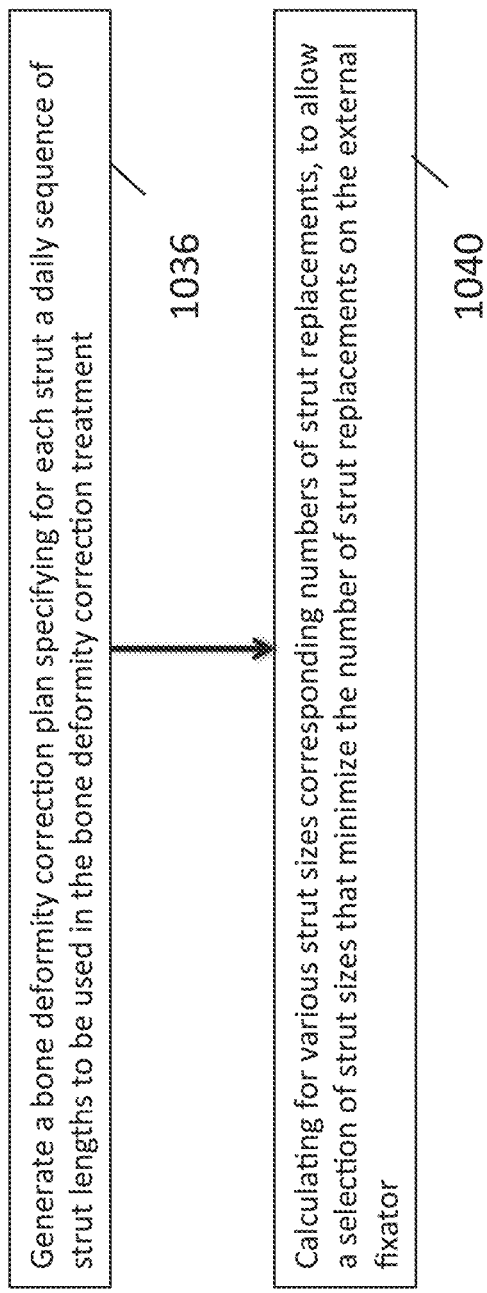
Figure 46F:
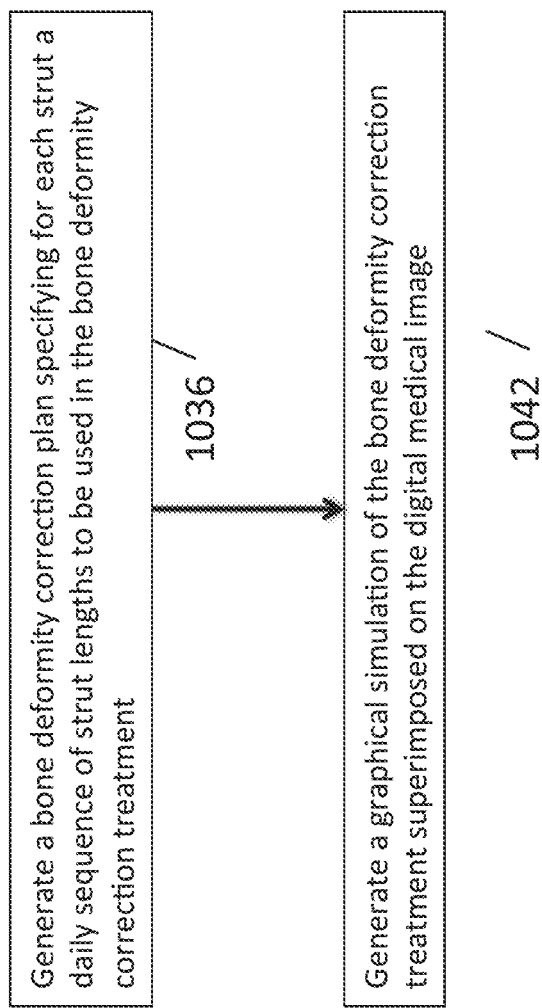

In some embodiments, generating a bone deformity correction plan specifying for each strut a daily sequence of strut lengths to be used in the bone deformity correction treatment 1036 further includes instructions to determine a preferred size for at least one strut according to the bone deformity correction plan to minimize a number of strut replacements for the external fixator over the bone deformity correction treatment 1038, as shown in FIG. 46D, calculate for various strut sizes corresponding numbers of strut replacements, to allow a selection of strut sizes that minimize the number of strut replacements on the external fixator 1040, as shown in FIG. 46E, and generate a graphical simulation of the bone deformity correction treatment superimposed on the digital medical image 1042, as shown in FIG. 46F.

Discussion

Exemplary systems and methods as described above allow accurate and user-friendly extraction of fixator ring and/or strut 3D position information using one or more radiographs of a patient's anatomy, and allow simulating ring and/or strut position sequences over a course of treatment overlaid on one or more radiographs. Exemplary systems and methods as described above, in particular methods relying on user-controlled axial and azimuthal rotations of fixator rings, can be significantly more convenient than fully-manual, pen-and-paper methods, and at the same time do not rely on potentially-inaccurate edge detection techniques or other fully-automatic techniques that may exhibit limited accuracy in visually-crowded environments. Exemplary human-controlled, computer-assisted methods as described above leverage human pattern-recognition capabilities to identify ring positions overlaid on radiographs, in conjunction with superior computer position-computation capabilities to determine 3D ring positions and corresponding courses of treatment once desired ring locations on one or more radiographs have been identified by a human. Such desired ring locations may be locations that match existing fixator structures already attached to the patient, or simulated locations for a fixator to be attached to the patient.

Exemplary systems and methods as described above do not necessarily require that fixator rings be orthogonal to corresponding bone segments, or that AP and lateral x-rays be perfectly mutually orthogonal. Planning and simulating sequential bone and ring manipulation sequences (i.e. concatenating multiple courses of treatment into one simulation) can allow improving clinical outcomes. Visual (graphical) simulation of a course of treatment overlaid on patient radiographs can provide ready confirmation that the prescribed course of treatment matches the patient's anatomy. Exemplary templating methods as described above allow preparing accurate ring/strut configurations pre-operatively and thus allow reducing the amount of time needed during surgery. In addition, minimizing the number of strut exchanges (replacements) for a given course of treatment allows savings in physician time and allows reducing patient suffering or discomfort.

It will be clear to one skilled in the art that the above embodiments may be altered in many ways without departing from the scope of the invention. Accordingly, the scope of the invention should be determined by the following claims and their legal equivalents.

What is claimed is:

1. A computer-implemented method comprising employing at least one processor to execute instructions to:
    generate a display of an ellipse superimposed on a display of at least one digital medical image, the at least one digital medical image displaying a view of a patient's anatomical structure, the ellipse being a graphical representation of a first ring of a synthetic external fixator representing a physical external fixator attached to the patient's anatomical structure, the physical external fixator comprising first and second rings interconnected by a plurality of struts;
    generate a display of a first line segment extending along an axis of a first bone segment shown in the display of the at least one digital medical image by detecting locations of corresponding bone segment graphical user input;
    for each strut, receive strut attachment point user input representing a first actual point of attachment of the strut to the first ring and a second actual point of attachment of the strut to the second ring;
    generate a strut line segment for each strut and displaying the strut line segment on the display such that the strut line segment overlies a corresponding one of the plurality of struts in the digital medical image; and
    generate a bone deformity correction plan specifying for each strut a sequence of strut lengths to be used in a bone deformity correction treatment.

2. The method of claim 1, wherein the bone segment graphical user input includes mouse clicks at opposite ends of the first bone segment shown in the display of the at least one digital medical image.

3. The method of claim 1, wherein the first actual point of attachment of the strut to the first ring is a hole in the first ring.

4. The method of claim 1, wherein the first actual point of attachment of the strut to the first ring is via an intermediary piece of hardware coupled to the first ring.

5. The method of claim 4, wherein the intermediary piece of hardware is a ring drop device adapted to position a corresponding one of the struts a predefined distance from the first ring.

6. The method of claim 1, wherein the display of the ellipse superimposed on the display of at least one digital medical image is displayed simultaneously with the strut line segments.

7. The method of claim 1, wherein the display of the at least one digital medical image comprises at least two digital medical images, each image displaying a view from a different angle of the patient's anatomical structure.

8. A computer system comprising at least one microprocessor configured to execute instructions to:
    generate a display of an ellipse superimposed on a display of at least one digital medical image, the at least one digital medical image displaying a view of a patient's anatomical structure, the ellipse being a graphical representation of a first ring of a synthetic external fixator representing a physical external fixator attached to the patient's anatomical structure, the physical external fixator comprising first and second rings interconnected by a plurality of struts;
    generate a display of a first line segment extending along an axis of a first bone segment shown in the display of the at least one digital medical image by detecting locations of corresponding bone segment graphical user input;
    for each strut, receive strut attachment point user input representing a first actual point of attachment of the strut to the first ring and a second actual point of attachment of the strut to the second ring;
    generate a strut line segment for each strut and displaying the strut line segment on the display such that the strut line segment overlies a corresponding one of the plurality of struts in the digital medical image; and
    generate a bone deformity correction plan specifying for each strut a sequence of strut lengths to be used in a bone deformity correction treatment.

9. The computer system of claim 8, wherein the bone segment graphical user input includes mouse clicks at opposite ends of the first bone segment shown in the display of the at least one digital medical image.

10. The computer system of claim 8, wherein the first actual point of attachment of the strut to the first ring is a hole in the first ring.

11. The computer system of claim 8, wherein the first actual point of attachment of the strut to the first ring is via an intermediary piece of hardware coupled to the first ring.

12. The computer system of claim 11, wherein the intermediary piece of hardware is a ring drop device adapted to position a corresponding one of the struts a predefined distance from the first ring.

13. The computer system of claim 8, wherein the display of the ellipse superimposed on the display of at least one digital medical image is displayed simultaneously with the strut line segments.

14. The computer system of claim 8, wherein the display of the at least one digital medical image comprises at least two digital medical images, each image displaying a view from a different angle of the patient's anatomical structure.

15. A non-transitory computer-readable medium encoding instructions which, when executed by a microprocessor of a computer system, cause the computer system to:
  generate a display of an ellipse superimposed on a display of at least one digital medical image, the at least one digital medical image displaying a view of a patient's anatomical structure, the ellipse being a graphical representation of a first ring of a synthetic external fixator representing a physical external fixator attached to the patient's anatomical structure, the physical external fixator comprising first and second rings interconnected by a plurality of struts;
  generate a display of a first line segment extending along an axis of a first bone segment shown in the display of the at least one digital medical image by detecting locations of corresponding bone segment graphical user input;
  for each strut, receive strut attachment point user input representing a first actual point of attachment of the strut to the first ring and a second actual point of attachment of the strut to the second ring;
  generate a strut line segment for each strut and displaying the strut line segment on the display such that the strut line segment overlies a corresponding one of the plurality of struts in the digital medical image; and
  generate a bone deformity correction plan specifying for each strut a sequence of strut lengths to be used in a bone deformity correction treatment.

16. The non-transitory computer-readable medium of claim 15, wherein the bone segment graphical user input includes mouse clicks at opposite ends of the first bone segment shown in the display of the at least one digital medical image.

17. The non-transitory computer-readable medium of claim 15, wherein the first actual point of attachment of the strut to the first ring is a hole in the first ring.

18. The non-transitory computer-readable medium of claim 15, wherein the first actual point of attachment of the strut to the first ring is via an intermediary piece of hardware coupled to the first ring.

19. The non-transitory computer-readable medium of claim 18, wherein the intermediary piece of hardware is a ring drop device adapted to position a corresponding one of the struts a predefined distance from the first ring.

20. The non-transitory computer-readable medium of claim 15, wherein the display of the ellipse superimposed on the display of at least one digital medical image is displayed simultaneously with the strut line segments.

21. The non-transitory computer-readable medium of claim 15, wherein the display of the at least one digital medical image comprises at least two digital medical images, each image displaying a view from a different angle of the patient's anatomical structure.

\* \* \* \* \*